(12) United States Patent
Abdo et al.

(10) Patent No.: US 12,379,378 B2
(45) Date of Patent: *Aug. 5, 2025

(54) SYSTEMS AND METHODS FOR BARRETT'S ESOPHAGUS PATHOGENESIS AND ESOPHAGEAL ADENOCARCINOMA PROGRESSION REVEALING MARKERS

(71) Applicant: PROPHASE LABS, INC., Garden City, NY (US)

(72) Inventors: Joe Abdo, Garden City, NY (US); Sumeet K. Mittal, Garden City, NY (US); Devendra K. Agrawal, Garden City, NY (US)

(73) Assignee: PROPHASE LABS, INC., Garden City, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/532,450

(22) Filed: Dec. 7, 2023

(65) Prior Publication Data

US 2024/0192217 A1  Jun. 13, 2024

Related U.S. Application Data

(62) Division of application No. 17/324,956, filed on May 19, 2021, now Pat. No. 11,874,277.

(60) Provisional application No. 63/026,818, filed on May 19, 2020.

(51) Int. Cl.
| | | |
|---|---|---|
| *G01N 33/574* | (2006.01) | |
| *G01N 33/543* | (2006.01) | |
| *G01N 33/68* | (2006.01) | |

(52) U.S. Cl.
CPC . *G01N 33/57484* (2013.01); *G01N 33/54306* (2013.01); *G01N 33/6848* (2013.01)

(58) Field of Classification Search
CPC ............................................. G01N 33/57484
USPC ...................................................... 435/7.23
See application file for complete search history.

(56) References Cited

U.S. PATENT DOCUMENTS

| | | | |
|---|---|---|---|
| 11,874,277 B2* | 1/2024 | Abdo | .......... C12Q 1/6886 |
| 2012/0264154 A1* | 10/2012 | Mann | .......... G01N 33/96 |
| | | | 435/23 |
| 2022/0334119 A1* | 10/2022 | Rodland | .......... G01N 33/57438 |

FOREIGN PATENT DOCUMENTS

| | | |
|---|---|---|
| WO | 2015103128 A1 | 7/2015 |
| WO | 2017137427 A1 | 8/2017 |

OTHER PUBLICATIONS

Ke et al (RSC Adv, 2016, 6: 12280-12285).*
Rolli-Derkinderen, M., et al., "ERK and p38 inhibit the expression of 4E-BP1 repressor of translation through induction of Egr-1," The Journal of Biological Chemistry, 278(21):18859-18867, May 23, 2003, 9 pages.
Sainz, B., et al., "ISG15 is a Critical Microenvironmental Factor for Pancreatic Cancer Stem Cells," Cancer Res., 74(24):7309-7320, Nov. 3, 2014, 13 pages.
Salcedo, R., et al., MyD88 and its divergent toll in carcinogenesis,: Trends Immonol., 34(8):379-389, Aug. 2013, 18 pages.
Shaheen, N.J., et al., "ACG Clinical Guideline: Diagnosis and Management of Barrett's Esophagus," Am. J. Gastroenterol., 111(1);30-50, 2016, 21 pages.
Sharma, A.K., et al., "Receptor for Advanced Glycation End Products (RAGE) on INKT Cells Mediates Lung Ischemia-Reperfusion Injury," Am. J. Transplant., 13(9):2255-2267, Sep. 2013, 21 pages.
Stella Diagnostics, Optimizing Patient Management Strategies for Esophageal Diseases, Feb. 2021, 26 pages.
Tong, X-M, et al., "Calcium-binding protein S100P is highly expressed during the implantation window in human endometrium," Fertil. Steril., 94(4):1510-1518, Sep. 2010, 9 pages.
Wakita, A., et al., "PD-L1 Expression is a Prognostic Factor in Patients with Thoracic Esophageal Cancer Treated Without Adjuvant Chemotherapy," Anticancer Research, 37(3):1433-1442, 2017, 9 pages.
Walmer, D.K., et al., "Malignant Transformaton of the Human Endometrium is Associated with Overexpression of Lactoferrin Messenger RNA and Protein," Cancer Research, 55(5):1168-1178, Mar. 1, 1995, 9 pages.
Wu, Z., et al., "Ubiquitin-conjugating enzyme complex Uev1A-Ubc13 promotes breast cancer metastasis through nuclear factor-kB mediated matrix metalloproteinase-1 gene regulation," Breast Cancer Research, 16(4):R75, 2014, 15 pages.
Xue, C., et al., "Up-regulation of CNDP2 facilitates the proliferation of colon cancer," BMC Gastroenterol, 14(1):96, 2014, 8 pages.
Yoon, J., et al., "Apoptosis-related mRNA expression profiles of ovarian cancer cell lines following cisplatin treatment," J. Gynecol. Oncol., 21(4):255-261, Dec. 30, 2010, 7 pages.
Zhang, Z., et al., "Epidemiology of esophageal cancer," World J. Gastroenterol., 19(34):5598-5606, Sep. 14, 2013, 10 pages.
Zhang, Z., et al., "Underexpressed CNDP2 Participates in Gastric Cancer Growth Inhibition through Activating the MAPK Signaling Pathway," Mol. Med., 20(1):17-28, 2014, 12 pages.
Zuo, C., et al., "ISG15 in the tumorigenesis and treatment of cancer: An emerging role in malignancies of the digestive system," Oncotarget, 7(45):74393-74409, Nov. 8, 2016, 17 pages.

(Continued)

*Primary Examiner* — Sean E Aeder
(74) *Attorney, Agent, or Firm* — POLSINELLI PC

(57) ABSTRACT

Methods are provided for assessing risk of developing esophageal adenocarcinoma in a subject using one or more of the following marker genes/proteins: ISG15, LTF, CNDP2, DAD1, SET, UBE2N, S100P, and GPI. Methods are also provided for determining expression of one or more esophageal adenocarcinoma risk factors in a subject. Methods are also provided for treating esophageal adenocarcinoma in a subject, for preventing esophageal adenocarcinoma in a subject, for inhibiting or decreasing proliferation of esophageal adenocarcinoma cells, for inhibiting or decreasing migration of esophageal adenocarcinoma cells, or for increasing susceptibility to cytotoxicity or inducing cell death of esophageal adenocarcinoma cells.

26 Claims, 91 Drawing Sheets
Specification includes a Sequence Listing.

(56) References Cited

OTHER PUBLICATIONS

Fleegel, J., et al., "Abstract 1976: Identification of 4 novel markers in the chemotherapy resistance of esophageal adenocarcinoma," Cancer Research, Jul. 1, 2018, [retrieved from the Internet Jul. 8, 2021: https://cancerres.accrjournals.org.content/78/13_Supplemental/1976], 2 pages.
Sabo, E., et al., "Expression Analysis of Barrett's Esophagus-Associated High-Grade Dysplasia in Laser Capture Microdissected Archival Tissue," Clin Cancer Res., 14(20):6440-6448, Oct. 15, 2008, 10 pages.
Olsen, et al., "Trypsin Cleaves Exclusively C-terminal to Arginine and Lysine Residues," Molecular & Cellular Proteomics 3.6, Mar. 19, 2004, 3:608-614, 7 pages.
Liebler, et al., "Targeted Quantitation of Proteins by Mass Spectrometry," Biochemistry, 2013, 52: 3797-3806, 10 pages.
Loeb, et al., "The Interferon-inducible 15-kDa Ubiquitin Homolog Conjugates to Intracellular Proteins," The Journal of Biological Chemistry, Apr. 15, 1992, 267(11): 7806-7813, 8 pages.
International Search Report and Written Opinion of the International Searching Authority for WIPO Application No. PCT/US2021/033248, mailed Jul. 19, 2021, pages.
Abdo, J., et al., "Neoadjuvant Therapy for Esophageal Adenocarcinoma in the Community Setting—Practice and Outcomes," Front Oncol., 7:151, 2017, 12 pages.
Abdo, J., et al., "Basis for molecular diagnostics and immunotherapy for esophageal cancer," Expert Rev. Anticancer Ther., 17(1):33-45, Jan. 2017, 27 pages.
Abdo, J., et al., "Discovery of Novel and Clinically Relevant Markers in Formalin-Fixed Paraffin-Embedded Esophageal Cancer Specimen," Frontiers in Oncology, 8(157):1-11, May 9, 2018, 11 pages.
Abdo, J., et al., "Retraction: Neoadjuvant Therapy for Esophageal Adenocarcinoma in the Community Setting—Practice and Outcomes," Frontiers in Oncology, 9(324):1, Apr. 2019, 1 page.
Arumugam, T., et al., "S100P promotes pancreatic cancer growth, survival and invasion," Clin. Cancer Res., 11(15):5356-5364, Aug. 1, 2005, 10 pages.
Arumugam, T., et al., "S100P: A novel therapeutic target for cancer," Amino Acids, 41(4):893-899, Oct. 2011, 11 pages.
Arumugam, T., et al., "S100P-Derived RAGE Antagonistic Peptide Reduces Tumor Growth and Metastasis," Clin. Cancer Res., 18(16):4356-4364, Aug. 15, 2012, 10 pages.
Ayyappan, S., et al., "Epidermal growth factor receptor (EGFR)-targeted therapies in esophagogastric cancer," Anticancer REs., 33(10):4139-4155, 2013, 17 pages.
Blomstrom, D.C., et al., "Molecular characterization of the interferon-induced 15-kDa protein. Molecular cloning and nucleotide and amino acid sequence," Journal of Biological Chemistry, 261(19);8811-8816, Jul. 5, 1986, 6 pages.
Cheng, J., et al., "A small-molecule inhibitor of UBE2N induces neuroblastoma cell death via activation of p53 and JNK pathways," Cell Death and Dis., 5(2):e1079, Feb. 20, 2014, 12 pages.
Czarnecki, O., et al., "A Dual Role of Strigolactones in Phosphate Acquisition and Utilizaton in Plants," Int. J. Mol. Sci., 14(4): 7681-7701, 2013, 21 pages.
Dau, T., et al., "Proteomics Using Protease Alternatives to Trypsin Benefits from Sequential Digestion with Trypsin," Analytical Chemistry, 92:9523-9527, 2020, 5 pages.
Deng, L., et al., "Activation of the IkappaB kinase complex by TRAF6 requires a dimeric ubiquitin-conjugating enzyme complex and a unique polyubiquitin cain," Cell, 103(2):351-361, Oct. 13, 2000, 11 pages.
Deng, M., et al., "MiR-214 promotes tumorigenesis by targeting lactotransferrin in nasopharyngeal carcinoma," Tumor Biol., 34(3): 1793-1800, 2013, 9 pages.
Desai, S.D., et al., "Elevated Expression of ISG15 in Tumor Cells Interferes with Ubiquitin/26S Proteasome Pathway," Cancer Res., 66(2):921-928, Jan. 2006, 9 pages.
Desai, S.D., "ISG15: Adouble edge sword in cancer," Oncoimmunology, 4(12):e1052935, Dec. 2015, 2 pages.
Diehl, J.A., et al., "Ubiquitin and Cancer: New Discussions for a New Journal," Genes & Cacner, 1(7):679-680, 2010, 2 pages.
Dong., L., et al., "Overexpression of S100P promotoes colorectal cancer metastasis and decreases chemosenitivity to 5-FU in vitro.," Mole. and Cell Biochem, 389(1-2): 257-264, 2014. 8 pages.
Feng, W., et al., "Morphoproteomic profile of mTOR, Ras/Raf kinase/ERK, and NF-kappaB pathways in human gastric adenocarcinoma," Ann Clin Lab. Sci., 38(3):195-209, 2008, 15 pages.
Gallo, L.H., et al., "The importance of regulatory ubiquitination in cancer and metastasis," Cell Cycle, 16(7):634-648, 2017, 15 pages.
Ge, F., et al., "S100P predicts prognosis and drug resistance in gastric cancer," Int. J. Biol. Markers, 28(4):e387-392, 2013, 6 pages.
Giansanti, P., et al., "Six alternative proteases for mass spectrometry-based proteomics beyond trypsin," Nature Protocol, 11(5):993-1006, Apr. 28, 2016, 14 pages.
Haverland, N.A., et al., "Quantitative Proteomics by SWATH-MS Reveals Altered Expression of Nucleic Acid Binding and Regulatory Proteins in HIV-1-Infected Macrophages," J. Proteome Research, 13(4):2109-2119, 2014, 11 pages.
He, M., et al., "The emerging role of deubiquitinating enzymes in genomic integrity, diseases, and therapeutics," Cell Bioscience, 6:62, Dec. 20, 2016, 15 pages.
Hedner, C., et al., "Expression and Prognostic Significance of Human Epidermal Growth Factor Receptors 1 and 3 in Gastric and Esophageal Adenocarcinoma," PLos One., 11(2):e0148101, 2016, 18 pages.
Howlader, N., et al., SEER Cancer Statistics Review, 1975-2011, National Cancer Institute, Bethesda, MD, 2014, 1 pages.
Hung, M.H., et al., "Reprogramming the oncogenic response: SET protein as a potential therapeutic target in cancer," Expert Opin. Ther. Targets, 21(7):685-694, 2017, 11 pages.
Jansen, R.S., et al., "N-lactoyl-amino acids are ubiquitous metabolites that originate from CNDP2-mediated reverse proteolysis lactate and amino acids," PNAS, 112(21):6601-6606, May 26, 2015, 6 pages.
Jardim, D.L.F., et al., "MET aberrations and c-MET inhibitors in patients with gastric and esophageal cancers in a phase 1 unit," Oncotarget., 5(7):1837-1845, 2014, 9 pages.
Jeon, Y.J., et al., "Chemosensitivity is controlled by p63 modification with ubiquitin-like protein ISG15," J. Clin. Invest., 122(7):2622-2636, Jul. 2, 2012, 15 pages.
Kalinina, T., et al., "Insulin-like growth factor-1 receptor as a novel prognostic marker and its implication as a cotarget in the treatment of human adenocarcinoma of the esophagus," International Journal of Cancer., 127(8), 2010, 10 pages.
Kelleher, D.J., et al., "DAD1, the defender against apoptotic cell death, is a subunit of the mammalian oligosaccharyltransferase," PNAS USA, 94(10):4994-4999, May 13, 1997, 6 pages.
Kim, Y.H., et al., "Combined microarry analysis of small cell lung cancer reveals altered apoptotic balance and distinct expression signatures of MYC family gene amplification," Oncogene, 25(1):130-138, Jan. 5, 2006, 9 pages.
Klein, C., et al., Monozygotic Twin Model Reveals Novel Embryo-Induced Transcriptome Changes of Bovine Endometrium in the Preattahment Period., Biology of Reproduction, 74(2):253-264, Feb. 1, 2006, 12 pages.
Lamberts, L.E., et al., "functional genomic mRNA profiliing of a large cancer data base demostrates mesothelin overexpression in a board range of tumor types," Oncotarget., 6(29):28164-28172, 2015, 9 pages.
Li, S., et al., "Ligand-dependent EphA7 signaling inhibits prostate tumor growth and progression," Cell Death and Dis., 8(10):e3122, Oct. 12, 2017, 11 pages.
Luo, G., et al., "Lactotransferrin expression is down regulated and effects the mitogen-activated protein kinase pathway in gastric cancer," Oncol. Let., 9)5):2409-2413, 2015, 5 pages.
Matsuzawa, S.I., et al., "Siah-1, SIP, and Ebi collaborate in a novel pathway for beta-catenin degradation linked to p53 responses," Molecular Cell., 7(5):915-926, May 2001, 12 pages.

(56) References Cited

OTHER PUBLICATIONS

Mittal, S., et al., "Discovery preteomics detects expression trends associated with resistance of the most commonly used chemotherapies in esophageal ademocarinoma," European Journal of Cancer, 138S2(S1-S62): S40, p. 148, Oct. 1, 2020, 2 pages.

Miura, J.T., et al., "Tumor profiling of gastric and esophageal carcinoma reveal different treatment options," Cancer Biol. Therapy, 16(5):764-769, May 2015, 6 pages.

Montgomery, E., et al., "Reproducibility of the diagnosis of dysplasia in Barrett esophagus: A reaffirmation," Human Pathol, 32(4):368-378, 2001, 11 pages.

Morales, D.J., et al., "The Antiviral Activities of ISG15," J. Mol Biol., 425(24):4995-5008, Dec. 13, 2013, 15 pages.

Moritz, R., "Mass spectrometry-based targeted proteomics," Nature Methods, 10(1):23, Jan. 2013, 1 pages.

Parkkila, S., et al., "The calcium-binding protein S100P in normal and malignant human tissues," BMC Clin. Pathol, 8(1):2, Feb. 18, 2008, 9 pages.

Pickart, C.M., et al., "Ubiquitin: structures, functions, mechanisms," Biochimica et Biophysica Acta-Mol. Cell Res., 1695(1-3):55-72, Nov. 29, 2004, 18 pages.

Prieto, D.A., et al., "Liquid Tissue: proteomic profiling of formalin-fixed tissues," Biotechniques, Suppl:32-35, Jun. 2005, 4 pages.

Prins, M.J.D., et al., "The significance of the HER-2 status in esophageal adenocarcinoma for survival: an immunohistochemical and an in situ hybridization study," Ann Oncol., 24(5):1290-1297, May 2013, 8 pages.

Rajagopal, P.S., et al., "Chemotherapy for advanced cancers," Ann Palliat, Med., 3(3)203-228, Jun. 16, 2014, 26 pages.

Rodriguez, H., et al., "The next horizon in precision oncology: Proteogenomics to inform cancer diagnosis and treatment," Cell, 184:1662-1670, Apr. 1, 2021, 10 pages.

\* cited by examiner

SYSTEMS AND METHODS FOR BARRETT'S ESOPHAGUS PATHOGENESIS AND ESOPHAGEAL ADENOCARCINOMA PROGRESSION REVEALING MARKERS

CROSS REFERENCE TO RELATED APPLICATIONS

This application is a divisional of U.S. application Ser. No. 17/324,956, filed May 19, 2021, which claims the benefit of U.S. Application No. 63/026,818, filed May 19, 2020, the entire disclosures of all of which are incorporated herein by reference.

REFERENCE TO A SEQUENCE LISTING

This application contains a Sequence Listing that has been submitted in XML format via Patent Center and is hereby incorporated by reference in its entirety. The XML copy, created on Dec. 7, 2023, is named 121413-774194_SL.xml and is 84,000 bytes in size.

BACKGROUND

Esophageal adenocarcinoma (EAC) has seen an aggressive increase in both incidence and prevalence since the 1970s and is now the eighth most common cancer in the world, with over half a million diagnosed per year. This upsurge in incidence is correlated with obesity and the increase in gastro-esophageal reflux disease which can lead to dysplasia of the lower esophagus known as Barrett's esophagus (BE), where roughly 2 million people in the US are currently living with this disease. Zhang (2013) *World J. Gastroenterol.* 19(34):5598-5606, herein incorporated by reference in its entirety for all purposes. Over time, as the number afflicted with esophageal adenocarcinoma has increased, proportional survival statistics with modern medicine have not. On average, death occurs 13 months after diagnosis, with less than 18% reaching the 5-year mark. This is a 5-year survival increase of only 10% from 1975. Howlader et al., SEER Cancer Statistics Review, 1975-2011, National Cancer Institute. Bethesda, MD (2014), herein incorporated by reference in its entirety for all purposes. Contrast this with increases of 50, 40, 50, and 70 percent of patients surviving 5-years compared to prognosis in 1975 for Leukemia, Non-Hodgkin's Lymphoma, Kidney and prostate cancer patients respectively. Not surprisingly, EAC has been found to resist many first-line chemotherapy tactics including, but not limited to, cisplatin, 5-FU, taxol, and carboplatin. In addition, one study suggested that there is indeed, no survival advantage for EAC patients treated with surgery plus chemotherapy versus surgery alone. Rajagopal et al. (2014) *Ann. Palliat. Med.* 3(3):203-228, herein incorporated by reference in its entirety for all purposes. A better understanding of what contributes to this rapidly metastatic and chemotherapy-resistant cancer is needed.

SUMMARY

Compositions and methods related to novel biomarkers for esophageal adenocarcinoma and progression from Barrett's esophagus to esophageal adenocarcinoma are provided.

In one aspect, provided are methods of assessing risk of developing esophageal adenocarcinoma in a subject. Some such methods comprise: (a) determining the expression level of one or more marker genes in a test esophageal tissue sample from the subject, wherein the one or more marker genes are selected from the group consisting of ISG15, LTF, CNDP2, DAD1, SET, UBE2N, S100P, GPI, and any combination thereof; and (b) comparing the expression level of the one or more marker genes in the test esophageal tissue sample to the expression level of the one or more marker genes in a control esophageal tissue sample, wherein increased expression of at least one of the one or more of marker genes in the test esophageal tissue sample relative to the control esophageal tissue sample indicates an increased risk of developing esophageal adenocarcinoma.

In some such methods, the one or more marker genes comprise ISG15. In some such methods, the one or more marker genes comprise LTF. In some such methods, the one or more marker genes comprise CNDP2. In some such methods, the one or more marker genes comprise DAD1. In some such methods, the one or more marker genes comprise SET. In some such methods, the one or more marker genes comprise UBE2N. In some such methods, the one or more marker genes comprise S100P. In some such methods, the one or more marker genes comprise GPI. In some such methods, the one or more marker genes comprise ISG15 and LTF. In some such methods, the one or more marker genes comprise ISG15 and DAD1. In some such methods, the one or more marker genes comprise LTF and DAD1. In some such methods, the one or more marker genes comprise ISG15, LTF, and DAD1. In some such methods, the one or more marker genes comprise ISG15 and CNDP2. In some such methods, the one or more marker genes comprise LTF and CNDP2. In some such methods, the one or more marker genes comprise ISG15, LTF, and CNDP2. In some such methods, the one or more marker genes comprise ISG15, LTF, DAD1, and CNDP2. In some such methods, the one or more marker genes comprise ISG15, LTF, DAD1, and SET. In some such methods, the one or more marker genes comprise ISG15, LTF, DAD1, and GPI. In some such methods, the one or more marker genes comprise ISG15, LTF, DAD1, CNDP2, and SET. In some such methods, the one or more marker genes comprise ISG15, LTF, DAD1, CNDP2, and GPI. In some such methods, the one or more marker genes comprise ISG15, LTF, DAD1, SET, and GPI. In some such methods, the one or more marker genes comprise ISG15, LTF, DAD1, CNDP2, SET, and GPI.

In some such methods, the one or more marker genes are selected from the group consisting of ISG15, LTF, DAD1, and any combination thereof. In some such methods, the one or more marker genes are selected from the group consisting of CNDP2, SET, GPI, and any combination thereof. In some such methods, the one or more marker genes are selected from the group consisting of ISG15, LTF, DAD1, CNDP2, SET, GPI, and any combination thereof. In some such methods, the one or more marker genes are selected from the group consisting of UBE2N, S100P, and any combination thereof. In some such methods, the one or more marker genes are selected from the group consisting of ISG15, CNDP2, DAD1, SET, UBE2N, GPI, and any combination thereof.

In some such methods, the subject has or is suspected of having gastroesophageal reflux disease or Barrett's esophagus. In some such methods, the subject has Barrett's esophagus, the test esophageal tissue sample is a Barrett's esophagus tissue sample, and the method assesses risk of progressing from Barrett's esophagus to esophageal adenocarcinoma. In some such methods, the subject is a human.

In some such methods, the test esophageal tissue sample comprises an isolated esophageal tissue sample. In some such methods, the test esophageal tissue sample comprises a biopsy sample. In some such methods, the test esophageal tissue sample comprises a fresh sample, a frozen sample, a preserved sample, a formalin-fixed sample, or a formalin-fixed paraffin-embedded (FFPE) sample. In some such methods, the test esophageal sample comprises a microdissected sample. In some such methods, the test esophageal tissue sample comprises a mucosa sample or a Barrett's esophagus mucosa sample. In some such methods, the test esophageal tissue sample comprises a mucosa sample or a Barrett's esophagus mucosa sample that has been separated from non-mucosal tissue. In some such methods, the test esophageal tissue sample comprises a Barrett's esophagus mucosa sample that has been separated from normal mucosal tissue. In some such methods, the test esophageal tissue sample comprises a Barrett's esophagus mucosa sample that has been separated from non-mucosal tissue and normal mucosal tissue. Optionally, the test esophageal tissue sample comprises a formalin-fixed paraffin-embedded (FFPE) mucosa sample or a FFPE Barrett's esophagus mucosa sample that has been separated from non-mucosal tissue, the test esophageal tissue sample comprises a FFPE Barrett's esophagus mucosa sample that has been separated from normal mucosal tissue, or the test esophageal tissue sample comprises a FFPE Barrett's esophagus mucosa sample that has been separated from non-mucosal tissue and normal mucosal tissue.

In some such methods, the method further comprises selectively isolating mucosal tissue from the test esophageal tissue sample to produce a test esophageal mucosa sample that has been separated from non-mucosal tissue prior to step (a), and the expression level of the one or more marker genes is determined in the test esophageal mucosa sample. In some such methods, the method further comprises selectively isolating Barrett's esophagus mucosal tissue from the test esophageal tissue sample to produce a test Barrett's esophagus mucosa sample that has been separated from normal mucosal tissue prior to step (a), and the expression level of the one or more marker genes is determined in the test Barrett's esophagus mucosa sample. In some such methods, the method further comprises selectively isolating Barrett's esophagus mucosal tissue from the test esophageal tissue sample to produce a test Barrett's esophagus mucosa sample that has been separated from non-mucosal tissue and normal mucosal tissue prior to step (a), and the expression level of the one or more marker genes is determined in the test Barrett's esophagus mucosa sample. In some such methods, the step of selectively isolating mucosal tissue comprises microdissection. In some such methods, the test esophageal tissue sample is a formalin-fixed paraffin-embedded (FFPE) sample.

In some such methods, the control esophageal tissue sample comprises normal esophageal mucosa. In some such methods, the control esophageal tissue sample is from the subject. In some such methods, the control esophageal tissue sample is from one or more control subjects that do not have gastroesophageal reflux disease, Barrett's esophagus, or esophageal adenocarcinoma.

In some such methods, determining the expression level of the one or more marker genes in the test esophageal tissue sample comprises performing an assay to measure the expression of messenger RNAs (mRNAs) encoded by the one or more marker genes. In some such methods, determining the expression level of the one or more marker genes in the test esophageal tissue sample comprises performing an assay to measure the expression of proteins encoded by the one or more marker genes. Optionally, the assay comprises a mass spectrometry assay, an immunohistochemistry assay, an immunoassay, an enzyme-linked immunosorbent assay (ELISA), an alphaLISA assay, or an enzyme-linked immune absorbent spot (ELISpot) assay.

In some such methods, the assay comprises the mass spectrometry assay. In some such methods, determining the expression level of the one or more marker genes in the test esophageal tissue sample comprises digesting the test esophageal tissue sample with one or more proteinases prior to performing the mass spectrometry assay. In some such methods, the test esophageal tissue sample is a formalin-fixed paraffin-embedded (FFPE) sample, and the method further comprises processing the FFPE sample to reverse formalin cross-links prior to performing the mass spectrometry assay, optionally wherein the processing comprises heating the FFPE sample in a detergent-free buffer. In some such methods, determining the expression level of the one or more marker genes in the test esophageal tissue sample comprises processing the FFPE sample to reverse formalin cross-links and subsequently digesting the test esophageal tissue sample with one or more proteinases prior to performing the mass spectrometry assay. Optionally, the one or more proteinases comprise trypsin.

In some such methods, the mass spectrometry assay comprises a targeted mass spectrometry assay. In some such methods, the mass spectrometry assay is done on a triple quadrupole mass spectrometer. In some such methods, the one or more marker genes comprise ISG15, and wherein determining the expression level of ISG15 comprises performing a targeted mass spectrometry assay for detection and quantification of the target peptide set forth in SEQ ID NO: 11 or SEQ ID NO: 12. In some such methods, the one or more marker genes comprise LTF, and wherein determining the expression level of LTF comprises performing a targeted mass spectrometry assay for detection and quantification of the target peptide set forth in SEQ ID NO: 54 or SEQ ID NO: 58. In some such methods, the one or more marker genes comprise CNDP2, and wherein determining the expression level of CNDP2 comprises performing a targeted mass spectrometry assay for detection and quantification of the target peptide set forth in SEQ ID NO: 20 or SEQ ID NO: 31. In some such methods, the one or more marker genes comprise DAD1, and wherein determining the expression level of DAD1 comprises performing a targeted mass spectrometry assay for detection and quantification of the target peptide set forth in SEQ ID NO: 7 or SEQ ID NO: 9. In some such methods, the one or more marker genes comprise SET, and wherein determining the expression level of SET comprises performing a targeted mass spectrometry assay for detection and quantification of the target peptide set forth in SEQ ID NO: 50. In some such methods, the one or more marker genes comprise UBE2N, and wherein determining the expression level of UBE2N comprises performing a targeted mass spectrometry assay for detection and quantification of the target peptide set forth in SEQ ID NO: 1 or SEQ ID NO: 5. In some such methods, the one or more marker genes comprise S100P, and wherein determining the expression level of S100P comprises performing a targeted mass spectrometry assay for detection and quantification of the target peptide set forth in SEQ ID NO: 67 or SEQ ID NO: 68. In some such methods, the one or more marker genes comprise GPI, and wherein determining the expression level of GPI comprises performing a targeted mass spectrometry assay for detection and quantification of the target peptide set forth in SEQ ID NO: 35 or SEQ ID NO: 39.

In some such methods, determining the expression level of the one or more marker genes in the test esophageal tissue sample comprises determining the expression level of two or more of ISG15, LTF, CNDP2, DAD1, SET, UBE2N, S100P, and GPI. In some such methods, determining the expression level of the one or more marker genes in the test esophageal tissue sample comprises determining the expression level of three or more of ISG15, LTF, CNDP2, DAD1, SET, UBE2N, S100P, and GPI. In some such methods, determining the expression level of the one or more marker genes in the test esophageal tissue sample comprises determining the expression level of four or more of ISG15, LTF, CNDP2, DAD1, SET, UBE2N, S100P, and GPI. In some such methods, determining the expression level of the one or more marker genes in the test esophageal tissue sample comprises determining the expression level of five or more of ISG15, LTF, CNDP2, DAD1, SET, UBE2N, S100P, and GPI. In some such methods, determining the expression level of the one or more marker genes in the test esophageal tissue sample comprises determining the expression level of six or more of ISG15, LTF, CNDP2, DAD1, SET, UBE2N, S100P, and GPI. In some such methods, determining the expression level of the one or more marker genes in the test esophageal tissue sample comprises determining the expression level of seven or more of ISG15, LTF, CNDP2, DAD1, SET, UBE2N, S100P, and GPI. In some such methods, determining the expression level of the one or more marker genes in the test esophageal tissue sample comprises determining the expression level of ISG15, LTF, CNDP2, DAD1, SET, UBE2N, S100P, and GPI.

In some such methods, increased expression of the majority of the one or more of marker genes in the test esophageal tissue sample relative to the control esophageal tissue sample indicates an increased risk of developing esophageal adenocarcinoma. In some such methods, increased expression of each of the one or more of marker genes in the test esophageal tissue sample relative to the control esophageal tissue sample indicates an increased risk of developing esophageal adenocarcinoma.

In some such methods, the subject is a human and has Barrett's esophagus, and the method assesses risk of progressing from Barrett's esophagus to esophageal adenocarcinoma, wherein the test esophageal tissue sample comprises an isolated Barrett's esophagus mucosa sample, and the control esophageal tissue sample comprises normal esophageal mucosa, wherein determining the expression level of the one or more marker genes in the test esophageal tissue sample comprises digesting the test esophageal tissue sample with trypsin and then performing a targeted mass spectrometry assay to measure the expression of proteins encoded by the one or more marker genes, wherein determining the expression level of the one or more marker genes in the test esophageal tissue sample comprises determining the expression level of ISG15, LTF, CNDP2, DAD1, SET, UBE2N, S100P, and GPI (or alternatively determining the expression level of ISG15, LTF, and DAD1; or alternatively determining the expression level of ISG15, LTF, DAD1, CNDP2, SET, and GPI), and wherein: (I) determining the expression level of ISG15 comprises performing a targeted mass spectrometry assay for detection and quantification of the target peptide set forth in SEQ ID NO: 11 or SEQ ID NO: 12; (II) determining the expression level of LTF comprises performing a targeted mass spectrometry assay for detection and quantification of the target peptide set forth in SEQ ID NO: 54 or SEQ ID NO: 58; (III) determining the expression level of CNDP2 comprises performing a targeted mass spectrometry assay for detection and quantification of the target peptide set forth in SEQ ID NO: 20 or SEQ ID NO: 31; (IV) determining the expression level of DAD1 comprises performing a targeted mass spectrometry assay for detection and quantification of the target peptide set forth in SEQ ID NO: 7 or SEQ ID NO: 9; (V) determining the expression level of SET comprises performing a targeted mass spectrometry assay for detection and quantification of the target peptide set forth in SEQ ID NO: 50; (VI) determining the expression level of UBE2N comprises performing a targeted mass spectrometry assay for detection and quantification of the target peptide set forth in SEQ ID NO: 1 or SEQ ID NO: 5; (VII) determining the expression level of S100P comprises performing a targeted mass spectrometry assay for detection and quantification of the target peptide set forth in SEQ ID NO: 67 or SEQ ID NO: 68; and (VIII) determining the expression level of GPI comprises performing a targeted mass spectrometry assay for detection and quantification of the target peptide set forth in SEQ ID NO: 35 or SEQ ID NO: 39. Optionally, the test esophageal tissue sample comprises a formalin-fixed paraffin-embedded (FFPE) Barrett's esophagus mucosa sample that has been separated from non-mucosal tissue and from normal mucosal tissue, and the method further comprises selectively isolating Barrett's esophagus mucosal tissue from the test esophageal tissue sample by microdissection to produce a test Barrett's esophagus mucosa sample that has been separated from non-mucosal tissue and from normal mucosal tissue and subsequently processing the test Barrett's esophagus mucosa sample to reverse formalin cross-links prior to the digesting.

In another aspect, provided are methods of determining expression of one or more esophageal adenocarcinoma risk factors in a subject. Some such methods comprise performing an assay to measure the expression level of the one or more esophageal adenocarcinoma risk factors in a test esophageal tissue sample obtained from the subject, wherein the one or more esophageal adenocarcinoma risk factors comprise one or more of ISG15, LTF, CNDP2, DAD1, SET, UBE2N, S100P, and GPI. Some such methods further comprise comparing the expression level of the one or more esophageal adenocarcinoma risk factors in the test esophageal tissue sample to the expression level of the one or more esophageal adenocarcinoma risk factors in a control esophageal tissue sample. In some such methods, the one or more esophageal adenocarcinoma risk factors comprise one or more of ISG15, LTF, and DAD1. In some such methods, the one or more esophageal adenocarcinoma risk factors comprise one or more of CNDP2, SET, and GPI. In some such methods, the one or more esophageal adenocarcinoma risk factors comprise one or more of ISG15, LTF, DAD1, CNDP2, SET, and GPI. In some such methods, the one or more esophageal adenocarcinoma risk factors comprise one or more of UBE2N and S100P. In some such methods, the one or more esophageal adenocarcinoma risk factors comprise one or more of ISG15, CNDP2, DAD1, SET, UBE2N, and GPI.

In some such methods, the one or more esophageal adenocarcinoma risk factors comprise ISG15. In some such methods, the one or more esophageal adenocarcinoma risk factors comprise LTF. In some such methods, the one or more esophageal adenocarcinoma risk factors comprise CNDP2. In some such methods, the one or more esophageal adenocarcinoma risk factors comprise DAD1. In some such methods, the one or more esophageal adenocarcinoma risk factors comprise SET. In some such methods, the one or more esophageal adenocarcinoma risk factors comprise UBE2N. In some such methods, the one or more esophageal adenocarcinoma risk factors comprise S100P. In some such methods, the one or more esophageal adenocarcinoma risk factors comprise GPI. In some such methods, the one or more esophageal adenocarcinoma risk factors comprise ISG15 and LTF. In some such methods, the one or more esophageal adenocarcinoma risk factors comprise ISG15 and DAD1. In some such methods, the one or more esophageal adenocarcinoma risk factors comprise LTF and DAD1. In some such methods, the one or more esophageal adenocarcinoma risk factors comprise ISG15, LTF, and DAD1. In some such methods, the one or more esophageal adenocarcinoma risk factors comprise ISG15 and CNDP2. In some such methods, the one or more esophageal adenocarcinoma risk factors comprise LTF and CNDP2. In some such methods, the one or more esophageal adenocarcinoma risk factors comprise ISG15, LTF, and CNDP2. In some such methods, the one or more esophageal adenocarcinoma risk factors comprise ISG15, LTF, DAD1, and CNDP2. In some such methods, the one or more esophageal adenocarcinoma risk factors comprise ISG15, LTF, DAD1, and SET. In some such methods, the one or more esophageal adenocarcinoma risk factors comprise ISG15, LTF, DAD1, and GPI. In some such methods, the one or more esophageal adenocarcinoma risk factors comprise ISG15, LTF, DAD1, CNDP2, and SET. In some such methods, the one or more esophageal adenocarcinoma risk factors comprise ISG15, LTF, DAD1, CNDP2, and GPI. In some such methods, the one or more esophageal adenocarcinoma risk factors comprise ISG15, LTF, DAD1, SET, and GPI. In some such methods, the one or more esophageal adenocarcinoma risk factors comprise ISG15, LTF, DAD1, CNDP2, SET, and GPI.

In some such methods, the one or more esophageal adenocarcinoma risk factors are selected from the group consisting of ISG15, LTF, DAD1, and any combination thereof. In some such methods, the one or more esophageal adenocarcinoma risk factors are selected from the group consisting of CNDP2, SET, GPI, and any combination thereof. In some such methods, the one or more esophageal adenocarcinoma risk factors are selected from the group consisting of ISG15, LTF, DAD1, CNDP2, SET, GPI, and any combination thereof. In some such methods, the one or more esophageal adenocarcinoma risk factors are selected from the group consisting of UBE2N, S100P, and any combination thereof. In some such methods, the one or more esophageal adenocarcinoma risk factors are selected from the group consisting of ISG15, CNDP2, DAD1, SET, UBE2N, GPI, and any combination thereof.

In some such methods, the subject has or is suspected of having gastroesophageal reflux disease or Barrett's esophagus, or wherein the subject has Barrett's esophagus and the test esophageal tissue sample is a Barrett's esophagus tissue sample. In some such methods, the subject is a human.

In some such methods, the test esophageal tissue sample comprises an isolated esophageal tissue sample. In some such methods, the test esophageal tissue sample comprises a biopsy sample. In some such methods, the test esophageal tissue sample comprises a fresh sample, a frozen sample, a preserved sample, a formalin-fixed sample, or a formalin-fixed paraffin-embedded (FFPE) sample. In some such methods, the test esophageal sample comprises a microdissected sample. In some such methods, the test esophageal tissue sample comprises a mucosa sample or a Barrett's esophagus mucosa sample. In some such methods, the test esophageal tissue sample comprises a mucosa sample or a Barrett's esophagus mucosa sample that has been separated from non-mucosal tissue. In some such methods, the test esophageal tissue sample comprises a Barrett's esophagus mucosa sample that has been separated from normal mucosal tissue. In some such methods, the test esophageal tissue sample comprises a Barrett's esophagus mucosa sample that has been separated from non-mucosal tissue and normal mucosal tissue. In some such methods, the test esophageal tissue sample comprises a formalin-fixed paraffin-embedded (FFPE) mucosa sample or a FFPE Barrett's esophagus mucosa sample that has been separated from non-mucosal tissue. In some such methods, the test esophageal tissue sample comprises a FFPE Barrett's esophagus mucosa sample that has been separated from normal mucosal tissue. In some such methods, the test esophageal tissue sample comprises a FFPE Barrett's esophagus mucosa sample that has been separated from non-mucosal tissue and normal mucosal tissue.

In some such methods, the method further comprises selectively isolating mucosal tissue from the test esophageal tissue sample to produce a test esophageal mucosa sample that has been separated from non-mucosal tissue prior to performing the assay to measure the expression level of the one or more esophageal adenocarcinoma risk factors, and the expression level of the one or more esophageal adenocarcinoma risk factors is measured in the test esophageal mucosa sample. In some such methods, the method further comprises selectively isolating Barrett's esophagus mucosal tissue from the test esophageal tissue sample to produce a test Barrett's esophagus mucosa sample that has been separated from normal mucosal tissue prior to performing the assay to measure the expression level of the one or more esophageal adenocarcinoma risk factors, and the expression level of the one or more esophageal adenocarcinoma risk factors is determined in the test Barrett's esophagus mucosa sample. In some such methods, the method further comprises selectively isolating Barrett's esophagus mucosal tissue from the test esophageal tissue sample to produce a test Barrett's esophagus mucosa sample that has been separated from non-mucosal tissue and normal mucosal tissue prior to performing the assay to measure the expression level of the one or more esophageal adenocarcinoma risk factors, and the expression level of the one or more esophageal adenocarcinoma risk factors is determined in the test Barrett's esophagus mucosa sample. In some such methods, the step of selectively isolating mucosal tissue comprises microdissection. In some such methods, the test esophageal tissue sample is a formalin-fixed paraffin-embedded (FFPE) sample.

In some such methods, the method further comprises comparing the expression level of the one or more esophageal adenocarcinoma risk factors in the test esophageal tissue sample to the expression level of the one or more esophageal adenocarcinoma risk factors in a control esophageal tissue sample. In some such methods, the control esophageal tissue sample comprises normal esophageal mucosa. In some such methods, the control esophageal tissue sample is from the subject. In some such methods, the control esophageal tissue sample is from one or more control subjects that do not have gastroesophageal reflux disease, Barrett's esophagus, or esophageal adenocarcinoma.

In some such methods, performing the assay to measure the expression level of the one or more esophageal adenocarcinoma risk factors in the test esophageal tissue sample comprises performing an assay to measure the expression of messenger RNAs (mRNAs) encoded by the one or more esophageal adenocarcinoma risk factors. In some such methods, performing the assay to measure the expression level of the one or more esophageal adenocarcinoma risk factors in the test esophageal tissue sample comprises performing assay to measure the expression of proteins encoded by the one or more esophageal adenocarcinoma risk factors.

Optionally, the assay comprises a mass spectrometry assay, an immunohistochemistry assay, an immunoassay, an enzyme-linked immunosorbent assay (ELISA), an alphaLISA assay, or an enzyme-linked immune absorbent spot (ELISpot) assay.

In some such methods, the assay comprises the mass spectrometry assay. In some such methods, performing the assay to measure the expression level of the one or more esophageal adenocarcinoma risk factors in the test esophageal tissue sample comprises digesting the test esophageal tissue sample with one or more proteinases prior to performing the mass spectrometry assay. In some such methods, the test esophageal tissue sample is a formalin-fixed paraffin-embedded (FFPE) sample, and the method further comprises processing the FFPE sample to reverse formalin cross-links prior to performing the mass spectrometry assay, optionally wherein the processing comprises heating the FFPE sample in a detergent-free buffer. In some such methods, performing the assay to measure the expression level of the one or more esophageal adenocarcinoma risk factors in the test esophageal tissue sample comprises processing the FFPE sample to reverse formalin cross-links and subsequently digesting the test esophageal tissue sample with one or more proteinases prior to performing the mass spectrometry assay. Optionally, the one or more proteinases comprise trypsin.

In some such methods, the mass spectrometry assay comprises a targeted mass spectrometry assay. In some such methods, the mass spectrometry assay is done on a triple quadrupole mass spectrometer. In some such methods, the one or more esophageal adenocarcinoma risk factors comprise ISG15, and wherein performing the assay to measure the expression level of ISG15 comprises performing a targeted mass spectrometry assay for detection and quantification of the target peptide set forth in SEQ ID NO: 11 or SEQ ID NO: 12. In some such methods, the one or more esophageal adenocarcinoma risk factors comprise LTF, and wherein performing the assay to measure the expression level of LTF comprises performing a targeted mass spectrometry assay for detection and quantification of the target peptide set forth in SEQ ID NO: 54 or SEQ ID NO: 58. In some such methods, the one or more esophageal adenocarcinoma risk factors comprise CNDP2, and wherein performing the assay to measure the expression level of CNDP2 comprises performing a targeted mass spectrometry assay for detection and quantification of the target peptide set forth in SEQ ID NO: 20 or SEQ ID NO: 31. In some such methods, the one or more esophageal adenocarcinoma risk factors comprise DAD1, and wherein performing the assay to measure the expression level of DAD1 comprises performing a targeted mass spectrometry assay for detection and quantification of the target peptide set forth in SEQ ID NO: 7 or SEQ ID NO: 9. In some such methods, the one or more esophageal adenocarcinoma risk factors comprise SET, and wherein performing the assay to measure the expression level of SET comprises performing a targeted mass spectrometry assay for detection and quantification of the target peptide set forth in SEQ ID NO: 50. In some such methods, the one or more esophageal adenocarcinoma risk factors comprise UBE2N, and wherein performing the assay to measure the expression level of UBE2N comprises performing a targeted mass spectrometry assay for detection and quantification of the target peptide set forth in SEQ ID NO: 1 or SEQ ID NO: 5. In some such methods, the one or more esophageal adenocarcinoma risk factors comprise S100P, and wherein performing the assay to measure the expression level of S100P comprises performing a targeted mass spectrometry assay for detection and quantification of the target peptide set forth in SEQ ID NO: 67 or SEQ ID NO: 68. In some such methods, the one or more esophageal adenocarcinoma risk factors comprise GPI, and wherein performing the assay to measure the expression level of GPI comprises performing a targeted mass spectrometry assay for detection and quantification of the target peptide set forth in SEQ ID NO: 35 or SEQ ID NO: 39.

In some such methods, performing the assay to measure the expression level of the one or more esophageal adenocarcinoma risk factors in the test esophageal tissue sample comprises measuring the expression level of two or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of three or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of four or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of five or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of six or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of seven or more of ISG15, LTF, CNDP2, DAD1, SET, UBE2N, S100P, and GPI. In some such methods, performing the assay to measure the expression level of the one or more esophageal adenocarcinoma risk factors in the test esophageal tissue sample comprises measuring the expression level of ISG15, LTF, CNDP2, DAD1, SET, UBE2N, S100P, and GPI.

In some such methods, the subject is a human and has Barrett's esophagus, wherein the test esophageal tissue sample comprises an isolated Barrett's esophagus mucosa sample, wherein performing the assay to measure the expression level of the one or more esophageal adenocarcinoma risk factors in the test esophageal tissue sample comprises digesting the test esophageal sample with trypsin and then performing a targeted mass spectrometry assay, wherein performing the assay to measure the expression level of the one or more esophageal adenocarcinoma risk factors in the test esophageal tissue sample comprises measuring the expression level of ISG15, LTF, CNDP2, DAD1, SET, UBE2N, S100P, and GPI (or alternatively measuring the expression level of ISG15, LTF, and DAD1; or alternatively measuring the expression level of ISG15, LTF, DAD1, CNDP2, SET, and GPI), and wherein: (I) measuring the expression level of ISG15 comprises performing a targeted mass spectrometry assay for detection and quantification of the target peptide set forth in SEQ ID NO: 11 or SEQ ID NO: 12; (II) measuring the expression level of LTF comprises performing a targeted mass spectrometry assay for detection and quantification of the target peptide set forth in SEQ ID NO: 54 or SEQ ID NO: 58; (III) measuring the expression level of CNDP2 comprises performing a targeted mass spectrometry assay for detection and quantification of the target peptide set forth in SEQ ID NO: 20 or SEQ ID NO: 31; (IV) measuring the expression level of DAD1 comprises performing a targeted mass spectrometry assay for detection and quantification of the target peptide set forth in SEQ ID NO: 7 or SEQ ID NO: 9; (V) measuring the expression level of SET comprises performing a targeted mass spectrometry assay for detection and quantification of the target peptide set forth in SEQ ID NO: 50; (VI) measuring the expression level of UBE2N comprises performing a targeted mass spectrometry assay for detection and quantification of the target peptide set forth in SEQ ID NO: 1 or SEQ ID NO: 5; (VII) measuring the expression level of S100P comprises performing a targeted mass spectrometry assay for detection and quantification of the target peptide set forth in SEQ ID NO: 67 or SEQ ID NO: 68; and (VIII) measuring the expression level of GPI comprises performing a targeted mass spectrometry assay for detection and quantification of the target peptide set forth in SEQ ID NO: 35 or SEQ ID NO: 39. Optionally, the test esophageal tissue sample comprises a formalin-fixed paraffin-embedded (FFPE) Barrett's esophagus mucosa sample that has been separated from non-mucosal tissue and from normal mucosal tissue, and the method further comprises selectively isolating Barrett's esophagus mucosal tissue from the test esophageal tissue sample by microdissection to produce a test Barrett's esophagus mucosa sample that has been separated from non-mucosal tissue and from normal mucosal tissue and subsequently processing the test Barrett's esophagus mucosa sample to reverse formalin cross-links prior to the digesting.

In another aspect, provided are isolated peptides comprising the sequence set forth in SEQ ID NO: 11 or 12 for use in a targeted mass spectrometry assay to determine expression of ISG15 in an isolated test esophageal tissue sample from a subject. Optionally, the isolated peptide is labeled with a heavy isotope.

In another aspect, provided are isolated peptides comprising the sequence set forth in SEQ ID NO: 54 or 58 for use in a targeted mass spectrometry assay to determine expression of LTF in an isolated test esophageal tissue sample from a subject. Optionally, the isolated peptide is labeled with a heavy isotope.

In another aspect, provided are isolated peptides comprising the sequence set forth in SEQ ID NO: 20 or 31 for use in a targeted mass spectrometry assay to determine expression of CNDP2 in an isolated test esophageal tissue sample from a subject. Optionally, the isolated peptide is labeled with a heavy isotope.

In another aspect, provided are isolated peptides comprising the sequence set forth in SEQ ID NO: 7 or 9 for use in a targeted mass spectrometry assay to determine expression of DAD1 in an isolated test esophageal tissue sample from a subject. Optionally, the isolated peptide is labeled with a heavy isotope.

In another aspect, provided are isolated peptides comprising the sequence set forth in SEQ ID NO: 50 for use in a targeted mass spectrometry assay to determine expression of SET in an isolated test esophageal tissue sample from a subject. Optionally, the isolated peptide is labeled with a heavy isotope.

In another aspect, provided are isolated peptides comprising the sequence set forth in SEQ ID NO: 1 or 5 for use in a targeted mass spectrometry assay to determine expression of UBE2N in an isolated test esophageal tissue sample from a subject. Optionally, the isolated peptide is labeled with a heavy isotope.

In another aspect, provided are isolated peptides comprising the sequence set forth in SEQ ID NO: 67 or 68 for use in a targeted mass spectrometry assay to determine expression of S100P in an isolated test esophageal tissue sample from a subject. Optionally, the isolated peptide is labeled with a heavy isotope.

In another aspect, provided are isolated peptides comprising the sequence set forth in SEQ ID NO: 35 or 39 for use in a targeted mass spectrometry assay to determine expression of GPI in an isolated test esophageal tissue sample from a subject. Optionally, the isolated peptide is labeled with a heavy isotope.

In another aspect, provided are methods of treating esophageal adenocarcinoma in a subject having esophageal adenocarcinoma or preventing esophageal adenocarcinoma in a subject at risk for developing esophageal adenocarcinoma. Some such methods comprise administering a therapeutically effective amount of one or more inhibitory agents to the subject, wherein the one or more inhibitory agents reduce expression or activity of one or more esophageal adenocarcinoma risk factors selected from ISG15, LTF, CNDP2, DAD1, SET, UBE2N, S100P, and GPI in esophageal tissue in the subject. In some such methods, the esophageal adenocarcinoma risk factors are selected from ISG15, DAD1, UBE2N, and S100P. In some such methods, the esophageal adenocarcinoma cells are in a subject with esophageal adenocarcinoma. In some such methods, the one or more inhibitory agents reduce expression of the one or more esophageal adenocarcinoma risk factors. In some such methods, the inhibitory agent comprises an RNAi agent or an antisense oligonucleotide.

In another aspect, provided are methods of inhibiting or decreasing proliferation of esophageal adenocarcinoma cells, comprising administering one or more inhibitory agents to the esophageal adenocarcinoma cells, wherein the one or more inhibitory agents reduce expression or activity of one or more esophageal adenocarcinoma risk factors selected from ISG15, UBE2N, and S100P. In some such methods, the esophageal adenocarcinoma cells are in a subject with esophageal adenocarcinoma. In some such methods, the one or more inhibitory agents reduce expression of the one or more esophageal adenocarcinoma risk factors. In some such methods, the inhibitory agent comprises an RNAi agent or an antisense oligonucleotide.

In another aspect, provided are methods of inhibiting or decreasing migration of esophageal adenocarcinoma cells, comprising administering one or more inhibitory agents to the esophageal adenocarcinoma cells, wherein the one or more inhibitory agents reduce expression or activity of one or more esophageal adenocarcinoma risk factors selected from ISG15, DAD1, UBE2N, and S100P. In some such methods, the esophageal adenocarcinoma cells are in a subject with esophageal adenocarcinoma. In some such methods, the one or more inhibitory agents reduce expression of the one or more esophageal adenocarcinoma risk factors. In some such methods, the inhibitory agent comprises an RNAi agent or an antisense oligonucleotide.

In another aspect, provided are methods of increasing susceptibility to cytotoxicity or inducing cell death of esophageal adenocarcinoma cells, comprising administering one or more inhibitory agents to the esophageal adenocarcinoma cells, wherein the one or more inhibitory agents reduce expression or activity of one or more esophageal adenocarcinoma risk factors selected from ISG15, UBE2N, and S100P. In some such methods, the esophageal adenocarcinoma cells are in a subject with esophageal adenocarcinoma. In some such methods, the one or more inhibitory agents reduce expression of the one or more esophageal adenocarcinoma risk factors. In some such methods, the inhibitory agent comprises an RNAi agent or an antisense oligonucleotide.

DEFINITIONS

Figure 1:
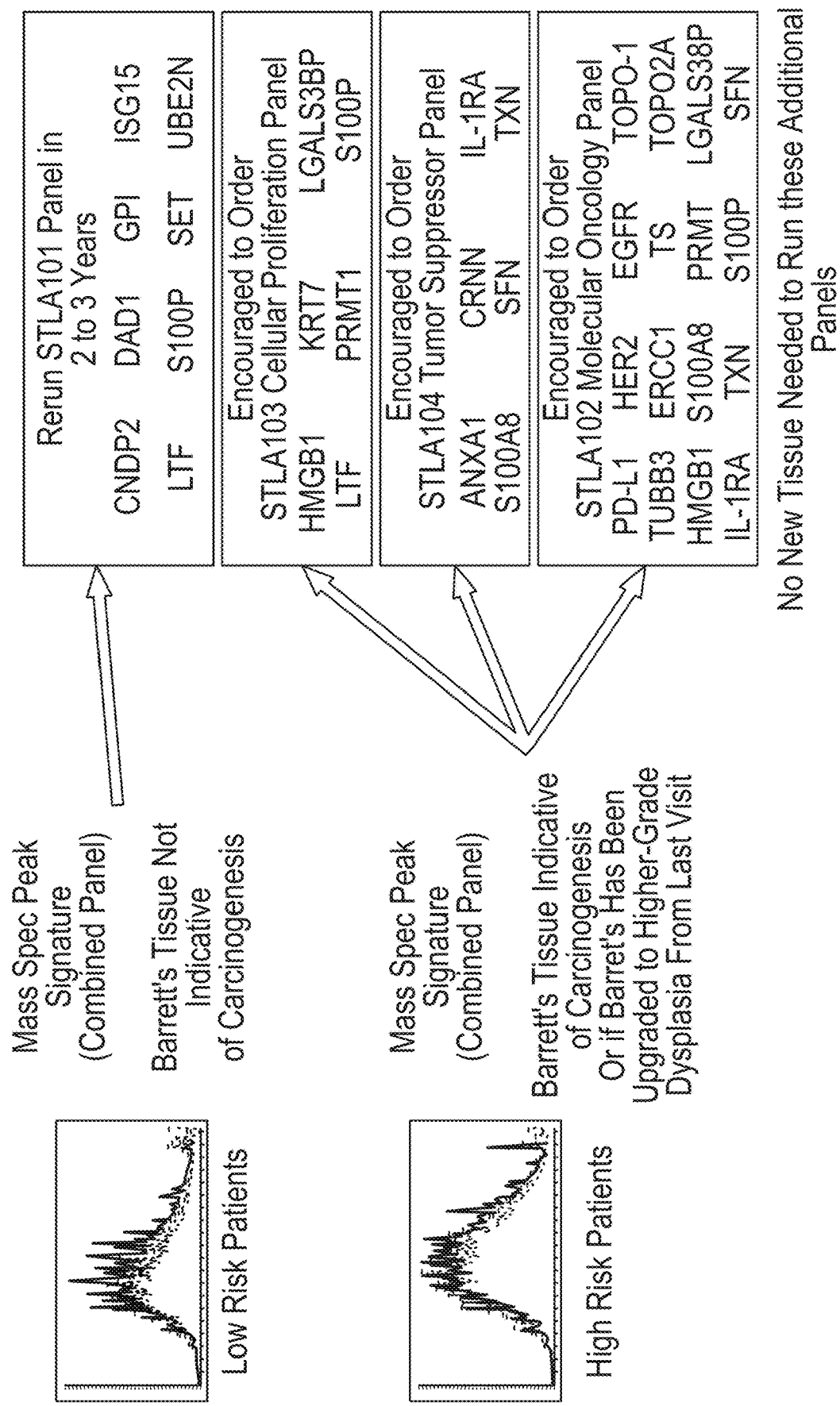
FIG. 1. Image illustrating a platform for detection and quantification for human proteomics using mass spectrometry. Depending on the results of the initial panel (top of figure), a recommendation to rerun the same panel 1-3 years after the first results could be made to assess if these disease drivers are remaining stable. Conversely, if the results indicate high or intermediate risk of disease progression, assessment of the biopsy with two other panels is recommended. These panels analyze six proliferation markers and six cell death markers to confirm that the patient's esophagus is indeed at risk for cancer. Lastly, another panel can be utilized for patients who are already diagnosed with esophageal adenocarcinoma (EAC) to optimize first-line therapy by quantifying proteomic expression patterns associated with increased benefit or resistance to all of the FDA-approved therapies for EAC.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" (amino-terminus) and a "C-terminus" (carboxy-terminus or carboxyl-terminus). The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "isolated" with respect to cells, tissues (e.g., liver samples), lipid droplets, proteins, and nucleic acids includes cells, tissues (e.g., liver samples), lipid droplets, proteins, and nucleic acids that are relatively purified with respect to other bacterial, viral, cellular, or other components that may normally be present in situ, up to and including a substantially pure preparation of the cells, tissues (e.g., liver samples), lipid droplets, proteins, and nucleic acids. The term "isolated" also includes cells, tissues (e.g., liver samples), lipid droplets, proteins, and nucleic acids that have no naturally occurring counterpart, have been chemically synthesized and are thus substantially uncontaminated by other cells, tissues (e.g., liver samples), lipid droplets, proteins, and nucleic acids, or has been separated or purified from most other components (e.g., cellular components or organism components) with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a rat cell or rat. For example, an endogenous Hsd17b13 sequence of a mouse refers to a native Hsd17b13 sequence that naturally occurs at the Hsd17b13 locus in the mouse.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A protein fragment can be, for example, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A nucleic acid fragment can be, for example, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

The term "in vitro" includes artificial environments and to processes or reactions that occur within an artificial environment (e.g., a test tube or an isolated cell or cell line). The term "in vivo" includes natural environments (e.g., an organism or body or a cell or tissue within an organism or body) and to processes or reactions that occur within a natural environment. The term "ex vivo" includes cells that have been removed from the body of an individual and processes or reactions that occur within such cells.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values ±5 of a stated value.

The term "and/or" refers to and encompasses any and all possible combinations of one or more of the associated listed items, as well as the lack of combinations when interpreted in the alternative ("or").

The term "or" refers to any one member of a particular list.

The singular forms of the articles "a," "an," and "the" include plural references unless the context clearly dictates otherwise. For example, the term "a protein" or "at least one protein" can include a plurality of proteins, including mixtures thereof.

Statistically significant means $p<0.05$.

DETAILED DESCRIPTION

I. Overview

Methods are provided for assessing risk of developing esophageal adenocarcinoma in a subject using one or more of the following marker genes/proteins: ISG15, LTF, CNDP2, DAD1, SET, UBE2N, S100P, and GPI. Methods are also provided for determining expression of one or more esophageal adenocarcinoma risk factors in a subject. Methods are also provided for treating esophageal adenocarcinoma in a subject, for preventing esophageal adenocarcinoma in a subject, for inhibiting or decreasing proliferation of esophageal adenocarcinoma cells, for inhibiting or decreasing migration of esophageal adenocarcinoma cells, or for increasing susceptibility to cytotoxicity or inducing cell death of esophageal adenocarcinoma cells.

The methods for assessing risk of developing esophageal adenocarcinoma or for determining expression of one or more esophageal adenocarcinoma risk factors in a subject are based on newly identified markers for progression from Barrett's esophagus to esophageal adenocarcinoma. These markers include ISG15, LTF, CNDP2, DAD1, SET, UBE2N, S100P, and GPI.

Every thirty minutes, someone in the United States dies from esophageal cancer, in part due to inefficient screening. The current pathology standard of prognosis for these diseases is gross and microscopic inspection of esophageal biopsies. Patients diagnosed with Barrett's esophagus receive endoscopic evaluation routinely ranging from every three months to every three years depending on the dysplastic severity of the distal esophagus. During these visits, the esophagus is observed grossly by the treating gastrointestinal (GI) physician, and biopsies retrieved during this procedure are stained by pathologists and aspects like cell structure, organization, are differentiation are noted and reported back to the GI physician. Very little, if any, molecular information is assessed with current standard screening protocols for this premalignant condition. The methods disclosed herein can provide robust molecular information using a small amount of leftover biopsy tissue taken during these procedures, seamlessly providing more information on the presence of disease drivers in Barrett's esophagus without disrupting the standard screening workflow and clinical histopathology. The methods disclosed herein can elucidate the expression trends of novel biomarkers that illuminate the carcinogenic proteomic environment that leads to an increase in cellular proliferation, invasion, migration, and cell survival. The presence and activity of the biomarkers in the panel may provide a colorful picture to physicians, showing if their patient's tissue is behaving normally or beginning to show molecular hallmarks of pathogenesis that sometimes goes undetected with traditional diagnostic approaches. The methods disclosed herein can, in some examples, utilize mass spectrometry to yield high-throughput, multiplexable, and confident data. Mass spectrometry produces extremely accurate and precise quantification of all biomarkers simultaneously utilizing the laws of physics (the mass and charge of each peptide) to quantify all markers of interest simultaneously, which reduces the amount of tissue needed and allows for a quick turnaround time. Therefore, the unique strengths of mass spectrometry allow the platform to circumvent standard antibody-based diagnostic limitations like nonspecific binding, subjective interpretation, and overstaining, which are issues with the current standard of care. Mass-spectrometry-based diagnostics are currently not utilized for monitoring precancerous conditions of proteomic signatures linked to malignant transformations that are undetectable via endoscopy and standard histopathology. The markers used in the methods disclosed herein have not been discovered as playing a role in the pathogenesis of Barrett's esophagus to esophageal adenocarcinoma. When using mass spectrometry, to assure highly accurate quantification, we discovered peptides that are identified as being uniquely present in our biomarker proteins of interest and performing well in mass spectrometry. A known amount of these synthesized markers can be spiked in, representing the biomarker proteins in our panel. The marker peptides can be isotopically labeled so they can be detected with ease, and the amount of protein spiked in can be subtracted from the endogenous signal, yielding extremely accurate and precise quantification of all biomarkers concurrently via targeted mass spectrometry.

Utilizing this method allows the delivery of accurate results void of subjective interpretation and false positives from a very small piece of fresh or fixed tissue in a timely manner. These tests require only 8 mm$^2$ of tissue and can deliver results to the ordering provider within one to two weeks of clinical biopsy retrieval. Using targeted mass spectrometry proteomics, physicians can be informed of the expression patterns playing a role in the pathogenesis of gastroesophageal reflux disease (GERD), Barrett's esophagus, and esophageal cancer early in treatment plans.

II. Methods of Determining Expression of Esophageal Adenocarcinoma Risk Factors in a Subject and Methods of Assessing Risk in a Subject to Develop Esophageal Adenocarcinoma Methods are provided for assessing risk of developing esophageal adenocarcinoma in a subject. Methods are also provided for determining expression of one or more marker genes (i.e., esophageal adenocarcinoma risk factors) in a subject. Such methods can comprise determining the expression level of one or more marker genes in a test esophageal tissue sample from the subject. Such methods can further comprise comparing the expression level of the one or more marker genes in the test esophageal tissue sample to the expression level of the one or more marker genes in a control esophageal tissue sample, wherein increased expression of at least one of the one or more of marker genes in the test esophageal tissue sample relative to the control esophageal tissue sample indicates an increased risk of developing esophageal adenocarcinoma. Increased risk means that the subject is more likely to develop esophageal adenocarcinoma than if there was not increased expression of the at least one of the one or more marker genes in the test esophageal tissue sample relative to the control esophageal tissue sample. In some methods, increased expression of the majority of the one or more of marker genes in the test esophageal tissue sample relative to the control esophageal tissue sample indicates an increased risk of developing esophageal adenocarcinoma. In some methods, increased expression of at least two of the one or more of marker genes in the test esophageal tissue sample relative to the control esophageal tissue sample indicates an increased risk of developing esophageal adenocarcinoma. In some methods, increased expression of at least three of the one or more of marker genes in the test esophageal tissue sample relative to the control esophageal tissue sample indicates an increased risk of developing esophageal adenocarcinoma. In some methods, increased expression of at least four of the one or more of marker genes in the test esophageal tissue sample relative to the control esophageal tissue sample indicates an increased risk of developing esophageal adenocarcinoma. In some methods, increased expression of at least five of the one or more of marker genes in the test esophageal tissue sample relative to the control esophageal tissue sample indicates an increased risk of developing esophageal adenocarcinoma. In some methods, increased expression of at least six of the one or more of marker genes in the test esophageal tissue sample relative to the control esophageal tissue sample indicates an increased risk of developing esophageal adenocarcinoma. In some methods, increased expression of at least seven of the one or more of marker genes in the test esophageal tissue sample relative to the control esophageal tissue sample indicates an increased risk of developing esophageal adenocarcinoma. In some methods, increased expression of at least eight of the one or more of marker genes in the test esophageal tissue sample relative to the control esophageal tissue sample indicates an increased risk of developing esophageal adenocarcinoma. In some methods, increased expression of each of the one or more of marker genes in the test esophageal tissue sample relative to the control esophageal tissue sample indicates an increased risk of developing esophageal adenocarcinoma.

In some methods, the increased expression in the test esophageal tissue sample relative to the control esophageal tissue sample is statistically significant. In some methods, the increased expression in the test esophageal tissue sample relative to the control esophageal tissue sample is at least about 1.1-fold, at least about 1.2-fold, at least about 1.3 fold, at least about 1.4-fold, at least about 1.5-fold, at least about 2-fold, at least about 3-fold, at least about 4-fold, at least about 5-fold, at least about 6-fold, at least about 7-fold, at least about 8-fold, at least about 9-fold, or at least about 10-fold (e.g., at least 1.1-fold, at least 1.2-fold, at least 1.3-fold, at least 1.4-fold, at least 1.5-fold, at least 2-fold, at least 3-fold, at least 4-fold, at least 5-fold, at least 6-fold, at least 7-fold, at least 8-fold, at least 9-fold, or at least 10-fold).

The marker genes can comprise, for example, one or more of ISG15, LTF, CNDP2, DAD1, SET, UBE2N, S100P, and GPI. The methods can comprise, for example, measuring the expression level (i.e., performing an assay to measure the expression level) of the one or more marker genes in a test esophageal tissue sample obtained from the subject, wherein the one or more marker genes (esophageal adenocarcinoma risk factors) comprise one or more of ISG15, LTF, CNDP2, DAD1, SET, UBE2N, S100P, and GPI or one or more of any other combination of marker genes described herein.

In some methods, determining the expression level of the one or more marker genes in the test esophageal tissue sample comprises determining the expression level of one or more of ISG15, LTF, CNDP2, DAD1, SET, UBE2N, S100P, and GPI or one or more of any other combination of marker genes described herein. In some methods, determining the expression level of the one or more marker genes in the test esophageal tissue sample comprises determining the expression level of two or more of ISG15, LTF, CNDP2, DAD1, SET, UBE2N, S100P, and GPI or two or more of any other combination of marker genes described herein (e.g., two or more of ISG15, LTF, and DAD1, or two or more of ISG15, LTF, DAD1, CNDP2, SET, and GPI). In some methods, determining the expression level of the one or more marker genes in the test esophageal tissue sample comprises determining the expression level of three or more of ISG15, LTF, CNDP2, DAD1, SET, UBE2N, S100P, and GPI or three or more of any other combination of marker genes described herein (e.g., three or more of ISG15, LTF, DAD1, CNDP2, SET, and GPI). In some methods, determining the expression level of the one or more marker genes in the test esophageal tissue sample comprises determining the expression level of four or more of ISG15, LTF, CNDP2, DAD1, SET, UBE2N, S100P, and GPI or four or more of any other combination of marker genes described herein (e.g., four or more of ISG15, LTF, DAD1, CNDP2, SET, and GPI). In some methods, determining the expression level of the one or more marker genes in the test esophageal tissue sample comprises determining the expression level of five or more of ISG15, LTF, CNDP2, DAD1, SET, UBE2N, S100P, and GPI or five or more of any other combination of marker genes described herein (e.g., five or more of ISG15, LTF, DAD1, CNDP2, SET, and GPI). In some methods, determining the expression level of the one or more marker genes in the test esophageal tissue sample comprises determining the expression level of six or more of ISG15, LTF, CNDP2, DAD1, SET, UBE2N, S100P, and GPI or six or more of any other combination of marker genes described herein. In some methods, determining the expression level of the one or more marker genes in the test esophageal tissue sample comprises determining the expression level of seven or more of ISG15, LTF, CNDP2, DAD1, SET, UBE2N, S100P, and GPI or seven or more of any other combination of marker genes described herein. In some methods, determining the expression level of the one or more marker genes in the test esophageal tissue sample comprises determining the expression level of each of ISG15, LTF, CNDP2, DAD1, SET, UBE2N, S100P, and GPI.

The one or more marker genes can be, for example, selected from the group consisting of ISG15, LTF, CNDP2, DAD1, SET, UBE2N, S100P, and GPI, and any combination thereof. In some methods the one or marker genes comprise UBE2N. In some methods, the one or marker genes comprise DAD1. In some methods, the one or marker genes comprise ISG15. In some methods, the one or marker genes comprise CNDP2. In some methods, the one or marker genes comprise GPI. In some methods, the one or marker genes comprise SET. In some methods the one or marker genes comprise LTF. In some methods, the one or marker genes comprise S100P. In some methods, the one or more marker genes comprise ISG15 and LTF. In some methods, the one or more marker genes comprise ISG15 and DAD1. In some methods, the one or more marker genes comprise LTF and DAD1. In some methods, the one or more marker genes comprise ISG15, LTF, and DAD1. In some methods, the one or more marker genes comprise ISG15 and CNDP2. In some methods, the one or more marker genes comprise LTF and CNDP2. In some methods, the one or more marker genes comprise ISG15, LTF, and CNDP2. In some methods, the one or more marker genes comprise ISG15, LTF, DAD1, and CNDP2. In some methods, the one or more marker genes comprise ISG15, LTF, DAD1, and SET. In some methods, the one or more marker genes comprise ISG15, LTF, DAD1, and GPI. In some methods, the one or more marker genes comprise ISG15, LTF, DAD1, CNDP2, and SET. In some methods, the one or more marker genes comprise ISG15, LTF, DAD1, CNDP2, and GPI. In some methods, the one or more marker genes comprise ISG15, LTF, DAD1, SET, and GPI. In some methods, the one or more marker genes comprise ISG15, LTF, DAD1, CNDP2, SET, and GPI.

In some methods, the one or more marker genes are selected from the group consisting of ISG15, CNDP2, DAD1, SET, UBE2N, GPI, and any combination thereof. In some methods, the one or more marker genes are selected from the group consisting of ISG15, DAD1, UBE2N, S100P, and any combination thereof. In some methods, the one or more marker genes are selected from the group consisting of ISG15, LTF, DAD1, and any combination thereof. In one example, the marker genes comprise ISG15 and LTF. In another example, the marker genes comprise ISG15 and DAD1. In another example, the marker genes comprise LTF and DAD1. In another example, the marker genes comprise ISG15, LTF, and DAD1. In some methods, the one or more marker genes are selected from the group consisting of ISG15, LTF, DAD1, CNDP2, SET, GPI, and any combination thereof.

Alternatively, the marker genes can comprise one or more of CNDP2, SET, GPI, and any combination thereof. Alternatively, the marker genes can comprise one or more of ISG15, LTF, DAD1, CNDP2, SET, GPI, and any combination thereof. Alternatively, the marker genes can comprise one or more of UBE2N, S100P, and any combination thereof. Alternatively, the marker genes can comprise one or more of ISG15, CNDP2, DAD1, SET, UBE2N, GPI, and any combination thereof.

ISG15 (UniProt Ref. P05161, also known as interferon-stimulating gene 15 or ubiquitin-like protein ISG15) is a ubiquitin-like protein that plays a key role in innate immune responses.

LTF (UniProt Ref. P02788, also known as lactotransferrin) is a major iron-binding and multifunctional protein found in exocrine fluids such as breast milk and mucosal secretions and possesses antimicrobial activity. LTF promotes binding of species C adenoviruses to epithelial cells, promoting adenovirus infection. LTF stimulates the TLR4 signaling pathway leading to NF-kappa-B activation and subsequent pro-inflammatory cytokine production while also interfering with the lipopolysaccharide (LPS)-stimulated TLR4 signaling. LTF inhibits neutrophil granulocyte migration to sites of apoptosis, when secreted by apoptotic cells and stimulates VEGF-mediated endothelial cell migration and proliferation.

CNDP2 (UniProt Ref. Q96KP4, also known as cytosolic non-specific dipeptidase) hydrolyzes a variety of dipeptides, preferentially hydrophobic dipeptides including prolyl amino acids. CNDP2 catalyzes the production of N-lactoyl-amino acids from lactate and amino acids by reverse proteolysis. An elevated level of CNDP2 activates p38 and JNK/MAPK pathways to induce cell apoptosis, and a lower level of CNDP2 activates the ERK MAPK pathway to promote cell proliferation.

DAD1 (UniProt Ref. P61803, also known as defender against cell death or dolichyl-diphosphooligosaccharide-protein glycosyltransferase subunit DAD1) is an enzyme required for efficient glycosylation.

SET nuclear proto-oncogene (UniProt Ref. Q01105, also known as protein SET) is transcribed into a multitasking protein involved in apoptosis, transcription, nucleosome assembly and histone chaperoning.

UBE2N (UniProt Ref. P61088, also known as ubiquitin-conjugating enzyme E2 N) has been found to be overexpressed in breast, pancreas, colon, prostate, and ovarian carcinomas. Overexpression of UBE2N has been found to be required for breast cancer metastasis to the lung. Inhibition of this marker caused cell death in neuroblastomas. UBE2N specifically builds ubiquitin chains that are critical for NFkβ inflammatory activation, a mechanism associated with carcinogenesis. UBE2N inhibition significantly altered the ubiquitination of ~140 proteins involved in innate immune signaling, cell survival, RNA splicing, and DNA damage response, indicating that it exerts its functions far upstream, respectively.

S100P (UniProt Ref. P25815, also known as protein S100-P) is localized in the cytoplasm and/or nucleus of a wide range of cells and is involved in the regulation of several cellular processes such as cell cycle progression and differentiation. S100P exerts its functions by binding to and activating RAGE, possibly causing cell division mechanisms to circumvent the classical tyrosine kinase/KRAS proliferation pathways often upregulated in many solid tumors.

GPI (UniProt Ref. P06744, also known as glucose-6-phosphate isomerase) catalyzes the conversion of glucose-6-phosphate to fructose-6-phosphate, the second step in glycolysis, and the reverse reaction during gluconeogenesis. It is a major glycolytic enzyme that is associated with the pathways involving the Warburg effect—the well-described avenue in which cancer cells produce energy at a high rate via glycolysis.

The subject in the described methods can be, for example, a healthy subject, a subject with a known familial risk for developing esophageal adenocarcinoma, a subject having one or more known risk factors for developing esophageal adenocarcinoma, or a subject having a precursor to esophageal adenocarcinoma. Various factors may raise a person's risk for developing esophageal adenocarcinoma, such as age (increased risk with greater age), gender (men are more likely than women to develop esophageal adenocarcinoma), obesity, genetic risk factors, or having gastroesophageal reflux disease (GERD) or Barrett's esophagus. For example, the subject can have GERD or Barrett's esophagus. In a particular example, the subject can have Barrett's esophagus. Esophageal adenocarcinoma occurs most commonly in people with GERD. GERD is distinguishable from normal mucosa via histopathology and sometimes via upper endoscopy (widening of cardiac sphincter and inflammation). The most common symptom of GERD is heartburn, a condition that 20 percent of adults in the U.S. experience at least twice per week. Although these individuals are at increased risk of developing esophageal cancer, the vast majority of them will never develop it. However, in approximately 10-15% of patients with GERD, a change in the esophageal lining develops, a condition called Barrett's esophagus. Most cases of adenocarcinoma of the esophagus begin in Barrett's tissue. Barrett's esophagus is a condition in which the esophageal lining changes, becoming similar to the tissue that lines the intestine. Barrett's esophagus is defined per the American College of Gastroenterology guidelines as intestinal metaplasia in areas of salmon-colored mucosa in the tubular esophagus. A complication of GERD, Barrett's is more likely to occur in patients who either experienced GERD first at a young age or have had a longer duration of symptoms. The frequency and or severity of GERD does not affect the likelihood that Barrett's may have formed. Although the risk of esophageal adenocarcinoma is higher in people with Barrett's esophagus, most patients with Barrett's esophagus will not develop cancer. In some patients, however, a precancerous change in the tissue, called dysplasia, will develop. That precancerous change is more likely to develop into esophageal cancer. Barrett's tissue is visible during endoscopy, although a diagnosis by endoscopic appearance alone is not sufficient. The definitive diagnosis of Barrett's esophagus requires biopsy confirmation. The risk of esophageal cancer in patients with Barrett's esophagus is quite low, approximately 0.5 percent per year (or 1 out of 200). The diagnosis of Barrett's esophagus is a reason for periodic endoscopies. If initial biopsies do not show dysplasia, endoscopy with biopsy should be repeated about every 3 years. In some of the methods disclosed herein, the subject has Barrett's esophagus, and the method assesses the risk of progressing from Barrett's esophagus to esophageal adenocarcinoma.

The subject in the methods can be, for example, a mammal, such as a non-human mammal or a human. In some methods, the mammal is a rodent, such as a rat or a mouse. In some methods, the subject is a human, such as a human with Barrett's esophagus.

The test esophageal tissue sample in the methods can be an esophageal tissue sample that was isolated from the subject (i.e., an isolated esophageal tissue sample). The isolated esophageal tissue sample can be a biopsy sample, such as a esophagogastroduodenoscopy biopsy sample or an esophagectomy sample. If the subject has Barrett's esophagus, the test esophageal tissue sample can be a test Barrett's esophagus tissue sample (i.e., pathologic tissue). The isolated sample can be in any form. For example, it can be a fresh esophageal tissue sample, a frozen esophageal tissue sample, a preserved esophageal sample, a formalin-fixed esophageal sample, or a formalin-fixed paraffin-embedded (FFPE) esophageal sample.

In a particular example, the isolated esophageal tissues sample is an FFPE sample. The vast majority of available cancer tissue specimens are fixed with formalin and embedded in paraffin for long-term preservation.

The isolated esophageal tissue sample can be a mucosa sample (e.g., Barrett's esophagus mucosa samples). The inner lining of the esophagus is known as the mucosa. The mucosa of the normal esophagus is composed of squamous cells (squamous mucosa) similar to those of the skin or mouth. Most of the esophagus is lined by squamous mucosa. Goblet cells normally line the intestines, not the esophagus. When goblet cells are found in a place where they are not supposed to be, like the lining of the esophagus, it is called intestinal metaplasia. Intestinal metaplasia can develop any place where squamous mucosa is normally found. When intestinal metaplasia replaces the squamous mucosa of the esophagus, it is called Barrett's esophagus. The isolated esophageal tissue sample (e.g., FFPE sample) in the methods can be, for example, a mucosa sample (e.g., Barrett's esophagus mucosa sample or FFPE Barrett's esophagus mucosa sample) that has been separated from non-mucosal tissue (e.g., by microdissection). In a specific example, the isolated esophageal tissue sample is an FFPE mucosa sample (e.g., an FFPE Barrett's esophagus mucosa sample) that has been separated from non-mucosal tissue such as stroma, microstructural cells (e.g., collagen, elastin, and fibrin), vascular cells, and immune cells.

In addition, biopsies (e.g., pinch biopsies) and esophagectomy specimens can also contain normal squamous esophageal epithelium. When assessing Barrett's esophagus tissue, microdissecting around the normal tissue can be beneficial because that the normal tissue can interfere with quantification of the expression patterns in the adjacent diseased tissue. Current diagnostic methods for Barrett's esophagus like histopathology and whole genome sequencing assess the entire specimen including the diseased, normal, and structural cells. Thus, the isolated esophageal tissue sample (e.g., FFPE sample) in the methods can be, for example, a Barrett's esophagus mucosa sample that has been separated from adjacent normal tissue (e.g., adjacent normal squamous esophageal epithelium). Similarly, the isolated esophageal tissue sample (e.g., FFPE sample) in the methods can be, for example, a Barrett's esophagus mucosa sample that has been separated from adjacent normal tissue (e.g., adjacent normal squamous esophageal epithelium) and/or has been separated from non-mucosal tissue such as stroma, microstructural cells (e.g., collagen, elastin, and fibrin), vascular cells, and immune cells. In a specific example, the isolated esophageal tissue sample (e.g., FFPE sample) in the methods is a Barrett's esophagus mucosa sample that has been separated from normal tissue and from non-mucosal tissue.

The isolated esophageal tissue samples can also be dissected (e.g., laser microdissected or needle dissected). That is, mucosa (e.g., squamous mucosa), Barrett's esophagus mucosa, or esophageal adenocarcinoma can be removed from the isolated esophageal tissue samples for proteomic analysis while avoiding cells of non-interest Microdissection refers to a variety of techniques where a microscope is used to assist in the separation of diseased tissue from normal or structural microenvironments. The cells of interest in an isolated esophageal tissue sample (e.g., FFPE sample, or slide) can be outlined with available software (e.g., Histokat Fusion or MMI CellCut), the sample (e.g., slide) can be turned upside-down, and a laser can knock the cells of interest off into a tube for sample preparation and analysis. Needle dissection refers to separation of the tissue of interest from cells of non-interest with a small-gauged needle. For example, the isolated esophageal tissue sample can be a dissected or microdissected mucosa sample (dissected or microdissected squamous mucosa sample), a dissected or microdissected Barrett's esophagus mucosa sample (e.g., a dissected or microdissected Barrett's esophagus mucosa sample), or dissected or microdissected esophageal adenocarcinoma cells.

The methods can further comprise a step of selectively isolating mucosal tissue from the test esophageal tissue sample (e.g., a test Barrett's esophagus tissue sample) to produce a test esophageal mucosa sample (e.g., a test Barrett's esophagus mucosa sample) that has been separated from non-mucosal tissue prior to determining the expression level of the one or marker genes. The expression level of the one or more marker genes is then determined in the test esophageal mucosa sample. For example, the step of selectively isolating mucosal tissue (e.g., Barrett's esophagus mucosal tissue) can comprise microdissection such as laser microdissection. For example, the mucosal cells or Barrett's esophagus mucosal cells of interest in a sample (e.g., FFPE sample, or slide) can separated from the rest of the sample using a laser (e.g., after outlining the cells of interest). Alternatively, the step of selectively isolating mucosal tissue (e.g., Barrett's esophagus mucosal tissue) can comprise needle dissection. For example, the mucosal cells or Barrett's esophagus mucosal cells of interest in a sample (e.g., FFPE sample, or slide) can be separated from the rest of the sample using a needle (e.g., a small-gauged needle). In a specific example, the test esophageal sample being used for selective isolation of mucosal tissue or Barrett's esophagus mucosa tissue is an FFPE sample.

Likewise, the methods can further comprise a step of selectively isolating Barrett's esophagus mucosal tissue from adjacent normal tissue (e.g., adjacent normal squamous esophageal epithelium) to produce a test Barrett's esophagus mucosa sample that has been separated from normal tissue prior to determining the expression level of the one or marker genes. The expression level of the one or more marker genes can then be determined in the test Barrett's esophagus mucosa sample. For example, the step of selectively isolating Barrett's esophagus mucosal tissue can comprise microdissection such as laser microdissection. Alternatively, it can comprise needle dissection. In a specific example, the test esophageal sample being used for selective isolation of Barrett's esophagus mucosal tissue is an FFPE sample. For example, the mucosal cells or Barrett's esophagus mucosal cells of interest in a sample (e.g., FFPE sample, or slide) can separated from the rest of the sample using a laser (e.g., after outlining the cells of interest). Alternatively, the step of selectively isolating mucosal tissue (e.g., Barrett's esophagus mucosal tissue) can comprise needle dissection. For example, the mucosal cells or Barrett's esophagus mucosal cells of interest in a sample (e.g., FFPE sample, or slide) can be separated from the rest of the sample using a needle (e.g., a small-gauged needle). In a specific example, the test esophageal sample being used for selective isolation of mucosal tissue or Barrett's esophagus mucosa tissue is an FFPE sample.

Likewise, the methods can further comprise a step of selectively isolating mucosal tissue from the test esophageal tissue sample (e.g., a test Barrett's esophagus tissue sample) and selectively isolating Barrett's esophagus mucosal tissue from adjacent normal tissue (e.g., adjacent normal squamous esophageal epithelium) to produce a test Barrett's esophagus mucosa sample that has been separated from non-mucosal tissue and normal tissue prior to determining the expression level of the one or marker genes. The expression level of the one or more marker genes can then be determined in the test Barrett's esophagus mucosa sample. For example, the step of selectively isolating Barrett's esophagus mucosal tissue can comprise microdissection such as laser microdissection. Alternatively, it can comprise needle dissection. In a specific example, the test esophageal sample being used for selective isolation of Barrett's esophagus mucosal tissue is an FFPE sample. For example, the mucosal cells or Barrett's esophagus mucosal cells of interest in a sample (e.g., FFPE sample, or slide) can separated from the rest of the sample using a laser (e.g., after outlining the cells of interest). Alternatively, the step of selectively isolating mucosal tissue (e.g., Barrett's esophagus mucosal tissue) can comprise needle dissection. For example, the mucosal cells or Barrett's esophagus mucosal cells of interest in a sample (e.g., FFPE sample, or slide) can be separated from the rest of the sample using a needle (e.g., a small-gauged needle). In a specific example, the test esophageal sample being used for selective isolation of mucosal tissue or Barrett's esophagus mucosa tissue is an FFPE sample.

The control esophageal tissue sample can comprise normal (non-cancerous, non-Barrett's) esophageal tissue (e.g., normal esophageal squamous epithelium). For example, the control esophageal tissue sample can comprise normal esophageal mucosa (e.g., squamous epithelium). In some methods, the control esophageal tissue sample is from the subject. For example, normal esophageal mucosa can be taken from the proximal resection margin to select tissue as far removed from the accompanying pathologic processes. In other methods, the control esophageal tissue sample can be from a control subject that does not have Barrett's esophagus or esophageal adenocarcinoma or that does not have does not have GERD, Barrett's esophagus, or esophageal adenocarcinoma. Some methods can also comprise a step of determining the expression level of the one or more marker genes in the control esophageal tissue sample.

Determining the expression level of the one or more marker genes in the test esophageal sample can comprise measuring the expression (i.e., performing an assay to measure the expression) of the one or more marker genes in the test esophageal sample. For example, determining the expression level of the one or more marker genes in the test esophageal tissue sample can comprise measuring the expression (i.e., performing an assay to measure the expression) of messenger RNAs (mRNAs) encoded by the one or more marker genes and/or can comprise measuring the expression (i.e., performing an assay to measure the expression) of proteins encoded by the one or more marker genes. In one example, determining the expression level of the one or more marker genes in the test esophageal tissue sample can comprise measuring the expression (i.e., performing an assay to measure the expression) of messenger RNAs (mRNAs) encoded by the one or more marker genes. For example, mRNA levels can be determined or measured by any known method, such as PCR, RT-PCR, quantitative RT-PCR, isothermal nucleic acid quantification, or next-generation sequencing (NGS). In another example, determining the expression level of the one or more marker genes in the test esophageal tissue sample can comprise measuring the expression (i.e., performing an assay to measure the expression) of proteins encoded by the one or more marker genes. For example, protein levels can be determined or measured by any known method, such as mass spectrometry, immunohistochemistry, an immunoassay, an enzyme-linked immunosorbent assay (ELISA), an alphaLISA, or an enzyme-linked immune absorbent spot (ELISpot) assay.

In a specific example, determining the expression level of the one or more marker genes (i.e., biomarkers) in the test esophageal tissue sample comprises measuring the expression of proteins encoded by the one or more marker genes using mass spectrometry. Mass spectrometry is high-throughput and multiplexable, assessing multiple disease-specific biomarkers simultaneously.

When mass spectrometry is used to determine the expression level of the one or more marker genes, the test esophageal tissue sample can be digested with one or more proteinases (e.g., after selectively isolating mucosal tissue or Barrett's esophagus mucosa from the test esophageal tissue sample), and the digested sample (i.e., the digested peptides) can then be analyzed by mass spectrometry. The proteinase can be any suitable proteinase for mass spectrometry, such as trypsin, chymotrypsin, LysC, LysN, AspN, GluC, or ArgC. In a particular example, the proteinase can be trypsin, which is a serine protease that cuts peptide chains mainly at the carboxyl side of lysine and arginine, but not before proline. In another example, the test esophageal sample can be digested sequentially with trypsin followed by any one of chymotrypsin, LysC, LysN, AspN, GluC, or ArgC.

If the test esophageal tissue sample is formalin-fixed (e.g., a formalin-fixed paraffin-embedded tissue), the sample can also be processed to reverse formalin cross-links prior to measuring the expression level of the one or more marker genes. In a specific example, this is done prior to digesting with the one or more proteinases. Formalin-fixed tissue has been typically incompatible with mass spectrometry platforms in the past. Clinically, mass spectrometry platforms typically utilize serum and fresh or frozen tissue specimen for proteomic scrutiny. Formalin cross-linked tissue samples have been found to not completely digest into a lysate compatible for mass spec, thereby increasing the risk of breaking expensive machinery. Some of the methods disclosed herein, however, allow the analysis of protein expression in new and old formalin-fixed paraffin-embedded (FFPE) tissue samples. Such methods disclosed herein can fully digest FFPE tissue into small, mass-spectrometry-friendly peptides. The methods can eliminate the effects of poor tissue fixation after surgery, as the mass spectrometry can measure a small, unique, identifying peptide within a large protein that only exists in the marker protein being detected. Therefore, protein degradation or breakage because of improper fixation has no bearing on the results. The process can take about 24 hours and completely reverses formalin cross-links of FFPE tissue while eliminating the need for protein epitope integrity for antibody recognition. The resulting liquid biopsies can also be stored indefinitely for future testing. Such methods disclosed herein make it possible to recover peptides from FFPE tissues that yield a reasonable representation of the proteins recovered from identical fresh or frozen specimens.

In a specific example, FFPE tissue is heated (e.g., in a buffer void of detergents), and the resulting sample is then treated with a proteinase (e.g., trypsin). The heating can reverse the formalin cross-links (e.g., untangle the bunched-up proteins caused by fixation). The proteinase treatment cuts the large proteins into smaller, mass-spectrometry-compatible peptides. The tissue can be heated, for example, to between about 90° C. to about 100° C., or to about 95° C. The heating can be, for example, for about 60 to about 120, for about 70 to about 110, for about 80 to about 100, or for about 90 minutes. In a specific example, the FFPE tissue is heated to about 95° C. (e.g., to 95° C.) for about 90 minutes (e.g., 90 minutes) in a buffer void of detergents reverse the formalin cross-links. A proteinase (e.g., trypsin) can then be added to cut the large proteins into smaller, mass-spectrometry-compatible peptides. The proteinase (e.g., trypsin) can be added, for example, at between about 35° C. to about 40° C., or at about 37° C. The proteinase (e.g., trypsin) can be added, for example, for about 14 to about 20, for about 15 to about 19, or for about 16 to about 18 hours. In a specific example, trypsin is added at about 37° C. (e.g., at 37° C.) for about 16 to about 18 hours (e.g., 16 to 18 hours) to cut the large proteins into smaller, mass-spectrometry-compatible peptides. The amount of protein in each sample can then be quantified (e.g., by a BCA (bicinchoninic acid) protein assay or via NanoDrop hardware/software). Finally, the sample can then be reduced (e.g., with 10% DTT (Dithiothreitol)). A selected amount of the sample (e.g., about 0.5 µg to about 1.5 µg, about 0.7 µg to about 1.3 g, about 0.8 µg to about 1.2 g, about 0.9 µg to about 1.1 µg, or about 1 µg of sample) can then be used for mass spectrometry analysis.

In a more specific example, the mass spectrometry can be targeted mass spectrometry. In a typical discovery-based mass spectrometry experiment, peptide ions are automatically selected in the mass spectrometer for fragmentation on the basis of their signal intensities. Fragmentation generates rich but complex tandem mass spectra for each peptide sequence. The experimental spectra are matched to library spectra to infer the peptide sequences and, by extension, the proteins—a process involving sophisticated bioinformatics tools and careful scrutiny of the results. In a targeted workflow, the mass spectrometer is programmed to detect specific peptide ions derived from proteins of interest. For example, to assure highly accurate quantification, a known amount of specific peptides unique to the proteins encoded by the one or more marker genes can be spiked in. The peptides can be isotopically labeled so they can be detected with ease. The amount of protein spiked in can be subtracted from the signal, yielding accurate and precise quantification of all markers concurrently.

In some methods, a triple quadrupole mass spectrometer (QQQ) is used. The triple quadrupole mass spectrometer (QQQ) operates as a dual mass filter that allows molecular ions of predetermined masses to be selected for fragmentation in the instrument. In a targeted proteome analysis, peptide ions travel into the first QQQ mass filter, which can be programmed to select specific precursor ions on the basis of their m/z ratio for fragmentation. In the second mass filter, target product ions are selected and then guided to the detector for quantification, resulting in a trace of signal intensity versus retention time for each precursor ion-product ion pair. This process is called selected reaction monitoring (SRM) or multiple reaction monitoring (MRM).

SRM assays can be generated by defining a signature set of peptide fragment coordinates. A detectable precursor ion-product ion pair is referred to as a transition, and several suitable transitions constitute an SRM assay for detection and quantification of a target peptide and, by extension, the target protein. By spiking the sample with heavy isotope-labeled reference peptides, it is possible to achieve absolute quantification of the targeted peptides. The SRM technique can analyze, for example, about 50 to about 100 proteins concurrently. Other mass spectrometry assays can also be used. With an approach called SWATH, complex mass spectra generated by data-independent acquisition (in which peptides are selected for fragmentation without regard to signal intensity) can be queried for the presence of specific peptides using libraries of qualified peptide fragment spectra. With another approach called parallel reaction monitoring, all transitions can be monitored in parallel in a single analysis.

Not all peptides are equally analyzed by mass spectrometry. Some are better separated, ionized, and detected than others owing to their physicochemical properties. Peptide sequences (proteotypic peptides) must also be carefully chosen to ensure that they uniquely represent one of the targeted proteins. Once proteotypic peptides have been chosen, the optimal SRM transitions must be determined and rigorously validated. In some methods, the one or more marker genes comprise UBE2N, and determining the expression level of UBE2N comprises targeted mass spectrometry (i.e., performing a targeted mass spectrometry assay) for detection and quantification of the target peptide set forth in SEQ ID NO: 1 or 5. In some methods, the one or more marker genes comprise UBE2N, and determining the expression level of UBE2N comprises targeted mass spectrometry (i.e., performing a targeted mass spectrometry assay) for detection and quantification of the target peptide set forth in SEQ ID NO: 1, 5, or 6. In some methods, the one or more marker genes comprise DAD1, and determining the expression level of DAD1 comprises targeted mass spectrometry (i.e., performing a targeted mass spectrometry assay) for detection and quantification of the target peptide set forth in SEQ ID NO: 7 or 9. In some methods, the one or more marker genes comprise ISG15, and determining the expression level of ISG15 comprises targeted mass spectrometry (i.e., performing a targeted mass spectrometry assay) for detection and quantification of the target peptide set forth in SEQ ID NO: 11 or 12. In some methods, the one or more marker genes comprise CNDP2, and determining the expression level of CNDP2 comprises targeted mass spectrometry (i.e., performing a targeted mass spectrometry assay) for detection and quantification of the target peptide set forth in SEQ ID NO: 20 or 31. In some methods, the one or more marker genes comprise CNDP2, and determining the expression level of CNDP2 comprises targeted mass spectrometry (i.e., performing a targeted mass spectrometry assay) for detection and quantification of the target peptide set forth in SEQ ID NO: 18, 19, 20, 24, 26, 28, 29, 31, 32, or 33. In some methods, the one or more marker genes comprise GPI, and determining the expression level of GPI comprises targeted mass spectrometry (i.e., performing a targeted mass spectrometry assay) for detection and quantification of the target peptide set forth in SEQ ID NO: 35 or 39. In some methods, the one or more marker genes comprise GPI, and determining the expression level of GPI comprises targeted mass spectrometry (i.e., performing a targeted mass spectrometry assay) for detection and quantification of the target peptide set forth in SEQ ID NO: 35, 39, 40, 42, 43, or 44. In some methods, the one or more marker genes comprise SET, and determining the expression level of SET comprises targeted mass spectrometry (i.e., performing a targeted mass spectrometry assay) for detection and quantification of the target peptide set forth in SEQ ID NO: 50. In some methods, the one or more marker genes comprise LTF, and determining the expression level of LTF comprises targeted mass spectrometry (i.e., performing a targeted mass spectrometry assay) for detection and quantification of the target peptide set forth in SEQ ID NO: 54 or 58. In some methods, the one or more marker genes comprise LTF, and determining the expression level of LTF comprises targeted mass spectrometry (i.e., performing a targeted mass spectrometry assay) for detection and quantification of the target peptide set forth in SEQ ID NO: 52, 53, 54, 57, 58, 59, 60, 62, 63, or 66. In some methods, the one or more marker genes comprise S100P, and determining the expression level of S100P comprises targeted mass spectrometry (i.e., performing a targeted mass spectrometry assay) for detection and quantification of the target peptide set forth in SEQ ID NO: 67 or 68.

Also provided herein are any of the peptides (e.g., isolated peptides) disclosed above, e.g., for use in targeted mass spectrometry (e.g., as heavy isotope-labeled reference peptides). For example, provided herein are any of the peptides (e.g., isolated peptides) disclosed above, e.g., for use in a targeted mass spectrometry assay (e.g., as heavy isotope-labeled reference peptides) to determine their expression in a test sample (e.g., a test esophageal tissue sample from a subject as disclosed in more detail elsewhere herein). In one example, a composition is provided comprising an isolated peptide comprising the sequence set forth in any one of SEQ ID NOS: 1, 5, 6, 7, 9, 11, 12, 18, 19, 20, 24, 26, 28, 29, 31, 32, 33, 35, 39, 40, 42, 43, 44, 50, 52, 53, 54, 57, 58, 59, 60, 62, 63, 66, 67, and 68. In one example, a composition is provided comprising an isolated peptide comprising the sequence set forth in any one of SEQ ID NOS: 1, 5, 7, 9, 11, 12, 20, 31, 35, 39, 50, 54, 58, 67, and 68. Such peptides can be isolated peptides and can be labeled with a heavy isotope.

In one example, provided herein is an isolated peptide comprising the sequence set forth in SEQ ID NO: 1 or 5 for use in a targeted mass spectrometry assay (e.g., as heavy isotope-labeled reference peptides) to determine expression of UBE2N in a test sample (e.g., test esophageal tissue sample from a subject). For example, the isolated peptide can be labeled with a heavy isotope.

In one example, provided herein is an isolated peptide comprising the sequence set forth in SEQ ID NO: 1, 5, or 6 for use in a targeted mass spectrometry assay (e.g., as heavy isotope-labeled reference peptides) to determine expression of UBE2N in a test sample (e.g., test esophageal tissue sample from a subject). For example, the isolated peptide can be labeled with a heavy isotope.

In one example, provided herein is an isolated peptide comprising the sequence set forth in SEQ ID NO: 7 or 9 for use in a targeted mass spectrometry assay (e.g., as heavy isotope-labeled reference peptides) to determine expression of DAD1 in a test sample (e.g., test esophageal tissue sample from a subject). For example, the isolated peptide can be labeled with a heavy isotope.

In one example, provided herein is an isolated peptide comprising the sequence set forth in SEQ ID NO: 11 or 12 for use in a targeted mass spectrometry assay (e.g., as heavy isotope-labeled reference peptides) to determine expression of ISG15 in a test sample (e.g., test esophageal tissue sample from a subject). For example, the isolated peptide can be labeled with a heavy isotope.

In one example, provided herein is an isolated peptide comprising the sequence set forth in SEQ ID NO: 18, 19, 20, 24, 26, 28, 29, 31, 32, or 33 for use in a targeted mass spectrometry assay (e.g., as heavy isotope-labeled reference peptides) to determine expression of CNDP2 in a test sample (e.g., test esophageal tissue sample from a subject). For example, the isolated peptide can be labeled with a heavy isotope.

In one example, provided herein is an isolated peptide comprising the sequence set forth in SEQ ID NO: 20 or 31 for use in a targeted mass spectrometry assay (e.g., as heavy isotope-labeled reference peptides) to determine expression of CNDP2 in a test sample (e.g., test esophageal tissue sample from a subject). For example, the isolated peptide can be labeled with a heavy isotope.

In one example, provided herein is an isolated peptide comprising the sequence set forth in SEQ ID NO: 35, 39, 40, 42, 43, or 44 for use in a targeted mass spectrometry assay (e.g., as heavy isotope-labeled reference peptides) to determine expression of GPI in a test sample (e.g., test esophageal tissue sample from a subject). For example, the isolated peptide can be labeled with a heavy isotope.

In one example, provided herein is an isolated peptide comprising the sequence set forth in SEQ ID NO: 35 or 39 for use in a targeted mass spectrometry assay (e.g., as heavy isotope-labeled reference peptides) to determine expression of GPI in a test sample (e.g., test esophageal tissue sample from a subject). For example, the isolated peptide can be labeled with a heavy isotope.

In one example, provided herein is an isolated peptide comprising the sequence set forth in SEQ ID NO: 50 for use in a targeted mass spectrometry assay (e.g., as heavy isotope-labeled reference peptides) to determine expression of SET in a test sample (e.g., test esophageal tissue sample from a subject). For example, the isolated peptide can be labeled with a heavy isotope.

In one example, provided herein is an isolated peptide comprising the sequence set forth in SEQ ID NO: 52, 53, 54, 57, 58, 59, 60, 62, 63, or 66 for use in a targeted mass spectrometry assay (e.g., as heavy isotope-labeled reference peptides) to determine expression of LTF in a test sample (e.g., test esophageal tissue sample from a subject). For example, the isolated peptide can be labeled with a heavy isotope.

In one example, provided herein is an isolated peptide comprising the sequence set forth in SEQ ID NO: 54 or 58 for use in a targeted mass spectrometry assay (e.g., as heavy isotope-labeled reference peptides) to determine expression of LTF in a test sample (e.g., test esophageal tissue sample from a subject). For example, the isolated peptide can be labeled with a heavy isotope.

In one example, provided herein is an isolated peptide comprising the sequence set forth in SEQ ID NO: 67 or 68 for use in a targeted mass spectrometry assay (e.g., as heavy isotope-labeled reference peptides) to determine expression of S100P in a test sample (e.g., test esophageal tissue sample from a subject). For example, the isolated peptide can be labeled with a heavy isotope.

Mass spectrometry has several advantages over typical diagnostic and prognostic assays for Barrett's esophagus. First, there is lower likelihood of false positives. Mass spectrometry detects all proteins by their mass/charge and does not rely on antibodies. Antibody-free detection and quantification avoids non-specific binding, overstaining, and subjective interpretation. Second, mass spectrometry requires very little sample (e.g., two FFPE slides or 8 mm$^2$ of tissue per run as compared to immunofluorescence or mutational load analysis, which require nine or more FFPE slides to yield proper results). Immunohistochemistry and immunofluorescence require one slide per biomarker if running in singlet, or two to three slides per biomarker if running duplicates or triplicates. Mass spectrometry allows for simultaneous quantification of all biomarkers concurrently from just 8 mm$^2$ of tissue, which can typically be retrieved from 1-2 FFPE pinch biopsy sections. Third, mass spectrometry has a quick turnaround time (e.g., one week from the day a biopsy specimen is received, as compared to three weeks for mutational load analysis via next generation sequencing or four weeks for multi-proteomic immunohistopathology techniques). Fourth, compared to diagnostic and prognostic assays looking at DNA (mutations) or RNA expression, proteomics is more clinically actionable because drugs in medical oncology typically target proteins, not the genes themselves.

If the subject in the methods described herein is identified as having an increased risk of developing esophageal adenocarcinoma, the methods can optionally further comprise monitoring the subject more closely or testing or screening the subject more frequently for progression to or development of esophageal adenocarcinoma.

If the subject in the methods described herein is identified as having an increased risk of developing esophageal adenocarcinoma, the methods can optionally further comprise determining the expression level of one or more cellular proliferation marker genes in a test esophageal tissue sample from the subject, and comparing the expression level of the one or more cellular proliferation marker genes in the test esophageal tissue sample to the expression level of the one or more cellular proliferation marker genes in a control esophageal tissue sample, wherein increased expression of at least one of the one or more of cellular proliferation marker genes in the test esophageal tissue sample relative to the control esophageal tissue sample indicates an increased risk for developing esophageal adenocarcinoma. The cellular proliferation marker genes can comprise, for example, one or more of HMGB1, KRT7, LGALS3BP, LTF, PRMT1, and S100P.

If the subject in the methods described herein is identified as having an increased risk of developing esophageal adenocarcinoma, the methods can optionally further comprise determining the expression level of one or more tumor suppressor marker genes in a test esophageal tissue sample from the subject, and comparing the expression level of the one or more tumor suppressor marker genes in the test esophageal tissue sample to the expression level of the one or more tumor suppressor marker genes in a control esophageal tissue sample, wherein decreased expression of at least one of the one or more of tumor suppressor marker genes in the test esophageal tissue sample relative to the control esophageal tissue sample indicates an increased risk for developing esophageal adenocarcinoma. The tumor suppressor marker genes can comprise, for example, one or more of ANXA1, CRNN, IL-1RA, S100A8, SFN, and TXN.

If the subject in the methods described herein is identified as having an increased risk of developing esophageal adenocarcinoma, the methods can optionally further comprise determining the expression level of one or more molecular oncology marker genes in a test esophageal tissue sample from the subject, and comparing the expression level of the one or more molecular oncology marker genes in the test esophageal tissue sample to the expression level of the one or more molecular oncology marker genes in a control esophageal tissue sample, wherein the expression levels of the molecular oncology marker genes in the test esophageal tissue sample relative to the control esophageal tissue sample provides information to optimize therapeutic treatments for esophageal adenocarcinoma by quantifying proteomic expression patterns associated with increased benefit or resistance to FDA-approved therapies for esophageal adenocarcinoma. The molecular oncology marker genes can comprise, for example, one or more of PD-L1, HER2, EGFR, TOPO-1, TUBB3, ERCC1, TS, TOPO2A, HMGB1, S100A8, PRMT, LGALS38P, IL-1RA, TXN, S100P, and SFN.

If the subject in the methods described herein is identified as having an increased risk of developing esophageal adenocarcinoma, the methods can optionally further comprise administering a therapeutically effective amount of one or more inhibitory agents to the subject, wherein the one or more inhibitory agents reduce expression or activity of one or more esophageal adenocarcinoma risk factors/marker genes selected from ISG15, LTF, CNDP2, DAD1, SET, UBE2N, S100P, and GPI in esophageal tissue in the subject. For example, if expression of UBE2N in the test esophageal tissue sample is increased relative to the control esophageal tissue sample, the inhibitory agent can be one that reduces expression or activity of UBE2N (e.g., a UBE2N RNAi agent or a UBE2N ASO as disclosed elsewhere herein). Similarly, if expression of DAD1 in the test esophageal tissue sample is increased relative to the control esophageal tissue sample, the inhibitory agent can be one that reduces expression or activity of DAD1 (e.g., a DAD1 RNAi agent or a DAD1 ASO as disclosed elsewhere herein). Similarly, if expression of ISG15 the test esophageal tissue sample is increased relative to the control esophageal tissue sample, the inhibitory agent can be one that reduces expression or activity of ISG15 (e.g., an ISG15 RNAi agent or an ISG15 ASO as disclosed elsewhere herein). Similarly, if expression of CNDP2 the test esophageal tissue sample is increased relative to the control esophageal tissue sample, the inhibitory agent can be one that reduces expression or activity of CNDP2 (e.g., a CNDP2 RNAi agent or a CNDP2 ASO as disclosed elsewhere herein). Similarly, if expression of GPI the test esophageal tissue sample is increased relative to the control esophageal tissue sample, the inhibitory agent can be one that reduces expression or activity of GPI (e.g., a GPI RNAi agent or a GPI ASO as disclosed elsewhere herein). Similarly, if expression of SET the test esophageal tissue sample is increased relative to the control esophageal tissue sample, the inhibitory agent can be one that reduces expression or activity of SET (e.g., a SET RNAi agent or a SET ASO as disclosed elsewhere herein). Similarly, if expression of LTF the test esophageal tissue sample is increased relative to the control esophageal tissue sample, the inhibitory agent can be one that reduces expression or activity of LTF (e.g., an LTF RNAi agent or an LTF ASO as disclosed elsewhere herein). Similarly, if expression of S100P the test esophageal tissue sample is increased relative to the control esophageal tissue sample, the inhibitory agent can be one that reduces expression or activity of S100P (e.g., an S100P RNAi agent or an S100P ASO as disclosed elsewhere herein). Such therapeutic methods are disclosed in more detail elsewhere herein.

III. Methods of Treating or Preventing Esophageal Adenocarcinoma, Inhibiting or Decreasing Proliferation or Migration of Esophageal Adenocarcinoma Cells, or Increasing Susceptibility to Cytotoxicity or Inducing Cell Death of Esophageal Adenocarcinoma Cells Methods of treating or preventing esophageal adenocarcinoma, methods of inhibiting or decreasing proliferation of esophageal adenocarcinoma cells, methods of inhibiting or decreasing migration of esophageal adenocarcinoma cells, and methods of increasing susceptibility to cytotoxicity or inducing cell death in esophageal adenocarcinoma cells are also provided.

Methods of treating esophageal adenocarcinoma in a subject having esophageal adenocarcinoma or preventing esophageal adenocarcinoma in a subject at risk for developing esophageal adenocarcinoma can comprise administering a therapeutically effective amount of one or more inhibitory agents to the subject, wherein the one or more inhibitory agents reduce expression or activity of one or more esophageal adenocarcinoma risk factors selected from ISG15, LTF, CNDP2, DAD1, SET, UBE2N, S100P, and GPI in esophageal tissue in the subject.

A therapeutically effective amount is an amount that produces the desired effect for which it is administered. The exact amount will depend on the purpose of the treatment, and will be ascertainable by one skilled in the art using known techniques. See, e.g., Lloyd (1999) The Art, Science and Technology of Pharmaceutical Compounding.

A subject can be a mammal, preferably a mammal (e.g., a human or a non-human mammal such as a rodent, mouse, or rat), more preferably a human, in need of amelioration, prevention, and/or treatment of esophageal adenocarcinoma. The term includes subjects (e.g., human subjects) who have or are at risk of having esophageal adenocarcinoma.

The terms treat, treating, or treatment refer to the reduction or amelioration of the severity of at least one symptom or indication of esophageal adenocarcinoma due to the administration of a therapeutic agent such as the inhibitory agents disclosed herein to a subject in need thereof. The terms include inhibition of progression of disease or of worsening of a symptom/indication. The terms also include positive prognosis of disease (i.e., the subject may be free of disease or may have reduced disease upon administration of a therapeutic agent). The therapeutic agent may be administered at a therapeutic dose to the subject. The terms prevent, preventing, or prevention refer to inhibition of manifestation of esophageal adenocarcinoma or any symptoms or indications of esophageal adenocarcinoma upon administration of therapeutic agent.

The one or more inhibitory agents in the methods reduce expression or activity of one or more esophageal adenocarcinoma risk factors. The esophageal adenocarcinoma risk factors can be, for example, selected from ISG15, DAD1, UBE2N, and S100P. In one example, the one or more esophageal adenocarcinoma risk factors comprise ISG15. In one example, the one or more esophageal adenocarcinoma risk factors comprise DAD1. In one example, the one or more esophageal adenocarcinoma risk factors comprise UBE2N. In one example, the one or more esophageal adenocarcinoma risk factors comprise S100P. The inhibitory agents can be administered by any suitable means. For example, the inhibitory agents can be administered to the esophagus of the subject or by a means suitable to reach the esophagus of the subject.

Methods of inhibiting or decreasing proliferation of esophageal adenocarcinoma cells can comprise administering one or more inhibitory agents to the esophageal adenocarcinoma cells, wherein the one or more inhibitory agents reduce expression or activity of one or more esophageal adenocarcinoma risk factors selected from ISG15, LTF, CNDP2, DAD1, SET, UBE2N, S100P, and GPI. For example, the one or more esophageal adenocarcinoma risk factors can be selected from ISG15, UBE2N, and S100P. In one example, the one or more esophageal adenocarcinoma risk factors comprise ISG15. In one example, the one or more esophageal adenocarcinoma risk factors comprise UBE2N. In one example, the one or more esophageal adenocarcinoma risk factors comprise S100P. In some methods, the esophageal adenocarcinoma cells are in a subject with esophageal adenocarcinoma (in vivo). In some methods, the cells are in vitro or ex vivo.

Methods of inhibiting or decreasing migration of esophageal adenocarcinoma cells can comprise administering one or more inhibitory agents to the esophageal adenocarcinoma cells, wherein the one or more inhibitory agents reduce expression or activity of one or more esophageal adenocarcinoma risk factors selected from ISG15, LTF, CNDP2, DAD1, SET, UBE2N, S100P, and GPI. For example, the one or more esophageal adenocarcinoma risk factors can be selected from ISG15, DAD1, UBE2N, and S100P. In one example, the one or more esophageal adenocarcinoma risk factors comprise ISG15. In one example, the one or more esophageal adenocarcinoma risk factors comprise DAD1. In one example, the one or more esophageal adenocarcinoma risk factors comprise UBE2N. In one example, the one or more esophageal adenocarcinoma risk factors comprise S100P. In some methods, the esophageal adenocarcinoma cells are in a subject with esophageal adenocarcinoma (in vivo). In some methods, the cells are in vitro or ex vivo.

Methods of increasing susceptibility to cytotoxicity or inducing cell death of esophageal adenocarcinoma cells can comprise administering one or more inhibitory agents to the esophageal adenocarcinoma cells, wherein the one or more inhibitory agents reduce expression or activity of one or more esophageal adenocarcinoma risk factors selected from ISG15, LTF, CNDP2, DAD1, SET, UBE2N, S100P, and GPI. For example, the one or more esophageal adenocarcinoma risk factors can be selected from ISG15, UBE2N, and S100P. In one example, the one or more esophageal adenocarcinoma risk factors comprise ISG15. In one example, the one or more esophageal adenocarcinoma risk factors comprise UBE2N. In one example, the one or more esophageal adenocarcinoma risk factors comprise S100P. In some methods, the esophageal adenocarcinoma cells are in a subject with esophageal adenocarcinoma (in vivo). In some methods, the cells are in vitro or ex vivo.

In any of the above methods, the one or more inhibitory agents can reduce expression of the one or more esophageal adenocarcinoma risk factors. Likewise, in any of the above methods, the one or more inhibitory agents reduce activity of the one or more esophageal adenocarcinoma risk factors. In one example, the one or more inhibitory agents can comprise an RNAi agent or an antisense oligonucleotide.

An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to, short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

In another example, the inhibitory agent can comprise an antisense oligonucleotide (ASO). Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
| --- | --- | --- |
| 1-6 | Protein | UBE2N Peptides |
| 7-9 | Protein | DAD1 Peptides |
| 10-16 | Protein | ISG15 Peptides |
| 17-33 | Protein | CNDP2 Peptides |
| 34-48 | Protein | GPI Peptides |
| 49-50 | Protein | SET Peptides |
| 51-66 | Protein | LTF Peptides |
| 67-68 | Protein | S100P Peptides |

EXAMPLES

Example 1. Identification of Novel Markers for Barrett's Esophagus Pathogenesis and Esophageal Adenocarcinoma Progression Large-scale mass spectrometric analyses were used to detect overexpression and downregulation patterns that contribute to the aggressiveness of esophageal adenocarcinoma (EAC). Formalin-fixed paraffin-embedded (FFPE) tissue samples, obtained from esophagectomy surgery before any chemotherapy or radiation had been administered, were used in analyzing EAC tissue, Barrett's esophagus (BE) tissue from subjects that progressed to EAC, and normal esophageal squamous epithelium from 50 patients. Our platform consisted of pathologist-guided microdissection, a Liquid Tissue® process turning FFPE tissue into a digested lysate, discovery mass spectrometry (TripleTOF 6600), and conservative biostatistics. Pathogenic processes that correlate with aggressiveness of this disease as well as EAC's proclivity to resist chemotherapeutic agents were identified. Twenty relevant proteomic events in which tumor suppressors were turned off, growth factors were overexpressed, chemoresistance markers were upregulated, and chemosensitivity markers were downregulated were identified. In addition, eight drug targets were identified in which therapeutic antagonism could slow tumorigenesis in EAC. Of the 20 proteins, eight (CNDP2, DAD1, GPI, ISG15, LTF, S100P, SET and UBE2N) were shown to be markers that significantly correlated with Barrett's esophagus pathogenesis into adenocarcinoma. Of the eight markers, four proteins, DAD1, ISG15, S100P and UBE2N, which have mutual intersections with diagnostic and therapeutic aspects of esophageal pathogenesis, were selected for further investigation. Overexpression of DAD1 (10 out of 10), ISG15 (9/10), S100P (8/10), and UBE2N (8/10) was discovered in BE tissue. In the adjacent EAC tissue, significant overexpression of DAD1 (20 out of 20), ISG15 (19/20), S100P (17/20) and UBE2N (18/20) proteins was observed. These expression levels spiked when transitioning from normal squamous epithelium to highly dysplastic BE tissue, demonstrating that BE starts to act like cancer by using more glucose for energy (Warburg effect), increasing proliferative measures, and suppressing apoptosis, which features carry over into the adenocarcinoma histology. Individual knockdown of ISG15, S100P and UBE2N yielded a significant decrease in cellular proliferation compared to untreated EAC cell lines (OE-33), while inducing a higher level of cytotoxicity over a 48-hour period. DAD1 knockdown demonstrated the slowest rate of EAC cell migration. Gene knockdown of DAD1, S100P, ISG15, and UBE21C improved the overall oncogenic milieu of interconnecting cancer pathways—significantly downregulating associated pro-tumoral genes while upregulating many anticancer factors. The sum of these findings demonstrates the diagnostic and therapeutic clinical utility of CNDP2, DAD1, GPI, ISG15, LTF, S100P, SET and UBE2N in assessing and treating Barrett's-related esophageal carcinogenesis.

Introduction

By identifying the proteomic environment that contributes to the metastatic and chemotherapy-resistant nature of esophageal adenocarcinoma, improved diagnostics and therapeutics can be developed. Unadulterated EAC samples from esophagectomies of patients who had never received chemotherapy were obtained. The samples were processed and microdissected. The microdissected samples were then digested into a Liquid Tissue® lysate and analyzed with a discovery mass spectrometry platform (TripleTOF 6600). 20 significant targets related to chemotherapy resistance and sensitivity, apoptosis suppression, and proliferation upregulation were identified. Eight targets (CNDP2, DAD1, GPI, ISG15, LTF, S100P, SET and UBE2N) were selected for further investigation based on their intersections with diagnostic and therapeutic aspects of molecular oncology. Notably, overproduction of DAD1 protein contributes to cisplatin resistance. Of note, 95% of 123 patients treated at Columbia University Medical Center (CUMC) for esophagectomy were placed on cisplatin by their community oncologist in the first-line setting.[4,5] S100P expression has been found to increase resistance to 5-FU (Fluorouracil) in colorectal cancer.[6] 5-FU was prescribed to 72% of the patients in our cohort (n=123). Our findings suggest that alternative patient management strategies are needed since EAC is likely to have resistance to the two most prescribed drugs for EAC.[4] In addition, we have identified eight diagnostic and therapeutic biomarkers with clinical utility for EAC. Targeting four of these proto-oncogenes was shown to diminish the proliferative and metastatic capabilities of EAC in vitro.

1.0. BE/EAC Markers

CNDP2, DAD1, GPI, ISG15, LTF, S100P, SET, and UBE2N have important microbiological functions in human physiology. 5100 proteins are involved in cellular regulatory roles, managing proliferation, differentiation, and apoptosis-usually in response to inflammation or cell damage. Ubiquitins are regulatory proteins that mark damaged cells for destruction and signal for cellular proliferative measures that promote healing-such as during inflammation or after bile-acidic assaults.[7] When these processes are dysfunctional or overactive, carcinogenesis can occur.

1.1. DAD1 (defender against cell death) is an enzyme required for efficient glycosylation. DAD1 has been found to be a negative regulator of programmed cell death and has been implicated in helping cancer cells evade apoptosis.[8] While DAD1 suppresses cellular apoptosis, reduction of DAD1 expression was found to more readily trigger cell death in a small cell lung carcinoma mice model.[9] 97% of EAC patients in our medical center were treated with cisplatin in the first line setting.[4] However, overexpression of DAD1 protein levels was found to contribute to cisplatin resistance and DAD1 was found to be overexpressed in 100% of our human EAC samples. We found DAD1 to be expressed at a 5.08× greater level in EAC tumors compared to normal esophagus tissue (P<0.0001). Our findings indicate that treatment with cisplatin may be inappropriate with patients having increases expression of DAD1. A role of DAD1 in EAC was previously unknown.

1.2. ISG15 (interferon-stimulating gene 15) is a ubiquitin-like protein that plays a key role in innate immune responses. Desai (2015) reports that "[ISG15 is] emerging as an important oncoprotein and a potential diagnostic and therapeutic target for cancer".[10] In pancreatic adenocarcinoma, tumor-associated macrophages secrete ISG15, thereby enhancing the phenotype of cancer stem cells in tumors—reinforcing cancer stem cell self-renewal, increasing invasive capacity, and increasing tumorigenic potential.[11] Recently, cancer stem cells have been found to play a major role in the development and metastatic progression of adenocarcinomas. ISG15 was also found to contribute to the malignant transformation of breast cells and is associated with a worse prognosis in colorectal cancer.[10, 12] Nevertheless, a role of ISG15 in EAC is currently unreported. Knockdown of ISG15 expression using ISG15-specific small interfering RNA (siRNA) was shown to increase the levels of polyubiquitinated proteins, suggesting an antagonistic role of ISG15 in regulating ubiquitin-mediated protein turnover.[10] ISG15 disrupts the process that ensures that virtually all peptide bonds within a protein marked for destruction are susceptible to cleavage.[13] While doxorubicin, which is FDA approved for EAC, was found to have greater efficacy in ISG15-rich tumors, only 6% of patients referred to our medical center for esophagectomy received doxorubicin in the first-line setting. Our finding that roughly 95% of EAC tumors overexpressed ISG15 suggests that doxorubicin may be beneficial in EAC patients that express high levels of ISG15.[4, 14] We found ISG15 to be expressed at a 7.29× greater level in EAC tumors compared to normal esophagus tissue (P<0.0001).

1.3. S100P is localized in the cytoplasm and/or nucleus of a wide range of cells and is involved in the regulation of several cellular processes such as cell cycle progression and differentiation.[15] S100P exerts its functions by binding to and activating RAGE, possibly causing cell division mechanisms to circumvent the classical tyrosine kinase/KRAS proliferation pathways often upregulated in many solid tumors. S100P-derived RAGE antagonistic peptide has been found to delay tumor growth and metastasis in pancreatic cancer.[16] A significant correlation was found between high expression of S100P and shorter overall survival (OS) and increased drug resistance in gastric and ovarian cancers.[17] S100P also plays a key role in the aggressiveness of pancreatic cancer, which is likely mediated by its ability to activate RAGE.[18] S100P knockdown was found to suppress cell proliferation while augmenting cellular apoptosis in endometrial cancer cell lines.[19] Expression of S100P increases drug resistance in gastric cancer and decreases chemosensitivity to 5-FU in vitro in colorectal cancer cells.[6] 87% of patients treated for EAC at our medical center were prescribed 5-FU in the first line setting.[4] We found S100P to be expressed at a 6.42× greater level in EAC tumors compared to normal esophagus tissue (P<0.0001). To our knowledge, a role of S100P in EAC has not been previously reported. Our findings suggest that EAC tumors can be monitored for S100P expression and that increased S100P expression indicates treatment other than with 5-FU.

1.4. UBE2N (ubiquitin-conjugating enzyme E2 N) has been found to be overexpressed in breast, pancreas, colon, prostate, and ovarian carcinomas. Overexpression of UBE2N has been found to be required for breast cancer metastasis to the lung.[21] Inhibition of this marker caused cell death in neuroblastomas.[21] UBE2N specifically builds ubiquitin chains that are critical for NFκβ inflammatory activation, a mechanism associated with carcinogenesis. Interestingly, UBE2N inhibition significantly altered the ubiquitination of ~140 proteins involved in innate immune signaling, cell survival, RNA splicing, and DNA damage response.[22] Our findings from the gene expression arm of this investigation corroborated the upstream position of UBE2N. Inhibition of UBE2N via siRNA-mediated knockdown had the largest effect of these tested markers on direct and peripheral cancer pathways. Over 50% of the pathways analyzed were positively affected by UBE2N knockdown. We found UBE2N to be expressed at a 6.88× greater level in EAC tumors compared to normal esophageal tissue (P<0.0001). Thus, increased expression of UBE2N indicates progression of normal tissue to EAC and may be used to monitor susceptibility to or risk of developing EAC or to diagnose EAC. To our knowledge, a role of UBE2N role in EAC progression has not been previously reported.

Figure 2:
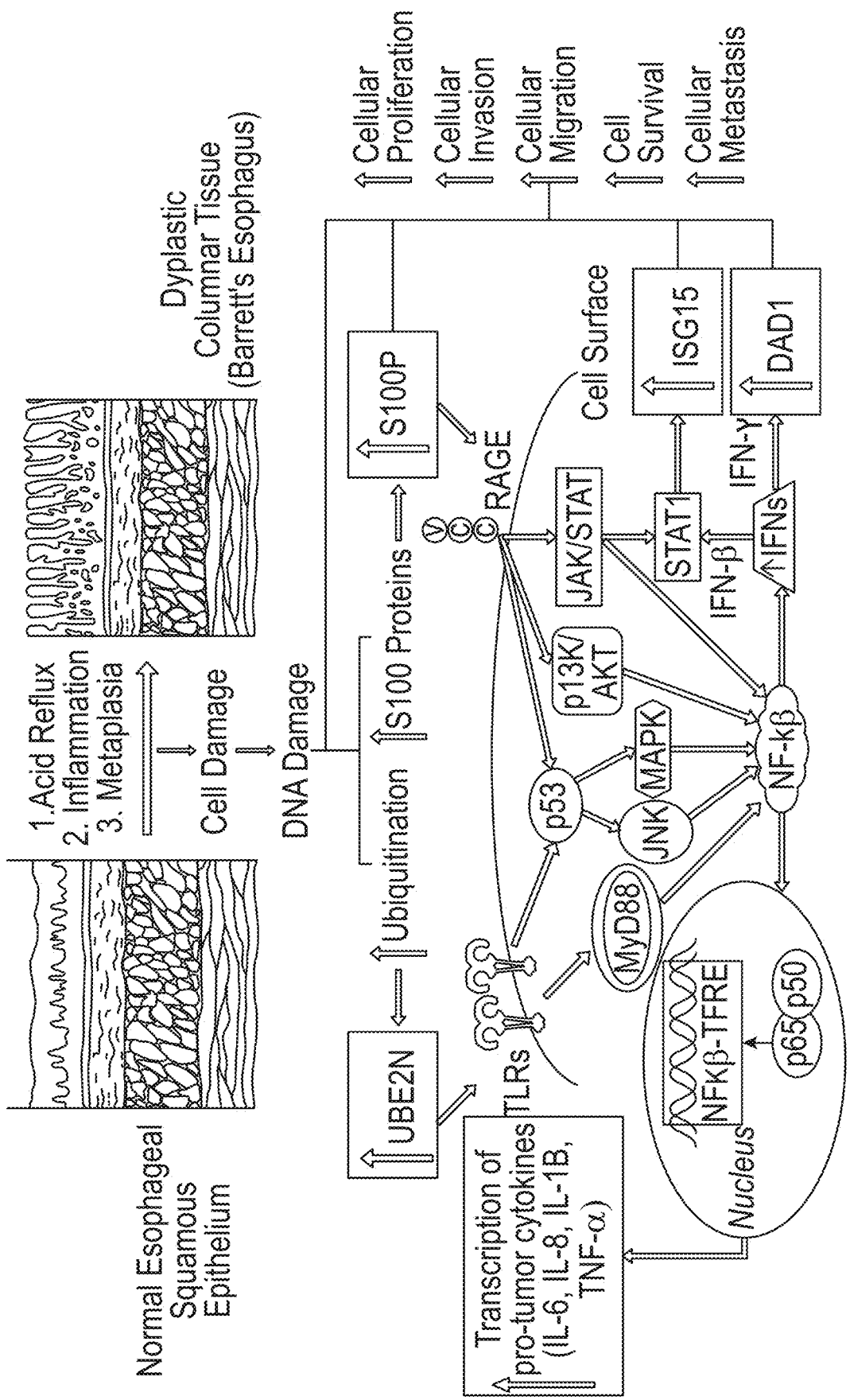
FIG. 2. Image illustrating pathways and roles of various genes in Barrett's esophagus progression and esophageal adenocarcinoma's aggression. UBE2N and S100P are upregulated during response to cell damage in the distal esophagus mucosa leading to pro-tumoral processes.

FIG. 2 shows an image illustrating pathways and roles of various genes in Barrett's esophagus progression and esophageal adenocarcinoma's aggression. UBE2N and S100P are upregulated during response to cell damage in the distal esophagus mucosa leading to pro-tumoral processes.[8,21,23-25]

1.5. CNDP2 (cytosolic non-specific dipeptidase) acts as a functional tumor suppressor in gastric cancer by activating MAPK pathway.[36] CNDP2 catalyzes the production of N-lactoyl-amino acids from lactate and amino acids by reverse proteolysis.[37] An elevated level of CNDP2 activates p38 and JNK/MAPK pathways to induce cell apoptosis. A lower level of CNDP2 activates the ERK MAPK pathway to promote cell proliferation. CNDP2 may play a role as tumor suppressor in hepatocellular carcinoma cells.[36] Notably, upregulation of CNPD2 facilitates the proliferation of colon cancer and conversely the underexpression of CNDP2 yields a more favorable prognosis for patients with gastric cancer.[36, 38] We found CNDP2 to be expressed at a 2.85× greater level in Barrett's tissue compared to normal esophageal tissue (P<0.0001). Thus, increased expression of CNDP2 indicates progression of normal tissue to Barrett's esophagus and/or EAC and may be used to monitor susceptibility to or risk of developing Barrett's esophagus and/or EAC. To our knowledge, a role of CNDP2 in EAC progression has not been previously reported.

1.6. GPI (glucose-6-phosphate isomerase) is a major glycolytic enzyme that is associated with the pathways involving the Warburg effect, in which cancer cells produce energy at a high rate via glycolysis. GPI can function as a tumor-secreted cytokine and an angiogenic factor (AMF) that stimulates endothelial cell motility. GPI enhances HER2 expression and HER2 overexpression enhances GPI expression. GPI likely confers resistance in breast cancer cells against HER2-based therapies using Trastuzumab and should be considered as an additional target when treating patients. The finding that GPI is upregulated as normal esophageal tissue progresses to precancerous and then cancerous esophageal tissue establishes that the Warburg effect is occurring in esophageal pathogenesis. Our findings suggest that cells from premalignant Barrett's esophagus tissue may adapt to an ever-changing selective microenvironment through changes in energy metabolic pathways typically associated with cancer cells. GPI proteomic expression trends have not yet been associated with EAC pathogenesis.

1.7. LTF, (lactotransferrin) is a major iron-binding and multifunctional protein found in exocrine fluids such as breast milk and mucosal secretions, and possesses antimicrobial activity. LTF promotes binding of species C adenoviruses to epithelial cells, promoting adenovirus infection. LTF stimulates the TLR4 signaling pathway leading to NFκB activation and subsequent pro-inflammatory cytokine production while also interfering with the lipopolysaccharide (LPS)-stimulated TLR4 signaling. LTF inhibits neutrophil granulocyte migration to sites of apoptosis when secreted by apoptotic cells, and stimulates VEGF-mediated endothelial cell migration and proliferation. LTF has been linked to malignant transformation of nasopharyngeal, gastric, and endometrial cancers.[39-41] We found LTF to be expressed 8.8× higher in BE and EAC tissue compared to normal esophageal tissue can be used as a marker in assessing BE and/or EAC or in assessing risk of developing BE and/or EAC. To our knowledge, LTF overexpression was not previously known to be not associated with promotion of tumorigenesis of BE.

1.8. SET nuclear proto-oncogene is transcribed into a multitasking protein involved in apoptosis, transcription, nucleosome assembly and histone chaperoning. SET promotes the initiation and progression of cancer.[42] SET inhibits apoptosis following attack by cytotoxic T lymphocytes, which is a hallmark of carcinogenesis. SET has also been shown to promote the development of therapeutic resistance in cancer cells. SET antagonists are currently under clinical study for a few cancers, but not EAC. SET is expressed at 2.5× greater levels in EAC compared to normal esophageal tissue. Therefore, analysis of SET expression can be used to assess EAC or risk of developing EAC. To our knowledge, SET upregulation has not previously been associated with BE dysplastic progression.

2.0. Materials and Methods 2.1. Patient Selection. Esophagectomy patient specimens from 82 patients that had not received neoadjuvant chemoradiation, collected between 2004-2015, were obtained. Most cases provided multiple blocks of tumor, Barrett's, and normal esophageal mucosa located in the proximal surgical margins taken from the distal esophagus. Of these 82 patients, about a dozen dropped out due to squamous cell carcinoma and gastric cancer histologies. For the mass spectrometry arm of our study, we utilized 20 esophageal adenocarcinoma samples, 10 Barrett's esophagus samples, and 20 normal squamous mucosa samples, all randomly selected. 15 of the 50 specimens (30%) were from female patients, which reflects the national percentages of gender manifestations for this disease. 9 of the 20 normal esophagus specimens and 10 of the 20 adenocarcinoma specimens were from patients with no visible Barrett's esophagus.

2.2. Tissue acquisition and processing. Formalin-fixed paraffin-embedded (FFPE) tissue was cut at 10 microns with one 5 m section stained with H&E. The paraffin blocks were selected, based on the available gross description of the specimens, to target normal stratified squamous esophageal mucosa, Barrett's esophagus, and invasive adenocarcinoma. Histologic slides of areas representing these gross pathologies were examined by a board-certified pathologist. If histologically confirmed to represent the desired pathology, the area of interest was circled. The serially sectioned unstained slide beneath that examined H&E was then microdissected from the circled area.

Barrett's esophagus was defined per the American College of Gastroenterology guidelines as intestinal metaplasia in areas of salmon colored mucosa in the tubular esophagus 43 Invasive adenocarcinoma areas were selected based on malignant cells clearly infiltrating through the basement membrane into underlying tissues. Areas of dysplasia, carcinoma in situ or with questionable infiltration were not selected as representative for analysis as either Barrett's esophagus or invasive adenocarcinoma.[44] Normal esophageal mucosa was taken from the proximal resection margin whenever possible to select tissue far removed from the accompanying pathologic processes. The squamous epithelium with some submucosa was selected for normal mucosa with muscularis propria. Adventitia was not included for analysis.

2.3. Preparation and staining of specimen, Formalin-fixed, paraffin embedded human tissue samples used for mass spec analysis were deparaffinized, rehydrated and stained with hematoxylin so topography of the tissue specimen could be used for accurate microdissection. Pre- and post-dissection images were taken to ensure samples were within the pathologist's designated margins (see section 2.2).

2.4. Tissue Processing. Clinically, mass spectrometry platforms typically utilize serum, urine, blood, and fresh or frozen tissue specimens for proteomic scrutiny. Formalin-cross-linked tissue samples have been found to not completely digest into a lysate compatible for mass spec and therefore increases the risk of not running properly or breaking expensive machinery. The methods disclosed herein can fully digest FFPE tissue into small, mass-spectrometry-friendly peptides. The method of processing FFPE tissue into a mass-spectrometry-compatible lysate takes about 24 hours and completely reverses formalin cross-links of FFPE tissue. Breaking the proteins into small peptides eliminates the effects of poor tissue fixation after surgery or endoscopy. There is no assurance that the specimen goes straight into a fresh or formalin fixative the minute it is resected from the patient and therefore could be subject to protein degradation that is outside the control of diagnosticians. Targeted mass spectrometry analysis measures a small unique identifying peptide within a large protein that only exists in the marker being detected. Hence, protein degradation or breakage because of improper fixation does not adversely affect results.[45] Mass spec analysis eliminates the need for protein epitope integrity required for antibody recognition. Additionally, liquid biopsies can be stored indefinitely for future testing.

2.5. SWATH-MS. Mass spectrometry: Data-independent acquisition (DIA) SWATH-MS experiments were performed as described previously.[46] All samples were analyzed by reverse-phase high-pressure liquid chromatography electrospray ionization tandem mass spectrometry (RP-HPLC-ESI-MS/MS) using a commercial 6600 TripleTOF® (Sciex) mass spectrometer. The mass spectrometer was coupled with nanoFlex cHiPLC system (Eksigent). All samples were loaded using a stepwise flow rate of 10 μL/min for 8.5 min and 2 μL/min for 1 min using 100% solvent A (0.1% (v/v) formic acid in HPLC water). Samples were eluted from the analytical column at a flow rate of 0.3 μL/min using a linear gradient of 5% solvent B (acetonitrile with 0.1% (v/v) formic acid) to 35% solvent B over duration of 180 min. The column was regenerated by washing with 90% solvent B for 15 min and re-equilibrated with 5% solvent B for 15 min. Autocalibration of spectra occurred after acquisition of every 6 samples using dynamic LC-MS and MS/MS acquisitions of 25 fmol 0-galactosidase. Samples used to generate the SWATH-MS spectral library were subjected to traditional, data-dependent acquisition (DDA) and a library was created using ProteinPilot software v. 4.2 (Sciex). Experimental samples were subjected to cyclic DIA of mass spectra using variable swaths. Ions were fragmented for each MS/MS experiment in the collision cell using rolling collision energy.

Targeted data extraction: Spectral alignment and targeted data extraction of DIA samples was performed using PeakView v.1.2 (Sciex) using the MDM reference spectral library generated above. All DIA files were loaded and exported in .txt format in unison using an extraction window of 10 min and the following parameters: 5 peptides, 5 transitions, peptide confidence of >99%, exclude shared peptides, and XIC width set at 50 ppm. This export results in the generation of three distinct files containing the quantitative output for (1) the area under the intensity curve for individual ions, (2) the summed intensity of individual ions for a given peptide, and (3) the summed intensity of peptides for a given protein. Laboratory contaminants and reversed sequences were removed from the data set prior to statistical analysis.

Figure 3:
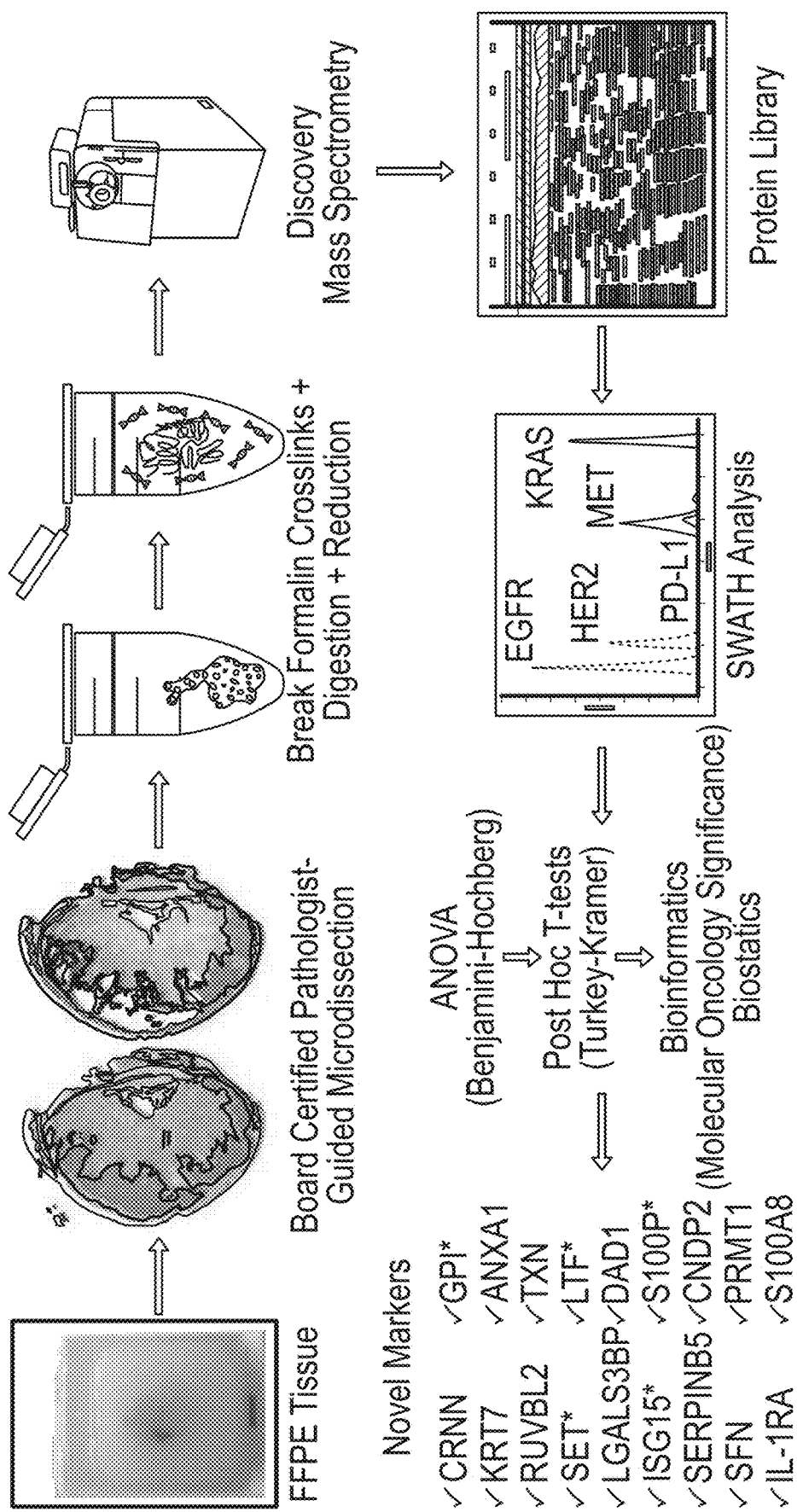
FIG. 3. Image illustrating an exemplary discovery LT-SWATH-MS workflow.

FIG. 3 shows a discovery LT-SWATH-MS workflow. H&E stained sections of the specimens were marked by a board-certified pathologist as described above and used as a guide for microdissections of serial sections stained with hematoxylin. About 2×4 mm from a 10 m section of pure tumor, Barrett's esophagus (precancerous tissue) or normal squamous esophageal epithelium was obtained for each sample. Pre- and post-microdissection images were taken to ensure tissue retrieval occurred within the specified margins. The microdissected formalin-fixed paraffin-embedded tissue was placed in Eppendorf tubes and covered in roughly 30 μL of detergent-free buffer and processed through a series of heating and digestion stages to generate samples suitable for mass spectrometry analysis. The sample is first incubated at 95° C. for 90 minutes, then cooled in ice. Trypsin is then added and incubated at 37° C. for 16-18 hours to break the large proteins into small peptides. The resultant digest was quantified for protein concentration via nanodrop, cleaned via MCX, reduced with 10% DTT at 95° C. for ten minutes, and analyzed by TripleTOF mass spectrometry. SWATH analysis and our outlined series of biostatistics (ANOVA, Benjamini-Hochberg procedure, post hoc T-tests, Tukey-Kramer range test), and simple bioinformatics yielded a set of eight markers associated with EAC pathogenesis. Four of these markers: DAD1, ISG15, S100P, and UBE2N were selected for further analyses, including immuno-fluorescence, siRNA knockdown model in EAC cell lines, colorimetric proliferation assays, fluorescent cytotoxicity assay, gene expression RT-PCR, and scratch migration assays. The results of these analyses validated the role of the proteins identified by mass spec analysis as playing a role in EAC pathogenesis. These protein are therefore useful as diagnostic markers and therapeutic targets for patients at risk of developing EAC, suspected of having EAC, or previously diagnosed as suffering from EAC.

2.6. Immunofluorescence. Standard deparaffinization and rehydration methods were used to expose our tissue to immunofluorescence. We performed antigen retrieval at 95° C. for 20 minutes in 2000 mL of Boster Immunoleader antigen solution dissolved in 2 L of water. Samples were blocked for 2 hours in 5% horse serum, and 0.25% triton buffer. We stained the samples with primary antibodies targeting four of the eight proteins overnight at 4° C. We utilized DAD1 (1:100 dilution) anti-rabbit polyclonal antibody (Thermo Fisher Scientific—PA5-20062), ISG15 (1:100 dilution) anti-rabbit polyclonal antibody (Thermo Fisher Scientific—PA5-31865), S100P (1:30 dilution) anti-mouse monoclonal antibody (Thermo Fisher Scientific—MA5-24106) and UBE2N (1:200 dilution) anti-rabbit polyclonal antibody (Thermo Fisher Scientific—PA5-29687), all diluted in blocking solution with the exception of S100P which was diluted with PBS. After washing off the primary antibody, DAD1, ISG15, and UBE2N samples received Alexa Fluor 594 donkey anti-rabbit secondary antibody (Invitrogen—A21207) and S100P received Alexa Fluor 488 donkey anti-mouse antibody (Invitrogen—A21202). Both secondary antibodies were diluted at 1:200 ratios in blocking solution and were left to stain the tissue for 1.5 hours at room temperature. DAPI enriched mounting serum was added before adding coverslips to our tissue sections. Post immunofluorescence imaging was done on an Olympus VS120 Slide Scanner, and immunofluorescence quantification was completed with ImageJ bundled with 64-bit Java 1.8.0_112 made available by the National Institute of Health.

2.7. Cell culture and siRNA knockdowns. The esophageal adenocarcinoma cell line that was used for in vitro studies was OE-33 from AddexBio (No. C0013003). The cells were grown in RPMI-1640 in 10% FBS. Prior to cell culture, cells were plated, and when 70% confluent, grown with OptiMEM and 25 nM siRNA or RNAiMAX lipofectamine alone. The siRNA treatments were siNEG, siPOS (GAPDH), siDAD1 (No. 145787), siS100P (No. 142895), siISG15 (No. 137859), and siUBE2N (No. 12328). The knockdown siRNA reagents utilized for these experiments were Silencer® Pre-designed siRNA from Ambion® (Cat #. AM16708A). The cells were incubated with the siRNA for 48-hours, after which they were washed with DPBS and lysed with lysis buffer. The cell lysates were then processed for simultaneous extraction of DNA, RNA, and protein.

2.8. RNA isolation, cDNA synthesis. After siRNA knockdown of the four markers, we isolated RNA, DNA, and protein from the various treated batches of esophageal adenocarcinoma cells using the AllPrep Mini Kit from Qiagen for simultaneous purification of components of the interactome. We utilized the QIAshredder to disrupt and homogenize the treated cells. RNA samples were then used to create a cDNA library for gene expression analysis. Protein and DNA material from these samples were stored at −20° C. RNA concentrations were quantified with a Nano-Drop 2000c spectrophotometer from Thermo Fisher Scientific. We used the RT² First Strand Kit from Qiagen, which is compatible with the RT² Profile PCR Array, optimizing results for detection of the reverse transcription controls contained in this platform.

2.9. Gene expression analysis. We mixed our cDNA templates with the appropriate ready-to-use PCR mastermix (SYBR® Green), then aliquoted equal volumes to each well of the same plate, and then ran the real-time PCR cycling program on a CFX96™ Real-Time system in a C100™ Thermal Cycler from Bio-Rad. We used the Cancer PathwayFinder RT² Profiler PCR Array, which simultaneously analyzes upregulation and downregulation patterns of genes linked to angiogenesis, apoptosis, cell cycle, DNA repair, etc. Treated EAC cell lines were normalized to multiple untreated EAC controls. The thermal cycle protocol had a 3 minute 95° C. warm up, and the cycled 40 times at 95° C. for 10 seconds followed by 55° C. for 30 seconds.

2.10. Proliferation, cytotoxicity and scratch assays. OE-33 adenocarcinoma cells were grown, trypsinized, counted and diluted into a 1,000,000 cells/μL concentration or 1,000 cells per L. This allowed us to standardize each well with 10,000 cells of OE-33 with just 10 μL of media/cells. Our siRNA stock for the DAD1, ISG15, S100P, UBE2N and our no vector negative control and GAPDH positive control was 5 micromolar. For the following experiments we utilized a concentration of 2.78 picomoles per cm² of siRNA for all target vectors in OE-33 esophageal adenocarcinoma cell line. We standardized all experiments using 57 μL of media, siRNA and lipofectamine per cm² depending on the size of the plate or wells.

2.10.1. 96-well plate prep protocol. Cells were grown to 70% confluency in T75 flasks. Cells were serum-starved in T75s for 16 hours to sync cell cycles. Cells were then detached with 1× trypsin EDTA by adding 5 mL per flask and incubating for 4 minutes at 37° C. The cells were then spun down at 800 rpm for 5 minutes. OE-33 cells were then resuspended in 1 mL of serum-free RPMI 1640 and counted using the Countess II FL automated cell counter (Thermo Fisher). The cells were diluted to a concentration of 1,000,000 cells per mL and 10 μL (10,000 cells) were added to each well in a 96-well plate. Each well contained serum free media with 2.78 picomoles per cm² siRNA with 57 μL total volume (media+cells+lipofectamine+siRNA) per cm². The cells were then incubated with the siRNA for 48 hours and then assayed.

2.10.2. Proliferation colorimetric assay. After gene knockdowns, cells were left to grow for 48 hours. Media was then decanted, and fresh serum-free media was added to each well. We added 10 μL of MTT (3-(4,5-dimethylthiazol-2-yl)-2,5-diphenyltetrazolium bromide), which is a yellow tetrazolium salt that is converted to formazan when in contact with NADPH, a byproduct of DNA synthesis, yielding a purple color in which its absorbance can serve as a surrogate for proliferation rates over a period of time. MTT was added directly to the media and left to incubate for 3.5 hours at 37° C. After allowing enough time for the MTT to convert to formazan we removed MTT/media and added 100 μL of DMSO (dimethylsulfoxide) to pull the formazan from the cells which allows a reliable colorimetric reading. The plate was placed on a slow gyration for 1 hour at room temperature. Upon solubilization, the amount of purple dye taken up by the monolayer can be quantitated in a plate reader at 570 nm.

2.10.3. Cytotoxicity Assay. Cell death over a period of time was measured using the Vybrant™ G6PD Release Cytotoxicity assay (Thermo Fisher—V23111) where resazurin, a blue dye, is reduced to resorufin, a red dye, which then can be measure by fluorescent plate reader to quantitate cell death rates post treatment. Resazurin is reduced when it comes in contact with G6PD (glucose-6-phosphate dehydrogenase) a molecule that is released when a cell membrane breaks, thereby serving as a surrogate for cell death rate. The cells were treated with respective siRNAs and incubated for 48 hours. 10,000 cells were then transferred to each well of a 96-well plate yielding an n=12 for each treatment group. 50 μL of resazurin was added to 10,000 cells per well of the knockdown treated cells and three controls (lysed untreated cells, positive and negative controls) and left to incubate at 37° C. for 24 hours. Fluorescent plate reading was done at 550 nm (excitation) and 590 nm (emission) to measure the level of resorufin (red) in each well. The plate was then assayed over 10-minute intervals for the first 30 minutes starting with T=0 and then at 1 hour.

2.10.4. Scratch migration assay. A scratch assay is a straightforward, inexpensive method to measure cell migration rates in vitro. Two 12-well plates were seeded with treated and untreated OE-33 cells. The media was then transfected with serum free RPMI-1640 with a siRNA negative control, siRNA positive control targeting GAPDH, and siDAD1, siUBE2N, siISG15, siS100P, or untreated, and grown for about 36-hours until 90% confluent. A vertical scratch was created with a 200 μL pipette tip. The media was removed and replaced with Opti-MEM and imaged at time 0 hours, 12 hours, and 16 hours to monitor the rate of wound closure at 4× magnification.

2.11. Western blot. Proteins concentrations were quantified with a NanoDrop™ One/OneC Microvolume UV Spectrophotometer. 25 μg of protein were loaded into each lane for each sample ran. We followed the Abcam general western blot protocol as described on their company website (http://www.abcam.com/protocols/general-western-blot-protocol). We ran an SDS-PAGE gel electrophoresis at 70 V for 30 minutes and then 100 V for 1 hour. We transferred the protein from the gel to a 0.45 m nitrocellulose membrane (Bio-Rad 162-0115) overnight at 30 V under cold running water. Next, we blocked the membranes for an hour at room temperature using 3% Bovine Serum Albumin (BSA) in TBST. For primary antibody staining we utilized DAD1 polyclonal antibody (Thermo Fisher Scientific—PA5-20062) diluted at a 1:500 ratio, ISG15 polyclonal antibody (Thermo Fisher Scientific—PA5-31865) diluted at a 1:1000 ratio, S100P monoclonal antibody (Thermo Fisher Scientific—MA5-24106) diluted at a 1:1000 ratio and UBE2N polyclonal antibody (Thermo Fisher Scientific—PA5-29687) diluted at a 1:1000 ratio to stain for their presence in the nitrocellulose membrane. Primary antibodies were allowed to react with the membrane overnight at 4° C. while gently rocking back and forth. Primary antibodies were washed off with TBST three times, for five minutes each. Secondary antibodies for DAD1, ISG15 and UBE2N were goat anti-rabbit (Novus Biologicals—NB7160) and S100P goat anti-mouse (Novus Biologicals—NB7539) which were diluted at a ratio of 1:10000 in blocking buffer at room temperature for 1 hour. For imaging signal development, we utilized Pierce® ECL Western Blotting Substrate (Thermo Scientific—32209), using 1 mL of peroxide solution mixed with 1 mL of luminol enhancer solution poured simultaneously onto the membrane within 1 minute of imaging, capturing the images with a ChemiDoc™ MP Imaging System from Bio-Rad. All four target proteins reside around 17 kDa.

2.12. Statistical analysis. 2.12.1. Mass spectrometry. A total of 617 proteins were identified and quantified by mass spectroscopy-SWATH analysis. Mass spectrometric values were converted to log base 2 prior to statistical analysis.

One-way fixed effect ANOVA was used to detect differences between the three tissue types (normal squamous esophageal epithelium, Barrett's esophagus, and adenocarcinoma tumor tissue). The Benjamini-Hochberg procedure was used to determine which of the ANOVA tests indicated a detectable association between protein expression and tissue type while controlling the false discovery rate at no more than 0.05. The post-hoc t-tests were allotted an alpha of 0.00085 and adjusted using the Tukey-Kramer adjustment for multiple comparisons. All our calculations were processed with SAS 9.4.

2.12.2. Immunofluorescence. 63 fluorescent intensity readings from Barrett's esophagus, normal squamous epithelia and adenocarcinoma tumors were quantified using ImageJ version 1.8.0_112 quantifying 5 areas of each section starting in a random section of the tissue and going clockwise around areas of interest (avoiding stroma areas of tissue). After quantification of fluorescent intensity, the values were averaged and SDs and SEM's for each of the proteins and treatment groups were calculated. 47 healthy mucosa fluorescent intensity readings from 4 Yucatán microswines with varying diets were utilized to calculate expression levels of four of the markers in a non-diseased control cohort.

2.12.3. Gene expression. Using the QIAGEN data analysis tool, PCR data was analyzed and compared to the siNEG control groups. The data was normalized using the geometric mean of 5 housekeeping controls (ACTB, B2M, GAPDH, HPRT1, and RPLP0). The fold regulation, fold change, average $\Delta C_T$ and the $2^{-\Delta C_T}$ were all calculated. Genes with significant changes compared to the controls were highlighted here.

2.12.4. Proliferation, Cytotoxicity, and Migration Assays. Means of the treatment groups were generated along with standard deviation and standard error calculations. From here we determined if the mean differences were significant among the groups with an ANOVA, and then P-values were generated with Tukey test. Outliers were determined with a Grubb's test, however we only had one outlier (S100P, MTT proliferation assay) during these series of experiments.

3.0. Results 3.1. Consistent and noteworthy overexpression. We designed a method to scrutinize thousands of proteins in FFPE tissue all using mass spectrometry. FFPE tissue samples were digested into mass spec compatible lysates, enabling simultaneously quantification of oncoproteins in three different histologies of the distal esophagus (normal squamous epithelium, precancerous Barrett's mucosa and esophageal adenocarcinoma tumor). Mass spec analysis provides a benefit over antibody-based assay in measuring peptides by their mass and charge. Mass spec analysis thus avoids problems associated with antibody-based assays such as non-specific binding or subjective interpretation.

Fifty samples were analyzed utilizing three different tissue types (20 EAC tumor, 10 Barrett's and 20 normal esophagus), which yielded a library of around 1,100 quantifiable proteins. 179 markers were deemed statistically significant when comparing expression levels of the various histologies. After a series of bioinformatics, eight proteins were selected for further analyses. Our mass spec data revealed that DAD1 is expressed 5.08× more in EAC and 3.60× more in BE tissue compared to normal esophageal mucosa (P<0.0001). ISG15 was expressed 7.29× more in EAC and 4.35× more in BE compared to normal controls (P<0.0001). S100P was expressed 5.27× higher in EAC and 6.42× higher in BE compared to normal tissue (P<0.0001). UBE2N was expressed 6.88× more in EAC (P<0.0001) and 3.59× higher in BE (P<0.001) compared to the adjacent normal squamous epithelium. The heatmap in FIG. 4B highlights very few outliers in our cohort.

Figure 4A:
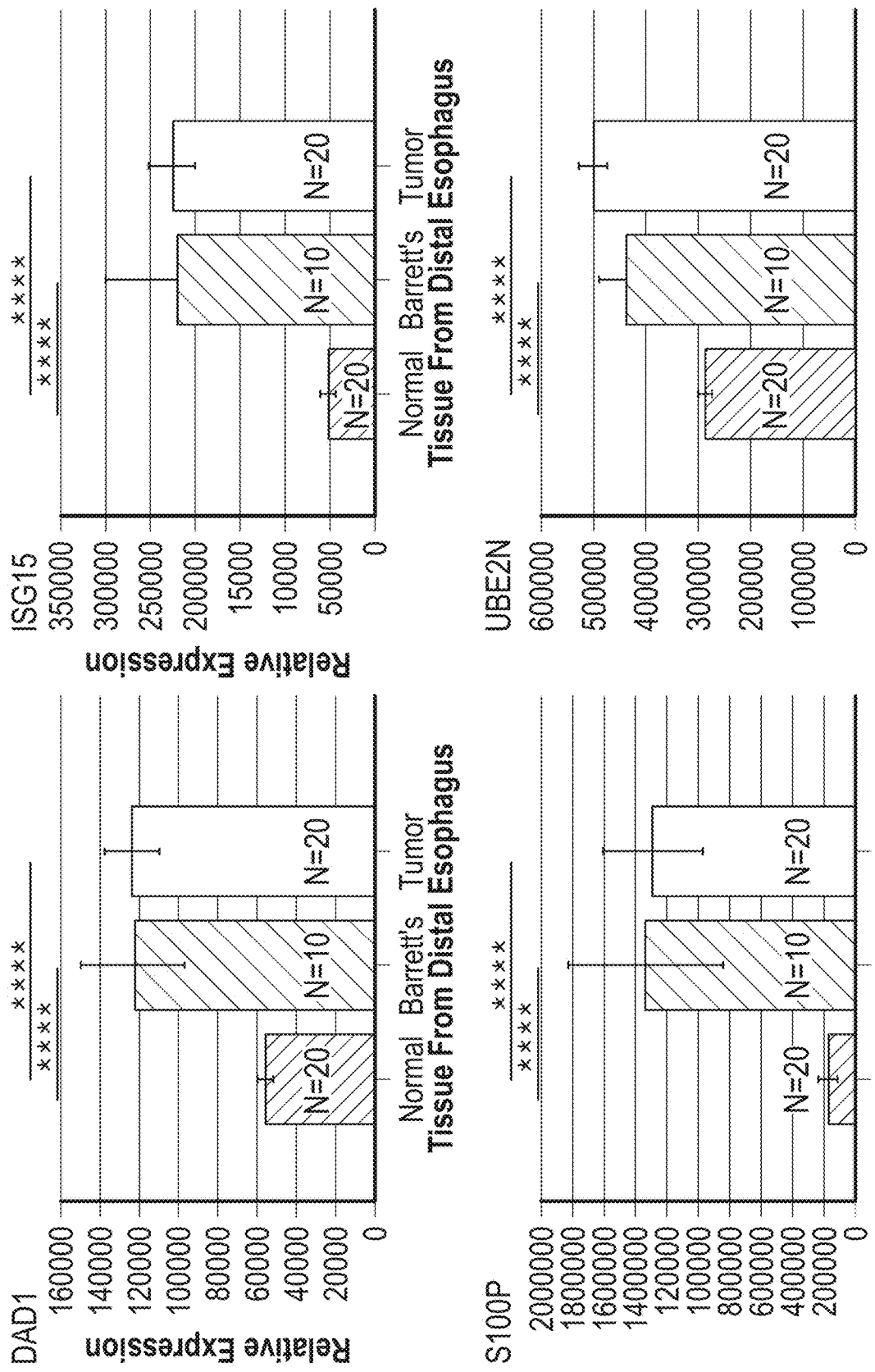
FIG. 4A. Graph illustrating expression of DAD1, S100P, ISG15, and UBE2N in normal squamous esophageal epithelium, Barrett's esophagus, and esophageal adenocarcinoma (** $P<0.0001$, * $P<0.001$, ** $P<0.01$, *$P<0.1$).
Figure 4B:
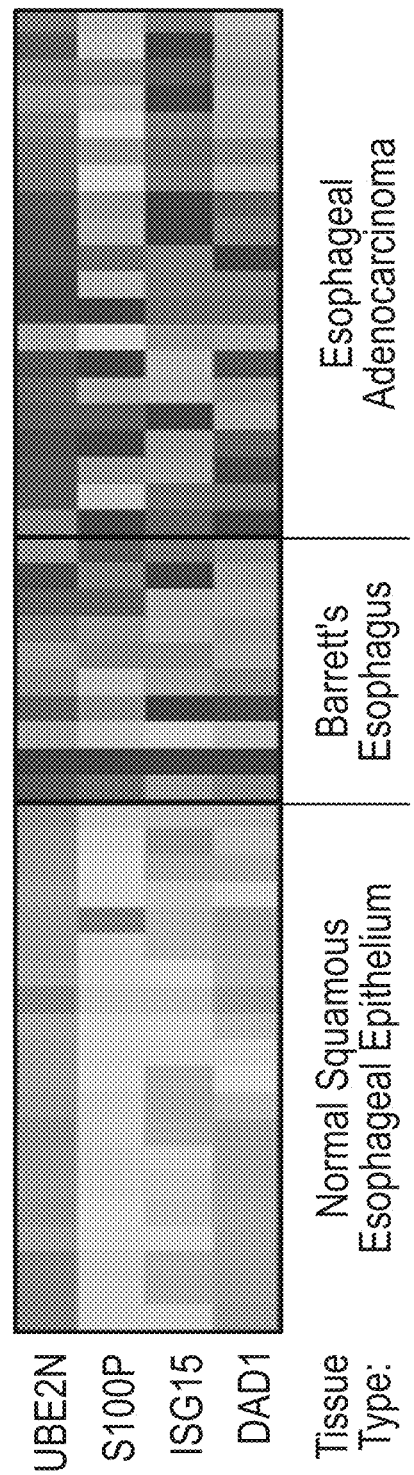
FIG. 4B Heat map illustrating expression of proteins in normal squamous esophageal epithelium, Barrett's esophagus, and esophageal adenocarcinoma.

3.1.1. Mass spectrometry proteomic expression quantification. FIG. 4A shows graphs illustrating expression of DAD1, S100P, ISG15, and UBE2N in normal squamous esophageal epithelium, Barrett's esophagus, and esophageal adenocarcinoma (** P<0.0001, * P<0.001, ** P<0.01, *P<0.1). FIG. 4B shows heat maps illustrating expression of proteins in normal squamous esophageal epithelium, Barrett's esophagus, and esophageal adenocarcinoma.

TABLE 2

Expression of DAD1, S100P, ISG15, and UBE2N in normal squamous esophageal epithelium, Barrett's esophagus, and esophageal adenocarcinoma.

| | Expression Level | | |
|---|---|---|---|
| Gene | Normal Squamous Esophageal Epithelium [a] | Barrett's Esophagus [b] | Esophageal Adenocarcinoma [a] |
| DAD1 | 56385 ± 3542 | 123542 ± 26366 [c] | 123896 ± 13688 [c] |
| S100P | 165206 ± 58897 | 1326063 ± 487967 [c] | 1284731 ± 318892 [c] |
| ISG15 | 51648 ± 6585 | 221555 ± 80921 [c] | 227040 ± 26429 [c] |
| UBE2N | 284480 ± 10736 | 433394 ± 55717 [c] | 497578 ± 26755 [c] |
| CNDP2 | 146276 ± 10324 | 395016 ± 61110 [c] | 294583 ± 32966 [c] |
| SET | 117064 ± 7797 | 159131 ± 28428 [c] | 249625 ± 27425 [c] |
| LTF | 49755 ± 8336 | 436619 ± 295689 [c] | 439873 ± 91500 [c] |
| G6PI | 372266 ± 17274 | 526476 ± 78394 [c] | 634425 ± 47698 [c] |

[a] n = 20
[b] n = 10
[c] P < 0.0001

Figure 5:
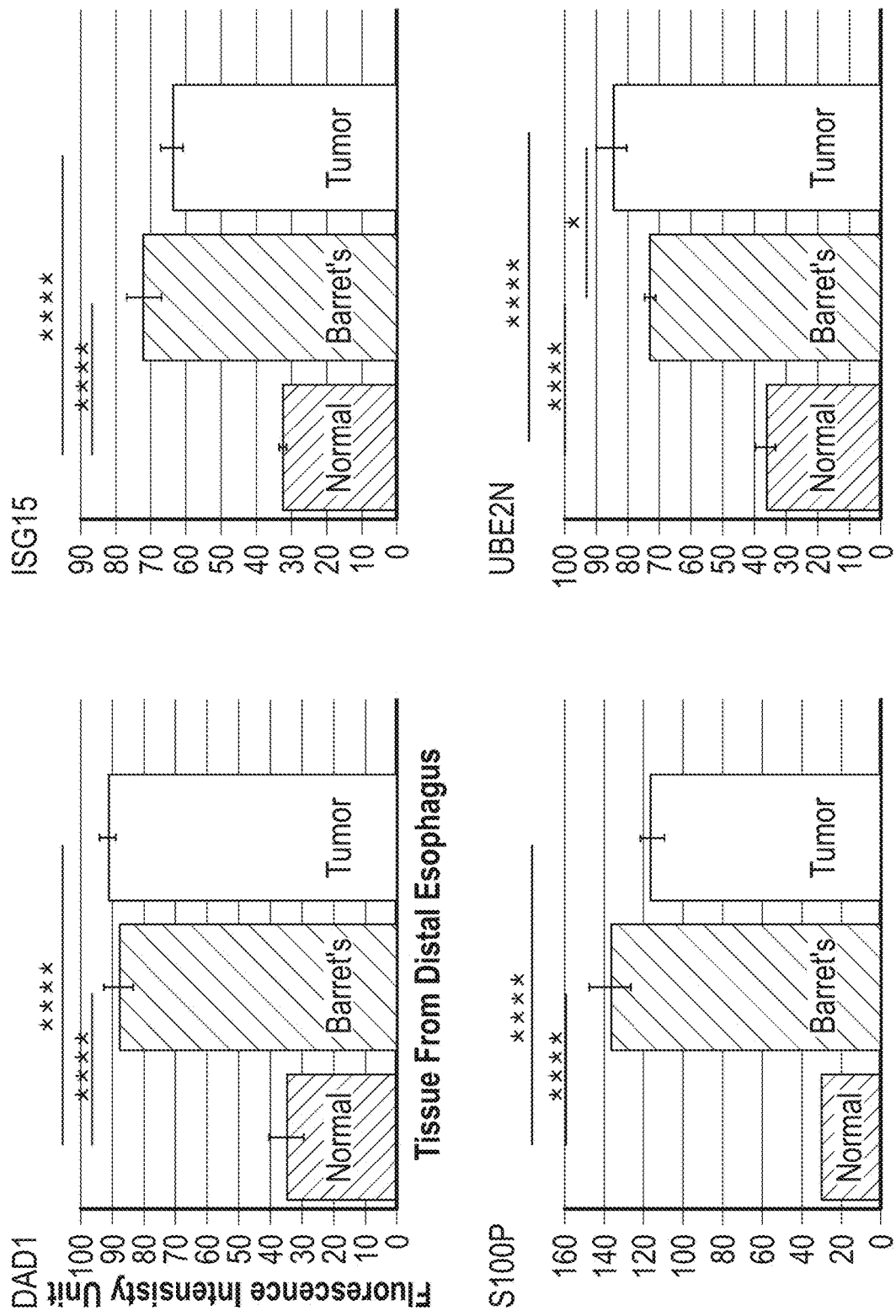
FIG. 5. Bar graphs illustrating immunofluorescence intensity quantification of the DAD1, ISG15, S100P and UBE2N in normal tissue, BE, and EAC. The expression trends observed in the discovery mass spectrometry study match the expression trends observed via antibody-based proteomic assays (immunofluorescence).

3.1.2. Immunofluorescent proteomic expression quantification. Immunofluorescence was used to provide a qualitative confirmation of the quantitative data obtained from mass spectrometry analysis. Using antibodies to DAD1, S100P, ISG15, and UBE2N, expression of the proteins was visualized in normal tissue, Barrett's esophageal tissue, and esophageal adenocarcinoma tissue. As expected, for each gene, increased fluorescence signal was observed in Barrett's esophageal tissue and esophageal adenocarcinoma tissue compared to normal tissue (see Table 3 and FIG. 5). Notably, S100P had a significantly higher expression in Barrett's tissue compared to esophageal adenocarcinoma tissue which may indicate it plays a larger role in progression from precancerous mucosa into a malignant histology.

Our results confirmed that the DAD1 proto-oncogene is upregulated during esophageal pathogenesis. EAC samples averaged a fluorescence intensity unit of 91.242, BE samples averaged a score of 87.634 FIU, compared to a mean FIU score of 34.167 in normal esophageal mucosa. The difference of the mean FIU score of both BE and EAC compared to the normal control samples had a p<0.0001. This expression pattern is indistinguishable compared to proteomic quantification of human FFPE tissue observed via mass spectrometry.

Our results also confirmed that the ISG15 proto-oncogene is upregulated during esophageal pathogenesis. EAC samples averaged a fluorescence intensity unit of 63.571, BE samples averaged a score of 71.827 FIU, compared to a mean FIU score of 31.626 in normal squamous esophageal epithelium. The difference of the mean FIU score of both BE and EAC compared to the normal control samples had a p<0.0001. This expression pattern is the same as the proteomic quantification of human FFPE tissue observed via mass spectrometry.

Our results also confirmed that the S100P proto-oncogene is upregulated during esophageal pathogenesis. EAC samples averaged a fluorescence intensity unit of 110.255, BE samples averaged a score of 136.331 FIU, compared to a mean FIU score of 32.339 in normal squamous esophageal mucosa. The difference of the mean FIU score of both BE and EAC compared to the normal control samples had a p<0.0001. This expression pattern is the same as the proteomic quantification of human FFPE tissue observed via mass spectrometry. Notably, S100P had a significantly higher expression in Barrett's tissue compared to esophageal adenocarcinoma tissue which may indicate it plays a larger role in progression from precancerous mucosa into a malignant histology.

Our results also confirmed that the UBE2N proto-oncogene is upregulated during esophageal pathogenesis. EAC samples averaged a fluorescence intensity unit of 84.849, BE samples averaged a score of 72.402 FIU, compared to a mean FIU score of 36.201 in normal squamous esophageal mucosa. The difference of the mean FIU score of both BE and EAC compared to the normal control samples had a p<0.0001. This expression pattern is the same as the proteomic quantification of human FFPE tissue observed via mass spectrometry.

TABLE 3

Protein expression in tissues as determined by immunofluorescence analysis.

| Gene | Average Fluorescence Intensity | | | |
|---|---|---|---|---|
| | DAD1 | S100P | ISG15 | UBE2N |
| Normal Tissue | 34.167 | 32.339 | 31.626 | 36.201 |
| Barrett's Esophagus Tissue | 87.634* | 136.331* | 71.827* | 72.402* |
| Esophageal Adenocarcinoma Tissue | 91.242* | 110.255* | 63.571* | 84.849* |

* p < 0.0001

3.5.2. Expression of DAD1, ISG15, S100P and UBE2N in healthy distal esophagus control. In order to assess DAD1, ISG15, S100P and UBE2N expression in the mucosa or non-diseased distal esophagus, an animal model was used. This analysis was performed to provide evidence that the increase expression observed in diseased tissue was not the result of an anomaly. Four different Yucatán microswines were fed diets categorized as high cholesterol, high fructose; vitamin D deficient; vitamin D sufficient; or vitamin D supplemental. Averaging data from the four animals, DAD1 had an average IF score of 22.48, ISG15 had a mean IF score of 27.73, S100P had a mean IF score of 22.33, and UBE2N had a mean IF score of 26.65 in the distal esophageal epithelium. The IF scores in the distal esophagus were comparable to the scores previously observed normal tissue samples, indicating the none of S100P, DAD1, ISG15, and UBE2N were highly expressed in normal esophageal tissue. DAD1 had an average IF score of 22.48 combining expression levels observed in the distal esophageal epithelium of the four pigs. DAD 1 received immunofluorescence scores of 91.24 in EAC, 87.63 in BE and 34.167 in normal mucosa of our human model. ISG15 had a mean IF score of 27.73 when combining the FIU of all four pigs with the various diets. Immunofluorescence for ISG15 were 71.83 in EAC samples, 63.57 in BE samples and 31.626 in normal squamous esophageal epithelium in our human FFPE study. S100P scored a 22.33 FIU in our pig model compared to 110.25 in EAC, 136.33 in BE and 32.34 in normal squamous esophageal mucosa of our human study. UBE2N scored a 26.65 FIU compared to 84.85 in EAC, 72.40 in BE, and 36.20 in normal human tissue.

Figure 6:
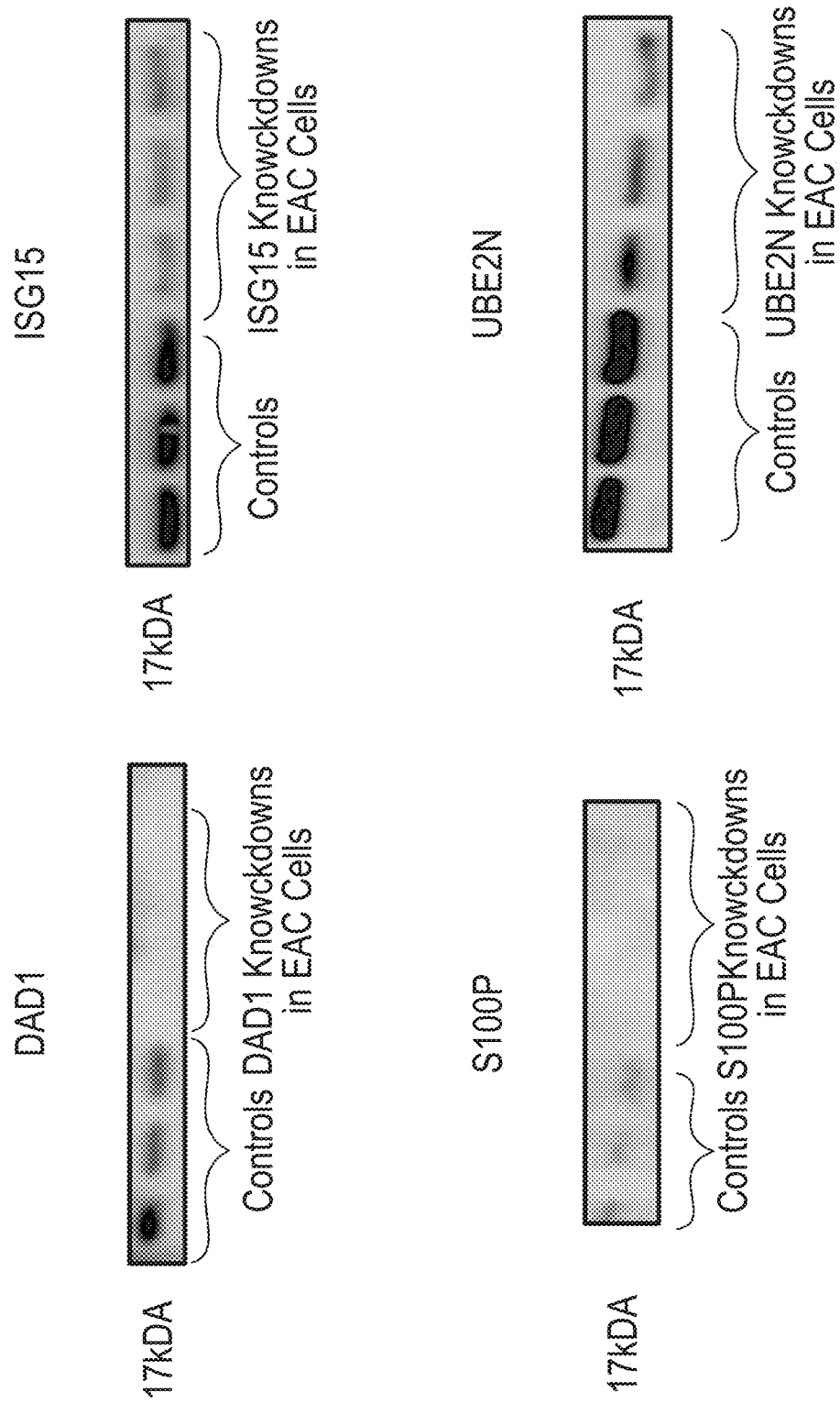
FIG. 6. Western blots illustrating protein abundance in esophageal adenocarcinoma cell lines in the presence or absence of siRNAs against DAD1, ISG15, S100P, and UBE2N.

3.5.3. Gene knockdown achieved in EAC cell line. siRNAs specific to DAD1, ISG15, S100P and UBE2N were analyzed for their ability to knock down expression of DAD1, ISG15, S100P and UBE2N in an EAC cell line. Cells were processed as described above and analyzed for protein expression by western blot. Four western blots of triplicate knockdown samples run next to triplicate untreated controls. As shown in FIG. 6, the siRNA significantly inhibited expression of each of DAD1, ISG15, S100P and UBE2N. Quantification of these knockdowns were normalized to GAPDH. All four markers had a molecular weight close to 17 kDa.

Figure 7:
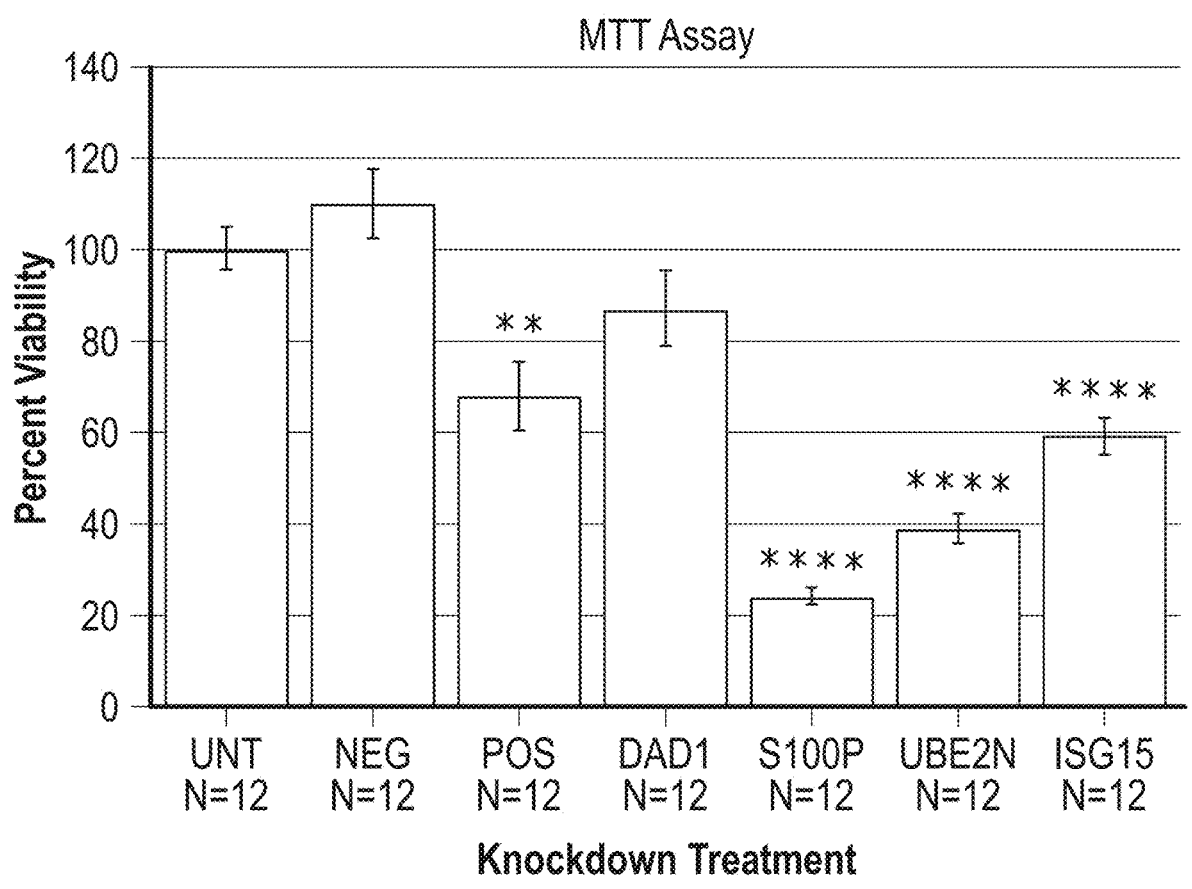
FIG. 7. Graph illustrating percent viability, as determined by MTT proliferation assay, of EAC cell line in cells treated with siRNA against DAD1, S100P, UBE2N, and ISG15. Statistical significance is in relation to the various treatment groups compared to untreated cells. Significance compared to untreated EAC cells ( $P<0.01$, ** $P<0.0001$).

3.5.4. S100P, UBE2N, and ISG15 gene knockdown inhibited cell proliferation in EAC cell line. MTT colorimetric assay demonstrated a decrease in cellular proliferation of EAC cells treated with siRNA against ISG15, S100P, and UBE2N (FIG. 7). Knockdown of S100P had the largest effect in reducing cell proliferation in esophageal adenocarcinoma cell line (OE-33). Knockdown of UBE2N and ISG15 also demonstrated statistically significant inhibition of cellular propagation compared to untreated cells. Knockdown of the positive control (GAPDH) had a statistically significantly reduction in cellular proliferation compared to the untreated and negative controls (P<0.01). Knockdown of DAD1 did not result in a statistically significant slower rate of proliferation compared to controls.

Figure 8:
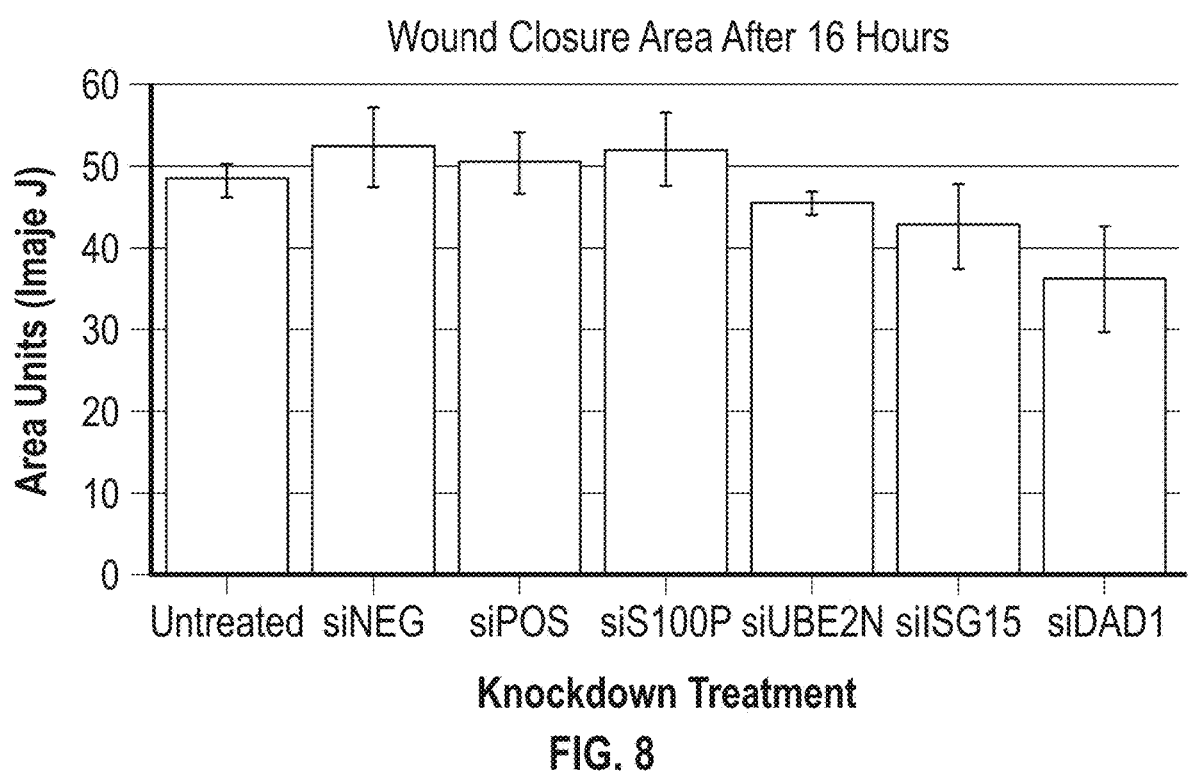
FIG. 8. Graph illustrating decreased cell migration as measured by scratch closure using EAC cells treated with siRNAs against DAD1, ISG15, S100P, and UBE2N, or control treated cells.

3.5.5. DAD1 knockdown inhibits migration in EAC cell line. One of the hallmarks of esophageal carcinogenesis is the adenocarcinoma cell's ability to migrate and spread rapidly throughout the body. Inhibiting migration of cancer cells typically yields extended overall survival rates in patients, assists in keeping the cancer localized, and slows down the spread to regional lymph nodes or distant organs. siRNA-mediated knockdown of DAD1, ISG15, S100P, and UBE2N in OE-33 cells was used to determine if suppression of these genes inhibited cellular migration compared to untreated and treated controls. Cellular migration was monitored using a scratch assay. Cells in 12-well plates were grown to 90% confluence and then a scratch was made vertically over the cells with a 200 μL pipette tip. Images were then captured at time 0 and after 12 and 16 hours to determine rate of wound closure. A higher percentage of scratch closure over 16 hours correlates to higher rates of migration. As shown in Table 4, the mean percentage of closure (N=3 for each knockdown) was lower in the four knockdowns compared to the four control groups (N=3 for each group). Although decreases in scratch closure were not statistically significant at 16 hours for any of the 4 genes tested in this initial experiment, the results nevertheless suggest inhibition of these four genes may decrease the rate of cellular migration in esophageal adenocarcinoma cells. DAD1 knockdown achieved the slowest rate of migration compared to controls and the other four markers. See FIG. 8 and Table 4. ISG15 and UBE2N knockdowns also demonstrated slower migration rates compared to controls. S100P knockdown had the least impact on migration rates with 78.0% wound closure after 16-hours compared to the other four gene knockdowns in OE-33 adenocarcinoma cells, but still showed less migration than the four controls. Both untreated cell lines (with or without lipofectamine) had the highest rates of migration of the 8 groups, with almost total wound closure after 16-hours post scratch. The siNEG control had a mean closure percentage of 94.6% compared to 39.1% (−DAD1), 73.2% (−ISG15), 78.0% (−S100P), and 73.6% (−UBE2N) after 16-hours. The siPOS control had a mean wound closure percentage of 89.8% which was a faster rate of migration compared to each of the four marker gene knockdowns.

TABLE 4

Cell migration assay results.

| Sample | Cell-Free Scratch Area | | | Percent Scratch Closure | Mean |
|---|---|---|---|---|---|
| | 0 hours | 12 hours | 16 hours | (16 hours) | Closure (n = 3) |
| Untreated control, No lipofectamine | 61.95 | 18.70 | 12.37 | 80.0 | 96.3 ± 2.5 |
| Untreated control, with lipofectamine | 55.70 | 10.65 | 3.28 | 94.1 | 95.5 ± 0.9 |
| siNEG control, no siRNA vector | 62.94 | 8.75 | 1.27 | 98.0 | 94.6 ± 2.9 |
| siPOS control, GADPH knockdown | 64.09 | 10.12 | 7.54 | 88.2 | 89.9 ± 2.4 |
| DAD1 | 54.44 | 32.88 | 27.80 | 48.9 | 39.3 ± 7.3 |
| ISG15 | 57.29 | 28.26 | 25.16 | 56.1 | 73.23 ± 8.7 |
| S100P | 55.62 | 19.20 | 12.81 | 77.0 | 78.0 ± 2.9 |
| UBE2N | 63.25 | 19.99 | 17.15 | 72.9 | 73.6 ± 0.7 |

Figure 9:
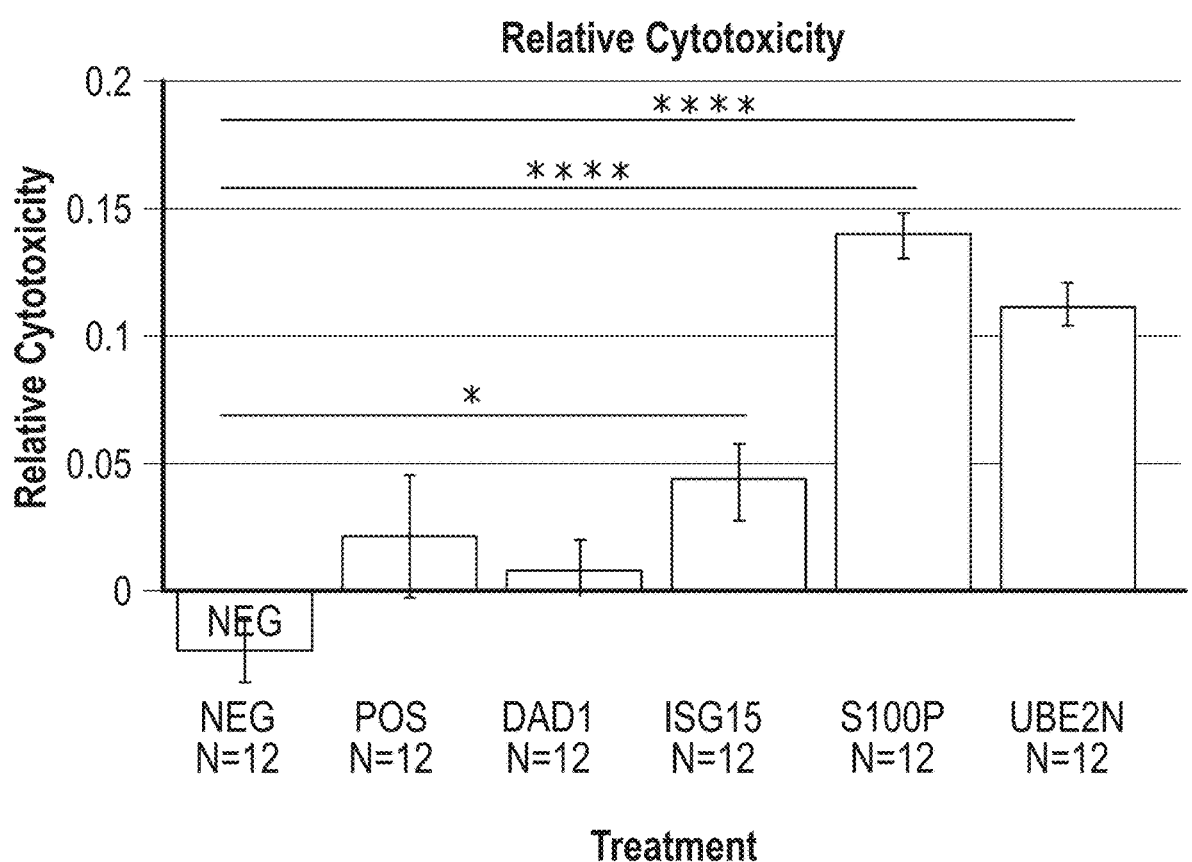
FIG. 9. Graph illustrating rate of cytotoxicity in EAC OE-33 cells treating with siRNA targeting DAD1, ISG15, S100P, and UBE2N.
Figure 10A:
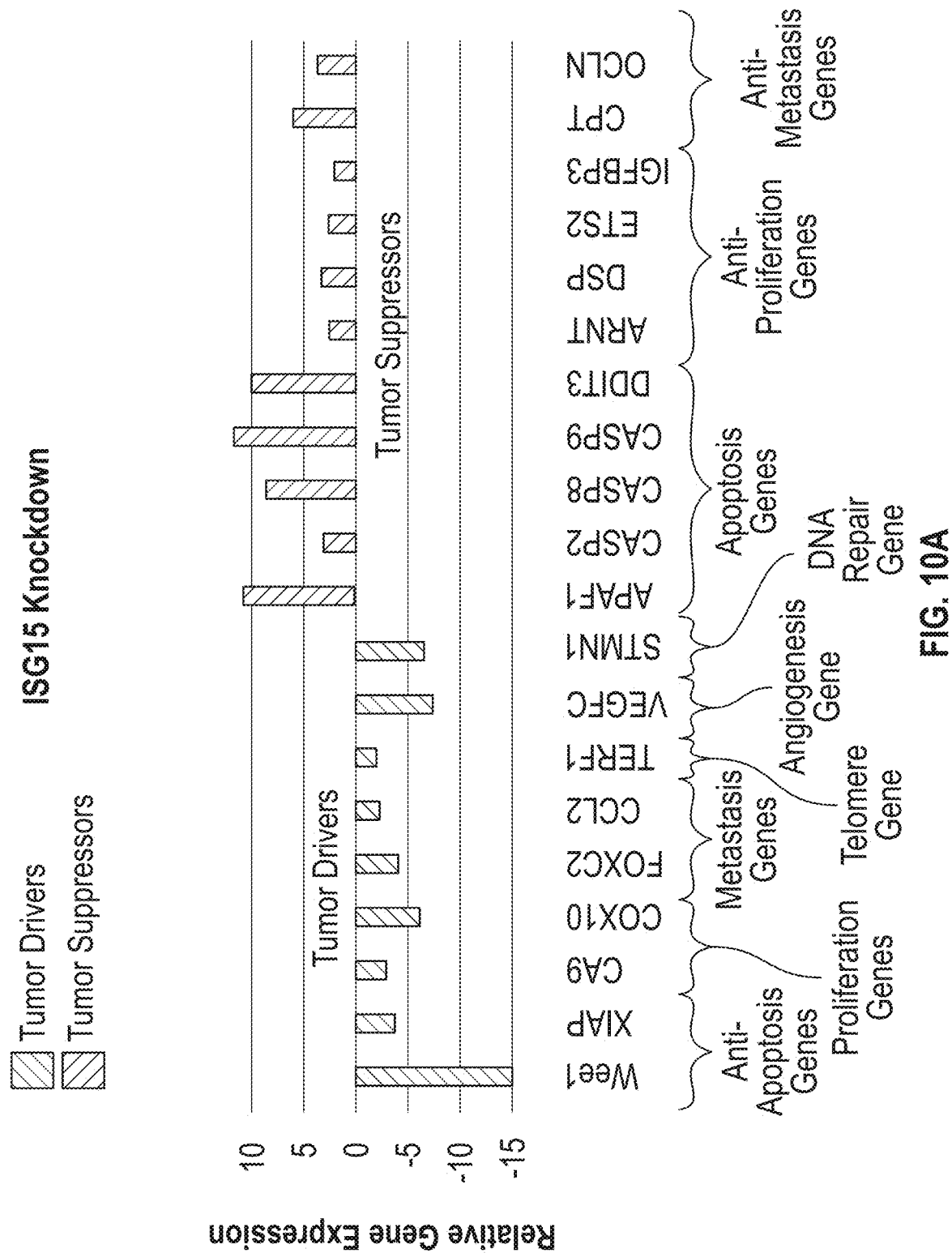
FIG. 10A. Graph illustrating decreased expression of tumor promoting genes and increased expression of tumor suppressor genes in response to knockdown of ISG15 gene in OE-33 cells.
Figure 10B:
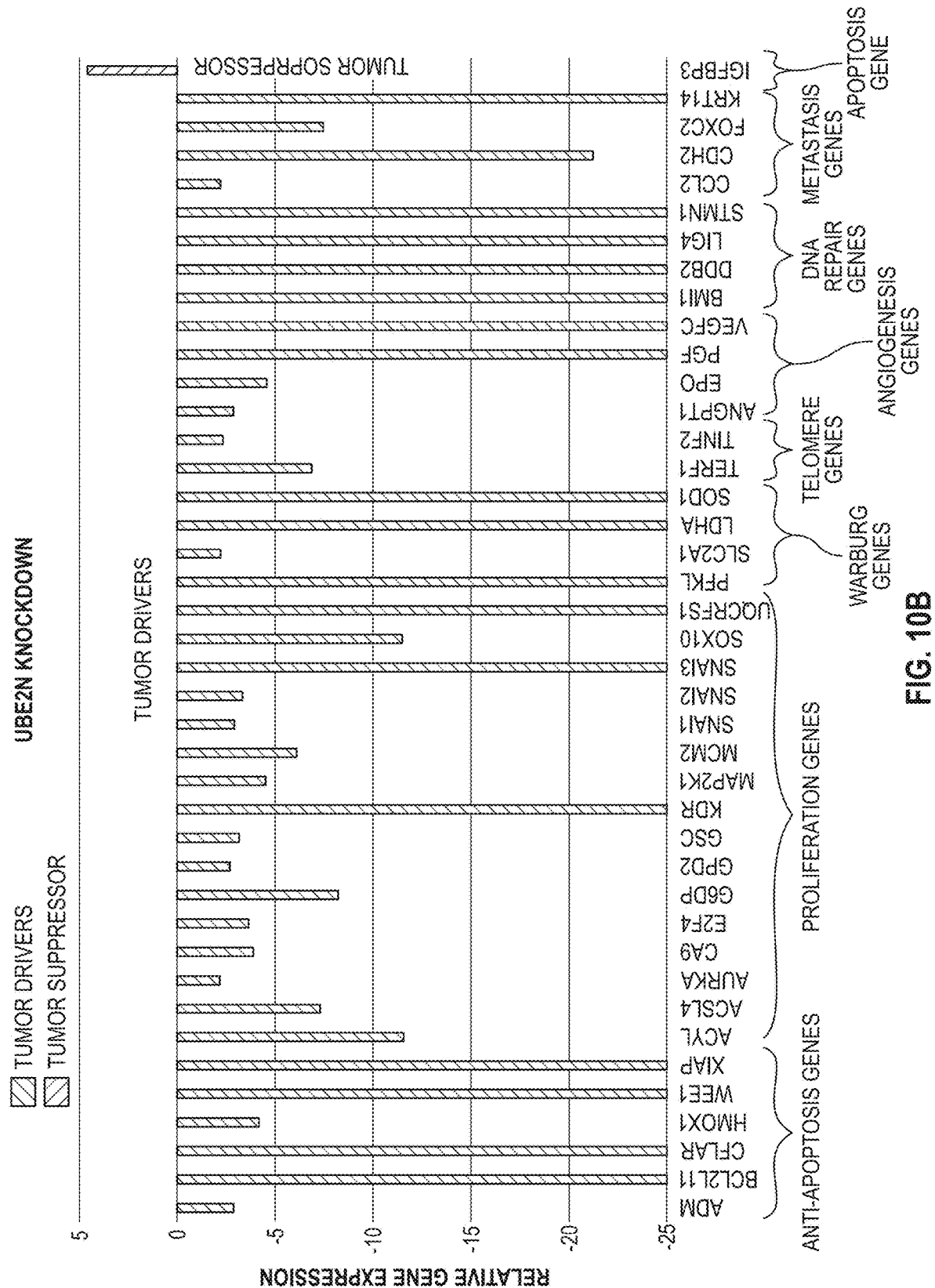
FIG. 10B. Graph illustrating decreased expression of tumor promoting genes and increased expression of tumor suppressor genes in response to knockdown of UBE2N gene in OE-33 cells.
Figure 10C:
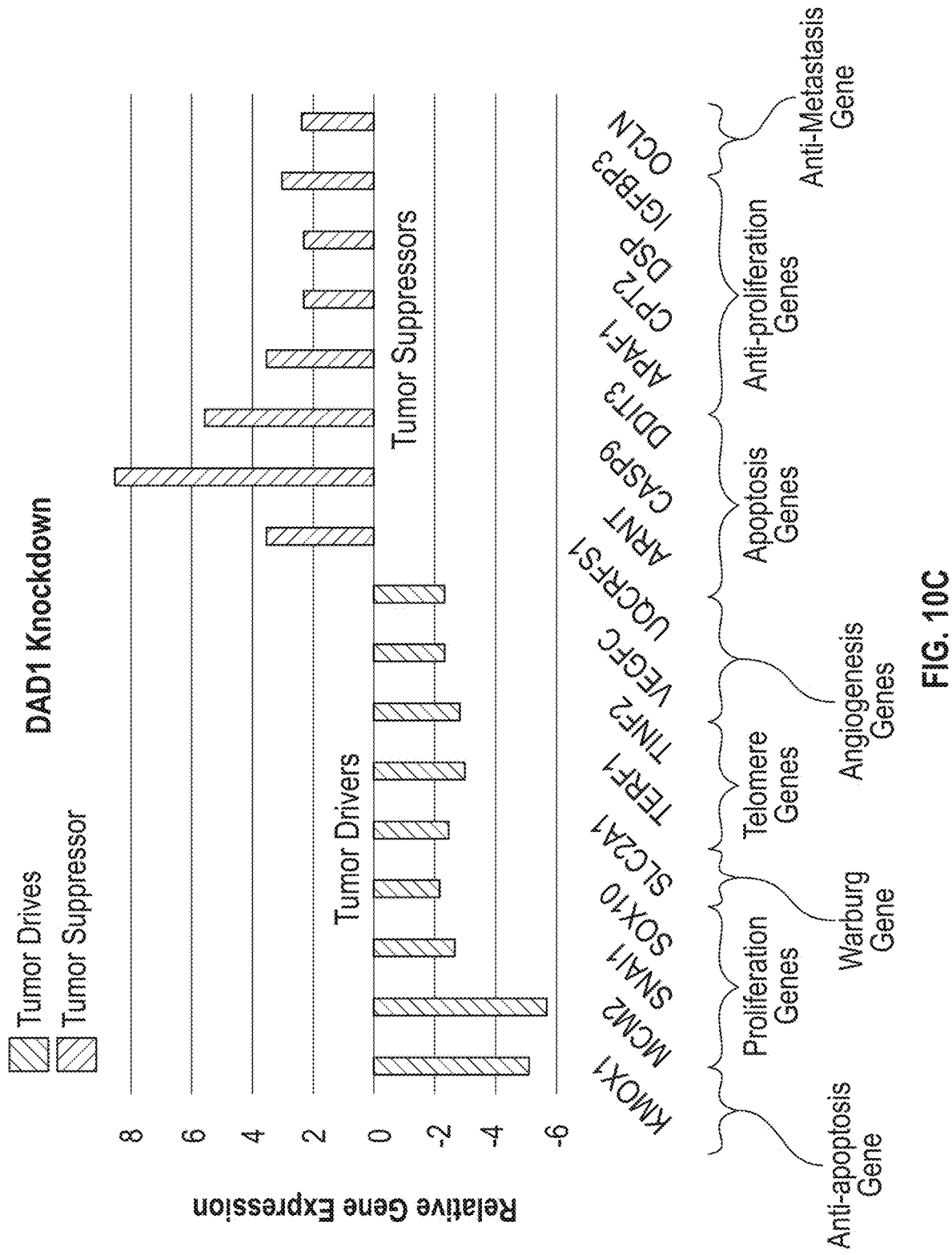
FIG. 10C. Graph illustrating decreased expression of tumor promoting genes and increased expression of tumor suppressor genes in response to knockdown of DAD1 gene in OE-33 cells.
Figure 10D:
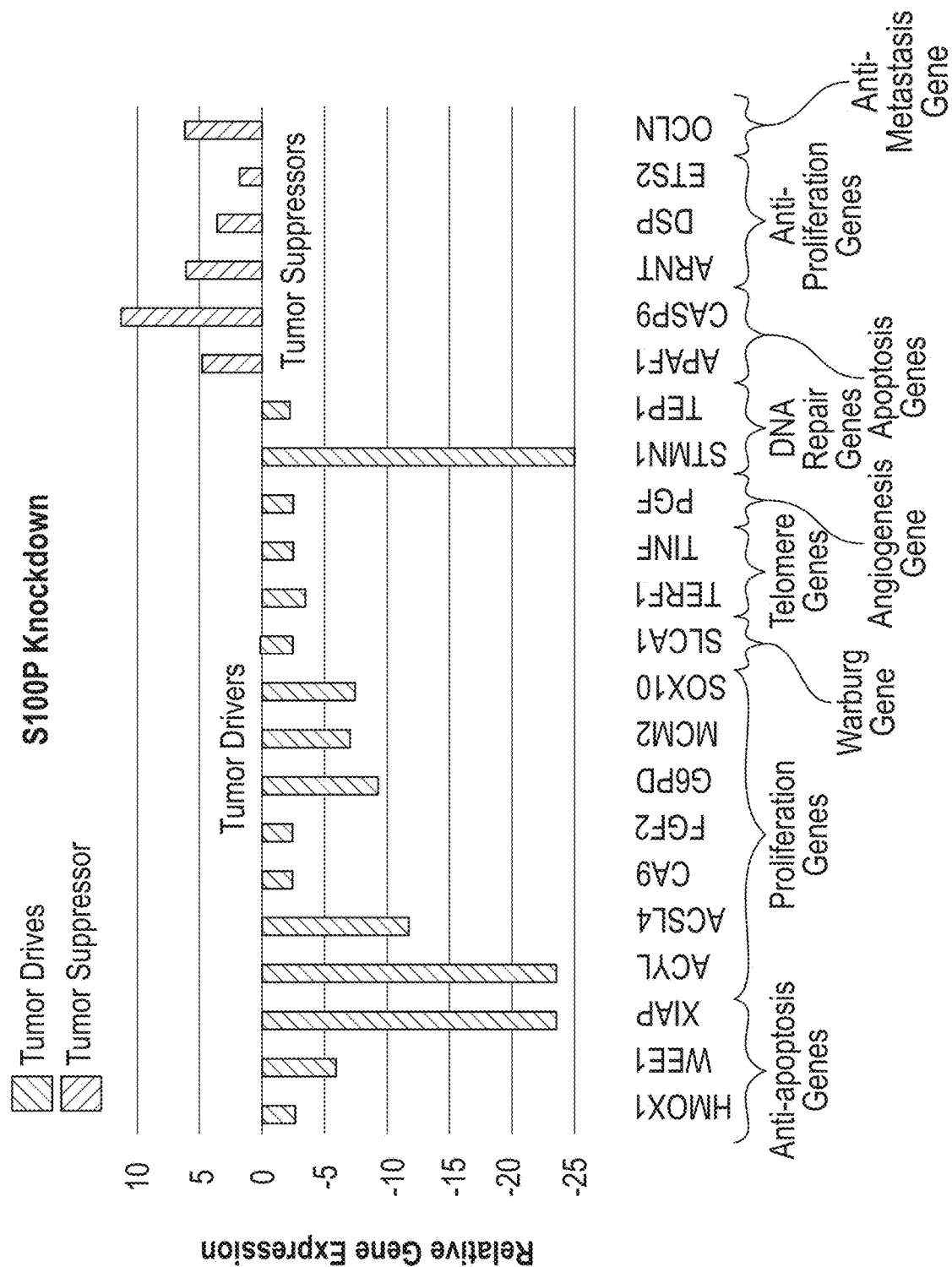
FIG. 10D. Graph illustrating decreased expression of tumor promoting genes and increased expression of tumor suppressor genes in response to knockdown of S100P gene in OE-33 cells.

3.5.6. ISG15, S100P, or UBE2N knockdown augments cytotoxicity in EAC cell line. Esophageal adenocarcinomas frequently evolve escape mechanisms that enable the cancerous cells to evade normal mechanisms that cause cell death. siRNA was used to knockdown DAD1, ISG15, S100P and UBE2N expression in EAC OE-33 cells. The treated cells were then analyzed to determine if knockdown increased cell death and/or increased susceptibility to cytotoxicity. Knockdown of S100P ($P<0.0001$), UBE2N ($P<0.0001$), and ISG15 ($P<0.01$) each showed increased rate of cytotoxicity compared to our negative control 48-hours post knockdown (FIG. 9). Knockdown of S100P and UBE2N in particular induced a rabid rate of cytotoxicity.

3.5.7. Cancer and immunity pathways affected by gene knockdown of DAD1, ISG15, S100P, or UBE2N. A Cancer PathwayFinder PCR array from QIAGEN, which quantifies downregulation and overexpression patterns of 84 genes representative of six biological pathways involved in transformation and tumorigenesis, was used to analyze the roles DAD1, ISG15, S100P or UBE2N play in the oncogenic environment. OE-33 adenocarcinoma cells transfected with siRNA targeting DAD1, ISG15, S100P and UBE2N were used. Knockdown of the four markers had a strong positive effect in downregulating pro-tumoral factors while upregulating tumor suppressing factors as depicted in FIGS. 10A-10D. These data demonstrate the utility of the described mass spec analysis methods in identifying genes involved in esophageal adenocarcinoma.

UBE2N siRNA was particularly effective in downregulating tumor drivers in well-described cancer pathways, reducing expression of 42 tumor drivers, including 18 proliferation genes. Conversely, ISG15 knockdown was the most effective in upregulating 11 tumor suppressors, including 5 inducers of apoptosis, 4 anti-proliferation genes and 2 metastatic suppressors. The effects of UBE2N siRNA in downregulating 42 tumor drivers and ISG15 siRNA in upregulating 11 tumor suppressors supports our observation that both UBE2N and ISG15 knockdown had an antiproliferative effect in our treated cell lines, while increasing cytotoxicity. UBE2N knockdown was found to downregulate MyD88 by a factor of 40.73×. Inhibition of MyD88 supports the roles of CNDP2, DAD1, GPI, ISG15, LTF, S100P, SET and UBE2N in Barrett's pathogenesis.[47] UBE2N knockdown affected 51.2% (43/84) of the genes in the Cancer PathwayFinder array, indicating a upstream role of this gene in BE/EAS pathogenesis.

Knockdown of DAD1 and S100P in EAC cell line OE-33 also established favorable anti-cancer effects representative of downregulation of oncogenes involved in DNA repair, proliferation, glycolysis (Warburg effect), angiogenesis, and anti-apoptotic factors. Knockdown of DAD1 and S100P both demonstrated an upregulation of three anticancer factors: apoptosis inducers, anti-proliferation regulators and anti-metastatic genes. S100P knockdown had a positive effect on 26.2% (22/84) of the oncogenes quantified in this assay, supporting it role in BE/EAS pathogenesis. The downregulation of well-described tumor drivers following treatment of cells with S100P siRNA may drive the antiproliferation effect observed in our MTT experiment.

In addition to the above, it was observed that some tumor suppressors were downregulated and some tumor drivers were upregulated in above gene expression (RT-PCR) experiments in each gene knockdown sample. Nevertheless, cellular proliferation and migration decreased while cytotoxicity increased when EAC cells incurred separate knockdown of each of the four markers.

4.0. Discussion.

Figure 11:
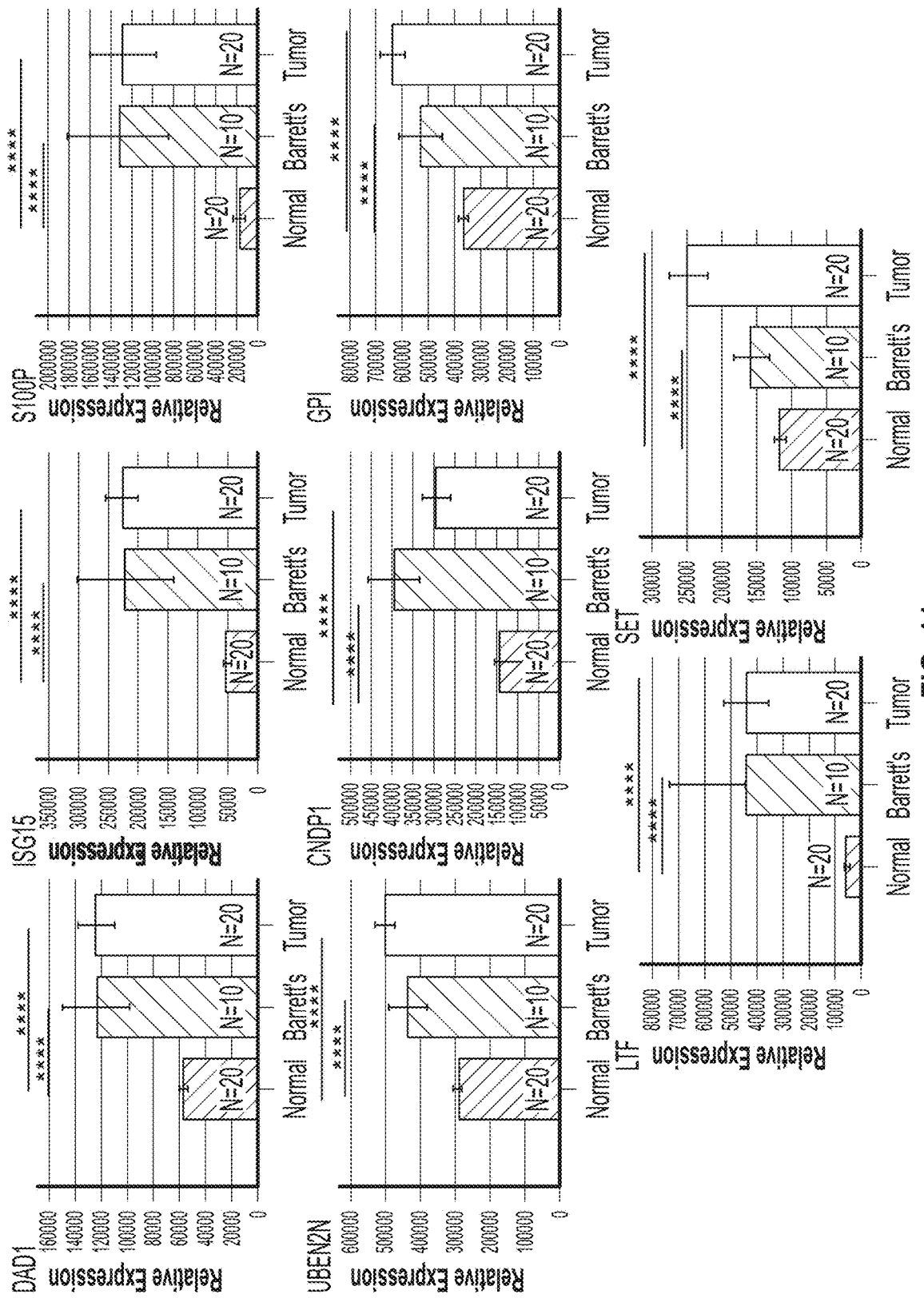
FIG. 11. Bar graphs illustrating increase expression of the indicated markers as esophageal tissue progresses from normal to precancerous (Barrett's esophagus) to cancer (esophageal adenocarcinoma).

CNDP2, DAD1, GPI, ISG15, LTF, S100P, SET and UBE2N provide for useful diagnostics in analyzing risk for developing EAC. Analyses of these gene also provides information that can guide clinical action on an individual subject basis. One of the challenges of EAC is that many people develop BE without developing cancer. Identifying subjects most likely at risk of developing EAS can be used detect malignant transformations at an earlier stage and improve outcomes. Compared to the eight most used markers for gastroesophageal cancers that are currently offered by molecular diagnostics, DAD1, ISG15, S100P, UBE2N are present in a much higher percentage of EAC (see Tables 5 and 6 and FIG. 11).[48-55] These markers therefore represent improved diagnostic utility in pathological analyses and clinical patient management strategies. We have shown that DAD1, ISG15, S100P, UBE2N are proto-oncogenes whose upregulation leads to proliferation of EAC cells by reducing apoptosis and inhibiting protein destruction, while promoting metastasis. Analyses of expression levels of these genes can thus serve as effective targets for therapeutic intervention, helping to sensitize these tumors to targeted therapy and chemotherapy.

TABLE 5

Markers overexpressed in esophageal adenocarcinoma (EAC) tumors.

| Markers routinely analyzed in EAC tumors | | Newly identified markers | |
|---|---|---|---|
| Marker | Overexpression in EAC tumors (% of tumors) | Marker | Overexpression in EAC tumors (% of tumors, n = 20) |
| EGFR1 | 28 | DAD1 | 100 |
| HER2 | 18 | ISG15 | 95 |
| HER3 | 20 | S100P | 85 |

TABLE 5-continued

Markers overexpressed in esophageal adenocarcinoma (EAC) tumors.

| Markers routinely analyzed in EAC tumors | | Newly identified markers | |
|---|---|---|---|
| Marker | Overexpression in EAC tumors (% of tumors) | Marker | Overexpression in EAC tumors (% of tumors, n = 20) |
| IGF1R | 52 | UBE2N | 90 |
| MET | 9 | | |
| MSLN | 13 | | |
| PD-L1 | 27 | | |
| TUBB3 | 7 | | |

TABLE 6

Expression of CNDP2, DAD1, GPI, ISG15, LTF, S100P, SET and UBE2N in normal squamous epithelium, BE, and EAC.

| | Protein Expression | | |
|---|---|---|---|
| Protein | Normal Squamous Epithelium | Barrett's Esophagus | Esophageal Adenocarcinoma |
| CNDP2 | 146,275 | 395,016 | 294,582 |
| DAD1 | 56,384 | 123,452 | 123,896 |
| GPI | 372,266 | 526,476 | 634,425 |
| ISG15 | 51,647 | 221,554 | 227,040 |
| LTF | 49,754 | 436,618 | 439,872 |
| S100P | 165,206 | 1,326,062 | 1,284,730 |
| SET | 117,063 | 159,130 | 249,625 |
| UBE2N | 284,480 | 433,394 | 497,577 |

EAC is a fatal disease lacking an effective standard of care outside of surgical extirpation, and its rising rate of incidence has become a considerable public health concern. Therefore, it is important that new drug targets and improved diagnostics be developed The eight markers disclosed herein, CNDP2, DAD1, GPI, ISG15, LTF, S100P, SET and UBE2N, are upregulated in 85% to 100% of BE and EAC and methods of identifying their upregulation in distal esophageal mucosa samples are useful in identifying progression or risk or progression from normal squamous epithelium to dysplastic Barrett's tissue and from BE to a malignant adenocarcinoma pathology.

From a molecular oncology perspective, we have proposed the mutual intersections of the disclosed markers in forming a carcinogenic proteomic milieu leading to an increase in proliferation, invasion, migration, metastasis, and cell survival as well as chemotherapeutic resistance to the most common prescribed neoadjuvant drugs FDA-approved for EAC. The therapeutic utility of these markers has been shown using siRNA-mediated knockdown of expression of proto-oncogenes ISG15, S100P and UBE2N. Knockdown of these genes led to a decrease in cellular proliferation compared to untreated esophageal adenocarcinoma cells. S100P knockdown resulting in the largest decrease in EAC cell growth (P<0.0001), growing at a rate roughly 75% less than untreated control cells. UBE2N and ISG15 knockdowns also showed statistically significant reduction in proliferation compared to controls. Knockdown of S100P and UBE2N also resulted in enhanced cytotoxicity in esophageal adenocarcinoma cell line OE-33 (P<0.0001). While DAD1 knockdown did not result in increased cell death in a G6PD cytotoxicity release assay, DAD1 knockdown may enhance cytotoxic effect in the presence of apoptotic pressure (i.e., chemotherapy) due to its role as a defender against apoptosis. Even though DAD1 had little effect on proliferation reduction or cell death induction, knockdown of DAD1 was effective in slowing migration. Cells treating with DAD1 siRNA exhibited only 39.3% wound closure after 16 hours, compared to 94.6% wound closure in negative control samples. Each of DAD1, ISG15, S100P and UBE2N contributed to aspects of anti-carcinogenesis. Thus, these four genes represent important diagnostic markers and therapeutic targets.

REFERENCES

1. Zhang Y. Epidemiology of esophageal cancer. World J Gastroenterol. 2013; 19(34):5598-5606. doi:10.3748/wjg.v19.i34.5598
2. Howlader N, Noone A M, Krapcho M, Garshell J, Miller D, Altekruse S F, Kosary C L, Yu M, Ruhl J, Tatalovich Z, Mariotto A, Lewis D R, Chen H S, Feuer E J, Cronin K A (eds). SEER Cancer Statistics Review, 1975-2011, National Cancer Institute. Bethesda, M D, http:/A 2014. SEER Cancer Statistics Review, 1975-2011. National Cancer Institute. Bethesda, M D.
3. Rajagopal P S, Nipp R D, Selvaggi K J. Chemotherapy for advanced cancers. Ann Palliat Med. 2014; 3(3):203-228.
4. Abdo J, Bertellotti C A, Cornell D L, Agrawal D K, Mittal S K. Neoadjuvant Therapy for Esophageal Adenocarcinoma in the Community Setting—Practice and Outcomes. Front Oncol. 2017; 7:151. doi:10.3389/fonc.2017.00151
5. Yoon J, Kim E-S, Lee S J, et al. Apoptosis-related mRNA expression profiles of ovarian cancer cell lines following cisplatin treatment. J Gynecol Oncol. 2010; 21(4):255-261. doi:10.3802/jgo.2010.21.4.255
6. Dong L, Wang F, Yin X, et al. Overexpression of S100P promotes colorectal cancer metastasis and decreases chemosensitivity to 5-F U in vitro. Mol Cell Biochem. 2014; 389(1-2):257-264. doi:10.1007/s11010-013-1947-5
7. Pickart C M, Eddins M J. Ubiquitin: structures, functions, mechanisms. Biochim Biophys Acta—Mol Cell Res. 2004; 1695(1-3):55-72. doi:10.1016/J.BBAMCR.2004.09.019
8. Kelleher D J, Gilmore R. DAD1, the defender against apoptotic cell death, is a subunit of the mammalian oligosaccharyltransferase. Proc Natl Acad Sci USA. 1997; 94(10):4994-4999. doi:10.1073/PNAS.94.10.4994
9. Kim Y H, Girard L, Giacomini C P, et al. Combined microarray analysis of small cell lung cancer reveals altered apoptotic balance and distinct expression signatures of MYC family gene amplification. Oncogene. 2006; 25(1):130-138. doi:10.1038/sj.onc.1208997
10. Desai S D. ISG15: A double edged sword in cancer. Oncoimmunology. 2015; 4(12):e1052935. doi:10.1080/2162402X.2015.1052935
11. Sainz B, Martin B, Tatari M, Heeschen C, Guerra S. ISG15 Is a Critical Microenvironmental Factor for Pancreatic Cancer Stem Cells. Cancer Res. 2014; 74(24): 7309-7320. doi:10.1158/0008-5472.CAN-14-1354
12. Zuo C, Sheng X, Ma M, Xia M, Ouyang L. ISG15 in the tumorigenesis and treatment of cancer: An emerging role in malignancies of the digestive system. Oncotarget. 2016; 7(45):74393-74409. doi:10.18632/oncotarget.11911
13. Desai S D, Haas A L, Wood L M, et al. Elevated Expression of ISG15 in Tumor Cells Interferes with the Ubiquitin/26S Proteasome Pathway. Cancer Res. 2006; 66(2):921-928. doi:10.1158/0008-5472.CAN-05-1123

14. Jeon Y J, Jo M G, Yoo H M, et al. Chemosensitivity is controlled by p63 modification with ubiquitin-like protein ISG15. J Clin Invest. 2012; 122(7):2622-2636. doi:10.1172/JCI61762
15. Arumugam T, Logsdon C D. S100P: A novel therapeutic target for cancer. Amino Acids. 2011; 41(4):893-899. doi:10.1007/s00726-010-0496-4
16. Arumugam T, Ramachandran V, Gomez S B, Schmidt A M, Logsdon C D. S100P-Derived RAGE Antagonistic Peptide Reduces Tumor Growth and Metastasis. Clin Cancer Res. 2012; 18(16):4356-4364. doi:10.1158/1078-0432.CCR-12-0221
17. Ge F, Wang C, Wang W, Wu B. S100P predicts prognosis and drug resistance in gastric cancer. Int J Biol Markers. 2013; 28(4):e387-92. doi:10.5301/jbm.5000034
18. Arumugam T, Simeone D M, Van Golen K, Logsdon C D. S100P promotes pancreatic cancer growth, survival, and invasion. Clin Cancer Res. 2005; 11(15):5356-5364. doi:10.1158/1078-0432.CCR-05-0092
19. Tong X-M, Lin X-N, Song T, Liu L, Zhang S. Calcium-binding protein S100P is highly expressed during the implantation window in human endometrium. Fertil Steril. 2010; 94(4):1510-1518. doi:10.1016/j.fertnstert.2009.07.1667
20. Wu Z, Shen S, Zhang Z, Zhang W, Xiao W. Ubiquitin-conjugating enzyme complex Uev1A-Ubc13 promotes breast cancer metastasis through nuclear factor-κB mediated matrix metalloproteinase-1 gene regulation. Breast Cancer Res. 2014; 16(4):R75. doi:10.1186/bcr3692
21. Cheng J, Fan Y-H, Xu X, et al. A small-molecule inhibitor of UBE2N induces neuroblastoma cell death via activation of p53 and JNK pathways. Cell Death Dis. 2014; 5(2):e1079-e1079. doi:10.1038/cddis.2014.54
22. He M, Zhou Z, Shah A A, et al. The emerging role of deubiquitinating enzymes in genomic integrity, diseases, and therapeutics. Cell Biosci. 2016; 6:62. doi:10.1186/s13578-016-0127-1
23. Deng L, Wang C, Spencer E, et al. Activation of the IkappaB kinase complex by TRAF6 requires a dimeric ubiquitin-conjugating enzyme complex and a unique polyubiquitin chain. Cell. 2000; 103(2):351-361.
24. Gallo L H, Ko J, Donoghue D J. The importance of regulatory ubiquitination in cancer and metastasis. Cell Cycle. 2017; 16(7):634-648. doi:10.1080/15384101.2017.1288326
25. Sharma A K, LaPar D J, Stone M L, Zhao Y, Kron I L, Laubach V E. Receptor for Advanced Glycation End Products (RAGE) on iNKT Cells Mediates Lung Ischemia-Reperfusion Injury. Am J Transplant. 2013; 13(9):2255-2267. doi:10.1111/ajt.12368
26. Diehl J A, Fuchs S Y, Haines D S. Ubiquitin and Cancer: New Discussions for a New Journal. Genes Cancer. 2010; 1(7):679-680. doi:10.1177/1947601910383565
27. Parkkila S, Pan P, Ward A, et al. The calcium-binding protein S100P in normal and malignant human tissues. BMC Clin Pathol. 2008; 8(1):2. doi:10.1186/1472-6890-8-2
28. Feng W, Brown R E, Trung C D, et al. Morphoproteomic profile of mTOR, Ras/Raf kinase/ERK, and NF-kappaB pathways in human gastric adenocarcinoma. Ann Clin Lab Sci. 2008; 38(3):195-209.
29. Li S, Wu Z, Ma P, et al. Ligand-dependent EphA7 signaling inhibits prostate tumor growth and progression. Cell Death Dis. 2017; 8(10):e3122. doi:10.1038/cddis.2017.507
30. Matsuzawa S I, Reed J C. Siah-1, SIP, and Ebi collaborate in a novel pathway for beta-catenin degradation linked to p53 responses. Mol Cell. 2001; 7(5):915-926.
31. Klein C, Bauersachs S, Ulbrich S E, et al. Monozygotic Twin Model Reveals Novel Embryo-Induced Transcriptome Changes of Bovine Endometrium in the Preattachment Period1. Biol Reprod. 2006; 74(2):253-264. doi:10.1095/biolreprod.105.046748
32. Blomstrom D C, Fahey D, Kutny R, Korant B D, Knight E. Molecular characterization of the interferon-induced 15-kDa protein. Molecular cloning and nucleotide and amino acid sequence. J Biol Chem. 1986; 261(19):8811-8816.
33. Morales D J, Lenschow D J. The Antiviral Activities of ISG15. J Mol Biol. 2013; 425(24):4995-5008. doi:10.1016/j.jmb.2013.09.041
34. Czarnecki O, Yang J, Weston D J, Tuskan G A, Chen J-G. A dual role of strigolactones in phosphate acquisition and utilization in plants. Int J Mol Sci. 2013; 14(4):7681-7701. doi:10.3390/ijms14047681
35. Rolli-Derkinderen M, Machavoine F, Baraban J M, Grolleau A, Beretta L, Dy M. ERK and p38 inhibit the expression of 4E-BP1 repressor of translation through induction of Egr-1. J Biol Chem. 2003; 278(21):18859-18867. doi:10.1074/jbc.M211696200
36. Zhang Z, Miao L, Xin X, et al. Underexpressed cndp2 participates in gastric cancer growth inhibition through activating the mapk signaling pathway. Mol Med. 2014; 20(1):17-28. doi:10.2119/molmed.2013.00102
37. Jansen R S, Addie R, Merkx R, et al. N-lactoyl-amino acids are ubiquitous metabolites that originate from CNDP2-mediated reverse proteolysis of lactate and amino acids. Proc Natl Acad Sci USA. 2015; 112(21):6601-6606. doi:10.1073/pnas.1424638112
38. Xue C, Zhang Z, Yu H, et al. Up-regulation of CNDP2 facilitates the proliferation of colon cancer. BMC Gastroenterol. 2014; 14(1):96. doi:10.1186/1471-230X-14-96
39. Luo G, Zhou Y, Yi W, Yi H. Lactotransferrin expression is downregulated and affects the mitogen-activated protein kinase pathway in gastric cancer. Oncol Lett. 2015; 9(5):2409-2413. doi:10.3892/ol.2015.3011
40. Deng M, Ye Q, Qin Z, et al. MiR-214 promotes tumorigenesis by targeting lactotransferrin in nasopharyngeal carcinoma. Tumor Biol. 2013; 34(3):1793-1800. doi:10.1007/s13277-013-0718-y
41. Walmer D K, Padin C J, Wrona M A, et al. Malignant transformation of the human endometrium is associated with overexpression of lactoferrin messenger RNA and protein. Cancer Res. 1995; 55(5):1168-1175. http://www.ncbi.nlm.nih.gov/pubmed/7867003. Accessed Mar. 16, 2020.
42. Hung M H, Chen K F. Reprogramming the oncogenic response: SET protein as a potential therapeutic target in cancer. Expert Opin Ther Targets. 2017; 21(7):685-694. doi:10.1080/14728222.2017.1336226
43. Shaheen N J, Falk G W, Iyer P G, Gerson L B, American College of Gastroenterology. ACG Clinical Guideline: Diagnosis and Management of Barrett's Esophagus. Am J Gastroenterol. 2016; 111(1):30-50. doi:10.1038/ajg.2015.322
44. Montgomery E, Bronner M P, Goldblum J R, et al. Reproducibility of the diagnosis of dysplasia in Barrett esophagus: A reaffirmation. Hum Pathol. 2001; 32(4):368-378. doi:10.1053/hupa.2001.23510
45. Prieto D A, Hood B L, Darfler M M, et al. Liquid Tissue: proteomic profiling of formalin-fixed tissues. Biotechniques. 2005; Suppl:32-35.

46. Haverland N A, Fox H S, Ciborowski P. Quantitative Proteomics by SWATH-MS Reveals Altered Expression of Nucleic Acid Binding and Regulatory Proteins in HIV-1-Infected Macrophages. J Proteome Res. 2014; 13(4):2109-2119. doi:10.1021/pr4012602
47. Salcedo R, Cataisson C, Hasan U, Yuspa S H, Trinchieri G. MyD88 and its divergent toll in carcinogenesis. Trends Immunol. 2013; 34(8):379-389. doi:10.1016/j.it.2013.03.008
48. Ayyappan S, Prabhakar D, Sharma N. Epidermal growth factor receptor (EGFR)-targeted therapies in esophagogastric cancer. Anticancer Res. 2013; 33(10):4139-4155.
49. Prins M J D, Ruurda J P, van Diest P J, van Hillegersberg R, ten Kate F J W. The significance of the HER-2 status in esophageal adenocarcinoma for survival: an immunohistochemical and an in situ hybridization study†. Ann Oncol. 2013; 24(5):1290-1297. doi:10.1093/annonc/mds640
50. Hedner C, Borg D, Nodin B, Karnevi E, Jirström K, Eberhard J. Expression and Prognostic Significance of Human Epidermal Growth Factor Receptors 1 and 3 in Gastric and Esophageal Adenocarcinoma. PLoS One. 2016; 11(2):e0148101. doi:10.1371/journal.pone.0148101
51. Kalinina T, Bockhorn M, Kaifi J T, et al. Insulin-like growth factor-1 receptor as a novel prognostic marker and its implication as a cotarget in the treatment of human adenocarcinoma of the esophagus. Int J Cancer. 2010; 127(8):1931-1940. doi:10.1002/ijc.25196
52. Jardim D L F, de Melo Gagliato D, Falchook G S, et al. MET aberrations and c-MET inhibitors in patients with gastric and esophageal cancers in a phase I unit. Oncotarget. 2014; 5(7):1837-1845. doi:10.18632/oncotarget.1828
53. Lamberts L E, de Groot D J A, Bense R D, de Vries E G E, Fehrmann R S N. Functional genomic mRNA profiling of a large cancer data base demonstrates mesothelin overexpression in a broad range of tumor types. Oncotarget. 2015; 6(29):28164-28172. doi:10.18632/oncotarget.4461
54. Wakita A, Motoyama S, Nanjo H, et al. PD-L1 Expression Is a Prognostic Factor in Patients with Thoracic Esophageal Cancer Treated Without Adjuvant Chemotherapy. Anticancer Res. 2017; 37(3):1433-1442. doi:10.21873/anticanres.11467
55. Miura J T, Xiu J, Thomas J, et al. Tumor profiling of gastric and esophageal carcinoma reveal different treatment options. Cancer Biol Ther. 2015; 16(5):764. doi:10.1080/15384047.2015.1026479

Example 2. Target Feasibility and Assay Development for Targeted Mass Spectrometry Target peptides for UBE2N, DAD1, ISG15, CNDP2, GPI, SET, LTF, and S100P were designed, generated, and evaluated for target feasibility and to develop assays for targeted mass spectrometry.

UBE2N

UBE2N (UniProt P61088) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 7, which are unique to UBE2N, were chosen.

TABLE 7

Unique UBE2N peptides.

| Sequence | UBE2N Isoform | Post-Translational Modifications | Start Position | End Position |
|---|---|---|---|---|
| LLAEPVPGIK (SEQ ID NO: 1) | 1 | K24-ub, K24-sm, K24-sc | 15 | 24 |
| AEPDESNAR (SEQ ID NO: 2) | 1 | | 25 | 33 |
| YFHVVIAGPQDSPFEGGTFK (SEQ ID NO: 3) | 1 | Y34-p, S45-p, K53-ac | 34 | 53 |
| IYHPNVDK (SEQ ID NO: 4) | 1 | K82-ac, K82-ub | 75 | 82 |
| WSPALQIR (SEQ ID NO: 5) | 1 | | 95 | 102 |
| TNEAQAIETAR (SEQ ID NO: 6) | 1 | T139-p, R141-m1 | 131 | 141 |

Figure 12A:
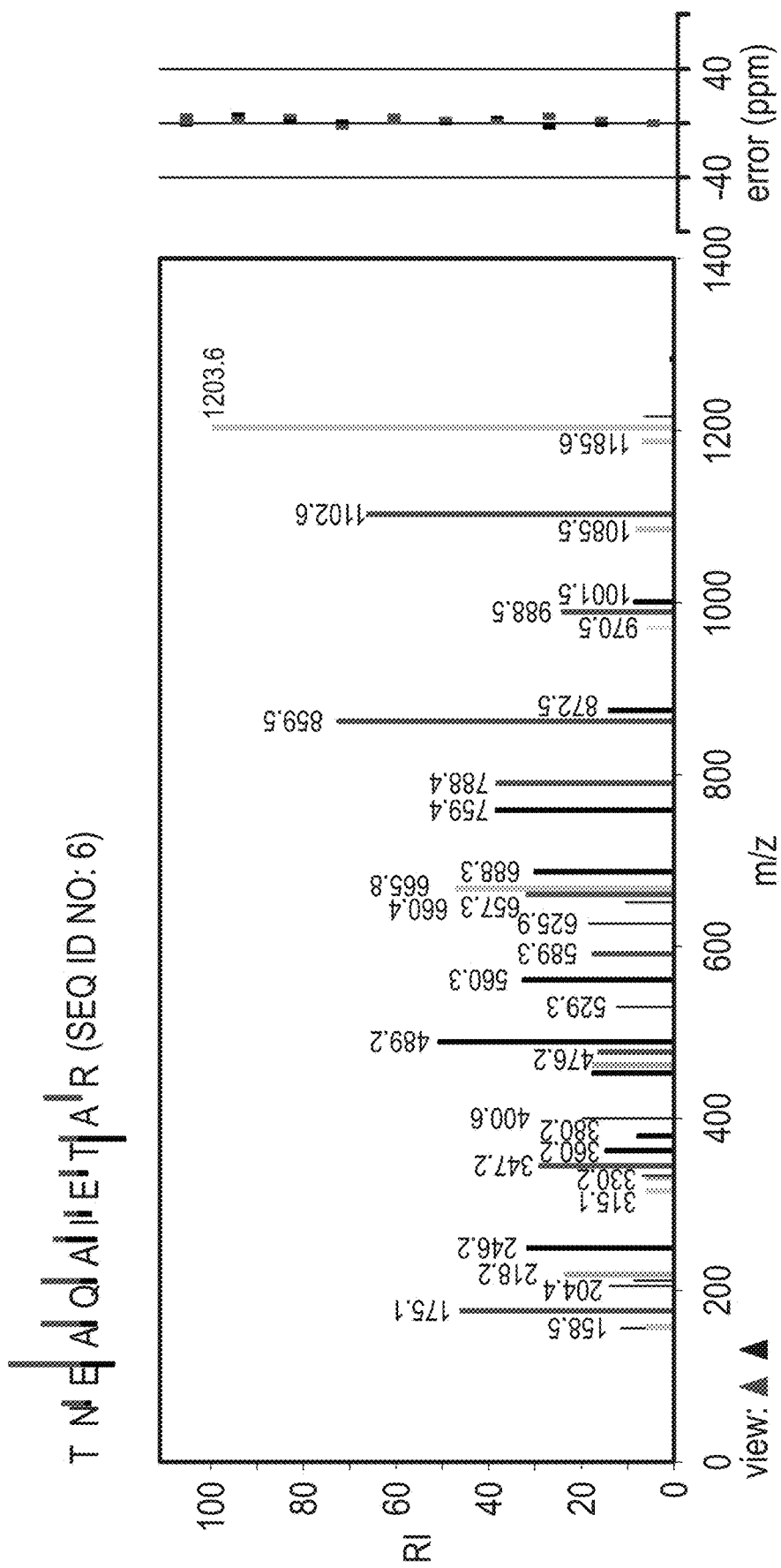
FIGS. 12A-12B. Representative tandem mass spectrometry spectra of the UBE2N protein in human samples using UBE2N peptides.
Figure 12B:
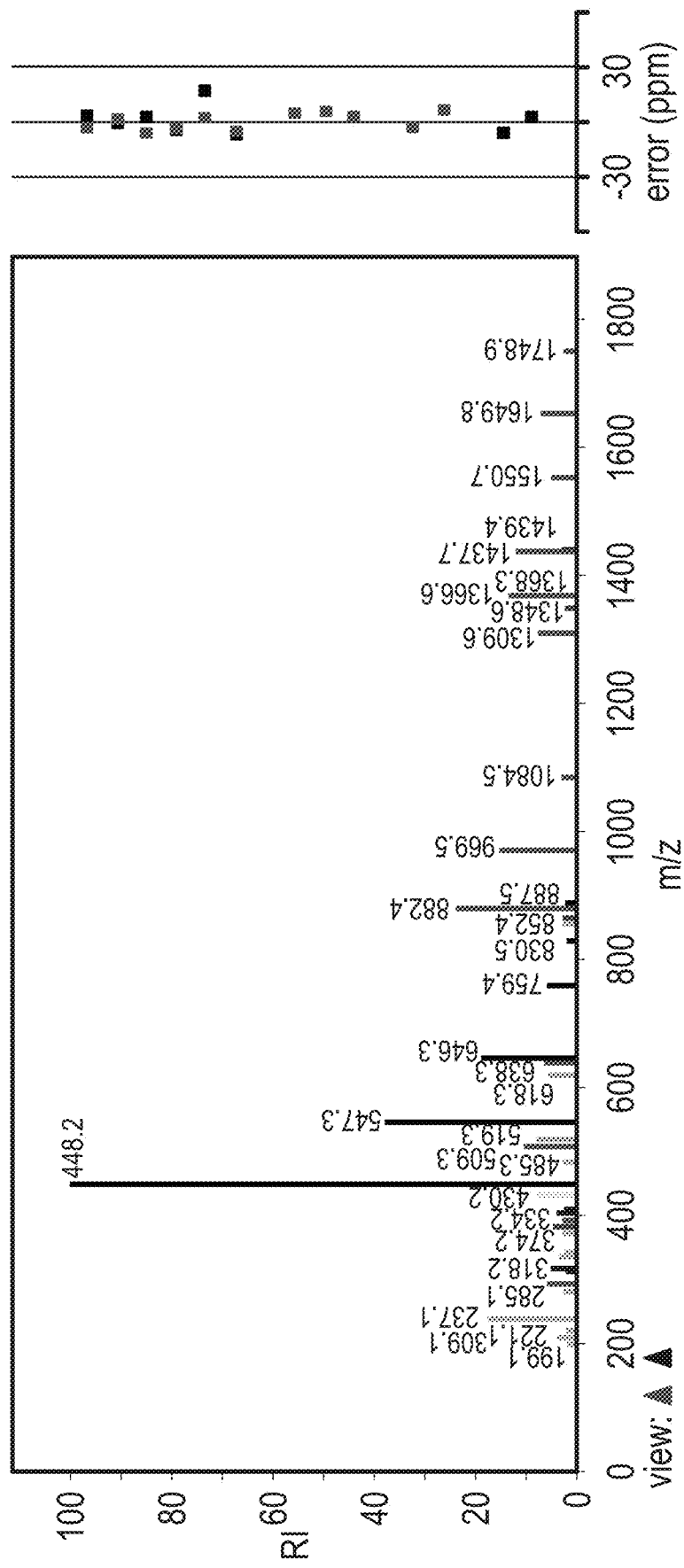
Figure 13A:
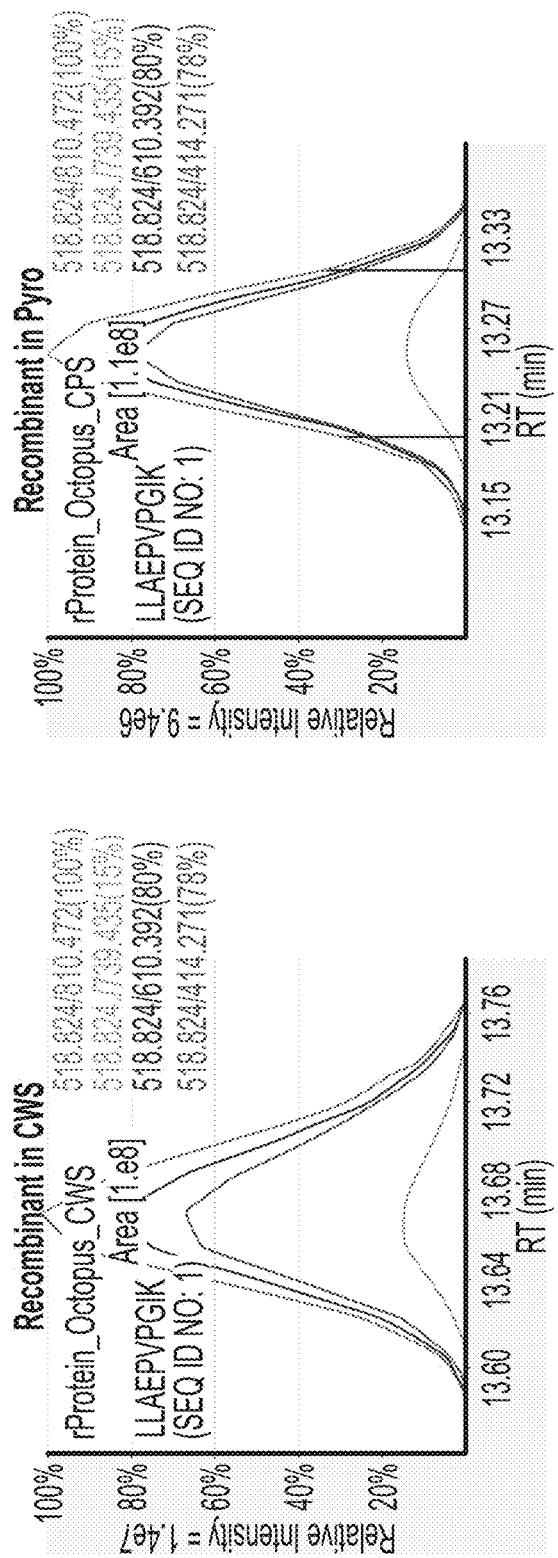
FIGS. 13A-13F. Detection of recombinant UBE2N peptides in carrier working solution (CWS) and a solution with *Pyrococcus* (pyro), and detection of UBE2N peptides in formalin-fixed paraffin-embedded esophageal adenocarcinoma tissues.
Figure 13A:
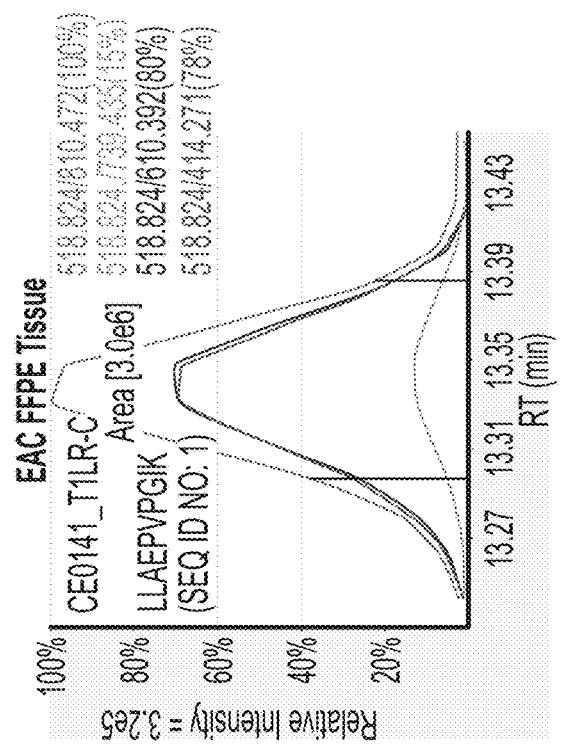
Figure 13B:
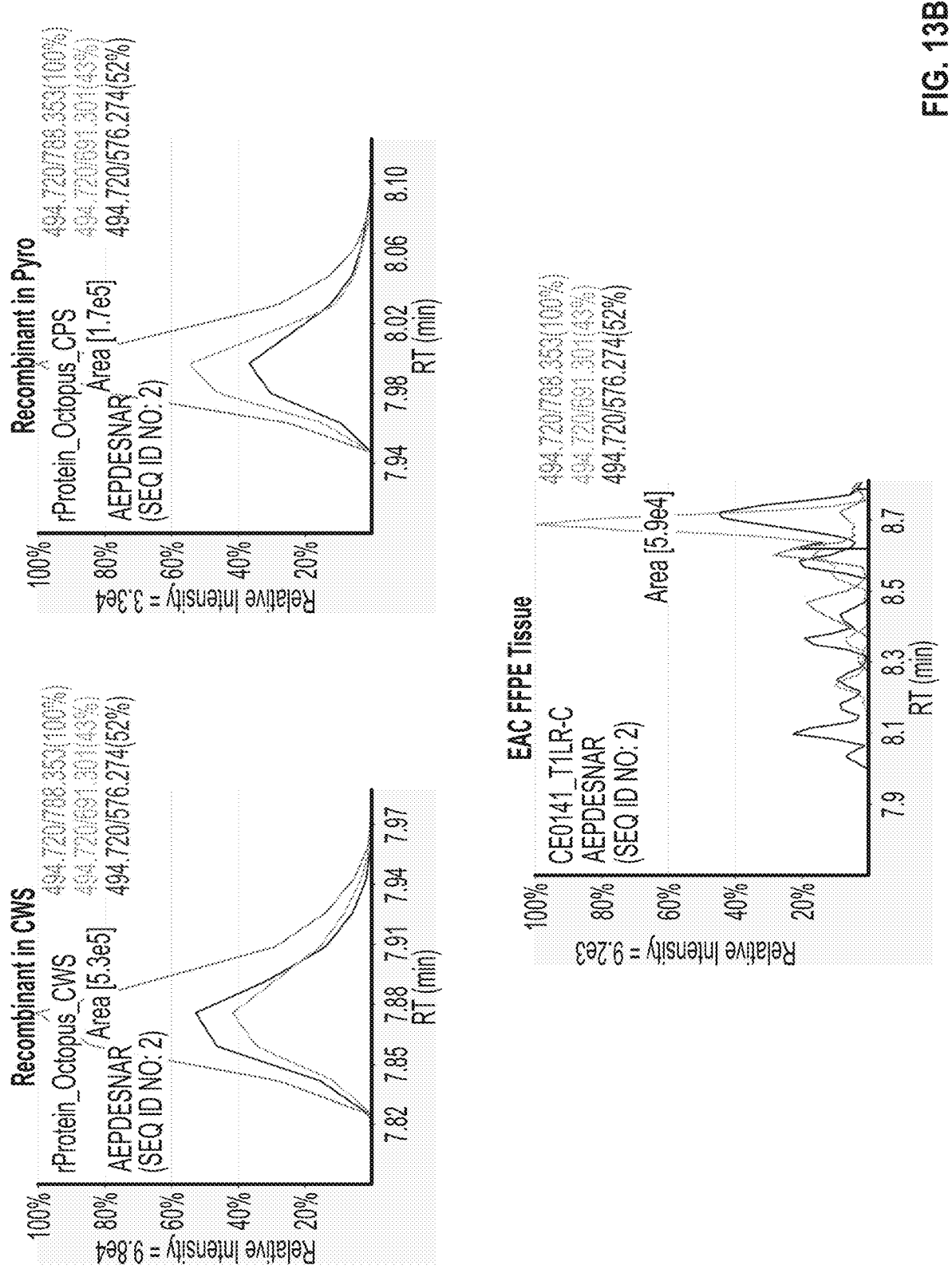
Figure 13C:
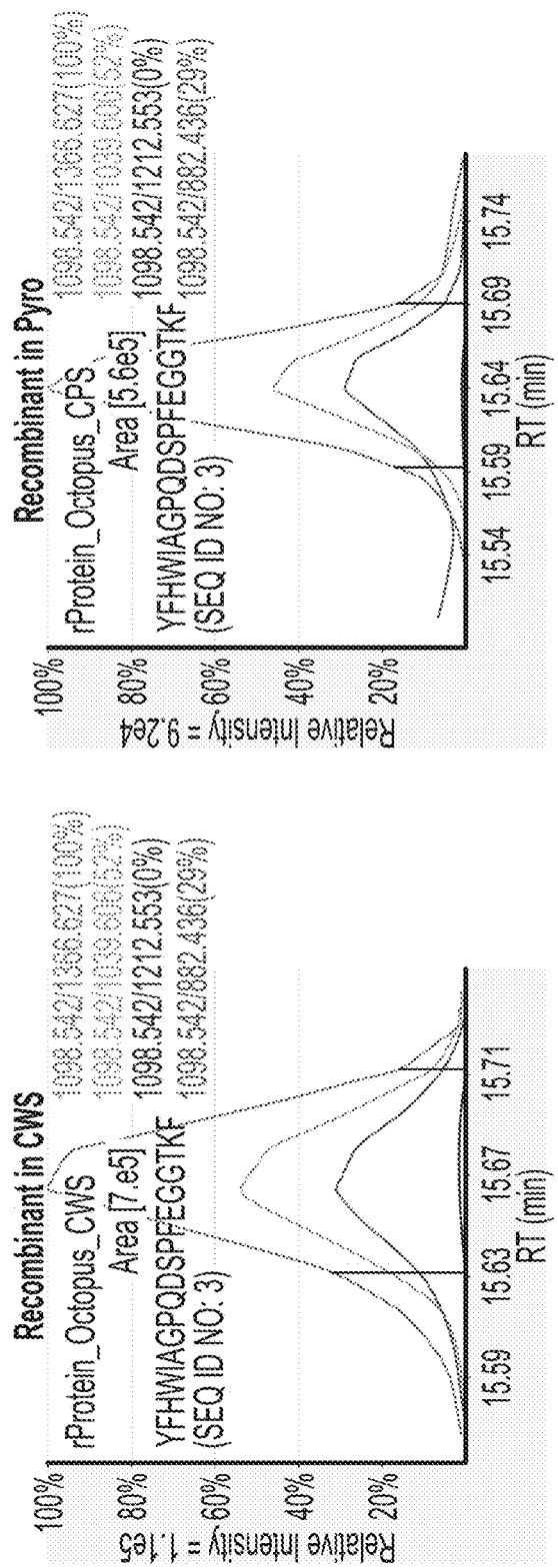
Figure 13C:
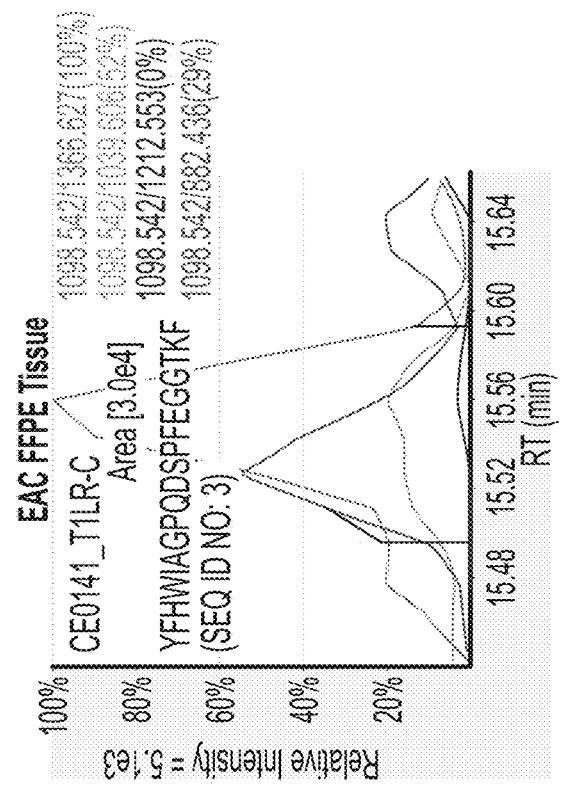
Figure 13D:
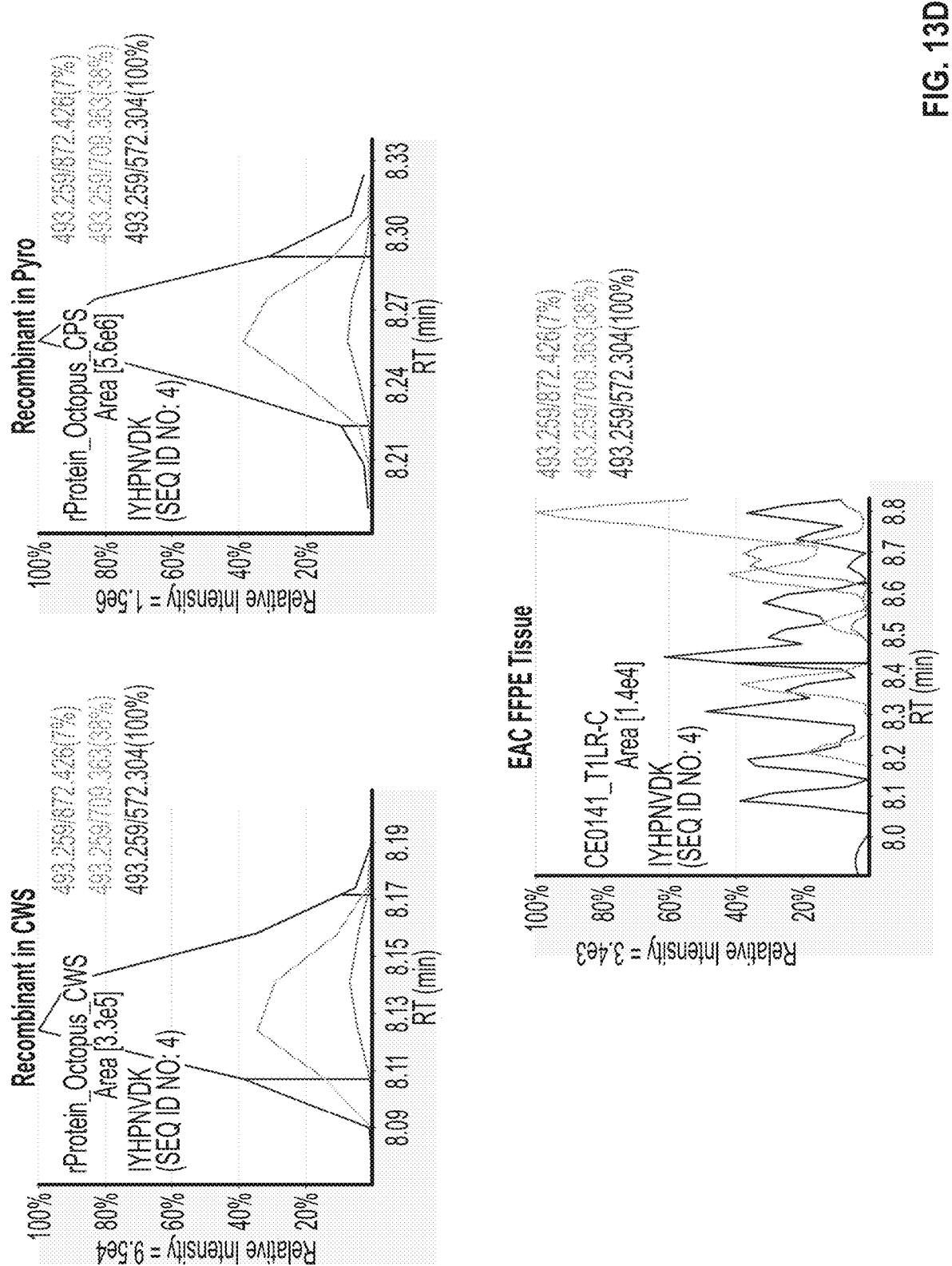
Figure 13E:
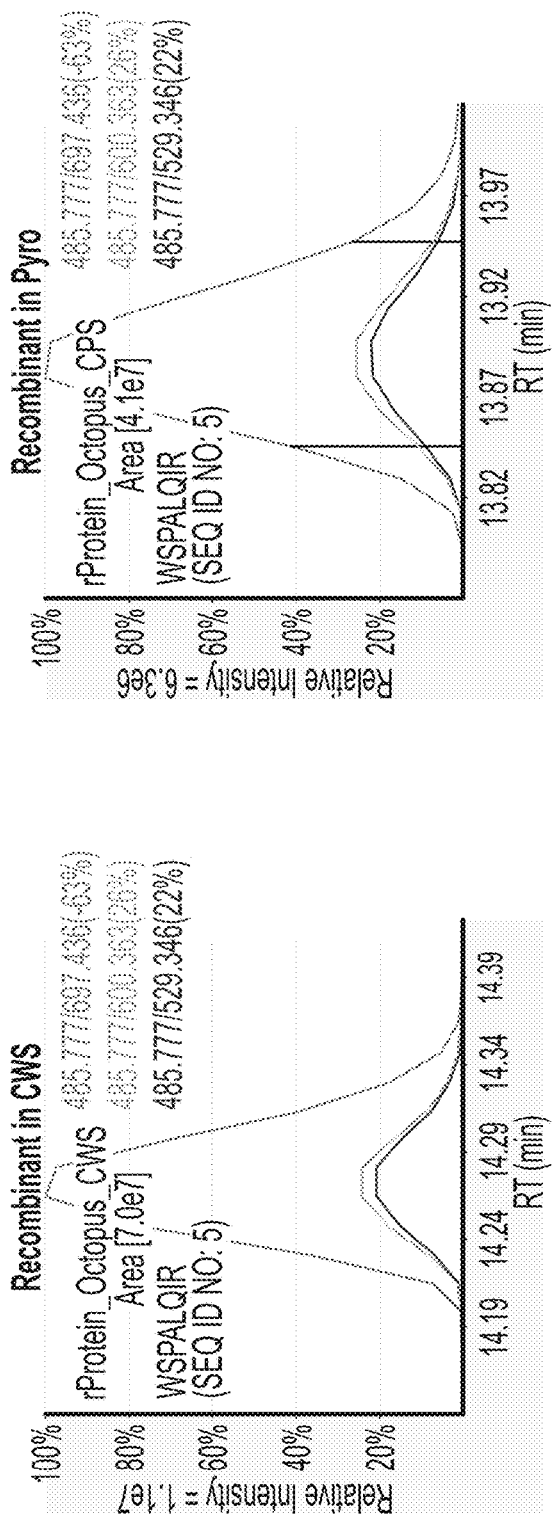
Figure 13E:
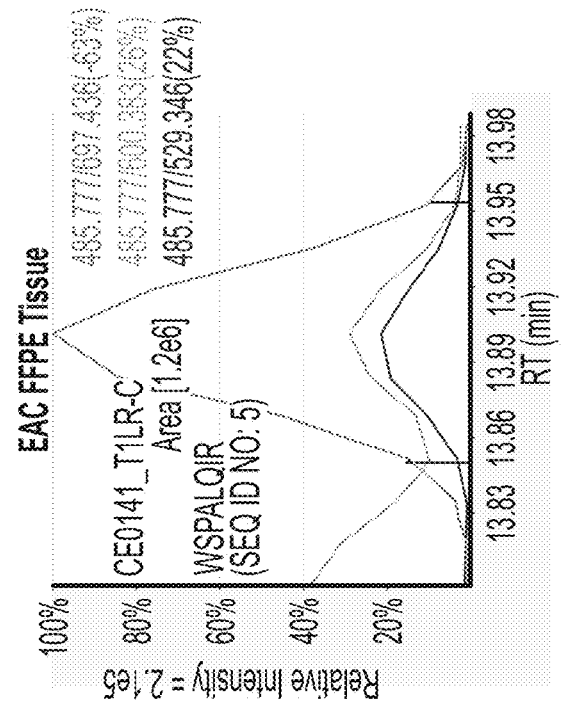
Figure 13F:
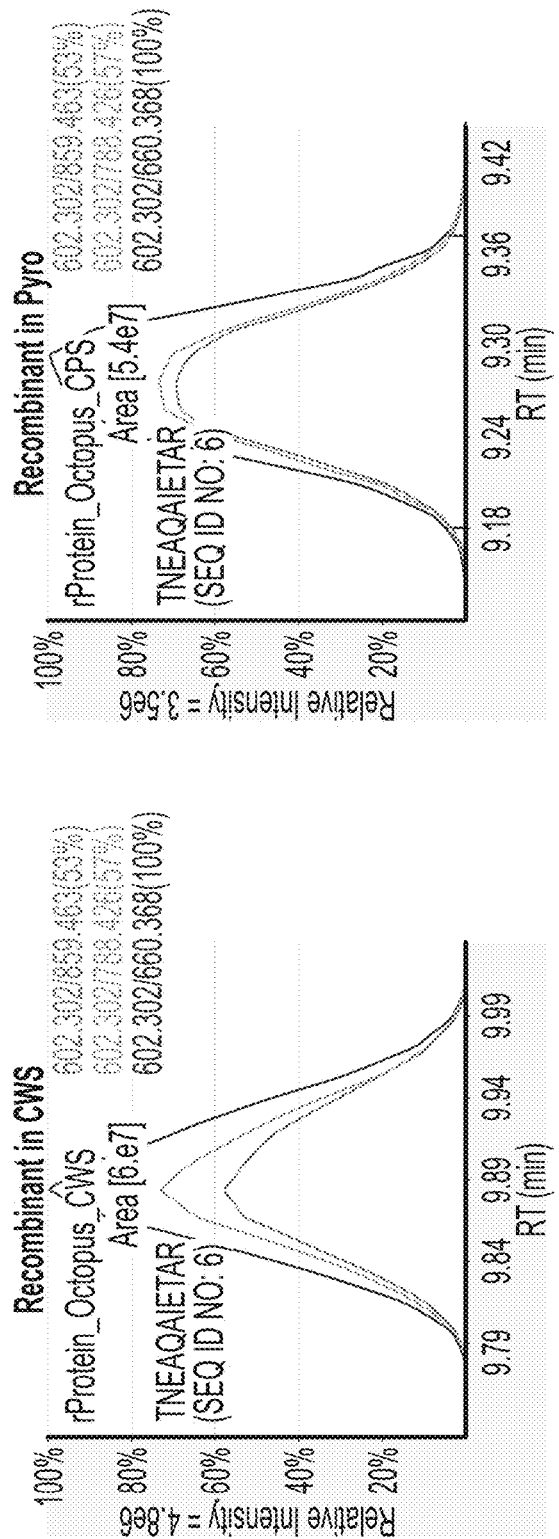
Figure 13F:
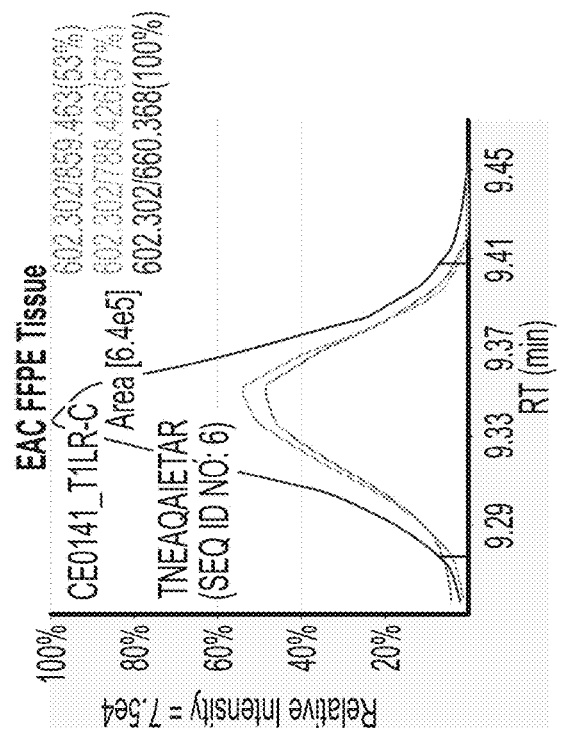

Representative tandem mass spectrometry spectra of the UBE2N protein in human samples using two of these peptides are shown in FIGS. 12A-12B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant UBE2N protein was used to screen unique peptides for SRM development. Specifically, 2 µg of human recombinant UBE2N protein was added to Liquid Tissue Buffer and treated with 0.5 µg of trypsin for 16 hours at 37° C. for a final concentration of 20 ng/µL. The reaction tube was heated at 95° C. for 5 minutes to inactivate trypsin. After hydrolysis, 2 µL of the UBE2N tryptic digests were mixed with 20 µL of carrier working solution (CWS), 5 µL HSM (to obtain retention time across the samples) and 23 µL of 0.1% formic acid of which 10 µL was injected for MS analysis. The data in Table 8 show the intensity that was observed in the MS analysis within this relatively simple matrix. In addition, 2 L of the UBE2N tryptic digests were mixed with 5 µg of *Pyrococcus* (to observe the performance of the peptide in a more complex matrix), 5 µL HSM and 0.1% formic acid to a final volume of 50 µL of which 10 µL was injected for MS analysis as well. The data in Table 8 show the intensity that was observed in the MS analysis within this more complex matrix. In addition, the data in Table 8 show the intensity that was observed in a very complex lysate containing FFPE tissue from an esophageal adenocarcinoma tumor sample.

Specifically, 2 μg of human recombinant DAD1 protein was added to Liquid Tissue Buffer and treated with 0.5 μg of trypsin for 16 hours at 37° C. for a final concentration of 20 ng/μL. The reaction tube was heated at 95° C. for 5 minutes

TABLE 8

Trypsin digestion mapping.

| Sequence | Recombinant Intensity in CWS | Recombinant Intensity in Pyro | FFPE EAC Intensity |
|---|---|---|---|
| LLAEPVPGIK (SEQ ID NO: 1) | 1e7 | 9e6 | 3e5 |
| AEPDESNAR (SEQ ID NO: 2) | 9e4 | 3e4 | ND |
| YFHVVIAGPQDSPFEGGTFK (SEQ ID NO: 3) | 1e5 | 9e4 | ND |
| IYHPNVDK (SEQ ID NO: 4) | 9e4 | 1e6 | ND |
| WSPALQIR (SEQ ID NO: 5) | 1e7 | 6e6 | 2e5 |
| TNEAQAIETAR (SEQ ID NO: 6) | 4e6 | 3e6 | 7e4 |

Detection of the peptides in the protein digest is shown in FIGS. 13A-13F. Of the six unique peptides screened, three peptides were observed in all seven FFPE ECA tissues screened. Peptides LLAEPVPGIK (SEQ ID NO: 1) and WSPALQIR (SEQ ID NO: 5) showed high intensity and consistent product ion ratios in the recombinant protein and FFPE ECA tissues.

DAD1

DAD1 (UniProt P61803) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 9, which are unique to DAD1, were chosen.

to inactivate trypsin. After hydrolysis, 2 μL of the DAD1 tryptic digests were mixed with 20 μL of carrier working solution (CWS), 5 μL HSM (to obtain retention time across the samples) and 23 μL of 0.1% formic acid of which 10 μL was injected for MS analysis. The data in Table 10 show the intensity that was observed in the MS analysis within this relatively simple matrix. In addition, 2 L of the DAD1 tryptic digests were mixed with 5 μg of *Pyrococcus* (to observe the performance of the peptide in a more complex matrix), 5 μL HSM and 0.1% formic acid to a final volume of 50 μL of which 10 μL was injected for MS analysis as well. The data in Table 10 show the intensity that was observed in the MS analysis within this more complex matrix. In addition, the data in Table 10 show the intensity that was observed in a very complex lysate containing FFPE tissue from an esophageal adenocarcinoma tumor sample.

TABLE 9

Unique DAD1 peptides.

| Sequence | DAD1 Isoform | Post-Translational Modifications | Start Position | End Position |
|---|---|---|---|---|
| FLEEYLSSTPQR (SEQ ID NO: 7) | 1 | Y16-p, S18-p, T20-p | 12 | 23 |
| IQINPQNK (SEQ ID NO: 8) | 1 | K82-ub | 75 | 82 |
| ADFQGISPER (SEQ ID NO: 9) | 1 | | 83 | 92 |

Figure 14A:
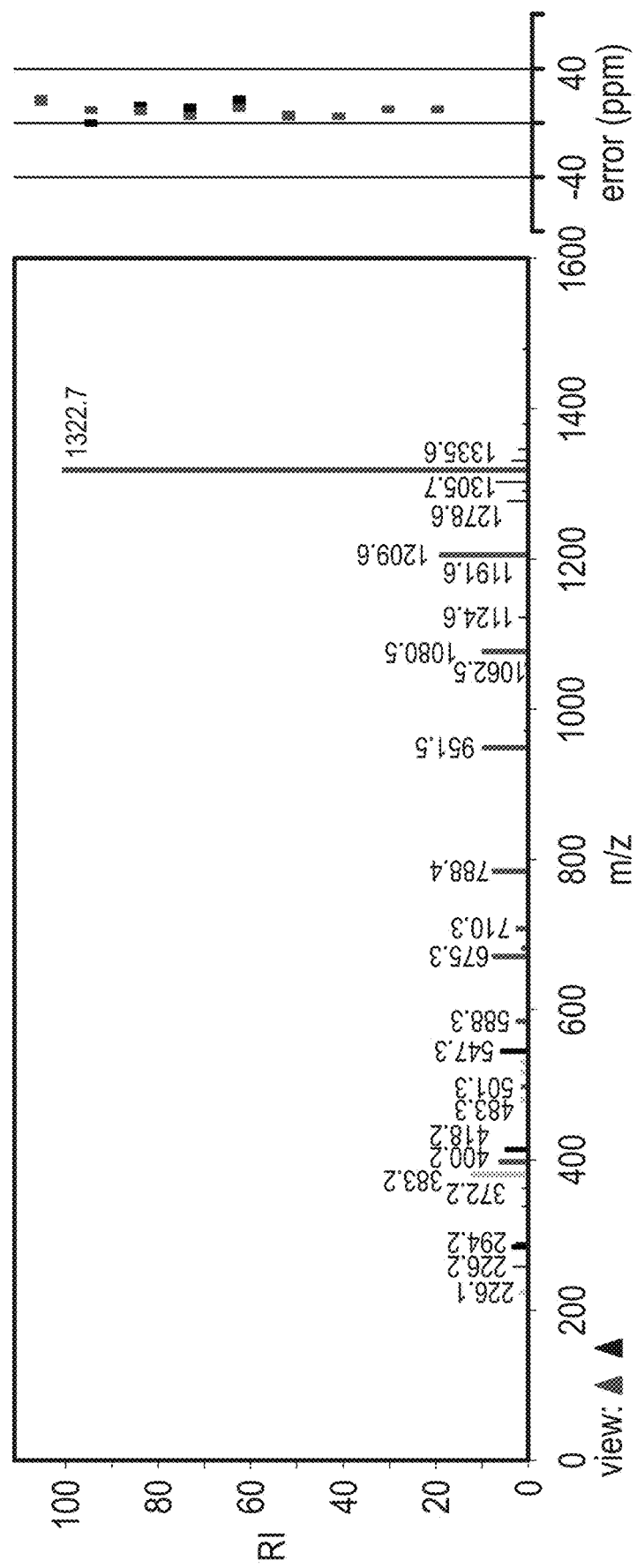
FIGS. 14A-14C. Representative tandem mass spectrometry spectra of the DAD1 protein in human samples using DAD1 peptides.
Figure 14B:
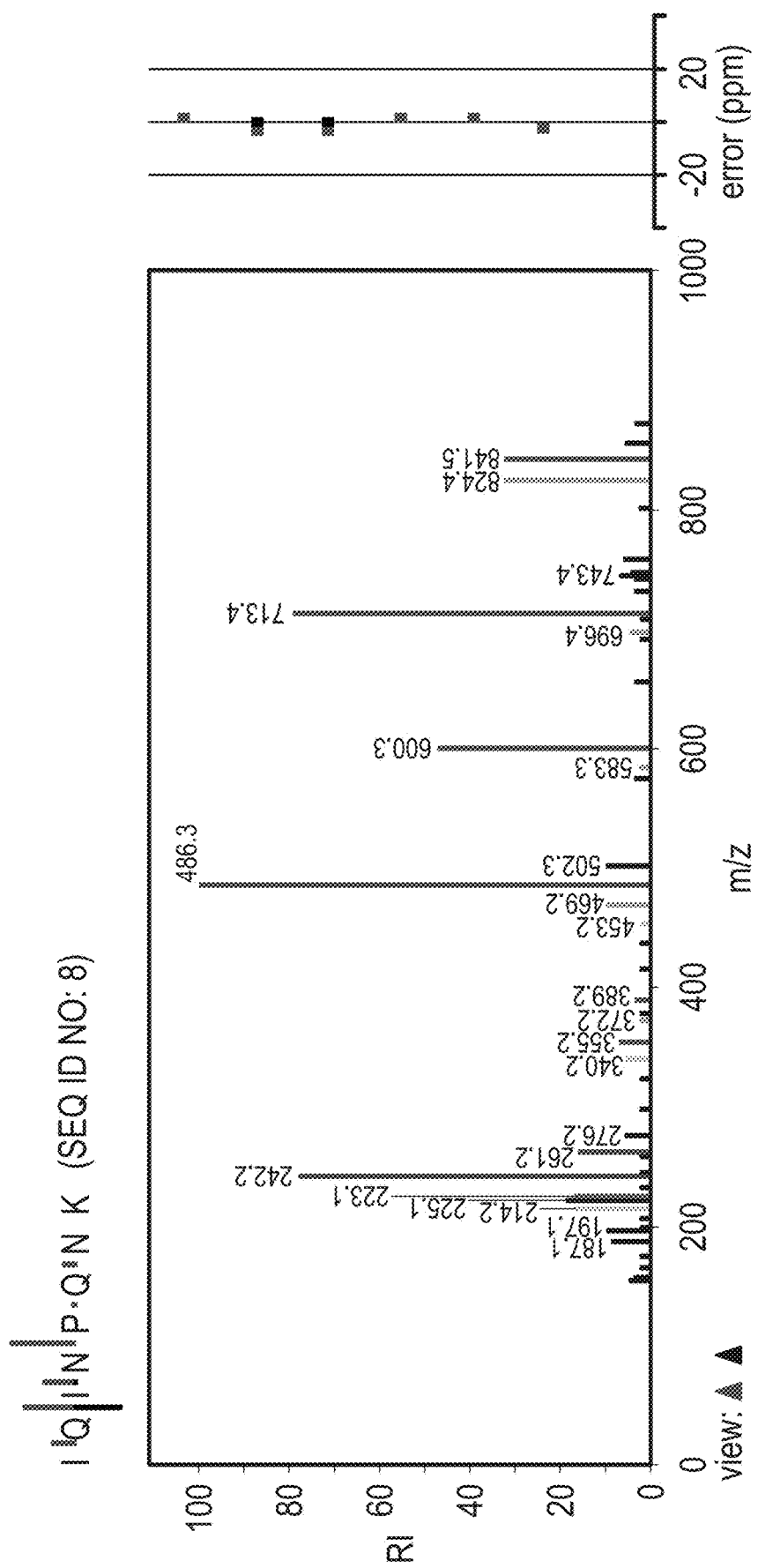
Figure 14C:
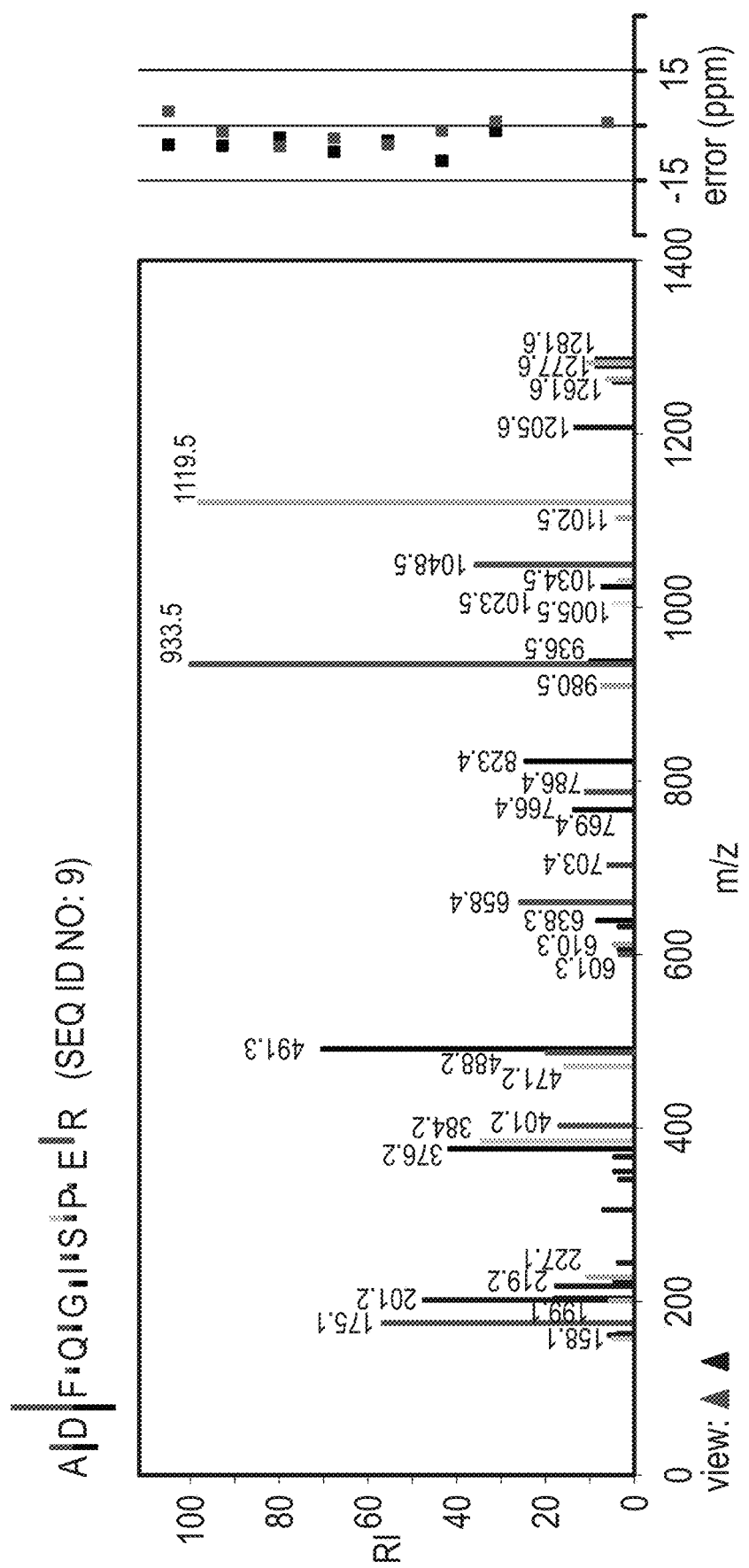

Representative tandem mass spectrometry spectra of the DAD1 protein in human samples using these peptides are shown in FIGS. 14A-14C. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant DAD1 protein was used to screen unique peptides for SRM development.

TABLE 10

Trypsin digestion mapping.

| Sequence | Recombinant Intensity in CWS | Recombinant Intensity in Pyro | FFPE EAC Intensity |
|---|---|---|---|
| FLEEYLSSTPQR (SEQ ID NO: 7) | 1e6 | 2e6 | 1e5 |

TABLE 10-continued

Trypsin digestion mapping.

| Sequence | Recombinant Intensity in CWS | Recombinant Intensity in Pyro | FFPE EAC Intensity |
|---|---|---|---|
| IQINPQNK (SEQ ID NO: 8) | 1e5 | 1e6 | ND |
| ADFQGISPER (SEQ ID NO: 9) | 4e6 | 3e6 | 1e5 |

Figure 15A:
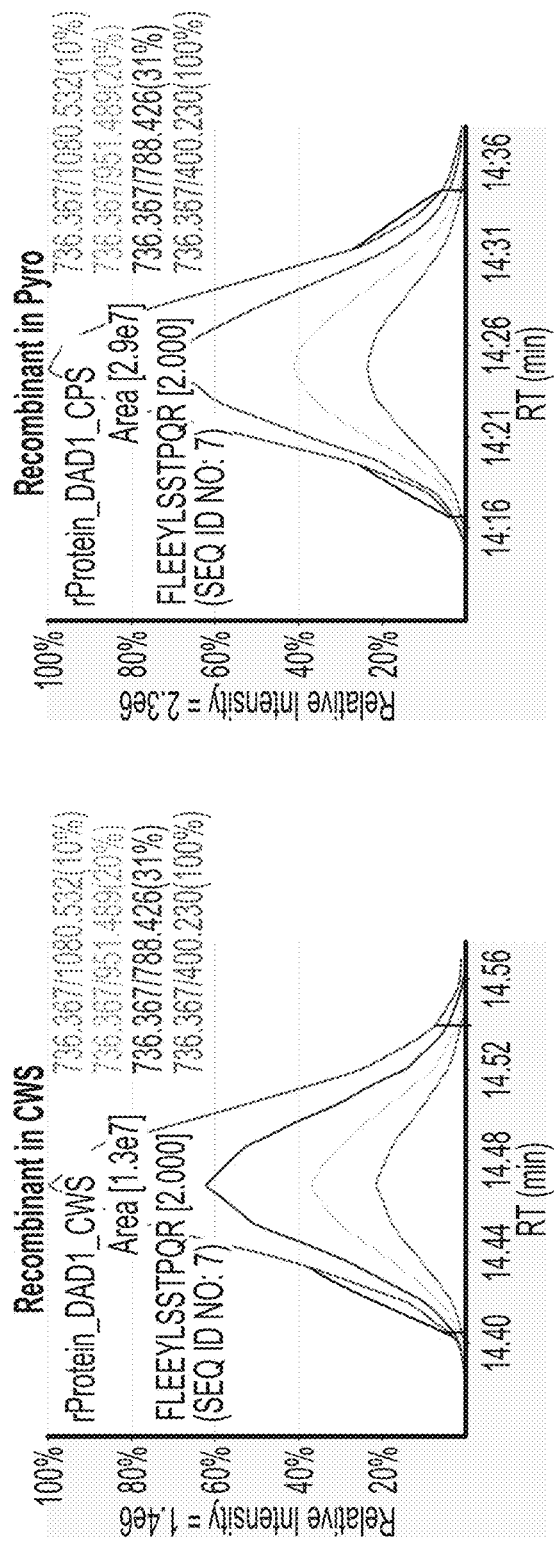
FIGS. 15A-15C. Detection of recombinant DAD1 peptides in carrier working solution (CWS) and a solution with *Pyrococcus* (pyro), and detection of DAD1 peptides in formalin-fixed paraffin-embedded esophageal adenocarcinoma tissues.
Figure 15A:
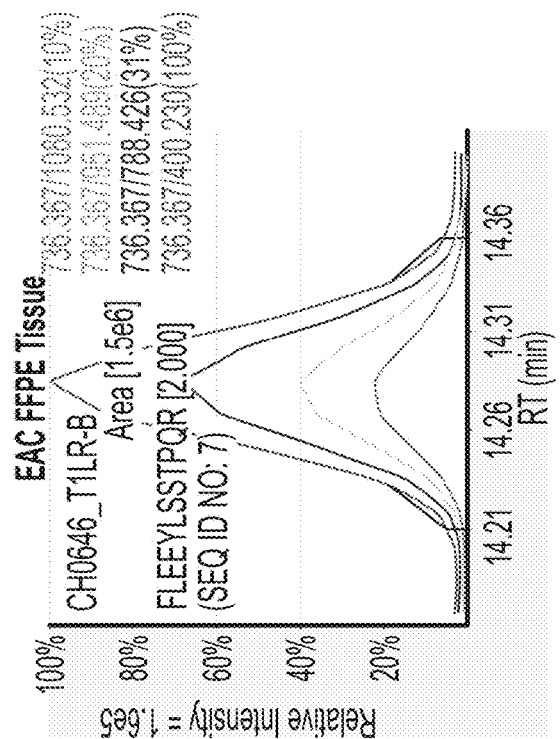
Figure 15B:
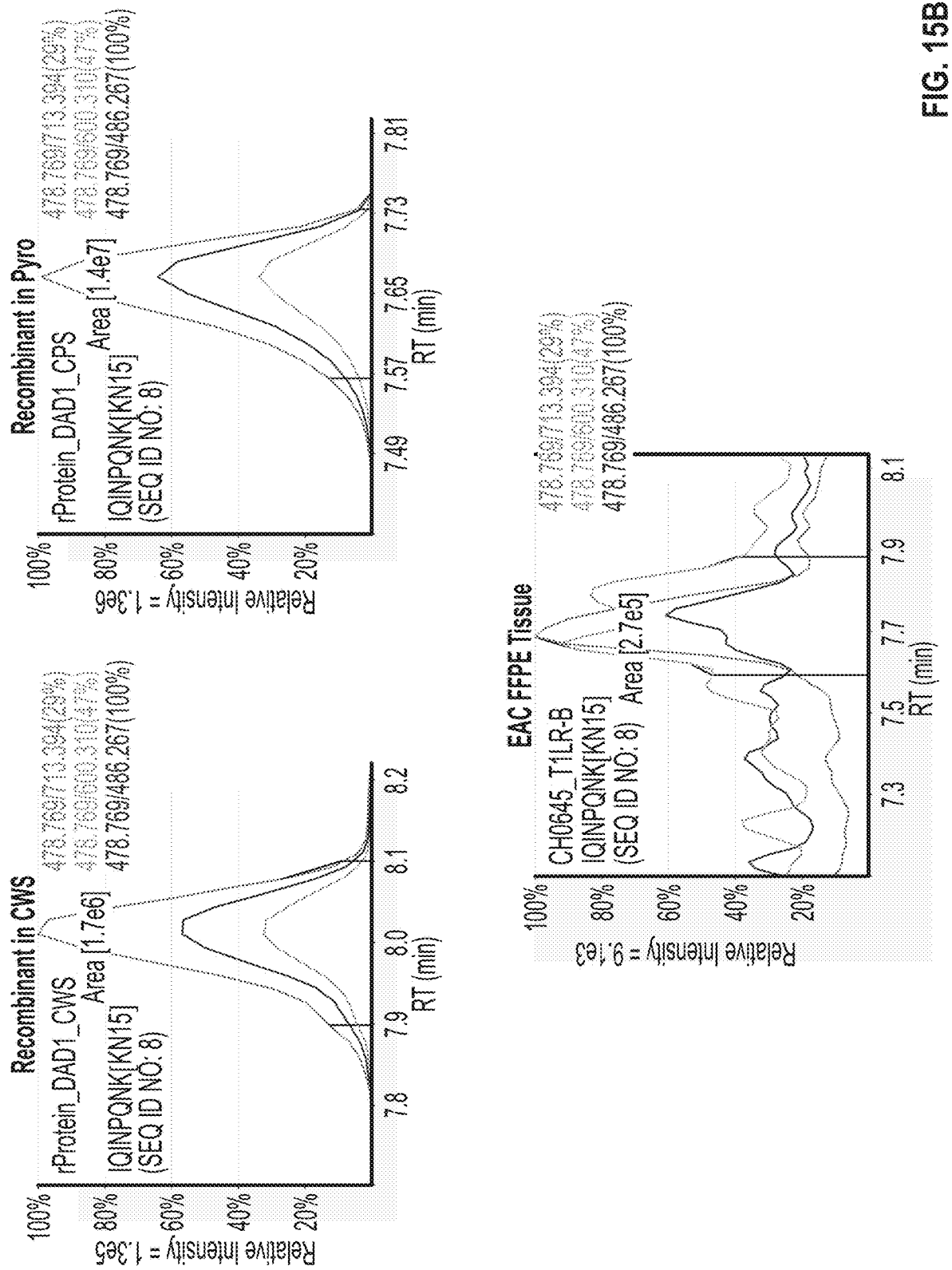
Figure 15C:
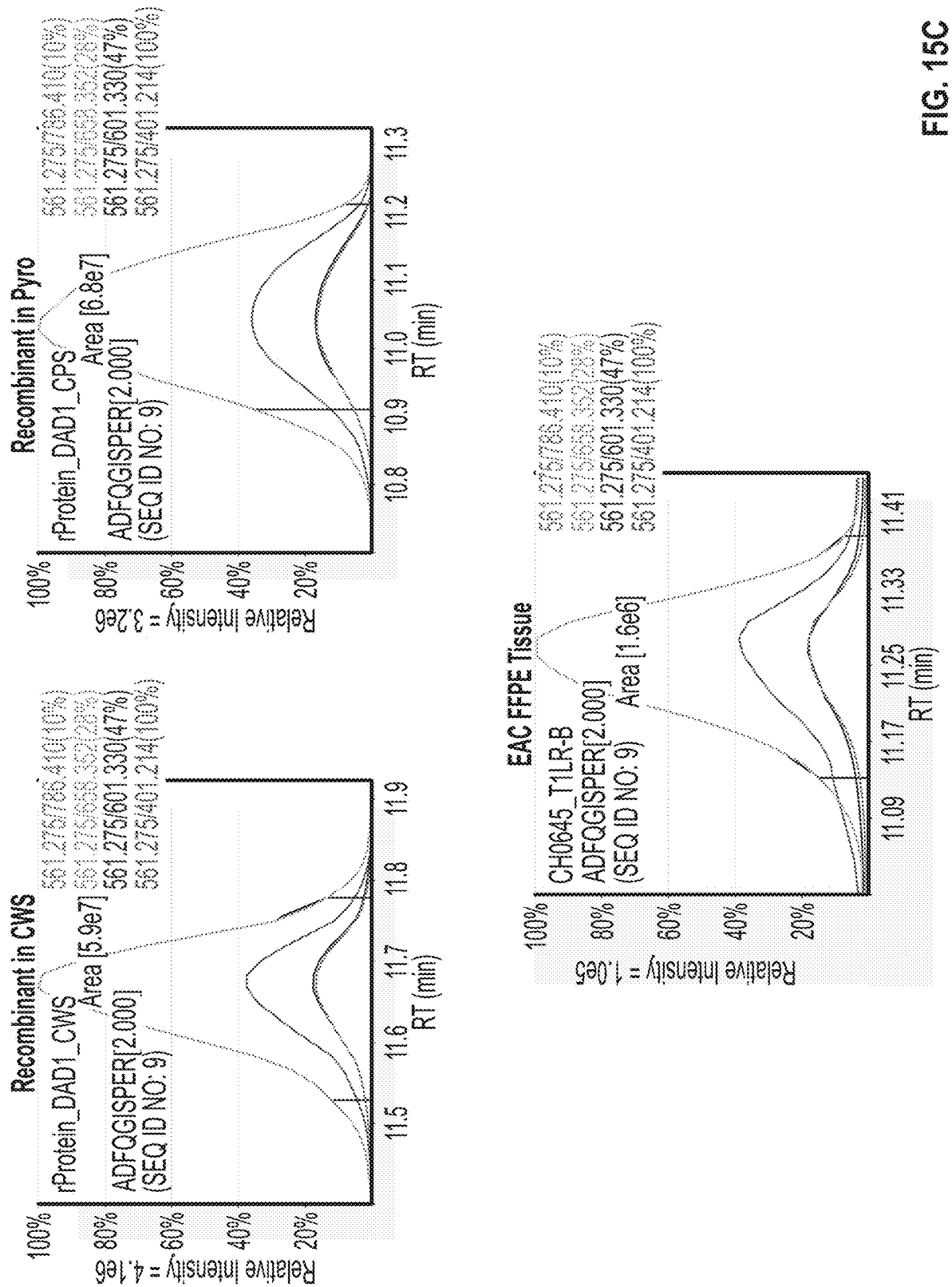

Detection of the peptides in the protein digest is shown in FIGS. 15A-15C. Of the three unique peptides screened, two peptides were observed in at least one FFPE ECA tissue. Peptides FLEEYLSSTPQR (SEQ ID NO: 7) and ADFQ-GISPER (SEQ ID NO: 9) showed high intensity and consistent product ion ratios in the recombinant protein and FFPE ECA tissues.

ISG15

ISG15 (UniProt P05161) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 11, which are unique to ISG15, were chosen.

TABLE 11

Unique ISG15 peptides.

| Sequence | ISG15 Isoform | Post-Translational Modifications | Start Position | End Position |
|---|---|---|---|---|
| AQITQK (SEQ ID NO: 10) | 1 | K35-ub | 30 | 35 |
| IGVHAFQQR (SEQ ID NO: 11) | 1 | | 36 | 44 |
| LAVHPSGVALQDR (SEQ ID NO: 12) | 1 | S50-p | 45 | 57 |
| VPLASQGLGPGSTVLLVVDK (SEQ ID NO: 13) | 1 | | 58 | 77 |
| SSTYEVR (SEQ ID NO: 14) | 1 | | 93 | 99 |
| LTQTVAHLK (SEQ ID NO: 15) | 1 | | 100 | 108 |
| GGGTEPGGR (SEQ ID NO: 16) | 1 | | 156 | 164 |

Figure 16A:
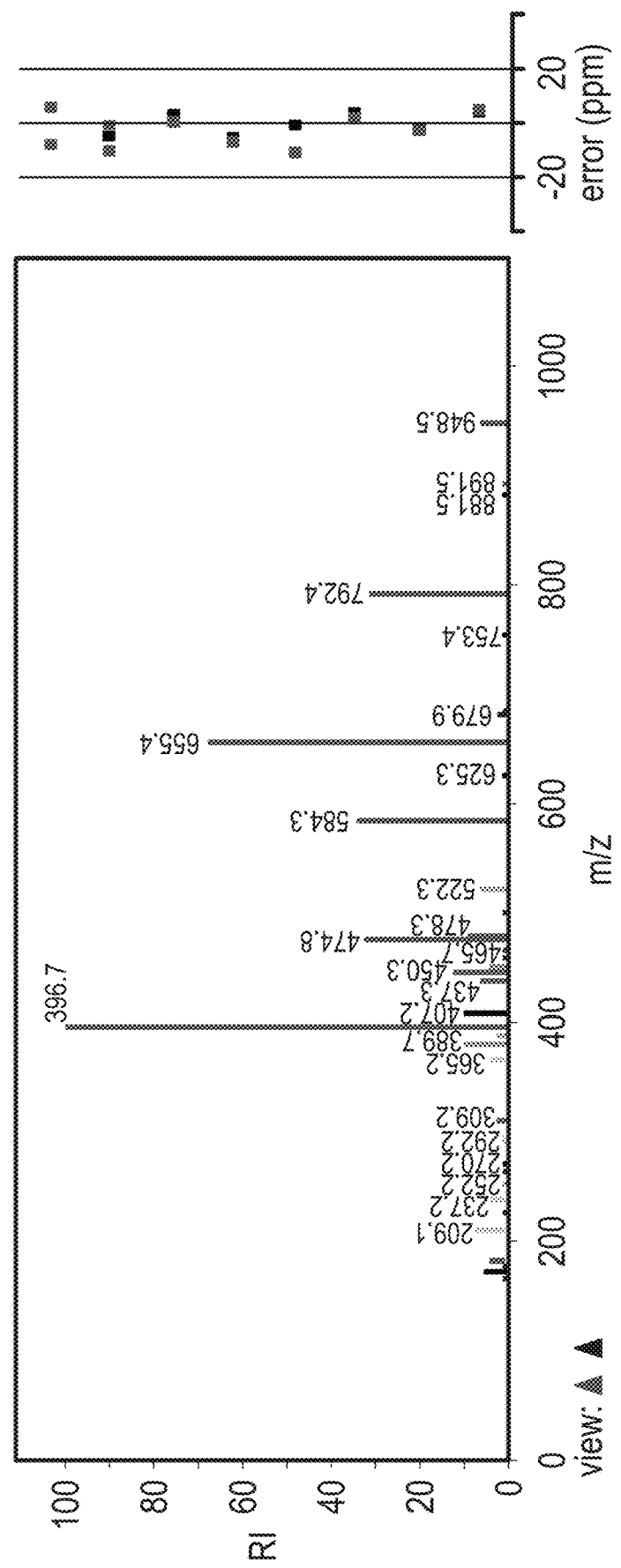
FIGS. 16A-16B. Representative tandem mass spectrometry spectra of the ISG15 protein in human samples using ISG15 peptides.
Figure 16B:
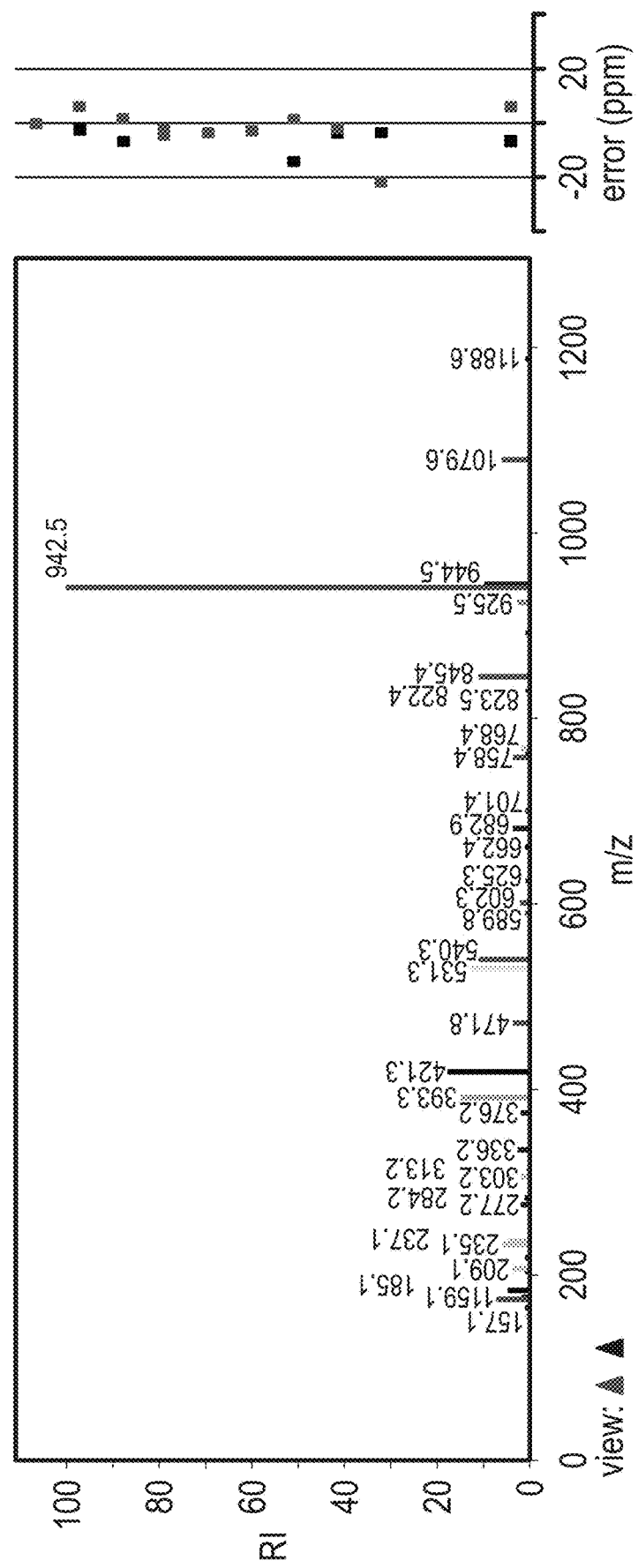
Figure 17A:
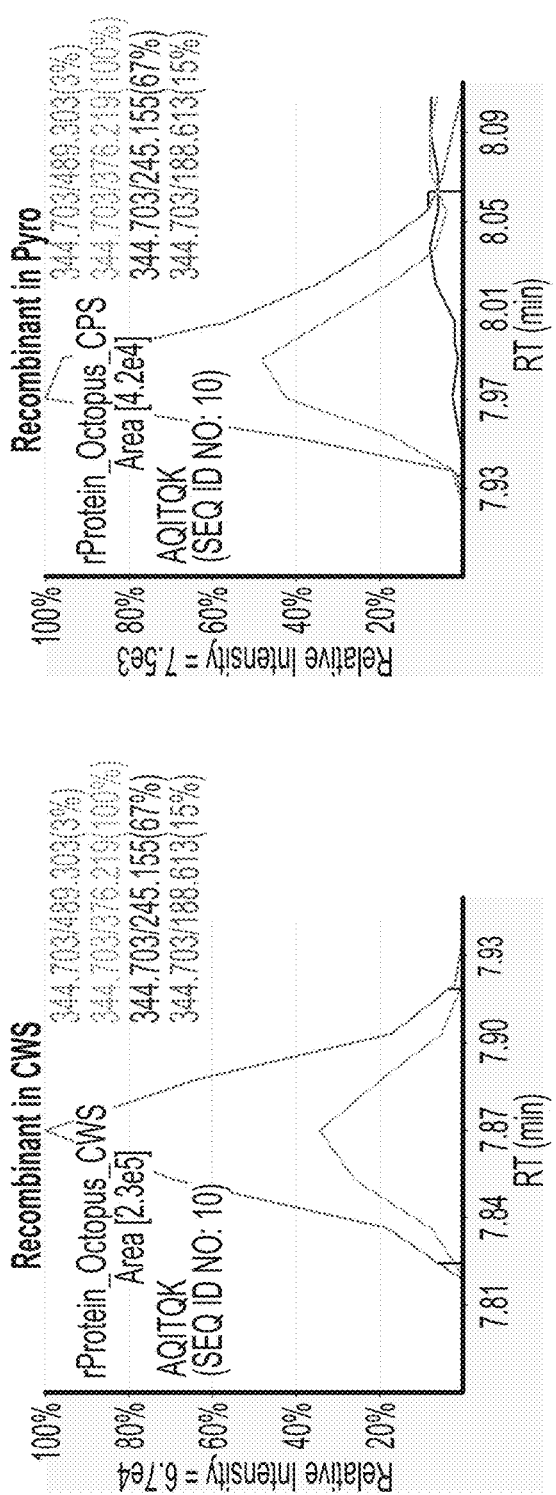
FIGS. 17A-17G. Detection of recombinant ISG15 peptides in carrier working solution (CWS) and a solution with *Pyrococcus* (pyro), and detection of ISG15 peptides in formalin-fixed paraffin-embedded esophageal adenocarcinoma tissues.
Figure 17A:
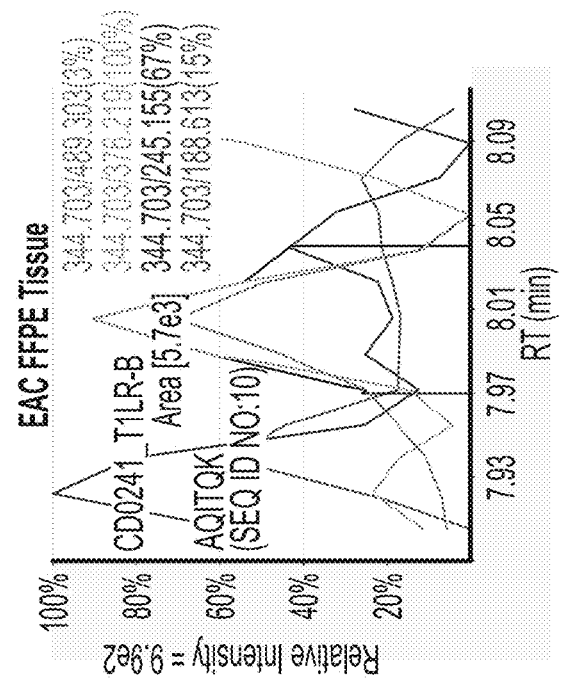
Figure 17B:
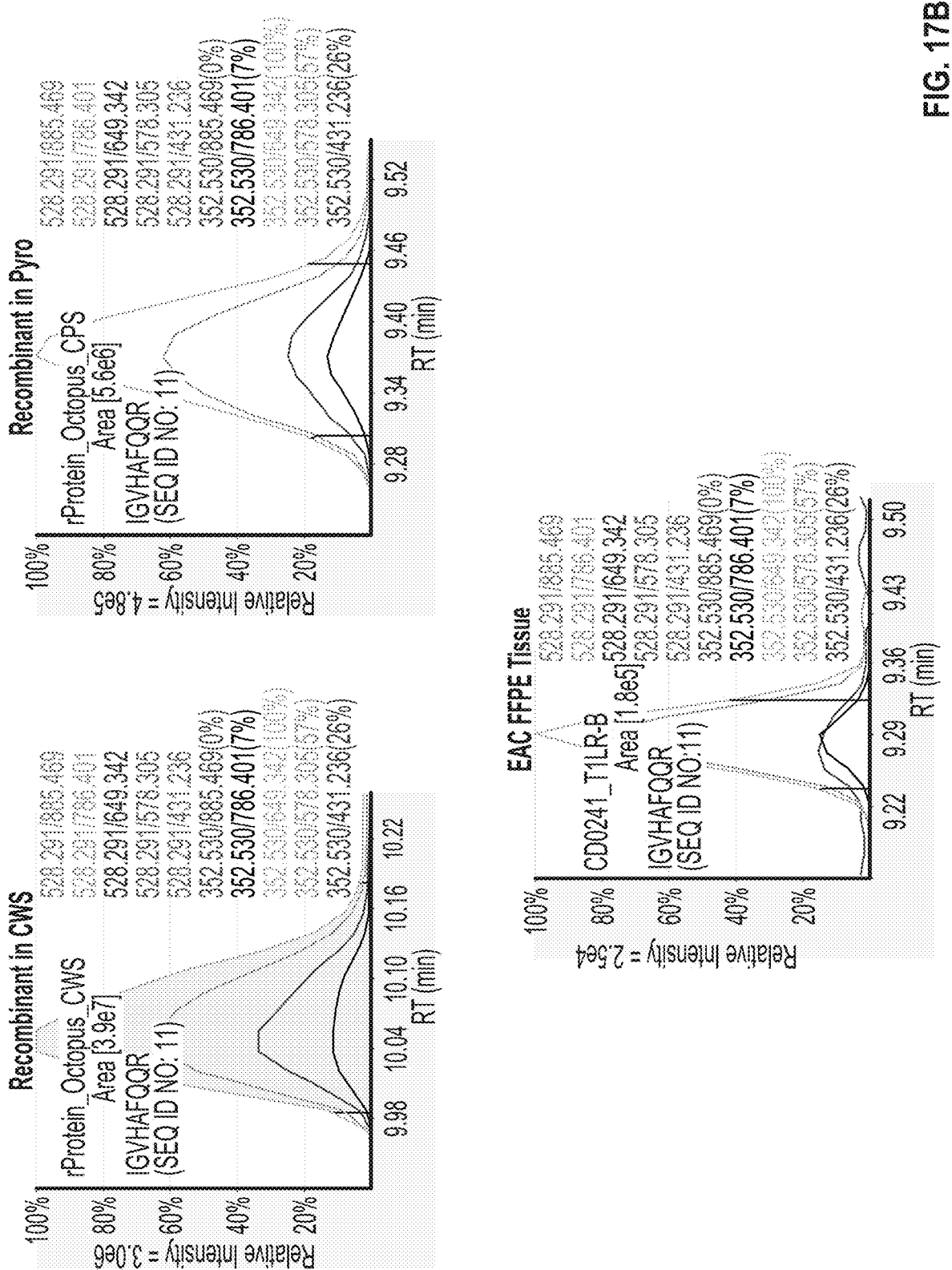
Figure 17C:
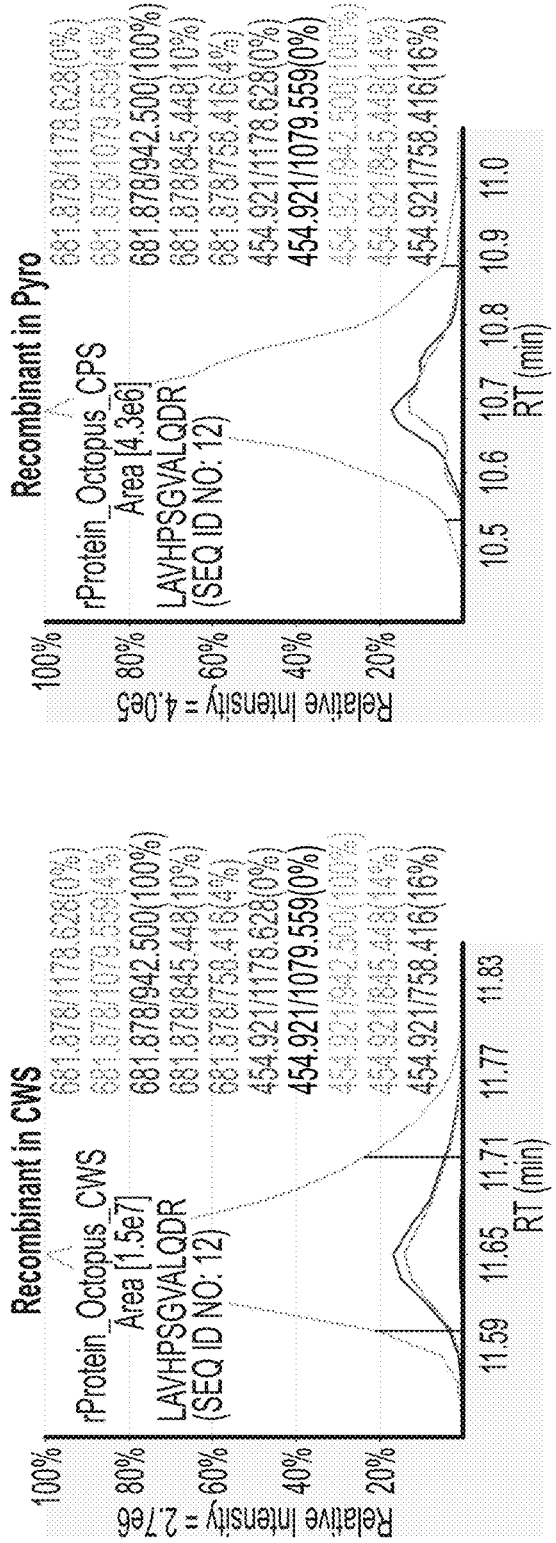
Figure 17C:
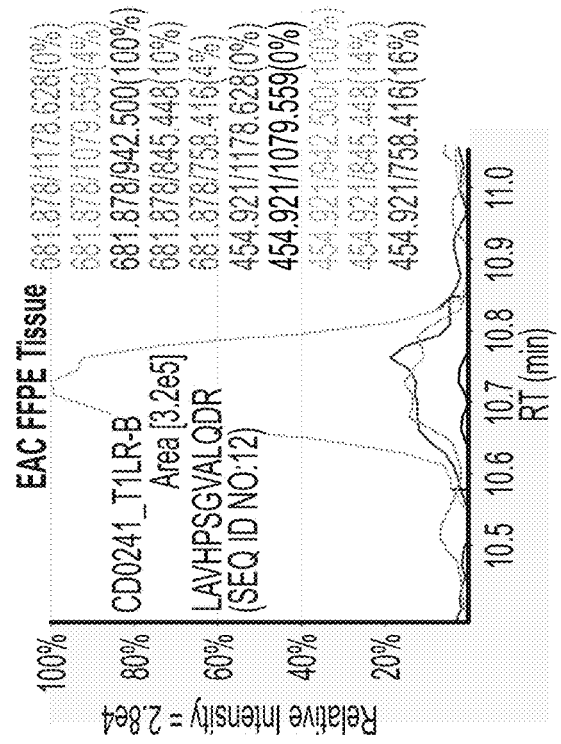
Figure 17D:
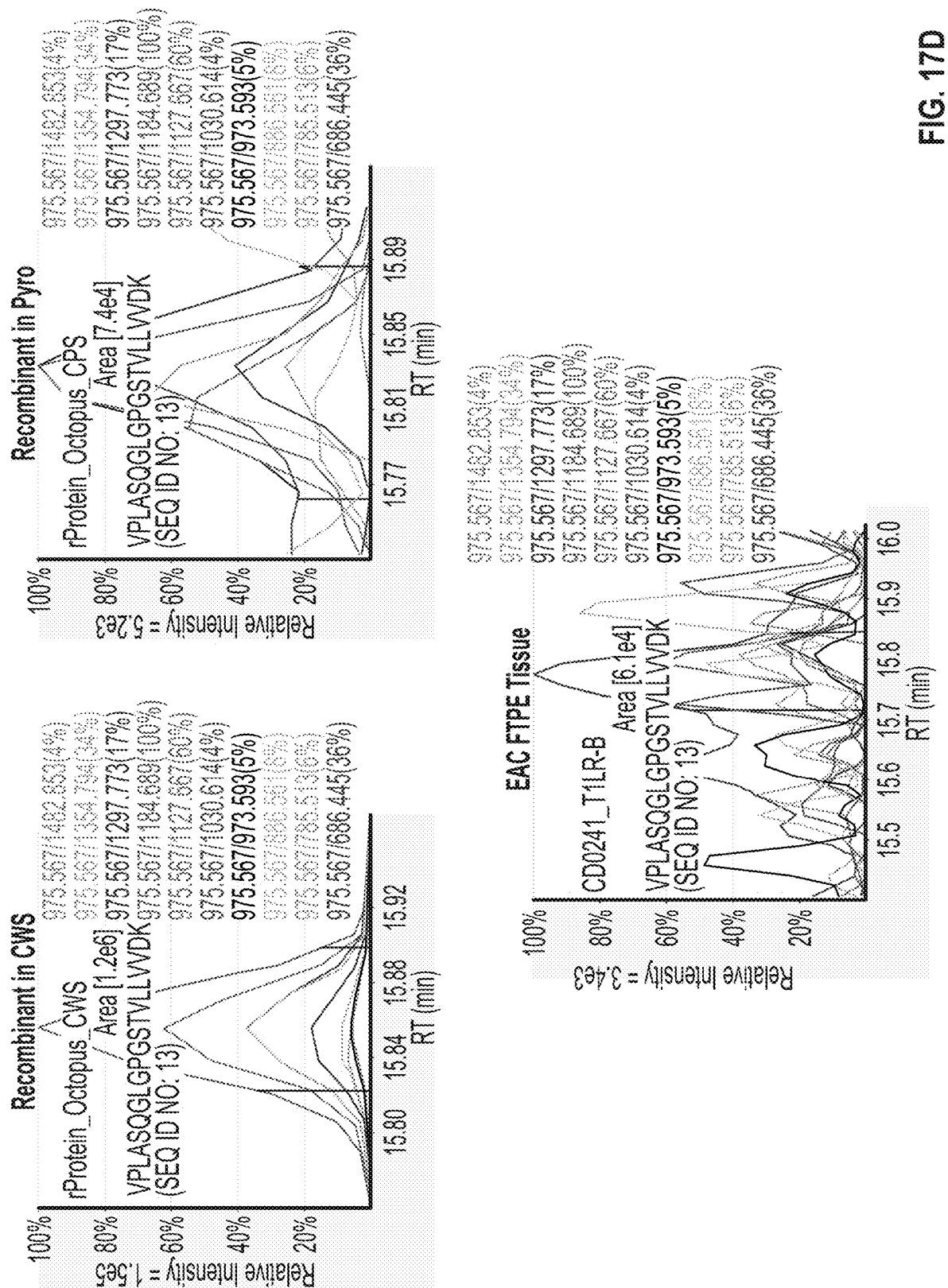
Figure 17E:
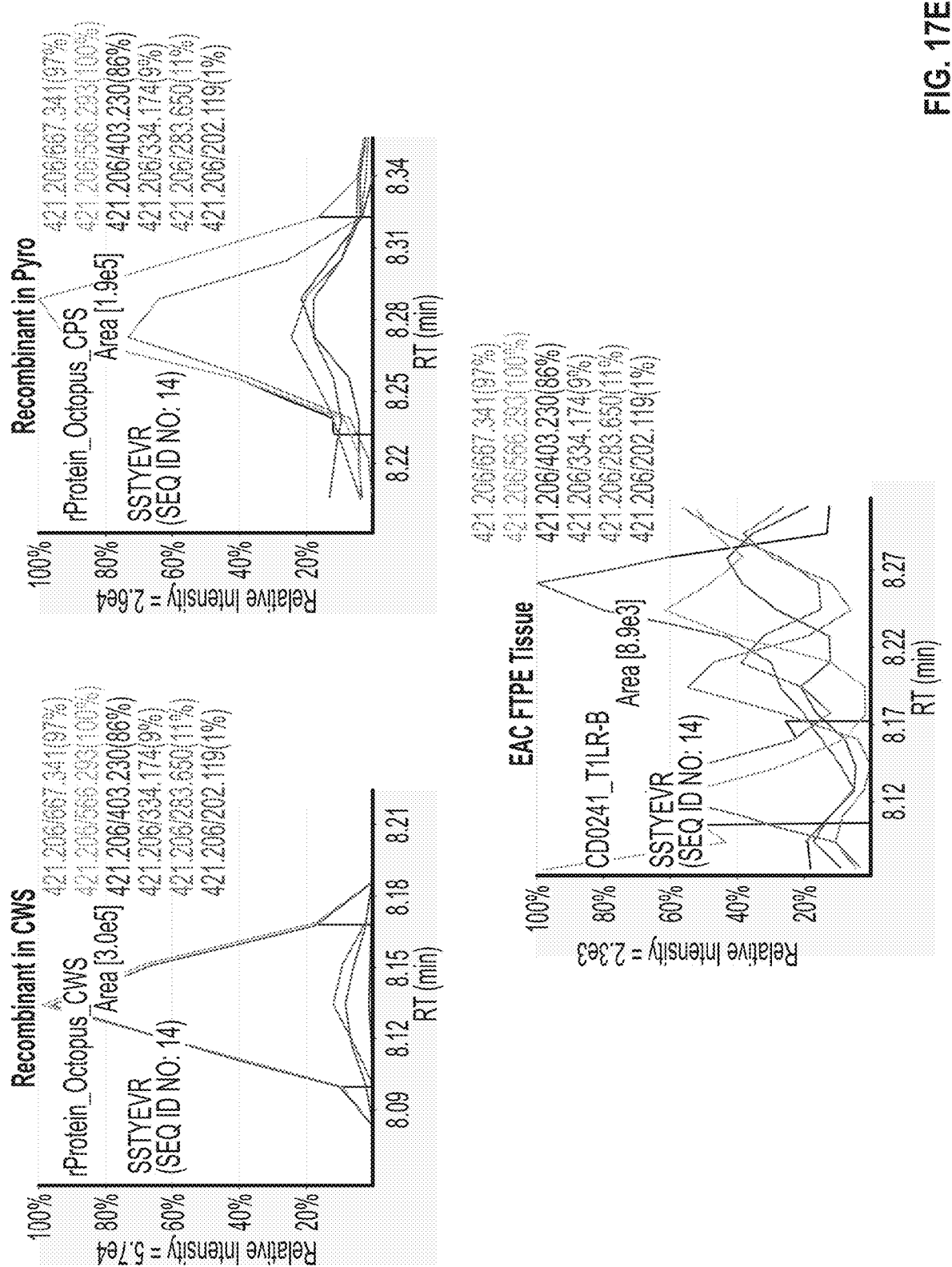
Figure 17F:
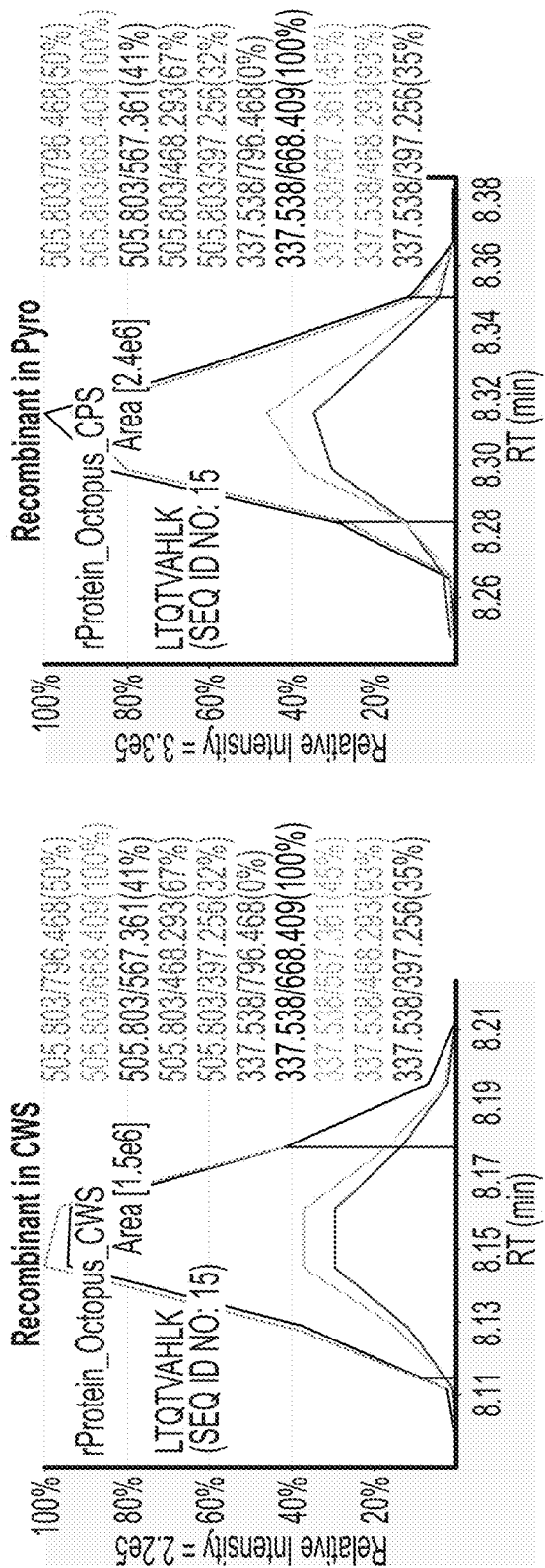
Figure 17F:
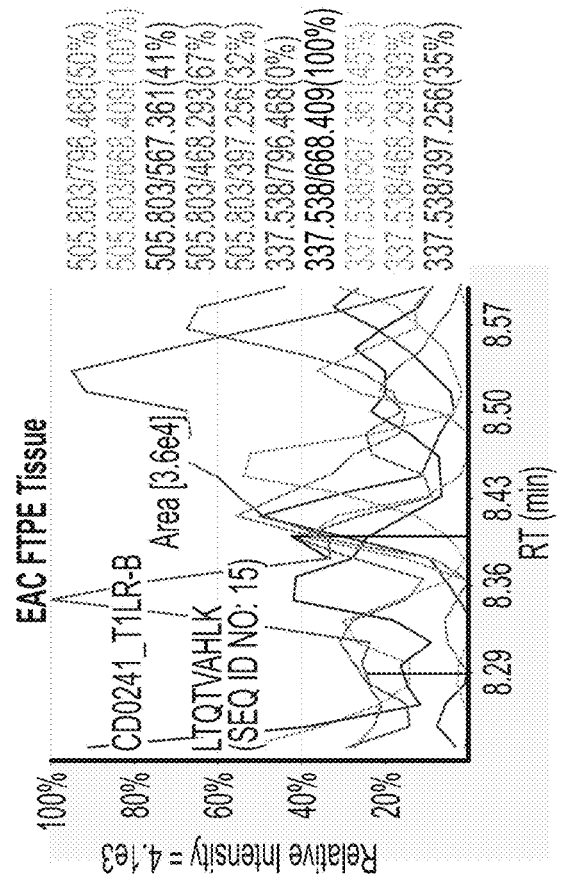
Figure 17G:
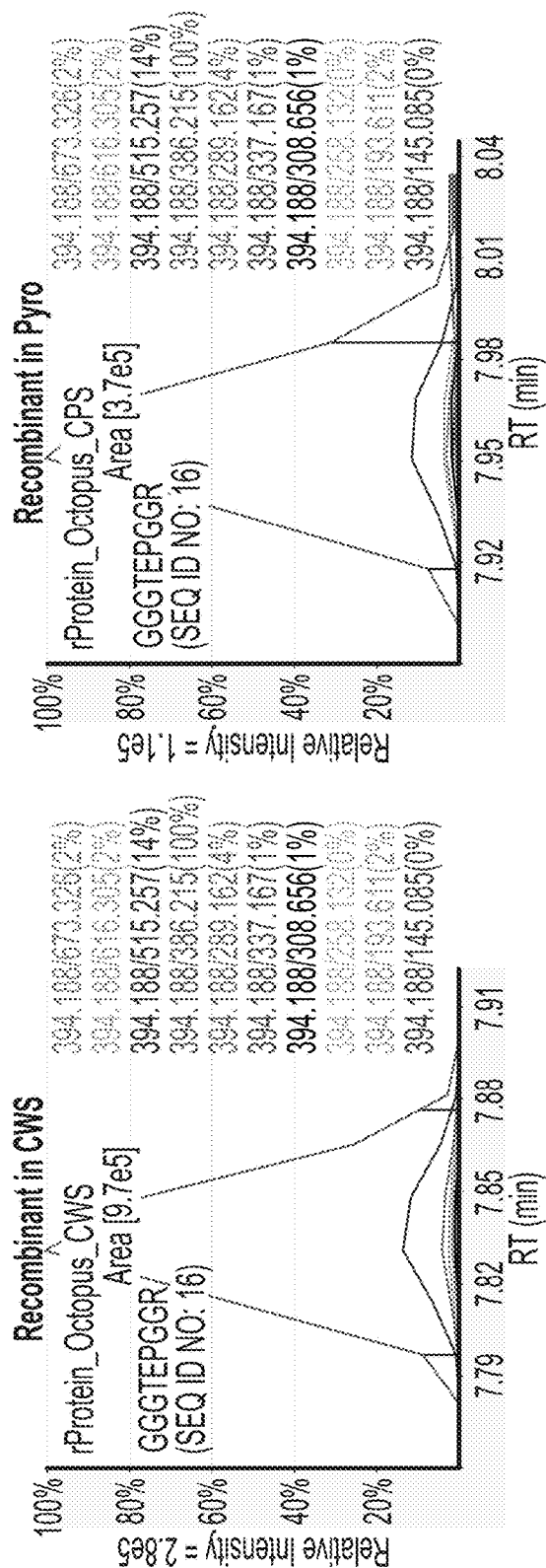
Figure 17G:
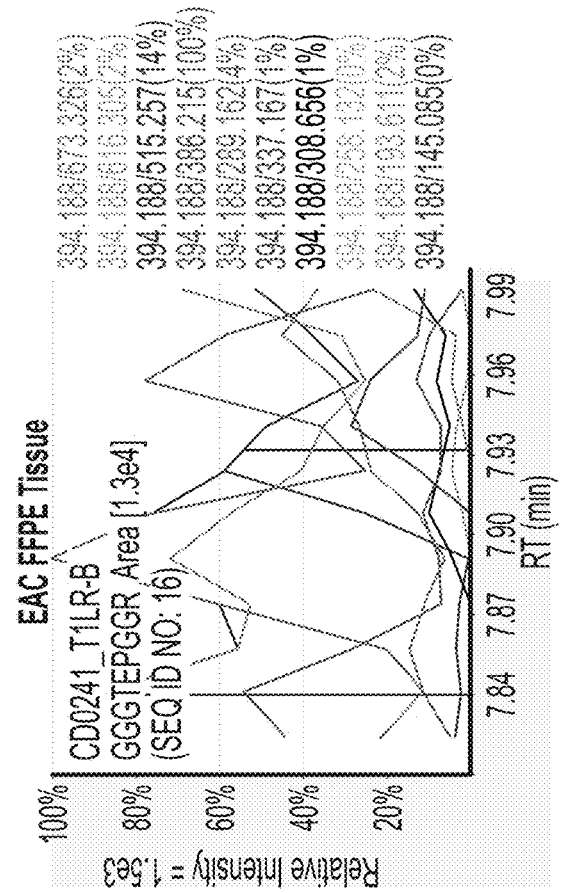

Representative tandem mass spectrometry spectra of the ISG15 protein in human samples using two of these peptides are shown in FIGS. 16A-16B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant ISG15 protein was used to screen unique peptides for SRM development. Specifically, 2 µg of human recombinant ISG15 protein was added to Liquid Tissue Buffer and treated with 0.5 µg of trypsin for 16 hours at 37° C. for a final concentration of 20 ng/µL. The reaction tube was heated at 95° C. for 5 minutes to inactivate trypsin. After hydrolysis, 2 µL of the ISG15 tryptic digests were mixed with 20 µL of carrier working solution (CWS), 5 µL HSM (to obtain retention time across the samples) and 23 µL of 0.1% formic acid of which 10 µL was injected for MS analysis. The data in Table 12 show the intensity that was observed in the MS analysis within this relatively simple matrix. In addition, 2 L of the ISG15 tryptic digests were mixed with 5 µg of *Pyrococcus* (to observe the performance of the peptide in a more complex matrix), 5 µL HSM and 0.1% formic acid to a final volume of 50 µL of which 10 µL was injected for MS analysis as well. The data in Table 12 show the intensity that was observed in the MS analysis within this more complex matrix. In addition, the data in Table 12 show the intensity that was observed in a very complex lysate containing FFPE tissue from an esophageal adenocarcinoma tumor sample.

TABLE 12

Trypsin digestion mapping.

| Sequence | Recombinant Intensity in CWS | Recombinant Intensity in Pyro | FFPE EAC Intensity |
|---|---|---|---|
| AQITQK (SEQ ID NO: 10) | 6e4 | 7e3 | ND |

TABLE 12-continued

Trypsin digestion mapping.

| Sequence | Recombinant Intensity in CWS | Recombinant Intensity in Pyro | FFPE EAC Intensity |
|---|---|---|---|
| IGVHAFQQR (SEQ ID NO: 11) | 3e6 | 4e5 | 2.5e4 |

TABLE 12-continued

Trypsin digestion mapping.

| Sequence | Recombinant Intensity in CWS | Recombinant Intensity in Pyro | FFPE EAC Intensity |
|---|---|---|---|
| LAVHPSGVALQDR (SEQ ID NO: 12) | 2e6 | 4e5 | 2.8e4 |
| VPLASQGLGPGSTVLLVVDK (SEQ ID NO: 13) | 1e5 | 5e3 | ND |
| SSTYEVR (SEQ ID NO: 14) | 5e4 | 2e4 | ND |
| LTQTVAHLK (SEQ ID NO: 15) | 2e5 | 3e5 | ND |
| GGGTEPGGR (SEQ ID NO: 16) | 2e5 | 1e5 | ND |

Detection of the peptides in the protein digest is shown in FIGS. 17A-17G. Of the seven unique peptides screened, two peptides were observed in at least one FFPE ECA tissue. Peptides IGVHAFQQR (SEQ ID NO: 11) and LAVHPSGVALQDR (SEQ ID NO: 12) showed high intensity and consistent product ion ratios in the recombinant protein and FFPE ECA tissues.

CNDP2

CNDP2 (UniProt Q96KP4) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 11, which are unique to CNDP2, were chosen.

TABLE 11

Unique CNDP2 peptides.

| Sequence | CNDP2 Isoform | Post-Translational Modifications | Start Position | End Position |
|---|---|---|---|---|
| YIDENQDR (SEQ ID NO: 17) | 1, 2 | R17-ml | 10 | 17 |
| WVAIQSVSAWPEK (SEQ ID NO: 18) | 1, 2 | | 25 | 37 |
| QLGGSVELVDIGK (SEQ ID NO: 19) | 1, 2 | S58-p, K66-ub | 54 | 66 |
| LPDGSEIPLPPILLGR (SEQ ID NO: 20) | 1 | | 69 | 84 |
| LGSDPQK (SEQ ID NO: 21) | 1 | S87-p | 85 | 91 |
| GSTDDK (SEQ ID NO: 22) | 1 | | 129 | 134 |
| GPVAGWINALEAYQK (SEQ ID NO: 23) | 1 | K149-ub | 135 | 149 |
| TGQEIPVNVR (SEQ ID NO: 24) | 1 | | 150 | 159 |
| DTFFK (SEQ ID NOI: 25) | 1, 2 | | 182 | 186 |
| GNILIPGINEAVAAVTEEEHK (SEQ ID NO: 26) | 1, 2 | | 255 | 275 |
| LYDDIDFDIEEFAK (SEQ ID NO: 27) | 1, 2 | Y277-p, K289-ub | 276 | 289 |
| DVGAQILLHSHK (SEQ ID NO: 28) | 1, 2 | S299-p, K301-ub | 290 | 301 |
| YPSLSLHGIEGAFSGSGAK (SEQ ID NO: 29) | 1, 2 | Y311-p | 311 | 329 |
| SPNEFK (SEQ ID NO: 30) | 1, 2 | | 370 | 375 |
| TVFGVEPDLTR (SEQ ID NO: 31) | 1, 2 | | 403 | 413 |

TABLE 11-continued

Unique CNDP2 peptides.

| Sequence | CNDP2 Isoform | Post-Translational Modifications | Start Position | End Position |
|---|---|---|---|---|
| EGGSIPVTLTFQEATGK (SEQ ID NO: 32) | 1, 2 | K430-ub | 414 | 430 |
| YNYIEGTK (SEQ ID NO: 33) | 1, 2 | | 454 | 461 |

Figure 18:
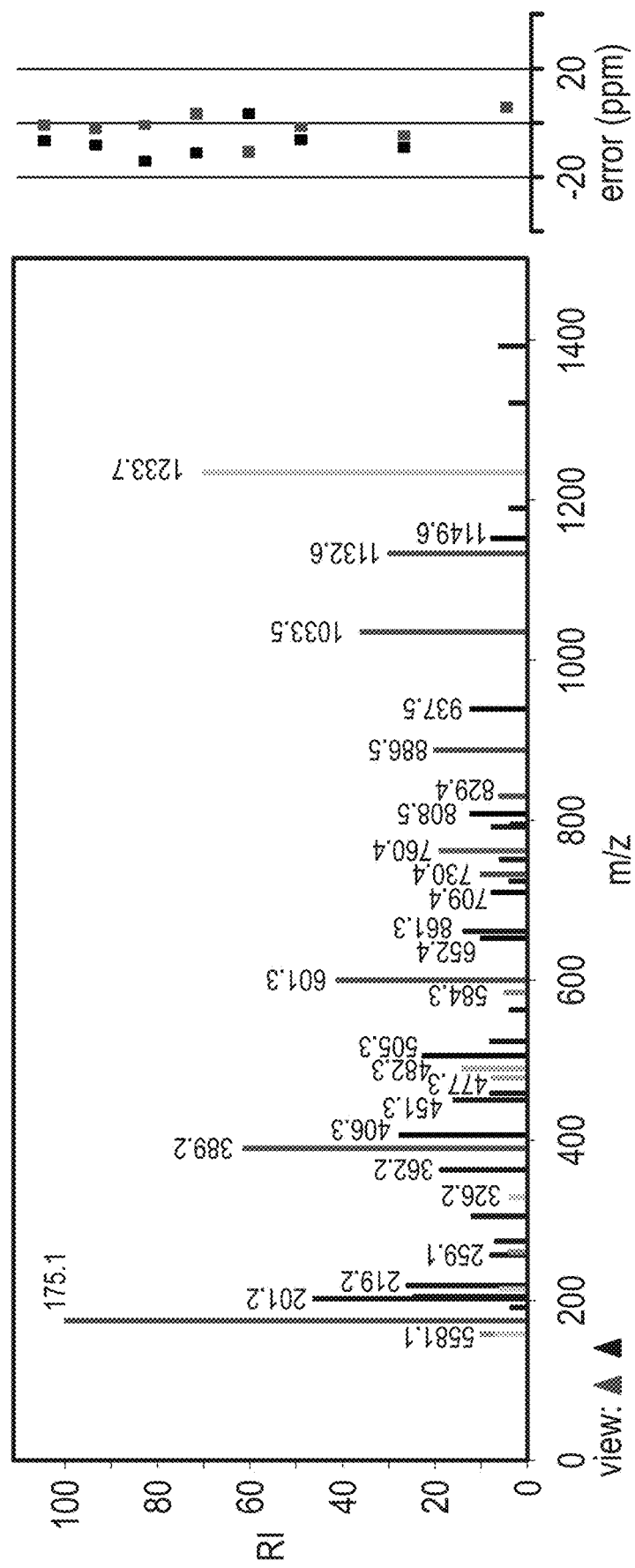
FIG. 18. Representative tandem mass spectrometry spectra of the CNDP2 protein in human samples using CNDP2 peptides.

Representative tandem mass spectrometry spectra of the CNDP2 protein in human samples using one of these peptides are shown in FIG. 18. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant CNDP2 protein was used to screen unique peptides for SRM development. Specifically, 2 µg of human recombinant CNDP2 protein was added to Liquid Tissue Buffer and treated with 0.5 µg of trypsin for 16 hours at 37° C. for a final concentration of 20 ng/µL. The reaction tube was heated at 95° C. for 5 minutes to inactivate trypsin. After hydrolysis, 2 µL of the CNDP2 tryptic digests were mixed with 20 µL of carrier working solution (CWS), 5 µL HSM (to obtain retention time across the samples) and 23 µL of 0.100 formic acid of which 10 µL was injected for MS analysis. The data in Table 14 show the intensity that was observed in the MS analysis within this relatively simple matrix. In addition, 2 µL of the CNDP2 tryptic digests were mixed with 5 µg of *Pyrococcus* (to observe the performance of the peptide in a more complex matrix), 5 µL HSM and 0.10% formic acid to a final volume of 50 µL of which 10 µL was injected for MS analysis as well. The data in Table 14 show the intensity that was observed in the MS analysis within this more complex matrix. In addition, the data in Table 14 show the intensity that was observed in a very complex lysate containing FFPE tissue from an esophageal adenocarcinoma tumor sample.

TABLE 14

Trypsin digestion mapping.

| Sequence | Recombinant Intensity in CWS | Recombinant Intensity in Pyro | FFPE EAC Intensity |
|---|---|---|---|
| YIDENQDR (SEQ ID NO: 17) | 7e4 | 2e4 | ND |
| WVAIQSVSAWPEK (SEQ ID NO: 18) | 8e5 | 6e3 | 3.7e4 |
| QLGGSVELVDIGK (SEQ ID NO: 19) | 6e5 | 3e5 | 4e4 |
| LPDGSEIPLPPILLGR (SEQ ID NO: 20) | 2e6 | 7e5 | 2e5 |
| LGSDPQK (SEQ ID NO: 21) | ND | ND | ND |
| GSTDDK (SEQ ID NO: 22) | ND | ND | ND |
| GPVAGWINALEAYQK (SEQ ID NO: 23) | 2e4 | ND | ND |
| TGQEIPVNVR (SEQ ID NO: 24) | 7e6 | 3e6 | 4e5 |
| DTFFK (SEQ ID NO: 25) | ND | ND | ND |
| GNILIPGINEAVAAVTEEEHK (SEQ ID NO: 26) | 2e5 | 1e5 | 9e3 |
| LYDDIDFDIEEFAK (SEQ ID NO: 27) | 3e5 | 2e5 | ND |
| DVGAQILLHSHK (SEQ ID NO: 28) | 2e5 | 5e4 | 1e4 |
| YPSLSLHGIEGAFSGSGAK (SEQ ID NO: 29) | 2e5 | 1e4 | 1e4 |
| SPNEFK (SEQ ID NO: 30) | 6e3 | 7e3 | ND |
| TVFGVEPDLTR (SEQ ID NO: 31) | 4e6 | 3e6 | 2.5e5 |
| EGGSIPVTLTFQEATGK (SEQ ID NO: 32) | 1e6 | 1e6 | 6e4 |
| YNYIEGTK (SEQ ID NO: 33) | 1e6 | 1e6 | 5.4e4 |

Figure 19A:
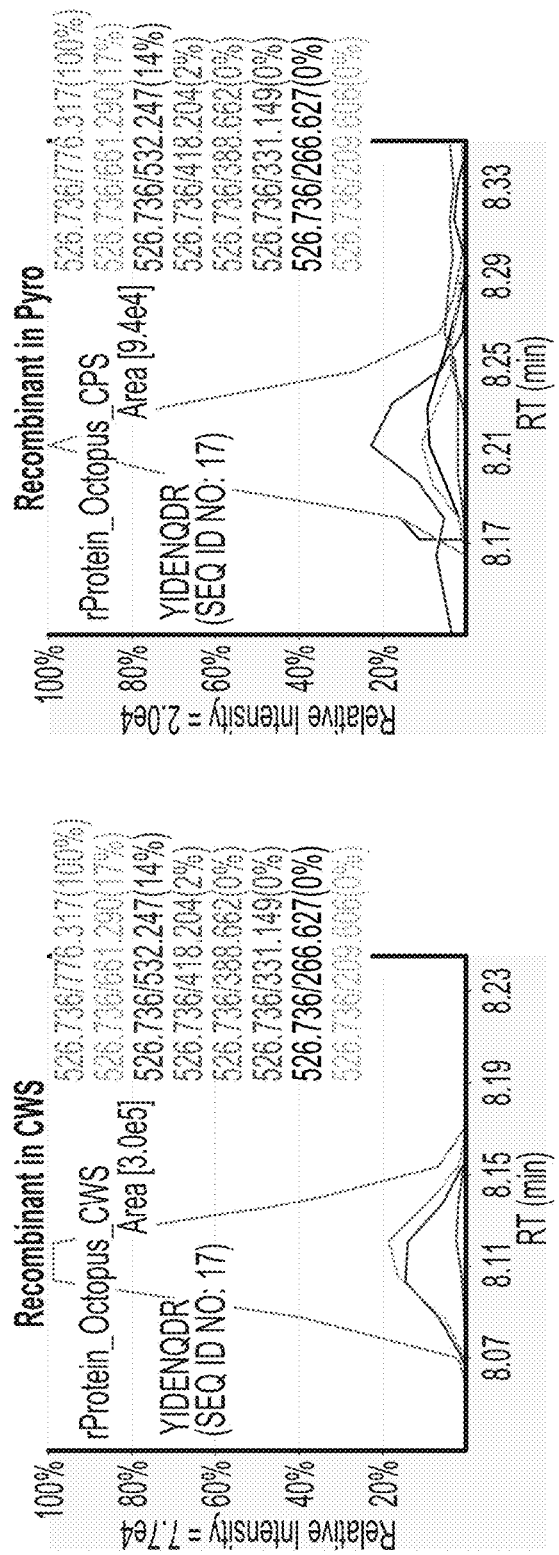
FIGS. 19A-19N. Detection of recombinant CNDP2 peptides in carrier working solution (CWS) and a solution with *Pyrococcus* (pyro), and detection of CNDP2 peptides in formalin-fixed paraffin-embedded esophageal adenocarcinoma tissues.
Figure 19A:
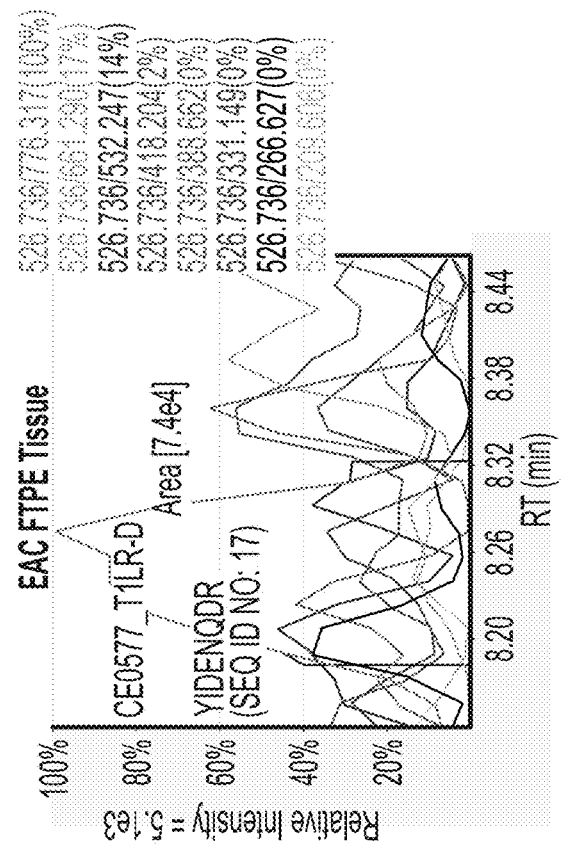
Figure 19B:
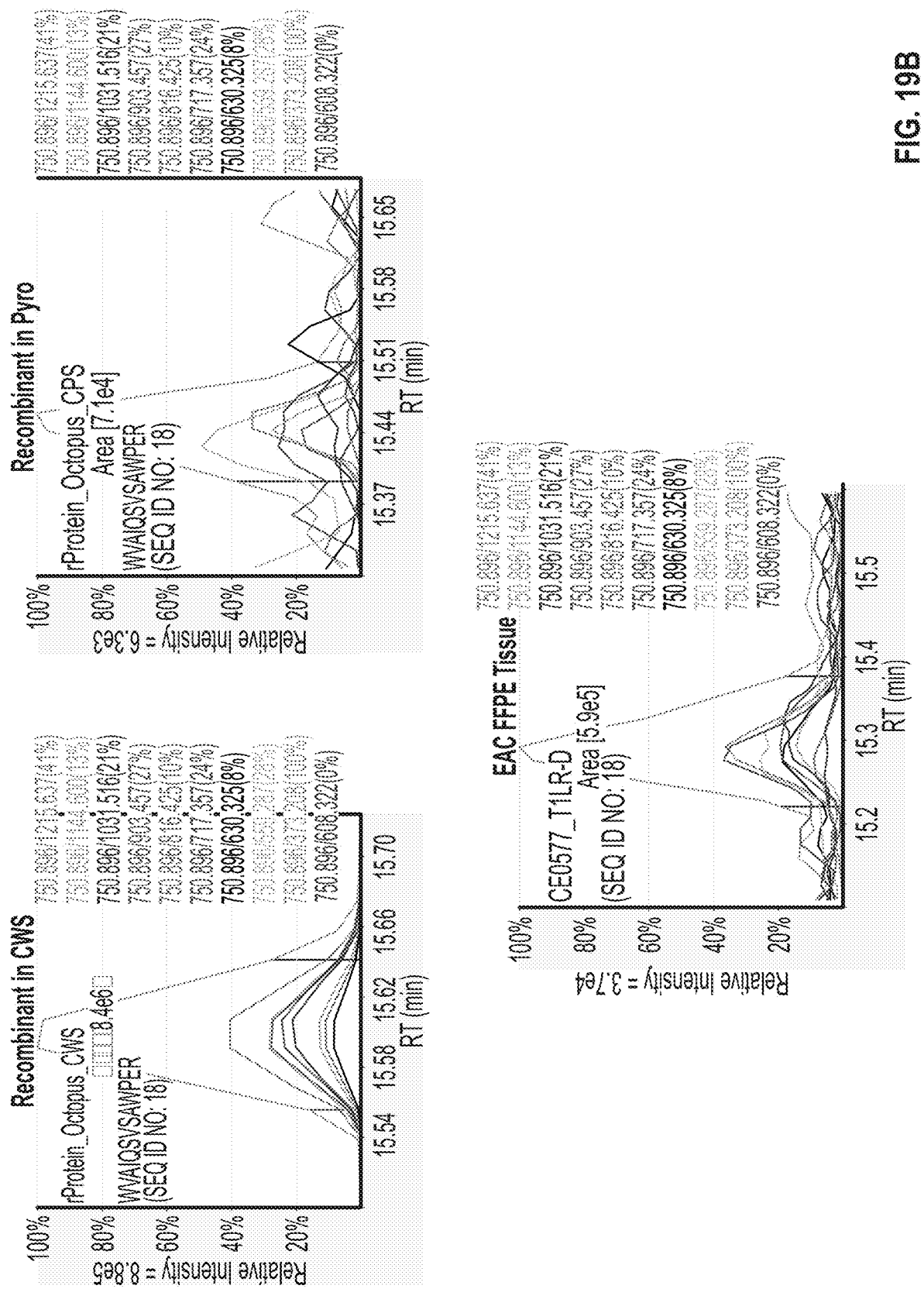
Figure 19C:
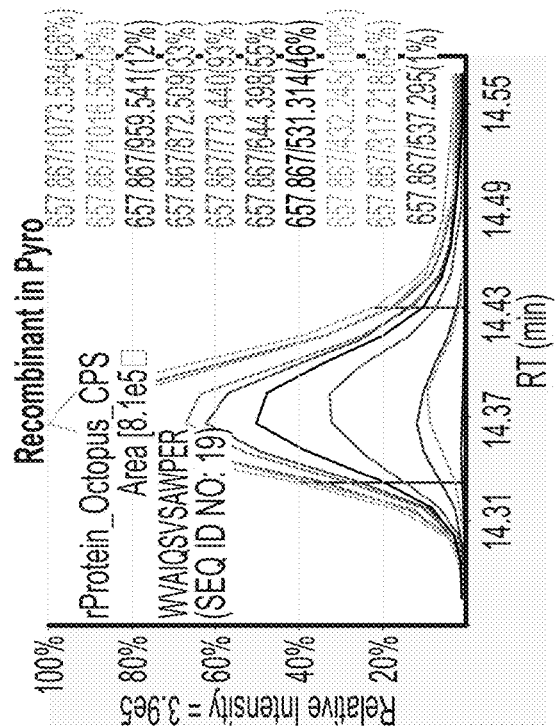
Figure 19C:
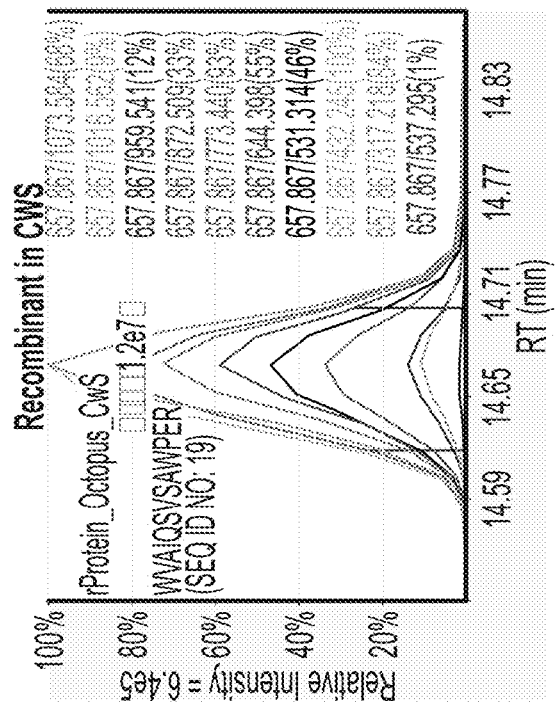
Figure 19C:
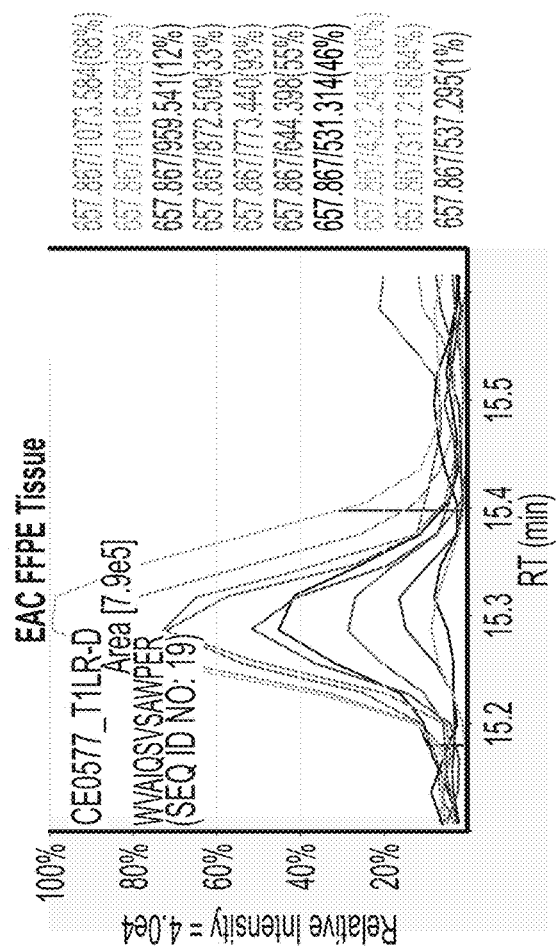
Figure 19D:
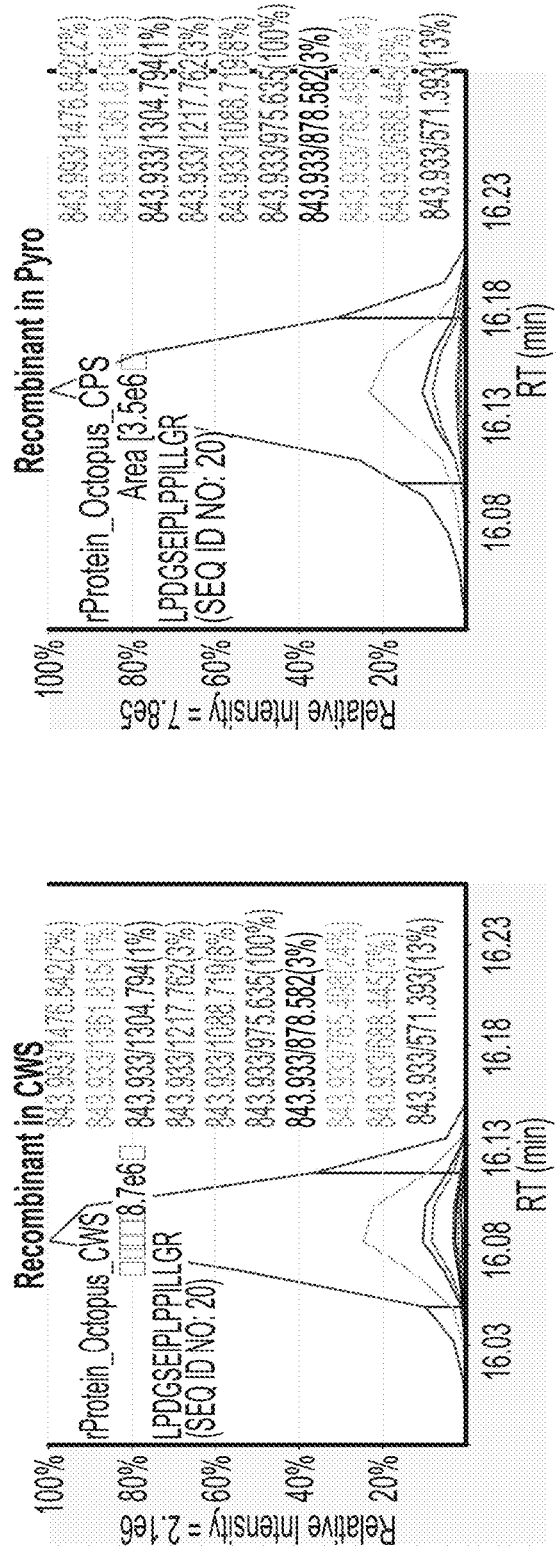
Figure 19D:
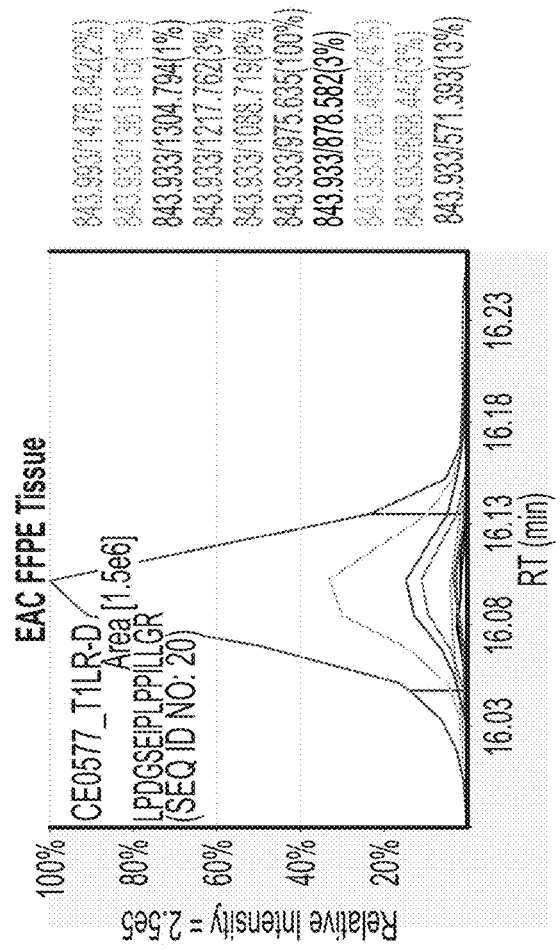
Figure 19E:
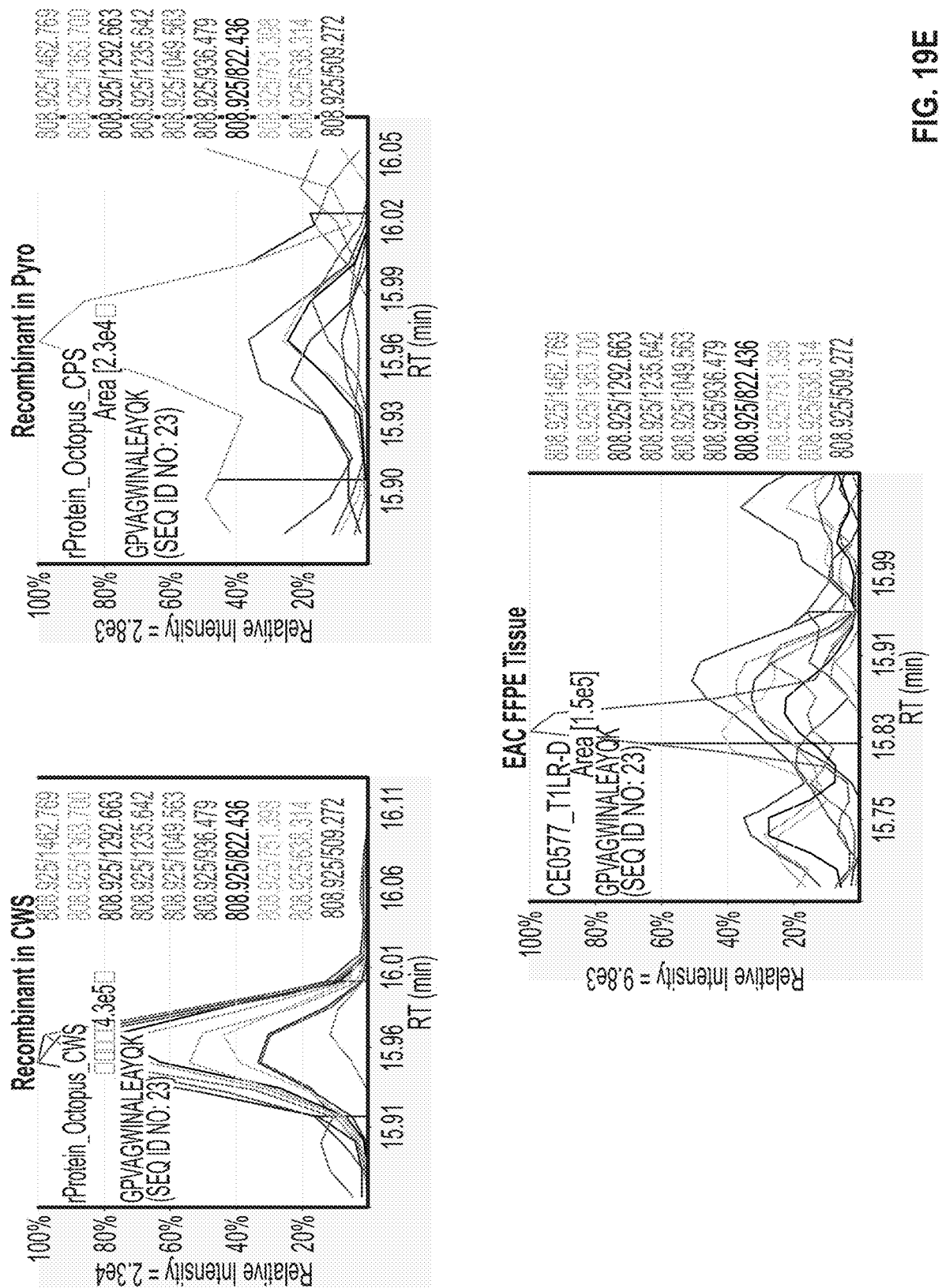
Figure 19F:
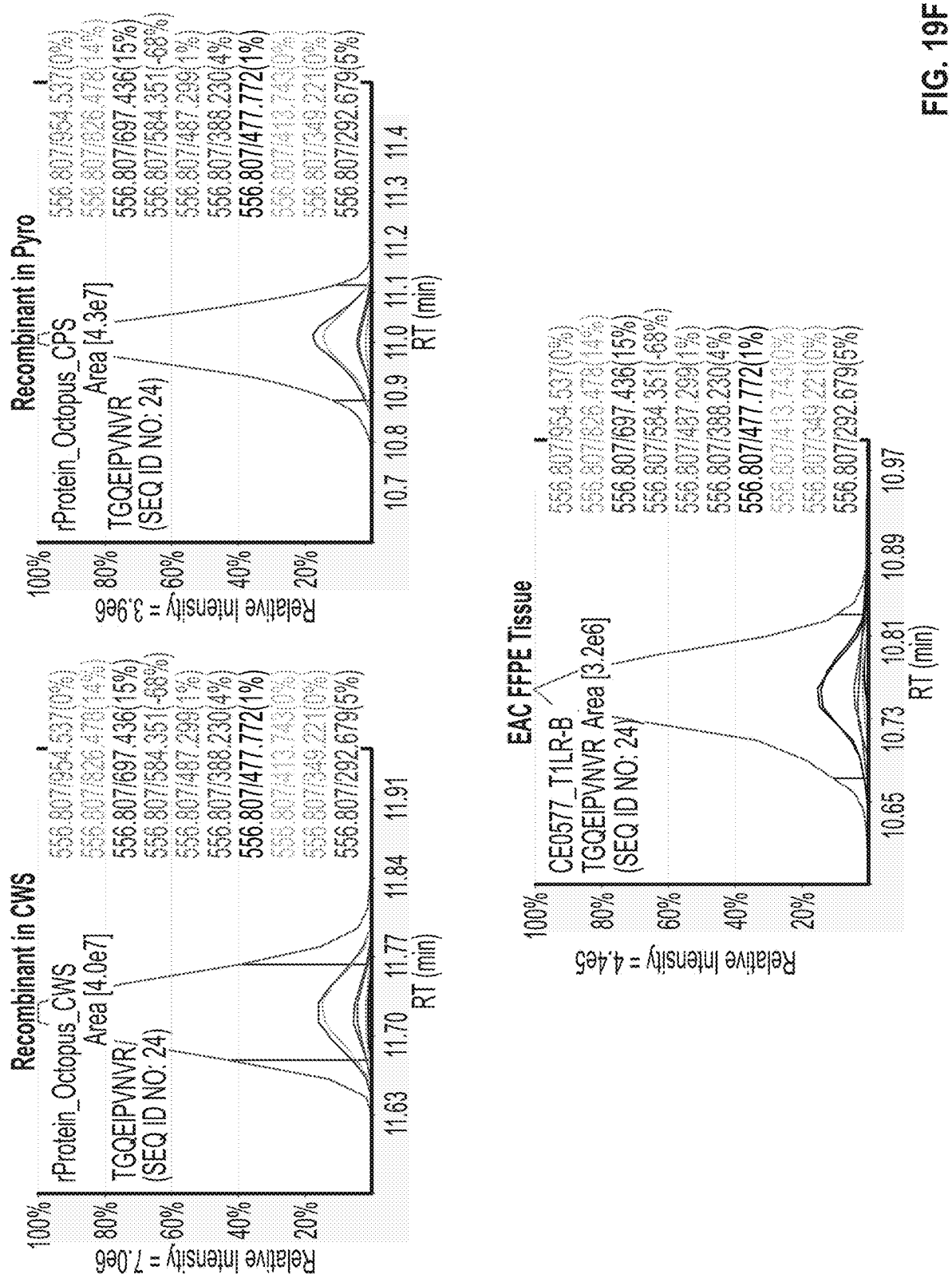
Figure 19G:
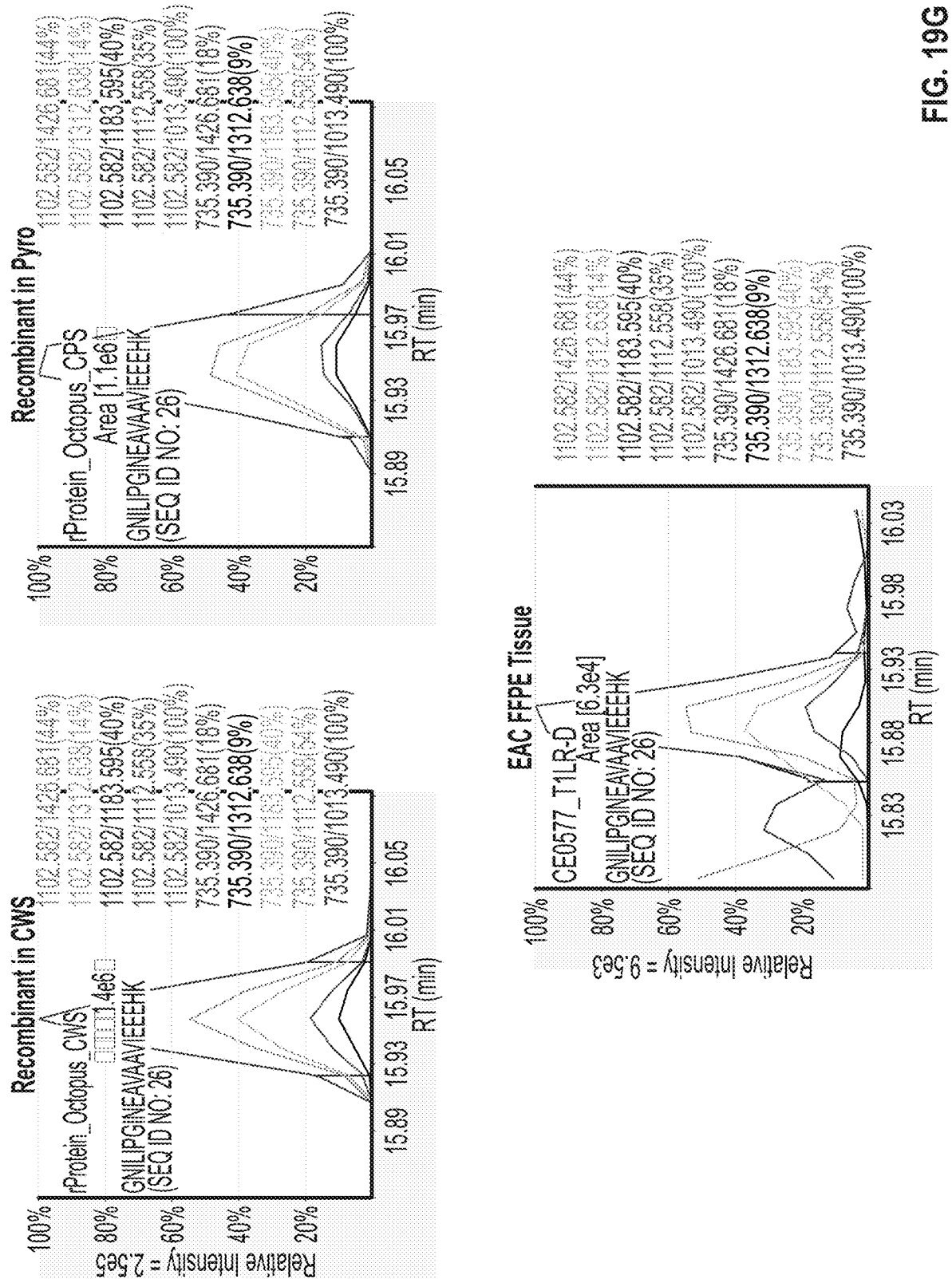
Figure 19H:
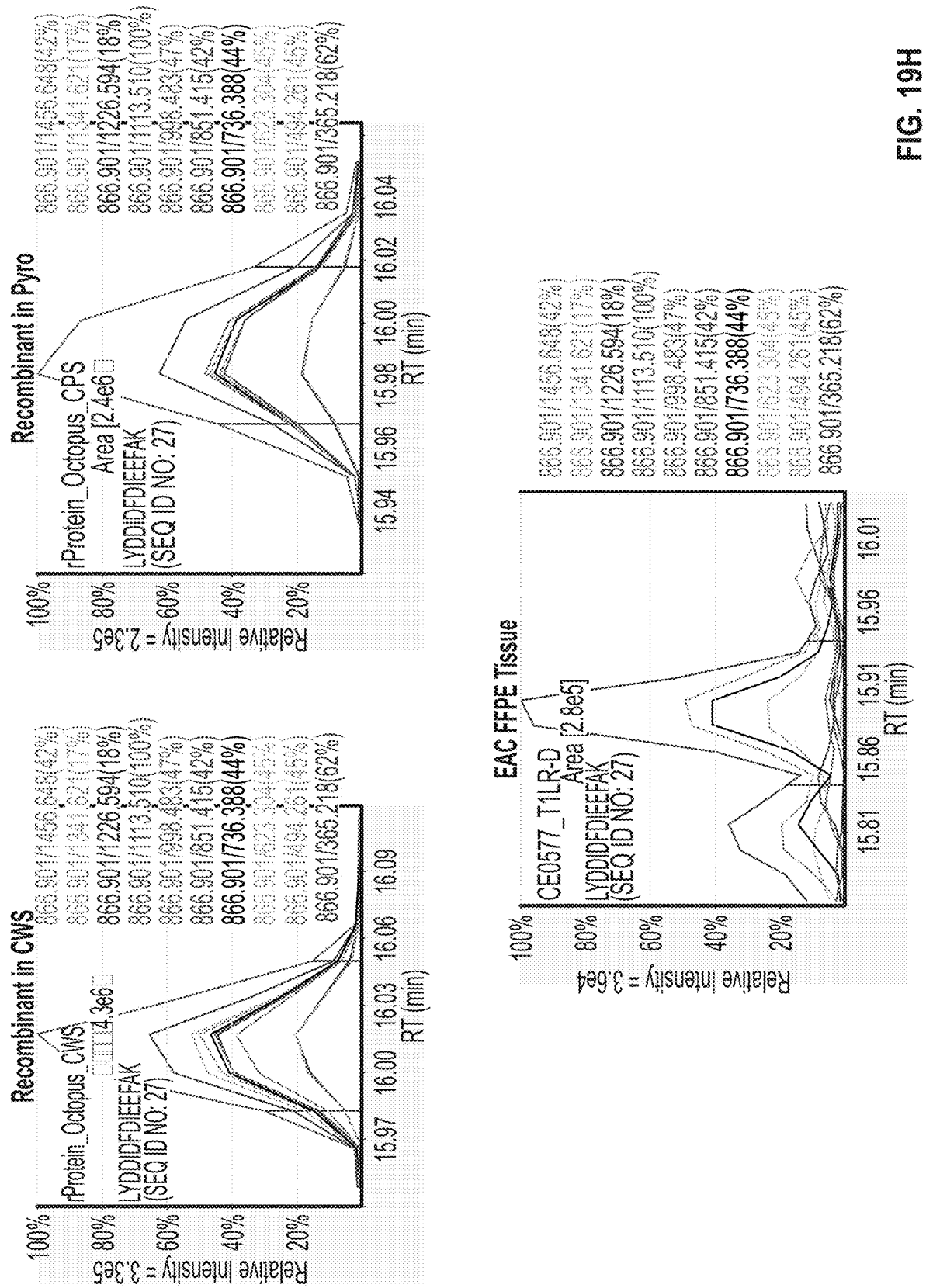
Figure 19I:
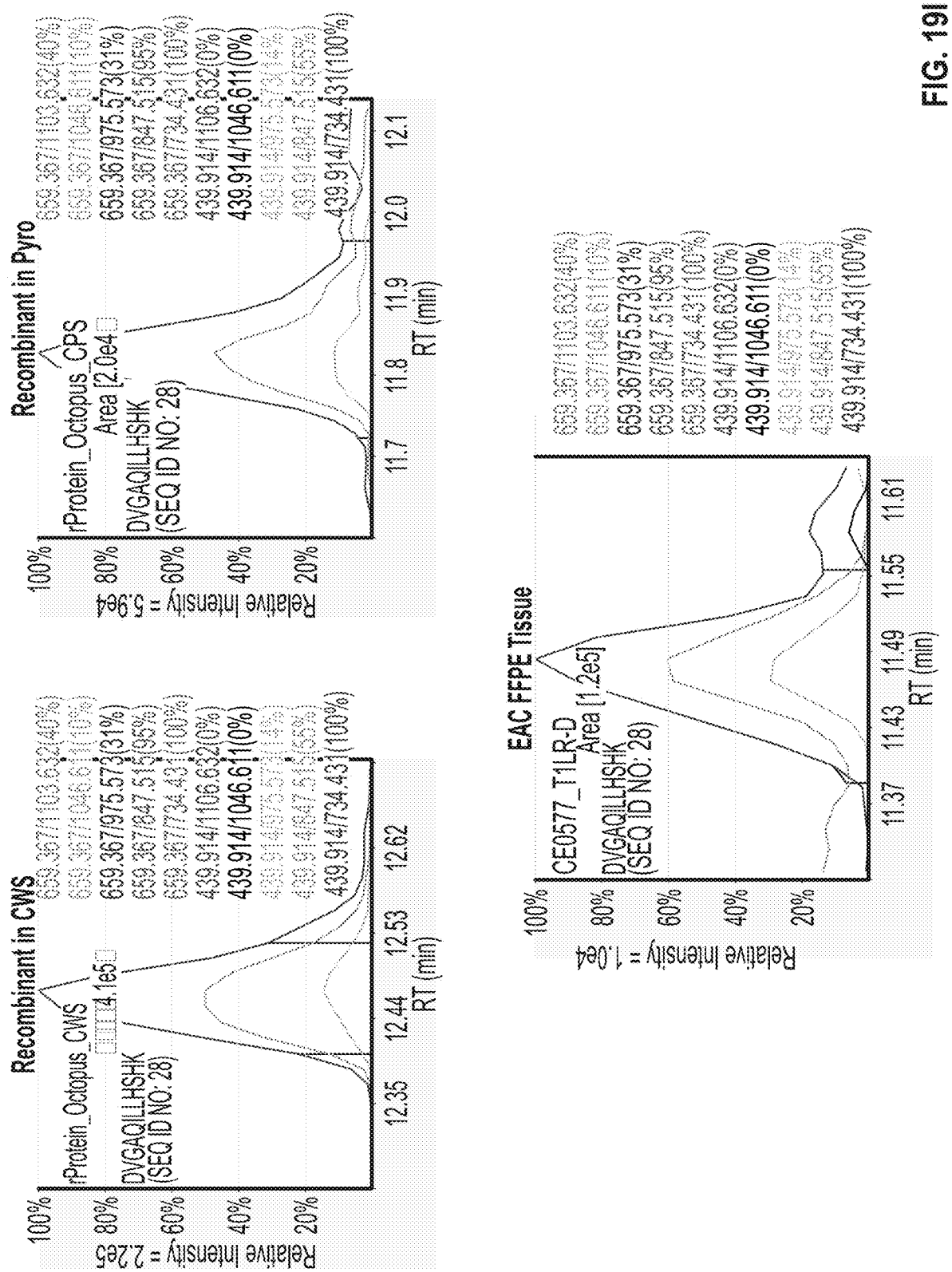
Figure 19J:
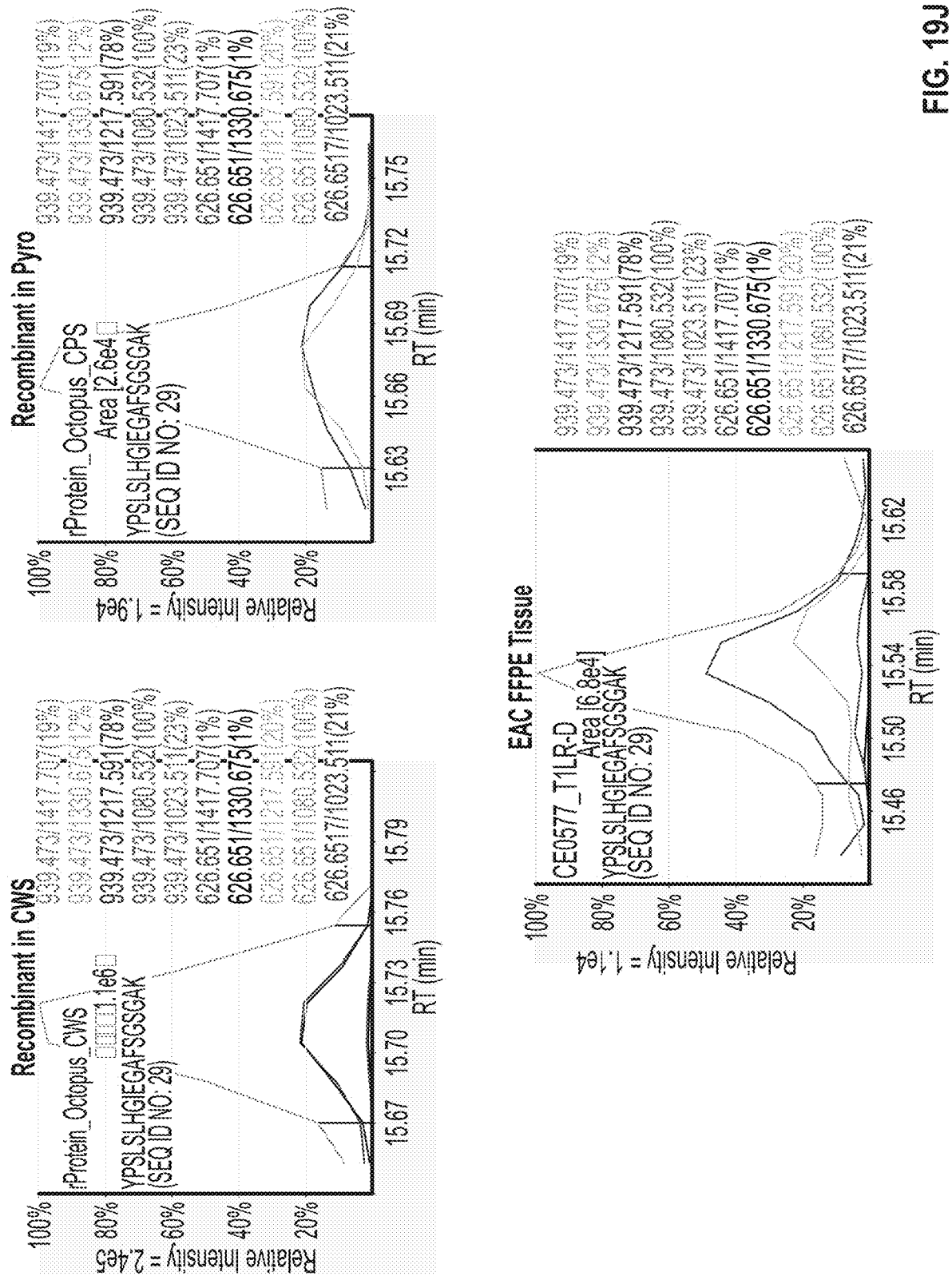
Figure 19K:
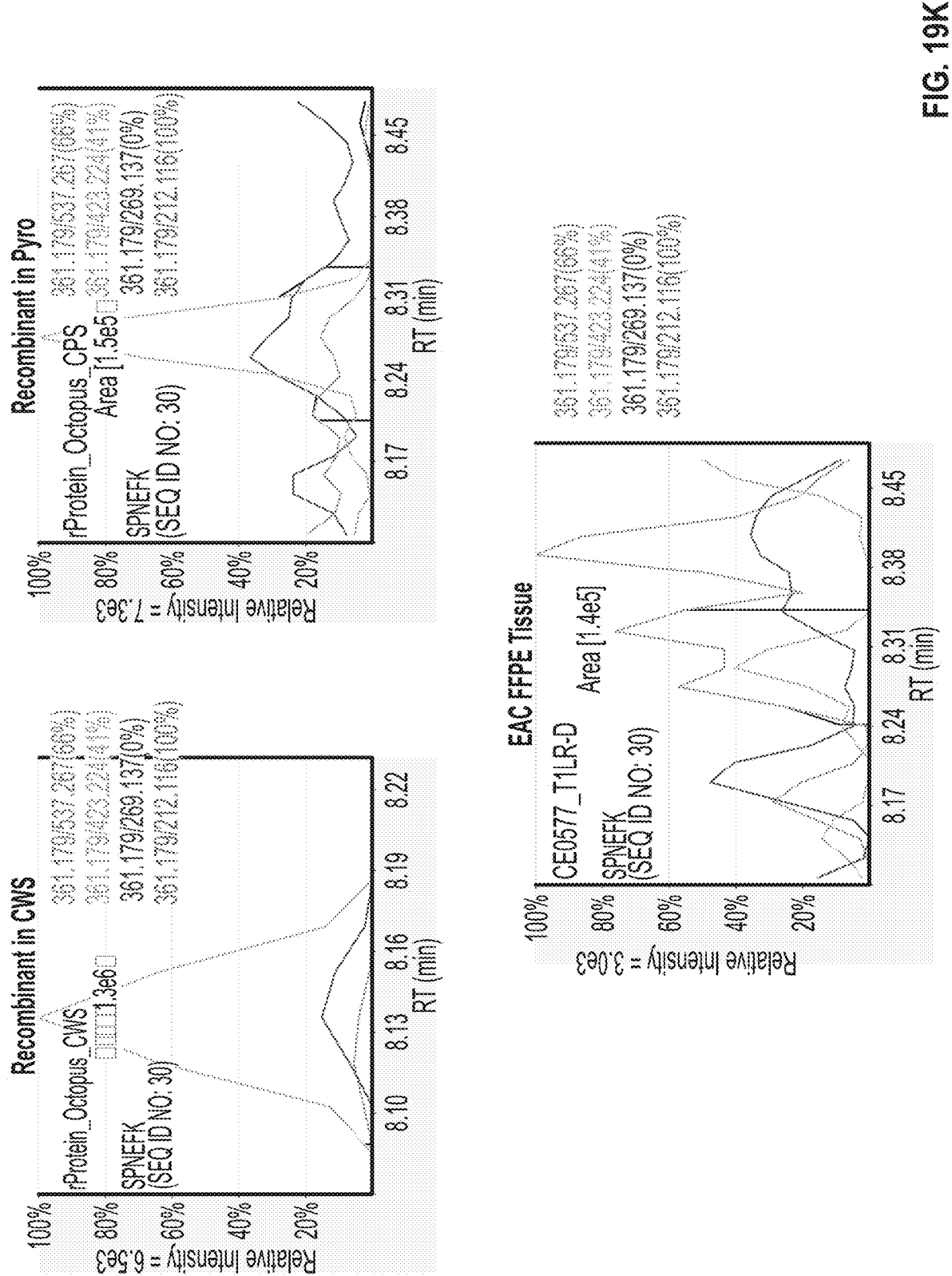
Figure 19L:
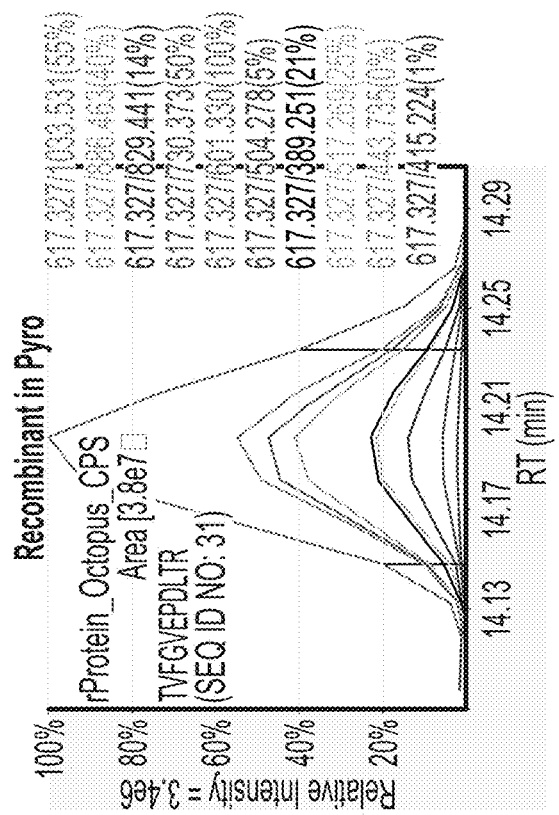
Figure 19L:
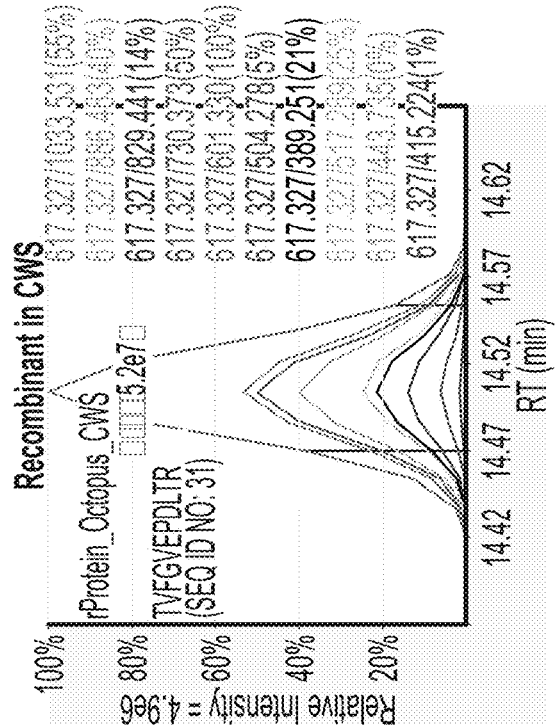
Figure 19L:
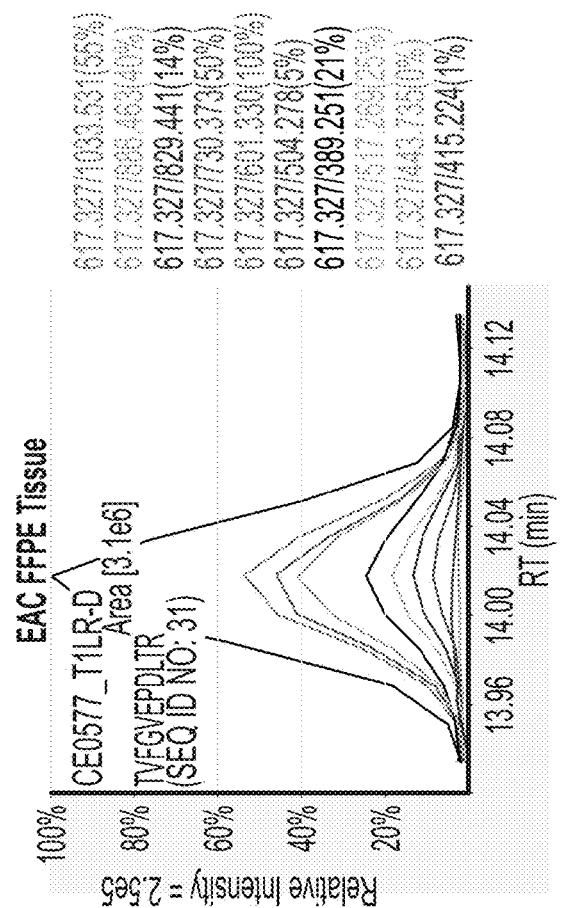
Figure 19M:
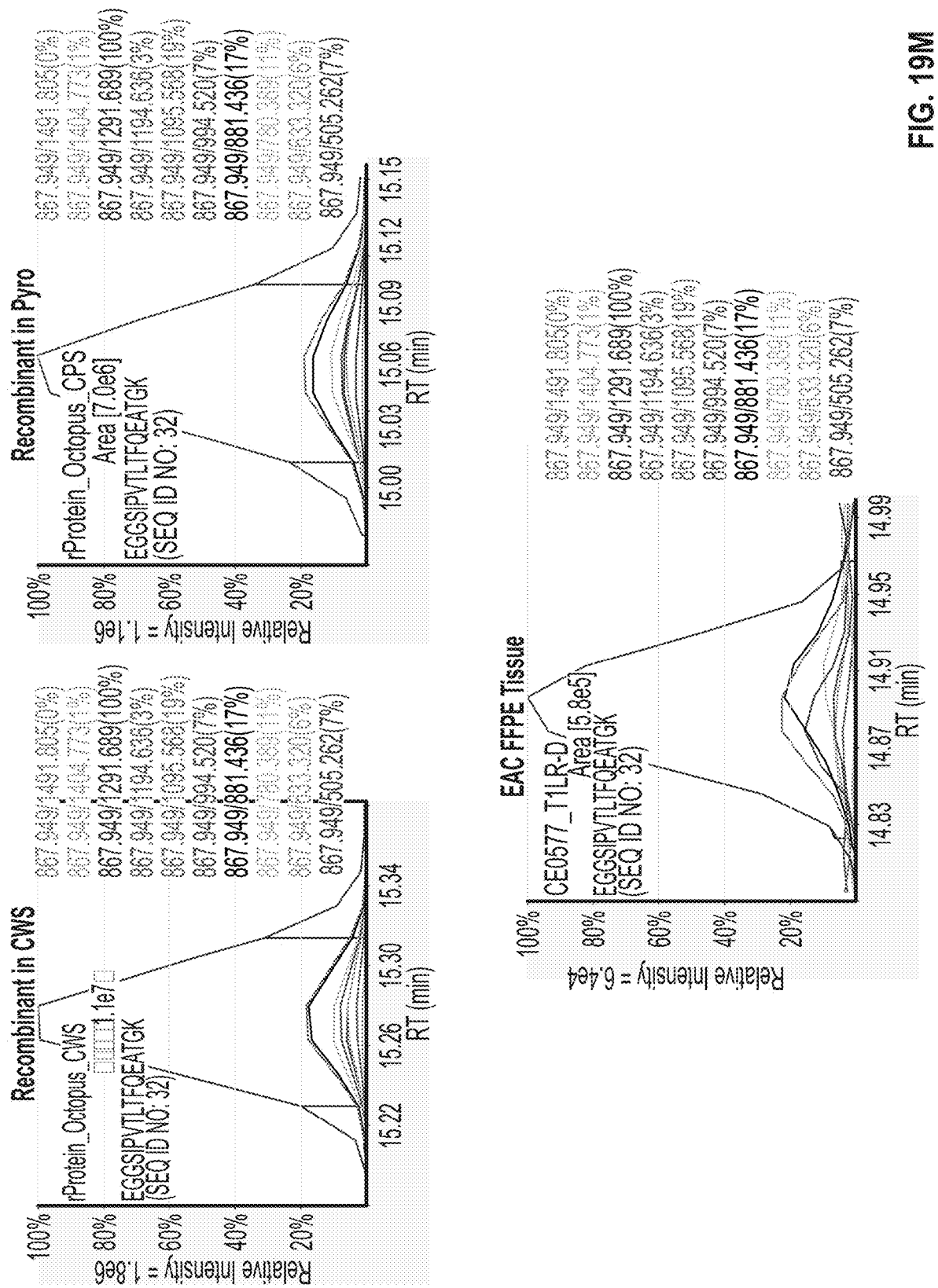
Figure 19N:
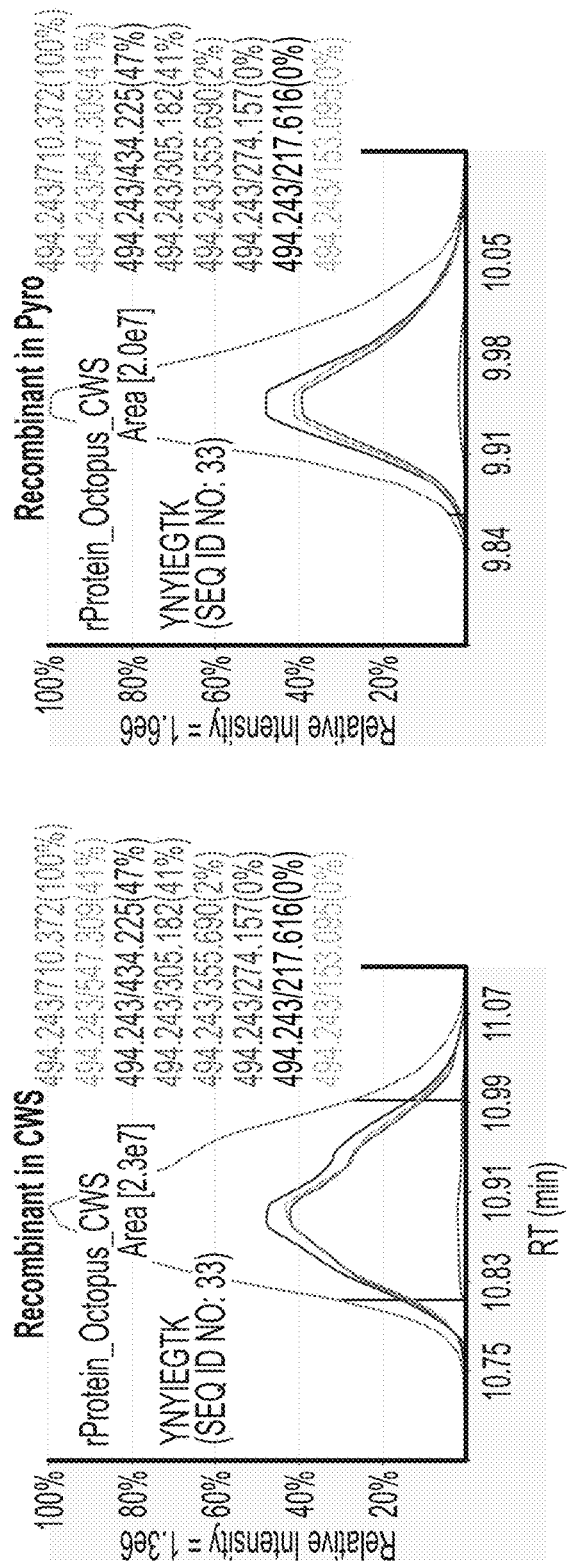
Figure 19N:
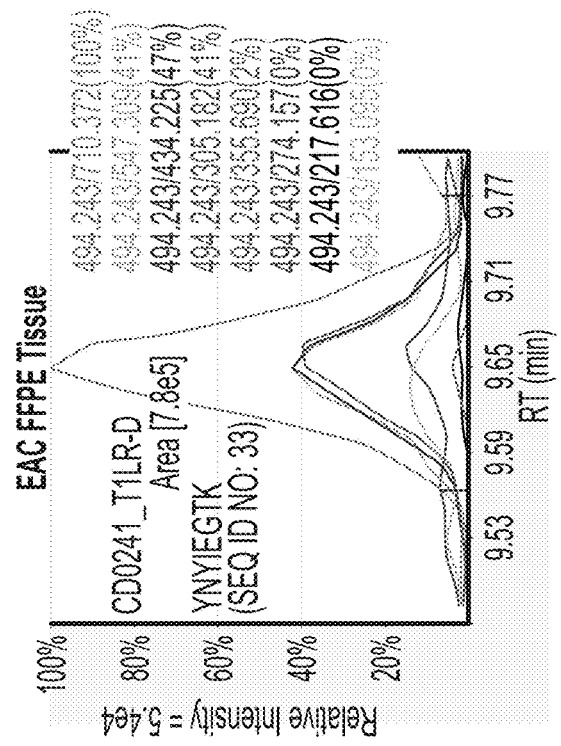

Detection of the peptides in the protein digest is shown in FIGS. 19A-19N. Of the seventeen unique peptides screened, ten peptides were observed in at least one FFPE ECA tissue. Peptides LPDGSEIPLPPILLGR (SEQ ID NO: 20) and TVFGVEPDLTR (SEQ ID NO: 31) showed high intensity and consistent product ion ratios in the recombinant protein and FFPE ECA tissues.

GPI

GPI (UniProt P06744) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 13, which are unique to GPI, were chosen. All fifteen peptides are common in all isoforms of GPI.

TABLE 13

Unique GPI peptides.

| Sequence | GPI Isoform | Post-Translational Modifications | Start Position | End Position |
|---|---|---|---|---|
| DPQFQK (SEQ ID NO: 34) | 1, 2 | K12-ac, K12-ml, K12-ub | 7 | 12 |
| LQQWYR (SEQ ID NO: 35) | 1, 2 | Y17-p | 13 | 18 |
| SELNLR (SEQ ID NO: 36) | 1, 2 | S22-p | 22 | 27 |
| FNHFSLTLNTNHGHILVDYSK (SEQ ID NO: 37) | 1, 2 | Y55-p, S56-p | 37 | 57 |
| INYTEGR (SEQ ID NO: 38) | 1, 2 | Y92-p, T93-p | 90 | 96 |
| AVLHVALR (SEQ ID NO: 39) | 1, 2 | | 97 | 104 |
| SNTPILVDGK (SEQ ID NO: 40) | 1, 2 | S107-p, T109-p, K116-ac, K116-ub | 107 | 116 |
| VWYVSNIDGTHIAK (SEQ ID NO: 41) | 1, 2 | Y183-p, S185-p, K194-ub | 181 | 194 |
| TLAQLNPESSLFIIASK (SEQ ID NO: 42) | 1, 2 | T195-p, S210-p, K211-ac, K211-ub | 195 | 211 |
| TFTTQETITNAETAK (SEQ ID NO: 43) | 1, 2 | T214-p, T215-p, K226-ub | 212 | 226 |
| EWFLQAAK (SEQ ID NO: 44) | 1, 2 | K234-ac, K234-ub, K234-sc | 227 | 234 |
| DPSAVAK (SEQ ID NO: 45) | 1, 2 | S237-p, K241-ub | 235 | 241 |
| HFVALSTNTTK (SEQ ID NO: 46) | 1, 2 | S247-p, T248-p, T250-p, T251-p, K252-ac, K252-ub | 242 | 252 |
| ELQAAGK (SEQ ID NO: 47) | 1, 2 | K454-ac, K454-ub, K454-sc | 448 | 454 |
| IFVQGHWDINSFDQWGVELGK (SEQ ID NO: 48) | 1, 2 | | 498 | 519 |

Figure 20A:
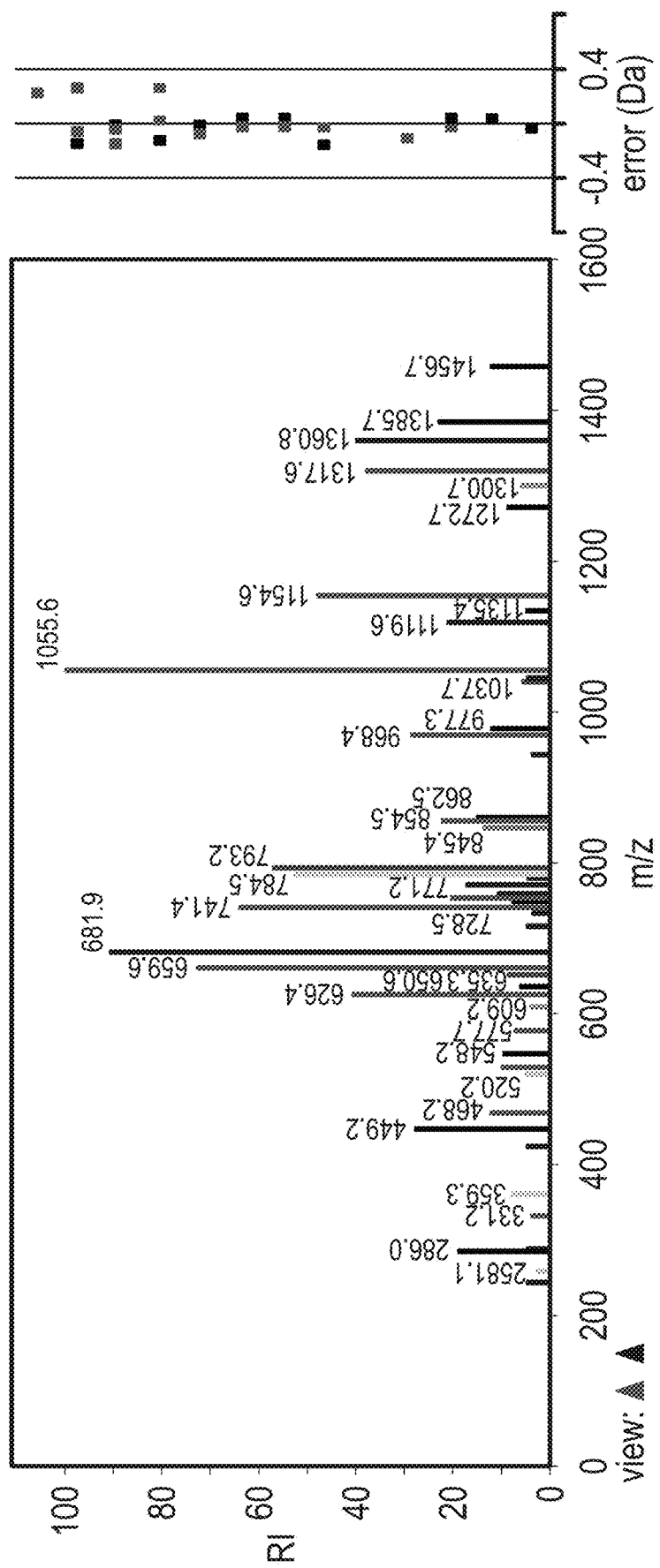
FIGS. 20A-20B. Representative tandem mass spectrometry spectra of the GPI protein in human samples using GPI peptides.
Figure 20B:
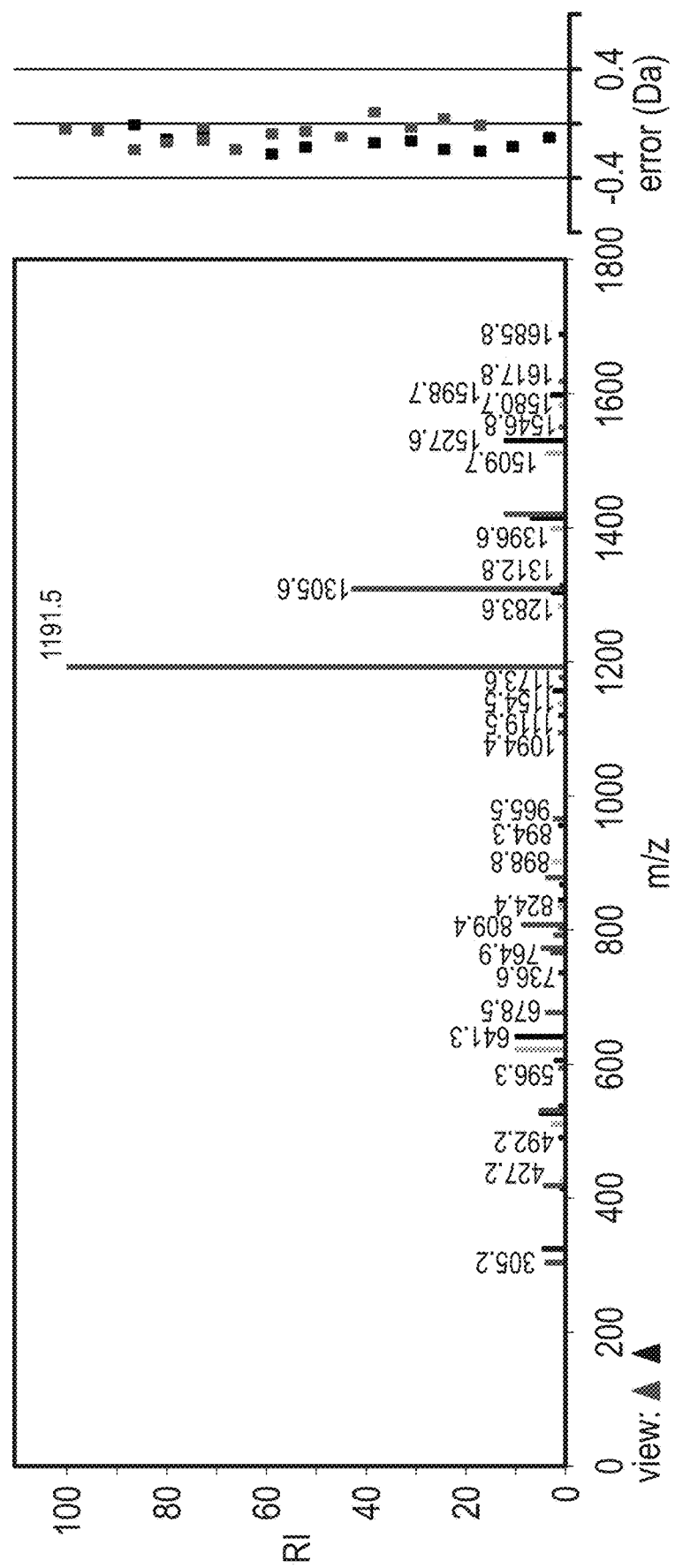
Figure 21A:
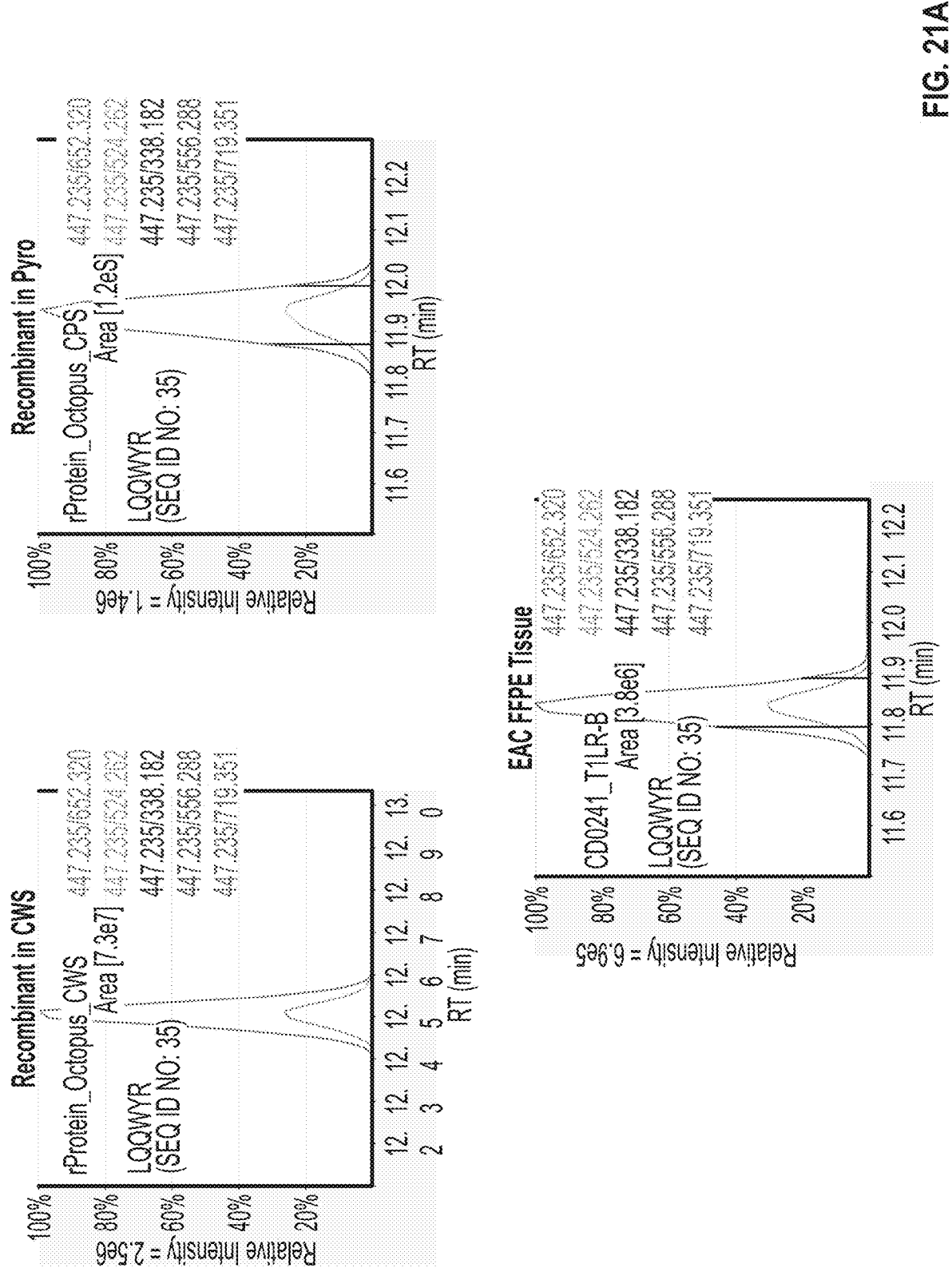
FIGS. 21A-21F. Detection of recombinant GPI peptides in carrier working solution (CWS) and a solution with *Pyrococcus* (pyro), and detection of GPI peptides in formalin-fixed paraffin-embedded esophageal adenocarcinoma tissues.
Figure 21B:
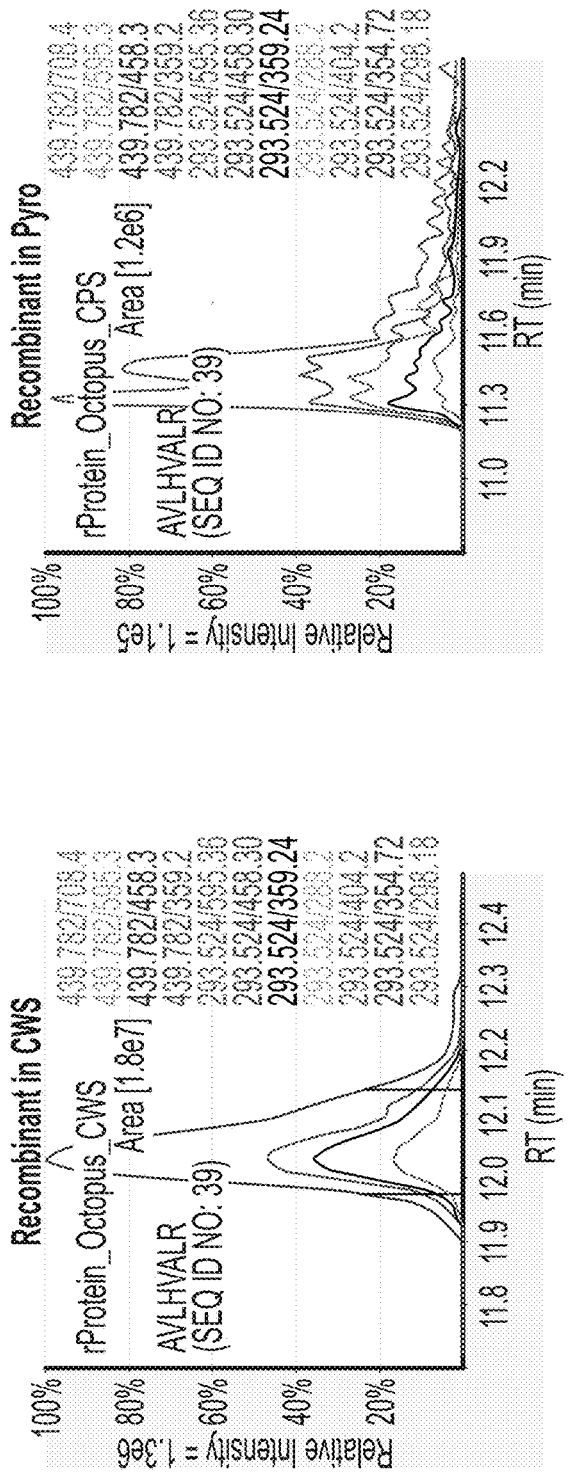
Figure 21B:
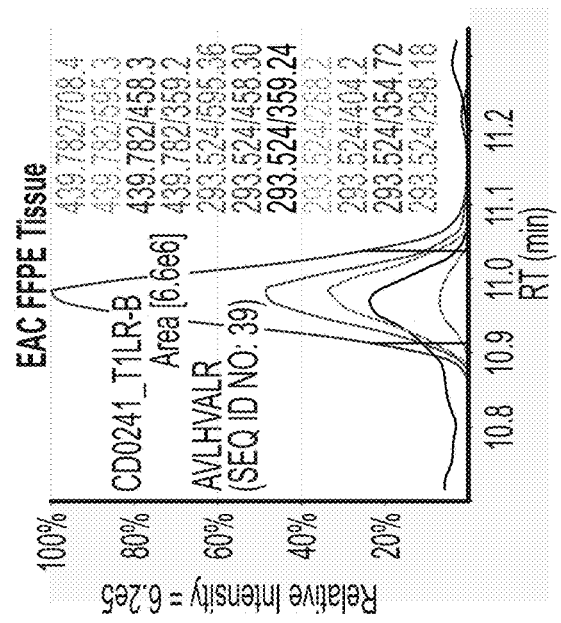
Figure 21C:
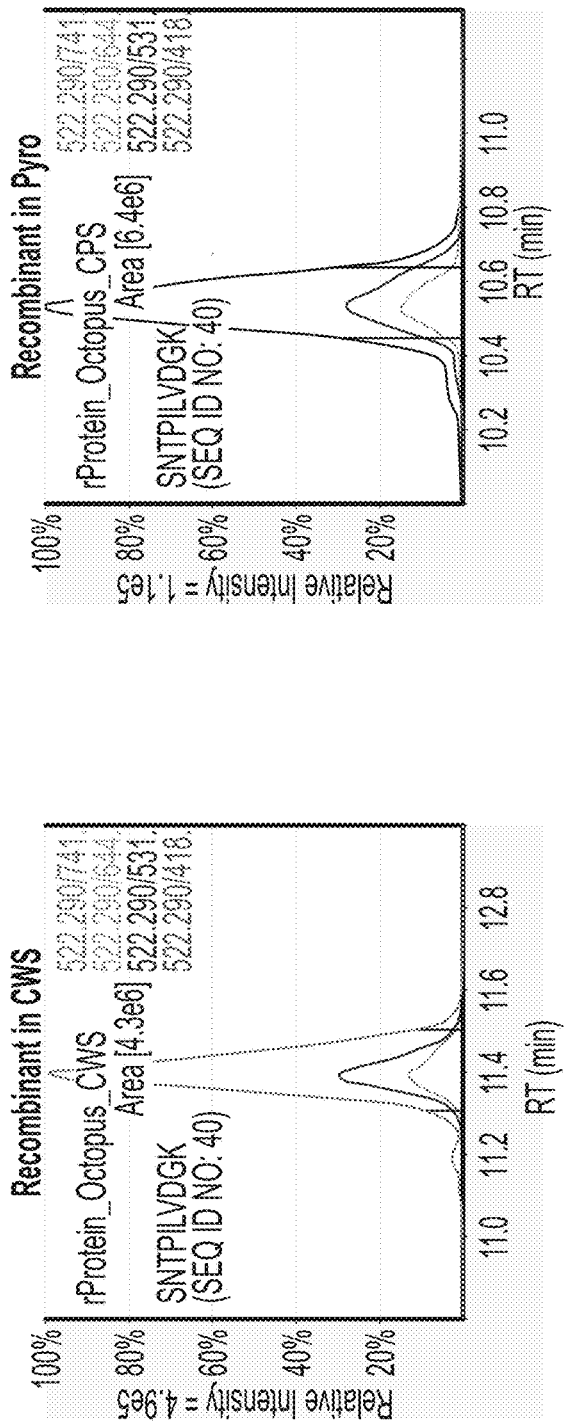
Figure 21C:
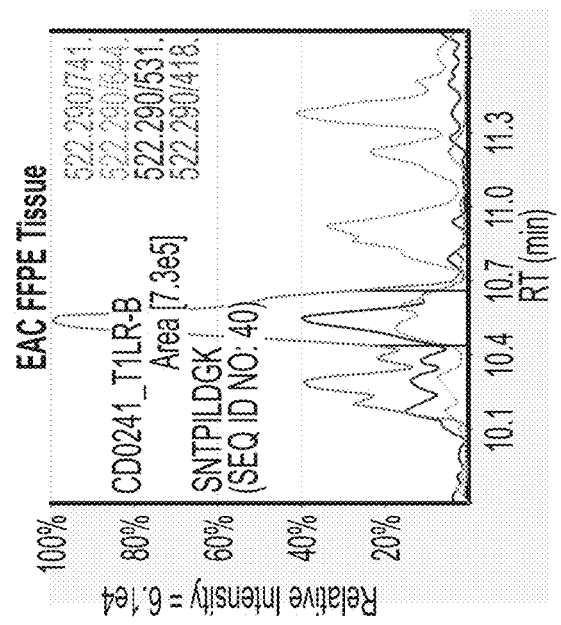
Figure 21D:
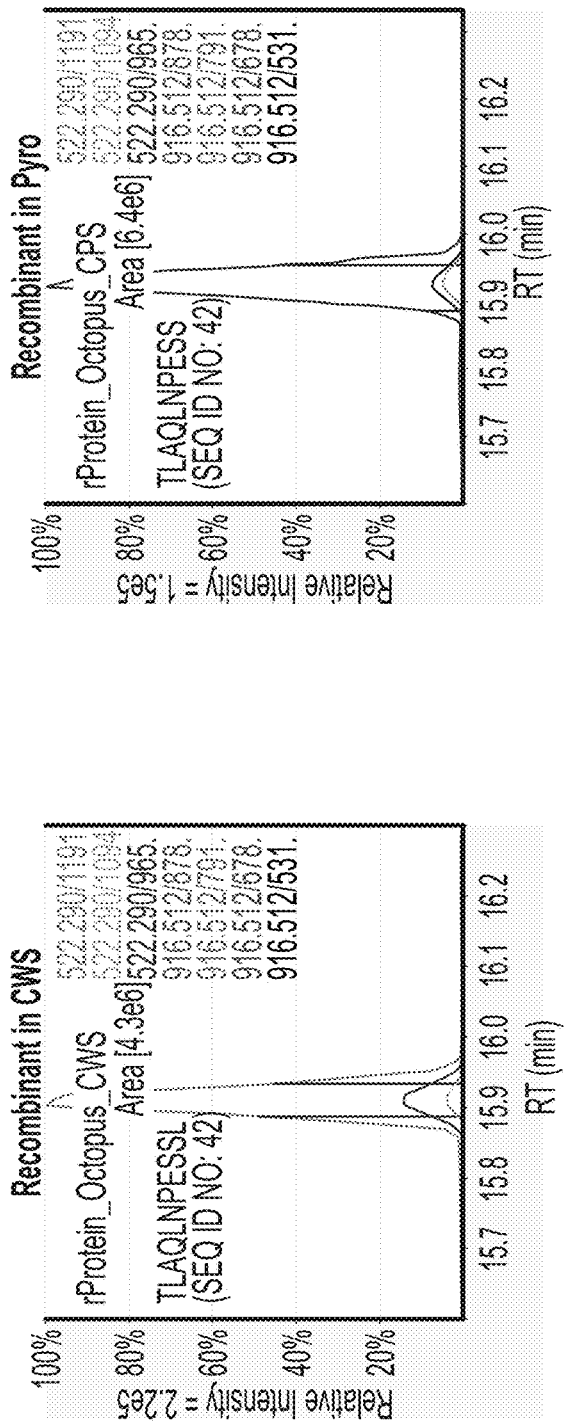
Figure 21D:
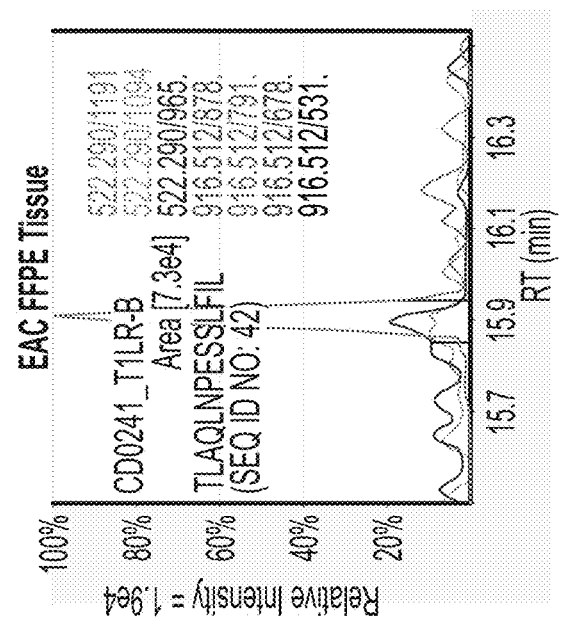
Figure 21E:
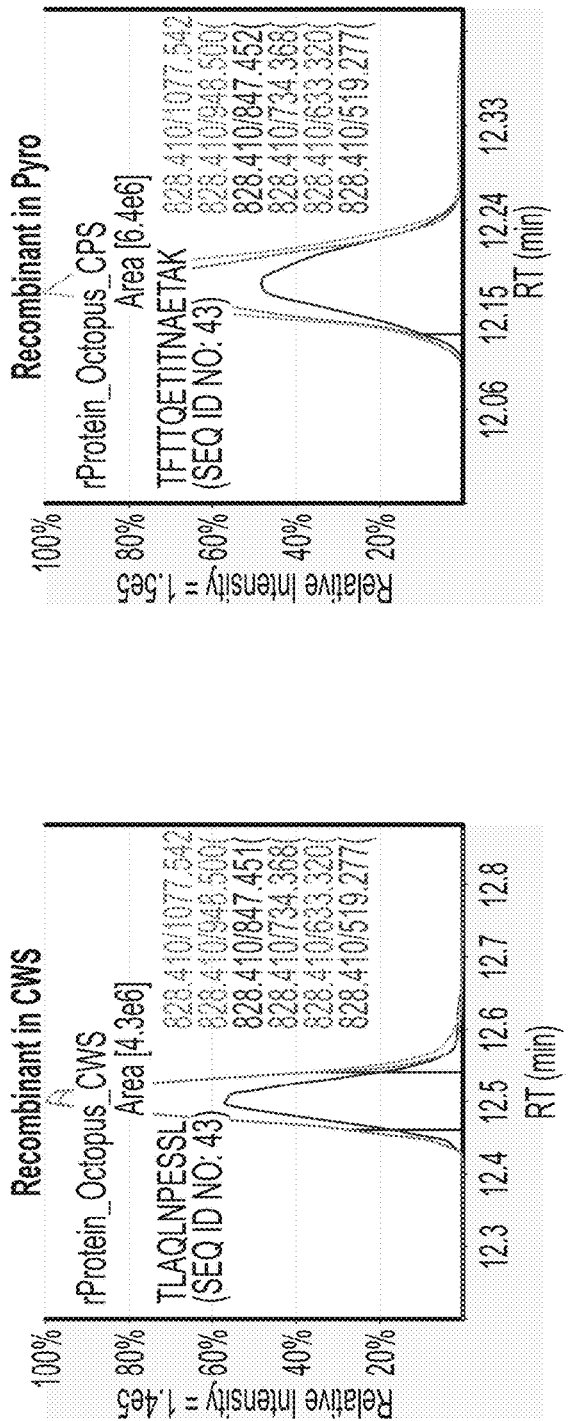
Figure 21E:
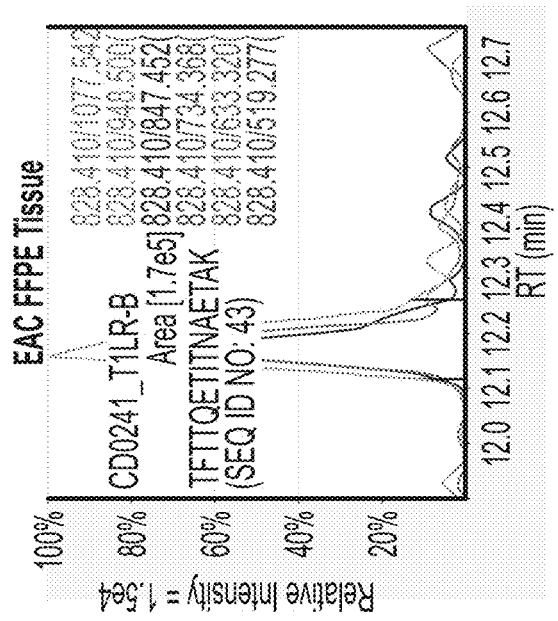
Figure 21F:
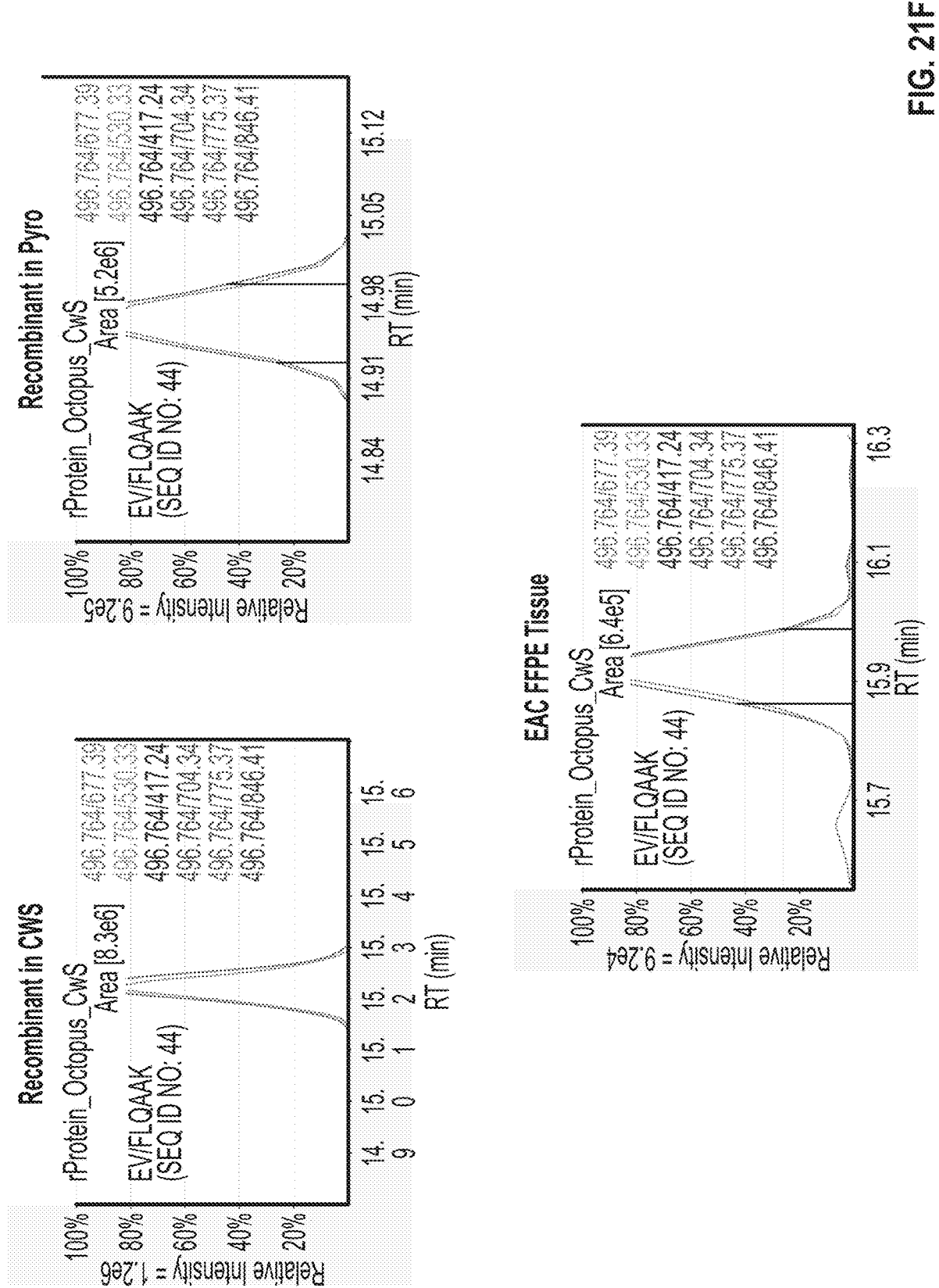

Representative tandem mass spectrometry spectra of the GPI protein in human samples using two of these peptides are shown in FIGS. 20A-20B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant GPI protein was used to screen unique peptides for SRM development. Specifically, 2 µg of human recombinant GPI protein was added to Liquid Tissue Buffer and treated with 0.5 µg of trypsin for 16 hours at 37° C. for a final concentration of 20 ng/µL. The reaction tube was heated at 95° C. for 5 minutes to inactivate trypsin. After hydrolysis, 2 µL of the GPI tryptic digests were mixed with 20 µL of carrier working solution (CWS), 5 µL HSM (to obtain retention time across the samples) and 23 µL of 0.100 formic acid of which 10 µL was injected for MS analysis. The data in Table 16 show the intensity that was observed in the MS analysis within this relatively simple matrix. In addition, 2 µL of the GPI tryptic digests were mixed with 5 µg of *Pyrococcus* (to observe the performance of the peptide in a more complex matrix), 5 µL HSM and 0.1% formic acid to a final volume of 50 µL of which 10 µL was injected for MS analysis as well. The data in Table 16 show the intensity that was observed in the MS analysis within this more complex matrix. In addition, the data in Table 16 show the intensity that was observed in a very complex lysate containing FFPE tissue from an esophageal adenocarcinoma tumor sample.

TABLE 16

Trypsin digestion mapping.

| Sequence | Recombinant Intensity in CWS | Recombinant Intensity in Pyro | FFPE EAC Intensity |
|---|---|---|---|
| DPQFQK (SEQ ID NO: 34) | ND | ND | ND |
| LQQWYR (SEQ ID NO: 35) | 2.5E6 | 1.4E6 | 6.9E5 |

TABLE 16-continued

Trypsin digestion mapping.

| Sequence | Recombinant Intensity in CWS | Recombinant Intensity in Pyro | FFPE EAC Intensity |
|---|---|---|---|
| SELNLR (SEQ ID NO: 36) | 7.3E4 | 2.9E6 | ND |
| FNHFSLTLNTNHGHILVDYSK (SEQ ID NO: 37) | ND | ND | ND |
| INYTEGR (SEQ ID NO: 38) | 2.4E4 | 7.5E5 | ND |
| AVLHVALR (SEQ ID NO: 39) | 1.3E6 (+3) | 1.1E5 (+3) | 6.2E5 (+3) |
| SNTPILVDGK (SEQ ID NO: 40) | 4.9E5 | 3.5E5 | 6E4 |
| VWYVSNIDGTHIAK (SEQ ID NO: 41) | 4E5 (+3) | 5.3E4 (+3) | ND |
| TLAQLNPESSLFIIASK (SEQ ID NO: 42) | 2.2E5 | 1.5E5 | 1.9E4 |
| TFTTQETITNAETAK (SEQ ID NO: 43) | 1.4E5 | 1.5E5 | 1.5E4 |
| EWFLQAAK (SEQ ID NO: 44) | 1.2E6 | 9.2E5 | 9.2E4 |
| DPSAVAK (SEQ ID NO: 45) | 6.4E3 | ND | ND |
| HFVALSTNTTK (SEQ ID NO: 46) | 1.5E5 (+2) | 1.5E4 (+2) | ND |
| ELQAAGK (SEQ ID NO: 47) | ND | ND | ND |
| IFVQGIIWDINSFDQWGVELGK (SEQ ID NO: 48) | ND | ND | ND |

Detection of the peptides in the protein digest is shown in FIGS. 21A-21F. Of the fifteen unique peptides screened, six peptides were observed in all FFPE ECA tissues screened. Peptides LQQWYR (SEQ ID NO: 35) and AVLHVALR (SEQ ID NO: 39) showed high intensity and consistent product ion ratios in the recombinant protein and FFPE ECA tissues.

SET

SET (UniProt Q01105) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 17, which are unique to SET, were chosen.

TABLE 17

Unique SET Peptides.

| Sequence | SET Isoform | Post-Translational Modifications | Start Position | End Position |
|---|---|---|---|---|
| QSPLPPQK (SEQ ID NO: 49) | 1 | S7-p | 6 | 13 |
| LNEQASEEILK (SEQ ID NO: 50) | 1, 2 | S63-p, K68-ub | 58 | 68 |

Figure 22A:
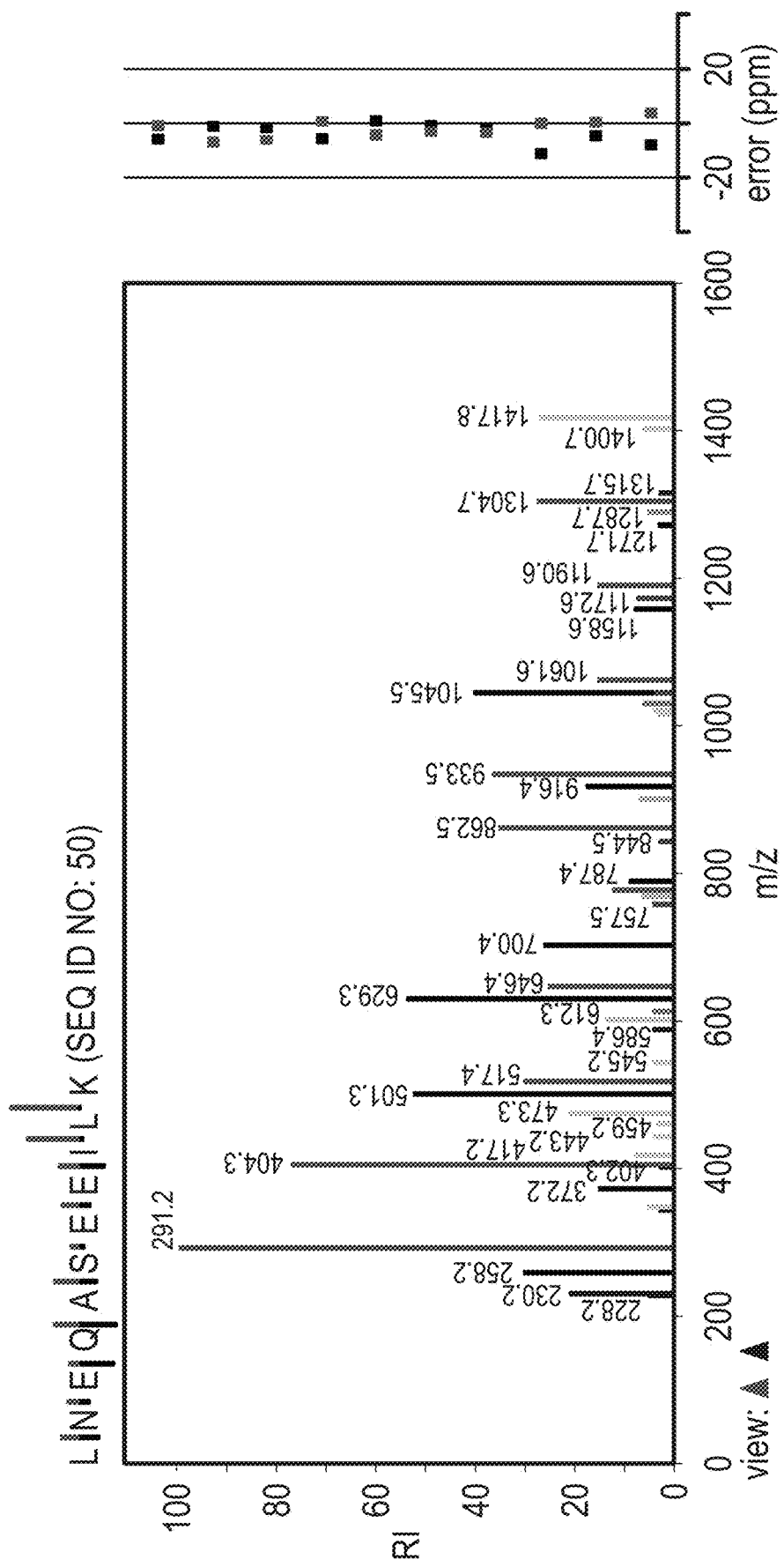
FIGS. 22A-22B. Representative tandem mass spectrometry spectra of the SET protein in human samples using SET peptides.
Figure 22B:
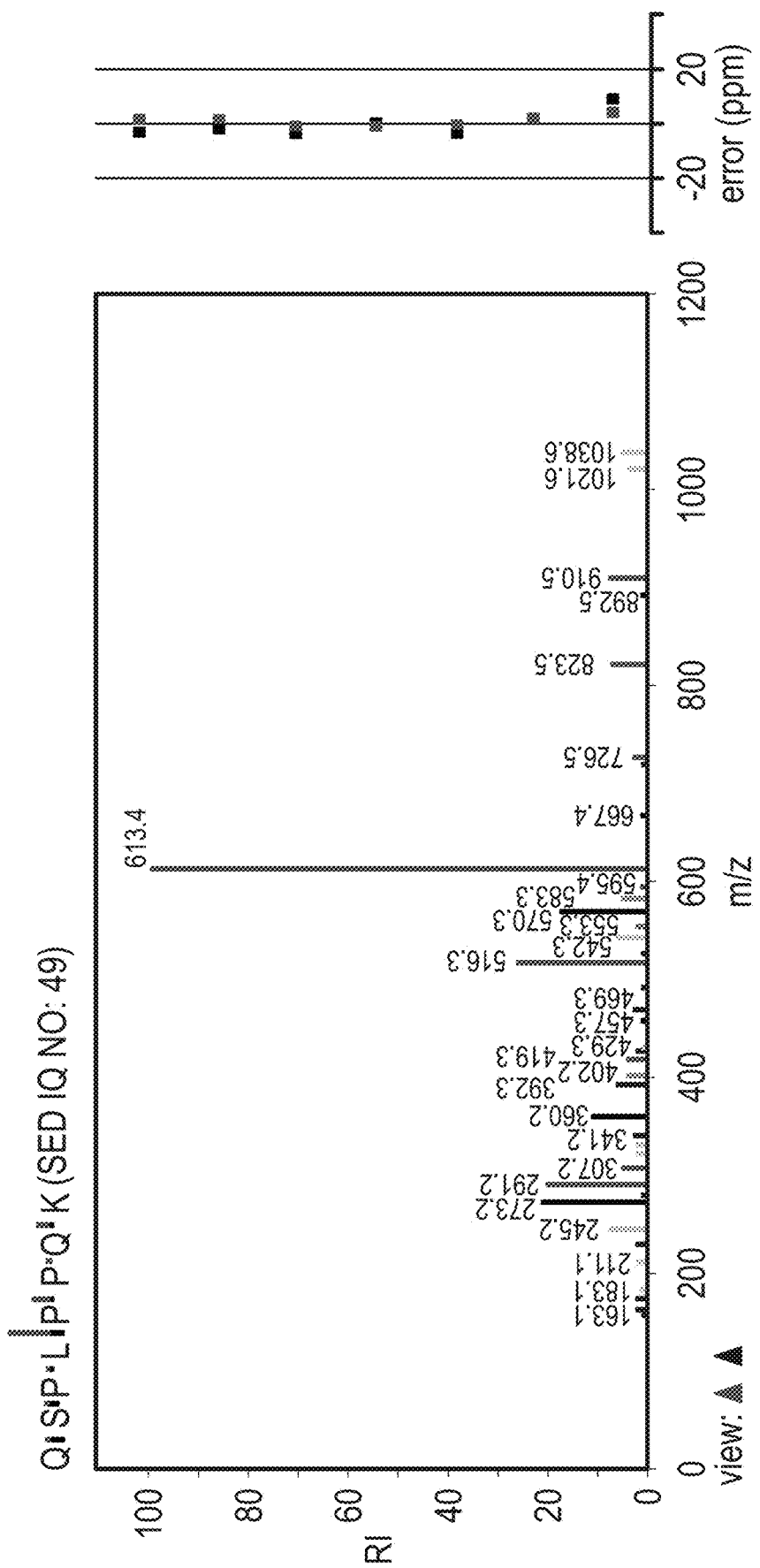

Representative tandem mass spectrometry spectra of the SET protein in human samples using these peptides are shown in FIGS. 22A-22B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant SET protein was used to screen unique peptides for SRM development. Specifically, 2 μg of human recombinant SET protein was added to 5 Liquid Tissue Buffer and treated with 0.5 μg of trypsin for 16 hours at 37° C. for a final concentration of 20 ng/μL. The reaction tube was heated at 95° C. for 5 minutes to inactivate trypsin. After hydrolysis, 2 μL of the SET tryptic digests were mixed with 20 μL of carrier working solution (CWS), 5 μL HSM (to obtain retention time across the samples) and 23 μL of 0.1% formic acid of which 10 μL was injected for MS analysis. The data in Table 18 show the intensity that was observed in the MS analysis within this relatively simple matrix. In addition, 2 L of the SET tryptic digests were mixed with 5 μg of *Pyrococcus* (to observe the performance of the peptide in a more complex matrix), 5 μL HSM and 0.1% formic acid to a final volume of 50 μL of which 10 μL was injected for MS analysis as well. The data in Table 18 show the intensity that was observed in the MS analysis within this more complex matrix. In addition, the data in Table 18 show the intensity that was observed in a very complex lysate containing FFPE tissue from an esophageal adenocarcinoma tumor sample.

TABLE 18

Trypsin Digestion Mapping.

| Sequence | Recombinant Intensity in CWS | Recombinant Intensity in Pyro | FFPE EAC Intensity |
|---|---|---|---|
| QSPLPPQK (SEQ ID NO: 49) | 6e4 | 8e4 | ND |
| LNEQASEEILK (SEQ ID NO: 50) | 1e6 | 1e6 | 7e4 |

Figure 23A:
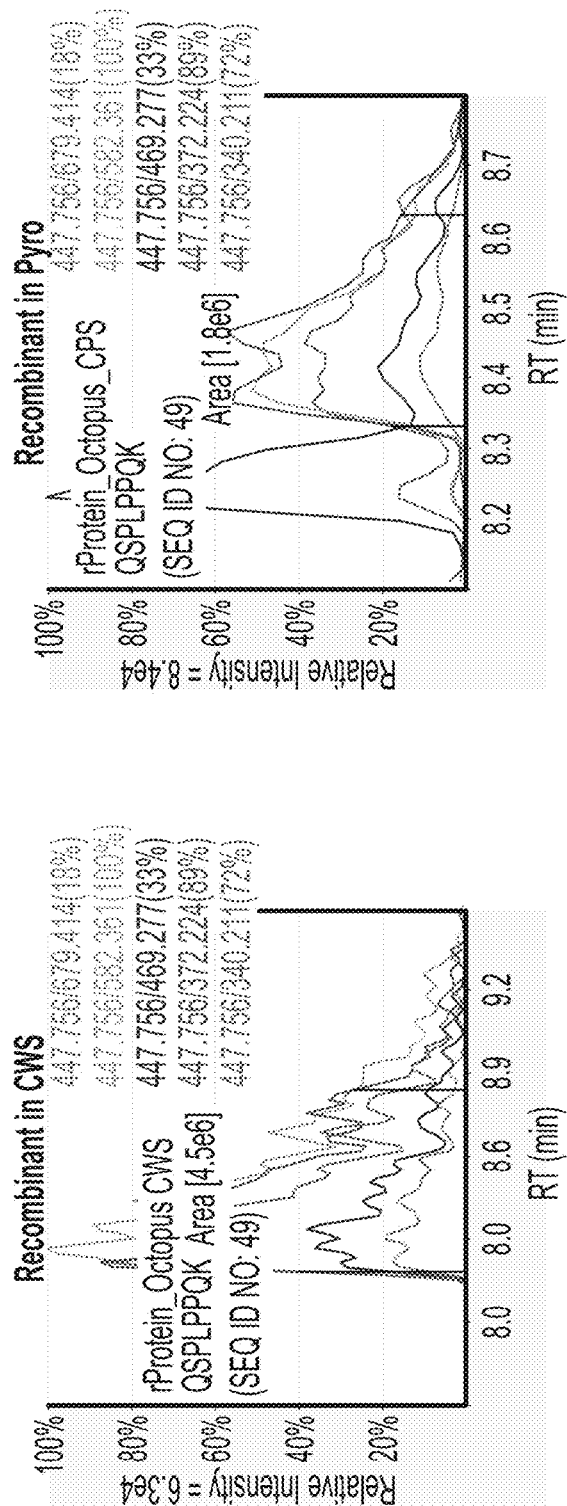
FIGS. 23A-23B. Detection of recombinant SET peptides in carrier working solution (CWS) and a solution with *Pyrococcus* (pyro), and detection of SET peptides in formalin-fixed paraffin-embedded esophageal adenocarcinoma tissues.
Figure 23A:
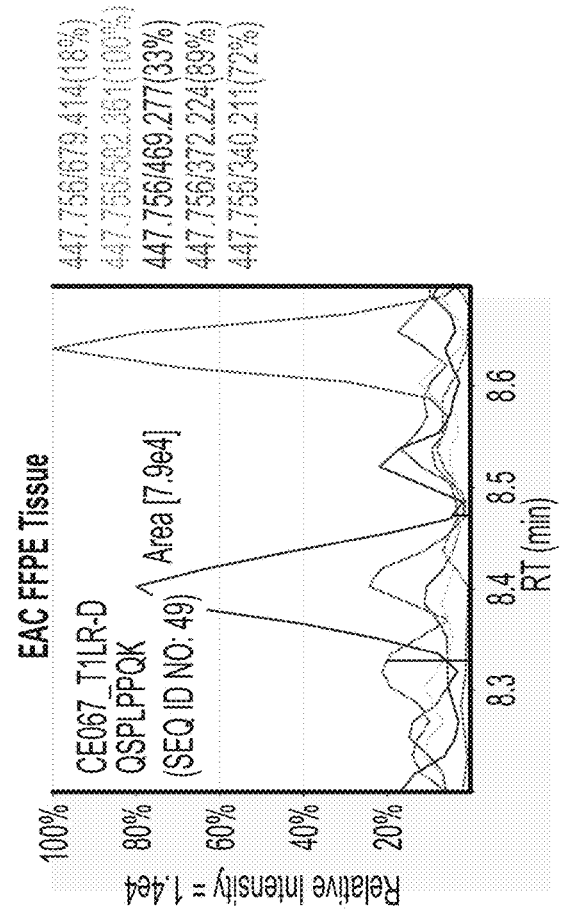
Figure 23B:
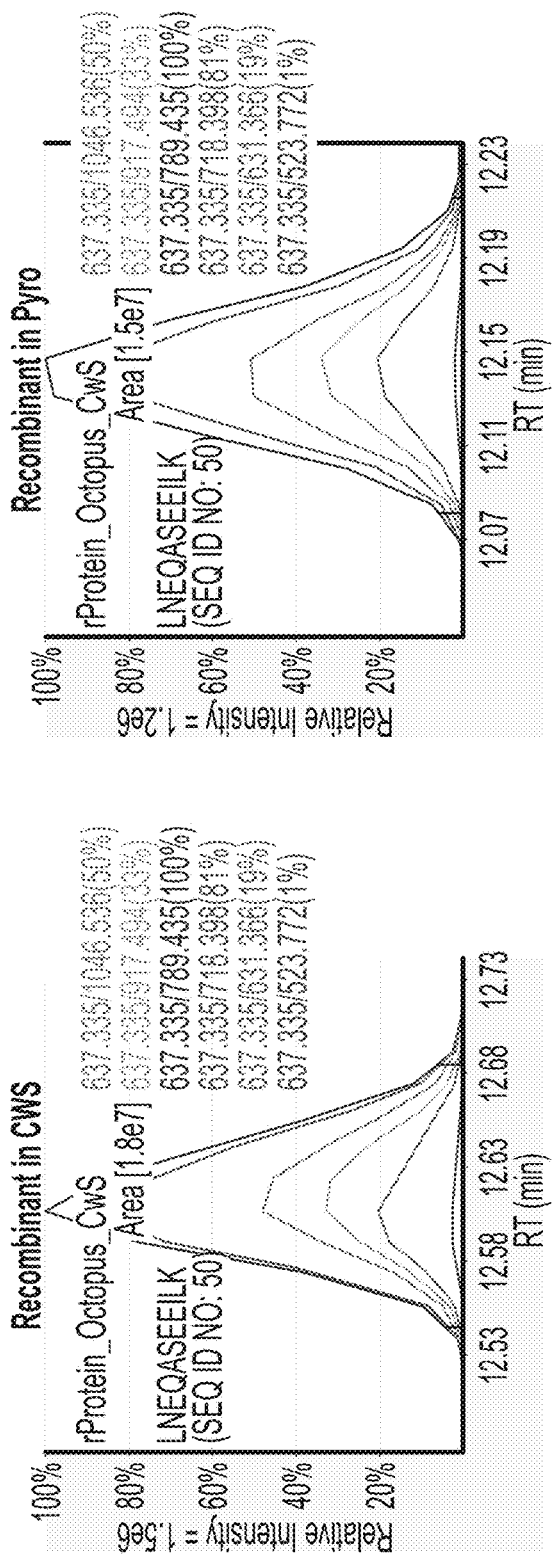
Figure 23B:
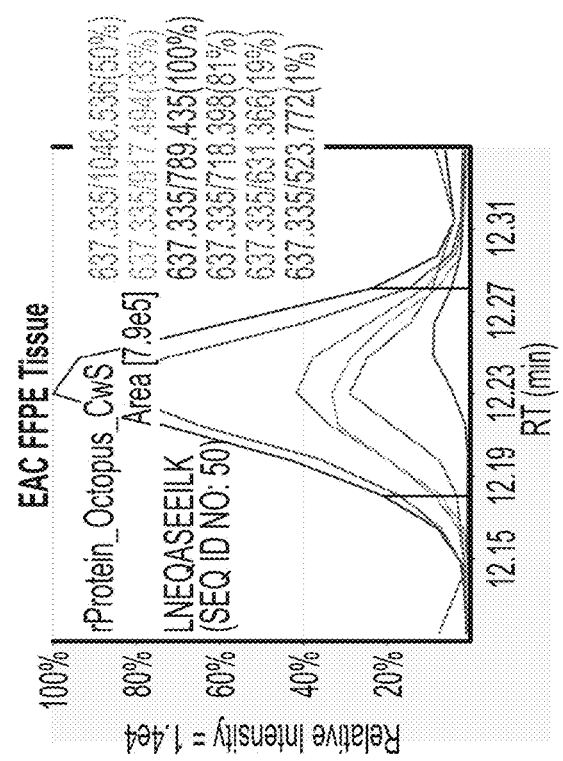

Detection of the peptides in the protein digest is shown in FIGS. 23A-23B. Of the two unique peptides screened, only one peptide was observed in FFPE ECA tissue. Peptide LNEQASEEILK (SEQ ID NO: 50) showed high intensity and consistent product ion ratios in the recombinant protein and FFPE ECA tissues.

LTF

LTF (UniProt P02788) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 19, which are unique to LTF, were chosen. All 16 peptides are common in all isoforms.

TABLE 19

Unique LTF Peptides.

| Sequence | LTF Isoform | Post-Translational Modifications | Start Position | End Position |
|---|---|---|---|---|
| ADAVTLDGGFIYEAGLAPYK (SEQ ID NO: 51) | 1, 2 | | 73 | 92 |
| THYYAVAVVK (SEQ ID NO: 52) | 1, 2 | Y111-p, Y112-p | 109 | 118 |
| GGSFQLNELQGLK (SEQ ID NO: 53) | 1, 2 | | 120 | 132 |
| DGAGDVAFIR (SEQ ID NO: 54) | 1, 2 | | 220 | 229 |
| ESTVFEDLSDEAER (SEQ ID NO: 55) | 1, 2 | | 230 | 243 |
| VPSHAVVAR (SEQ ID NO: 56) | 1, 2 | | 269 | 277 |
| EDAIWNLLR (SEQ ID NO: 57) | 1, 2 | | 283 | 291 |
| FQLFGSPSGQK (SEQ ID NO: 58) | 1, 2 | | 305 | 315 |
| DSAIGFSR (SEQ ID NO: 59) | 1, 2 | S327-p | 321 | 328 |

TABLE 19-continued

Unique LTF Peptides.

| Sequence | LTF Isoform | Post-Translational Modifications | Start Position | End Position |
|---|---|---|---|---|
| IDSGLYLGSGYFTAIQNLR (SEQ ID NO: 60) | 1, 2 | | 333 | 351 |
| SEEEVAAR (SEQ ID NO: 61) | 1, 2 | | 353 | 360 |
| GEADAMSLDGGYVYTAGK (SEQ ID NO: 62) | 1, 2 | K423-ub, K423-sm | 406 | 423 |
| SDTSLTWNSVK (SEQ ID NO: 63) | 1, 2 | | 463 | 473 |
| DVTVLQNTDGNNNEAWAK (SEQ ID NO: 64) | 1, 2 | | 566 | 583 |
| QVLLHQQAK (SEQ ID NO: 65) | 1, 2 | | 630 | 638 |
| YLGPQYVAGITNLK (SEQ ID NO: 66) | 1, 2 | | 681 | 694 |

Figure 24A:
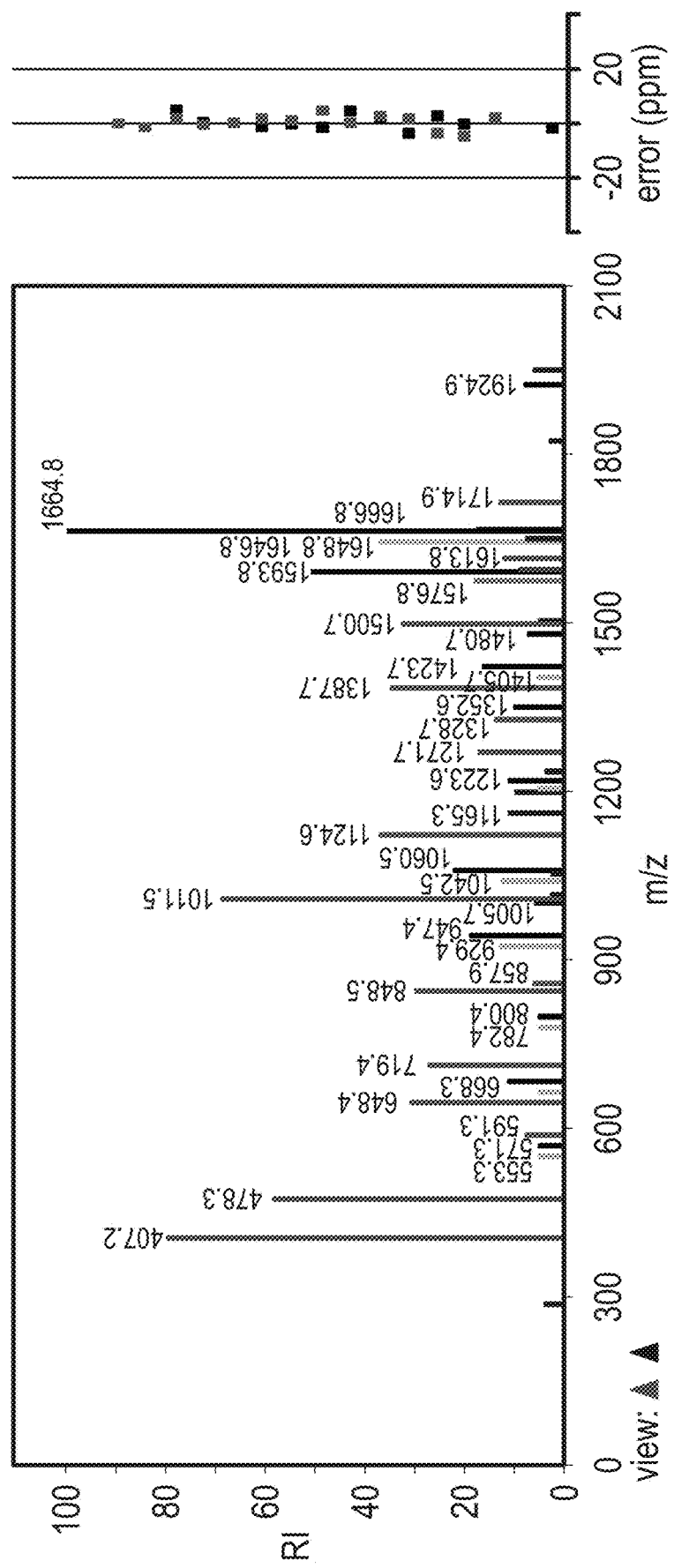
FIGS. 24A-24B. Representative tandem mass spectrometry spectra of the LTF protein in human samples using LTF peptides.
Figure 24B:
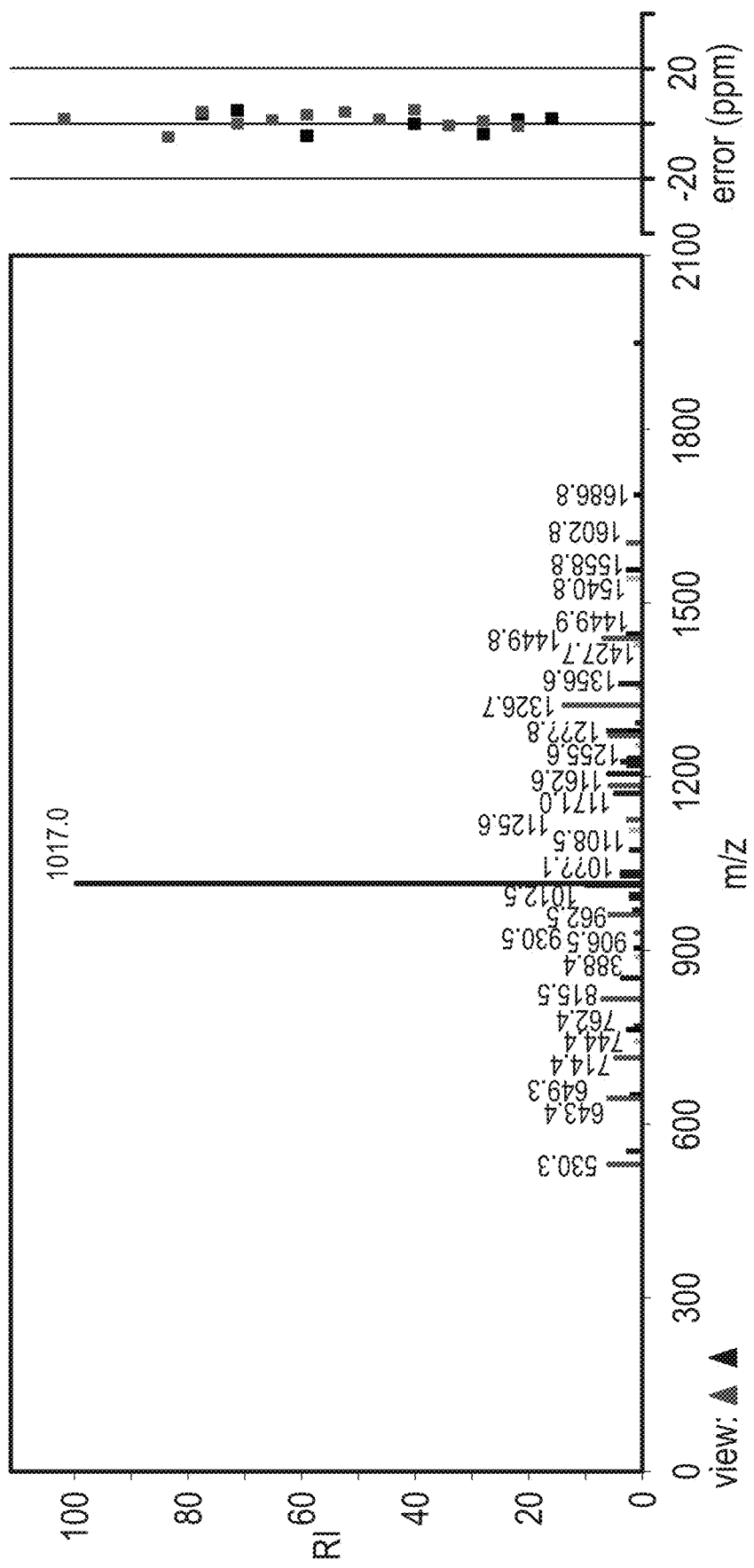
Figure 25A:
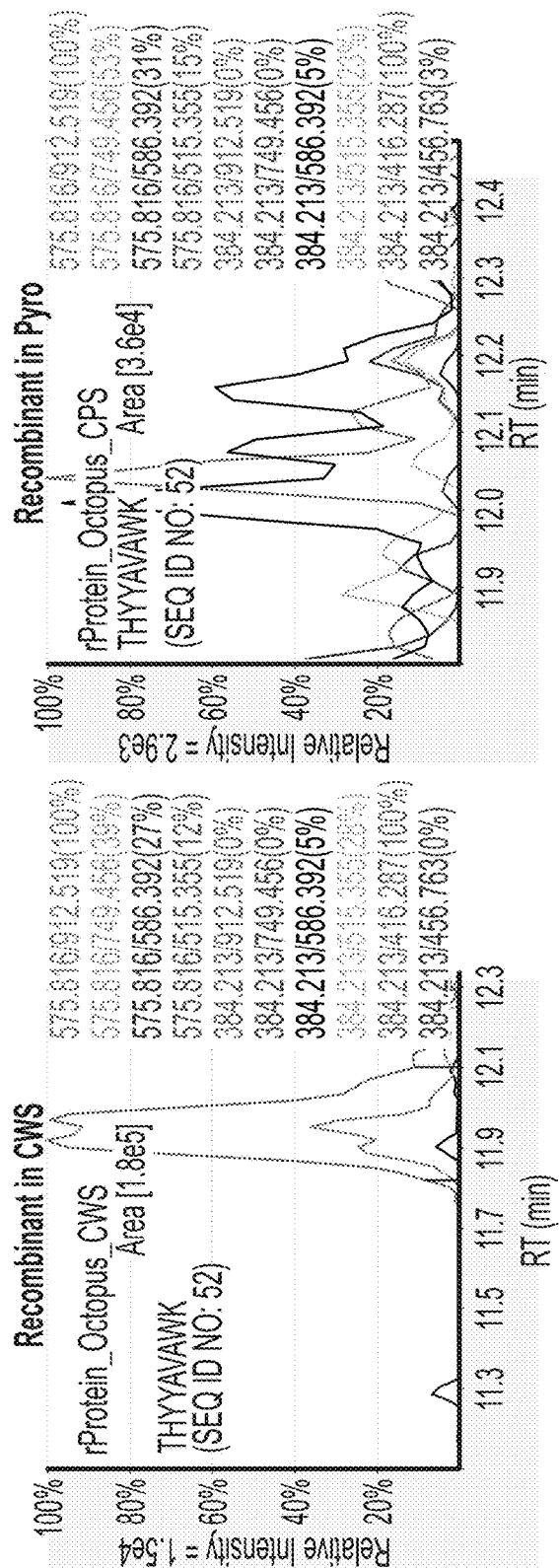
FIGS. 25A-25M. Detection of recombinant LTF peptides in carrier working solution (CWS) and a solution with *Pyrococcus* (pyro), and detection of LTF peptides in formalin-fixed paraffin-embedded esophageal adenocarcinoma tissues.
Figure 25A:
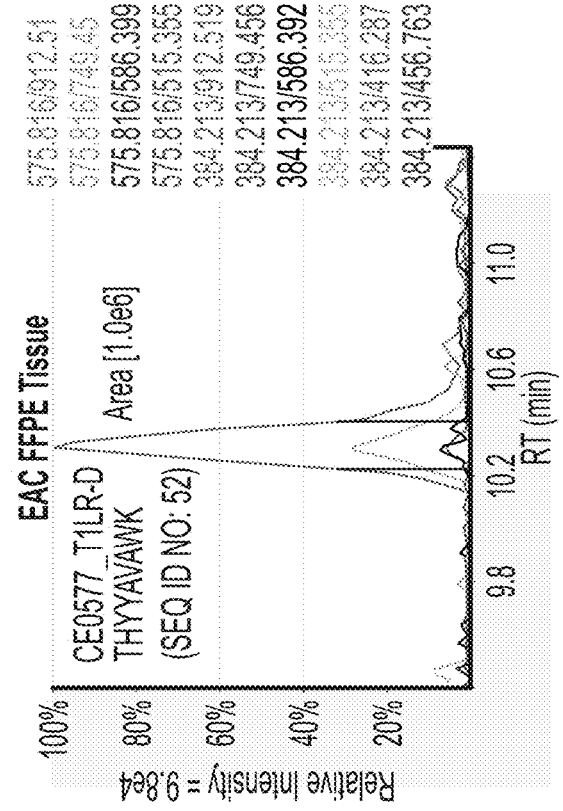
Figure 25B:
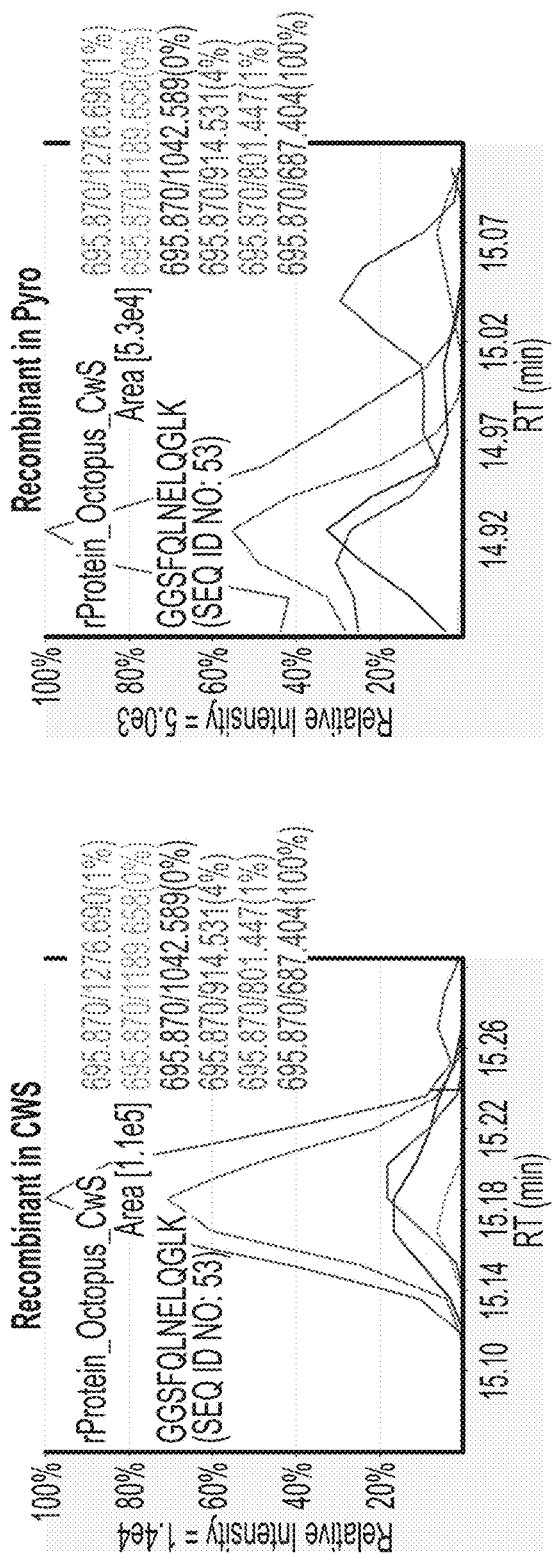
Figure 25B:
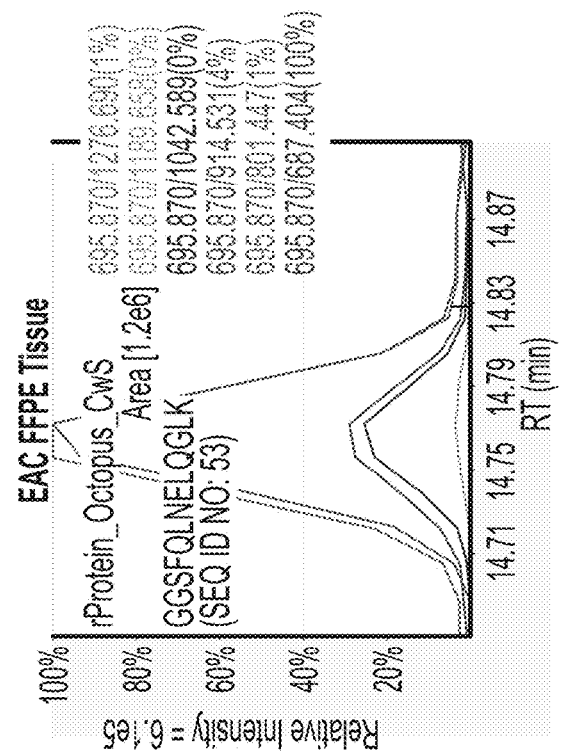
Figure 25C:
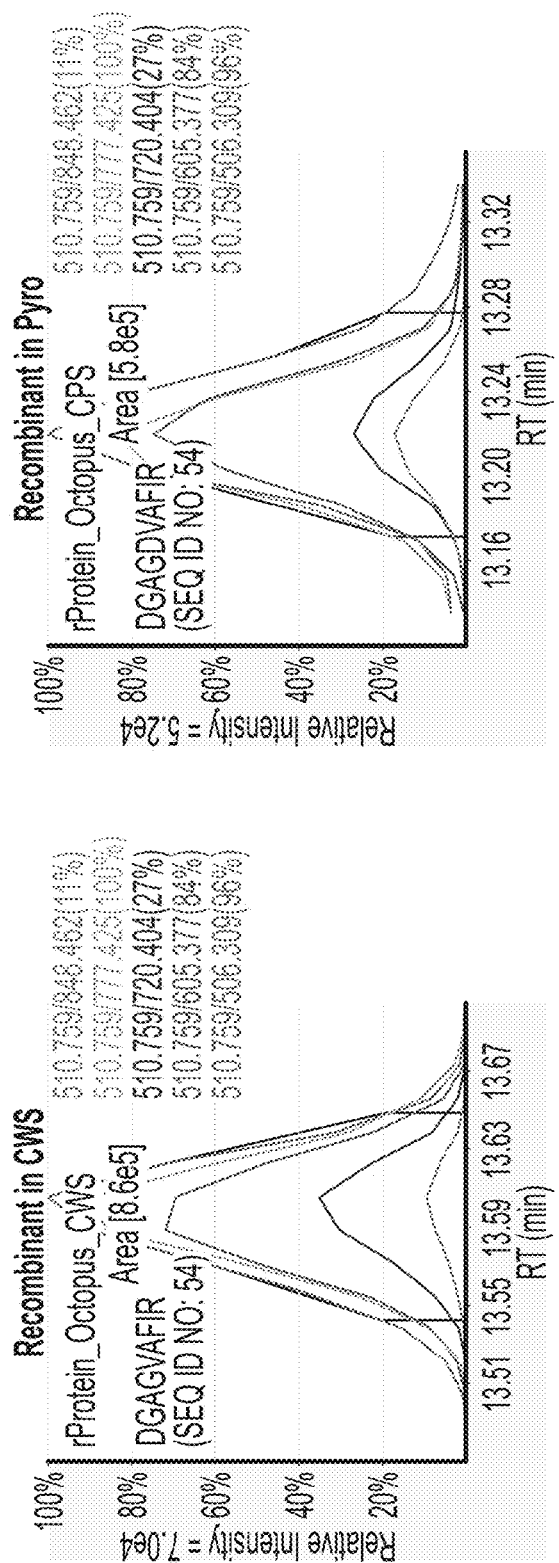
Figure 25C:
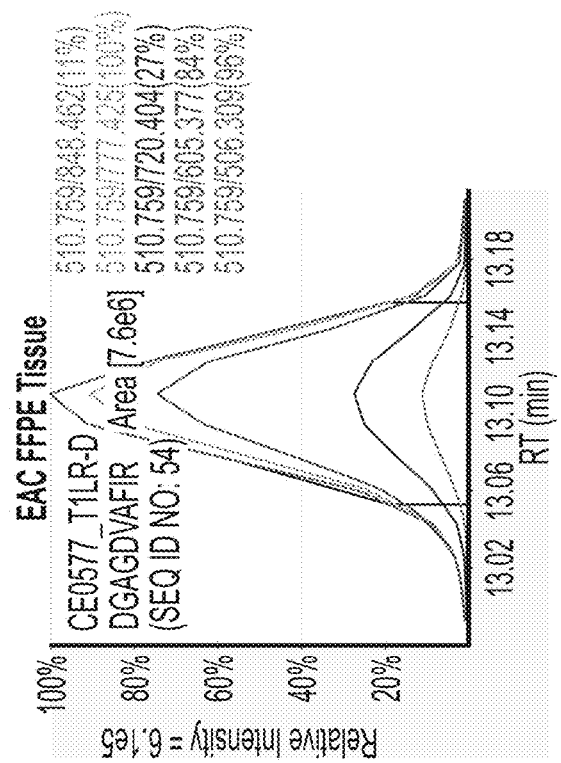
Figure 25D:
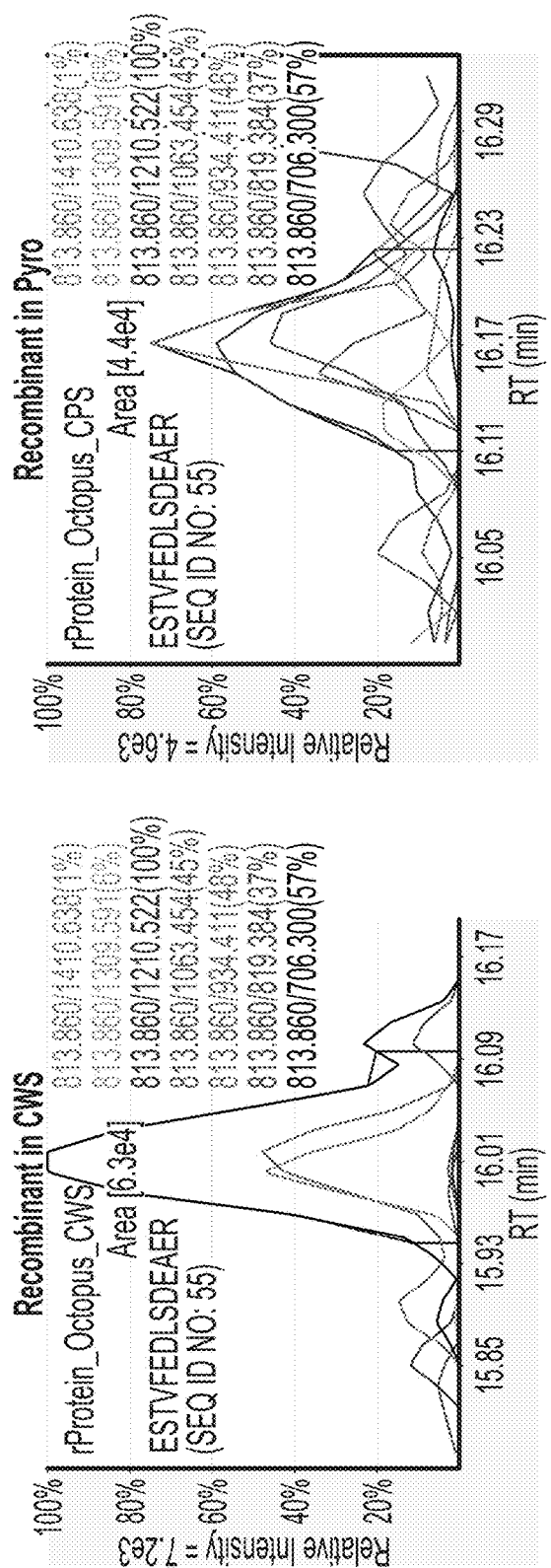
Figure 25D:
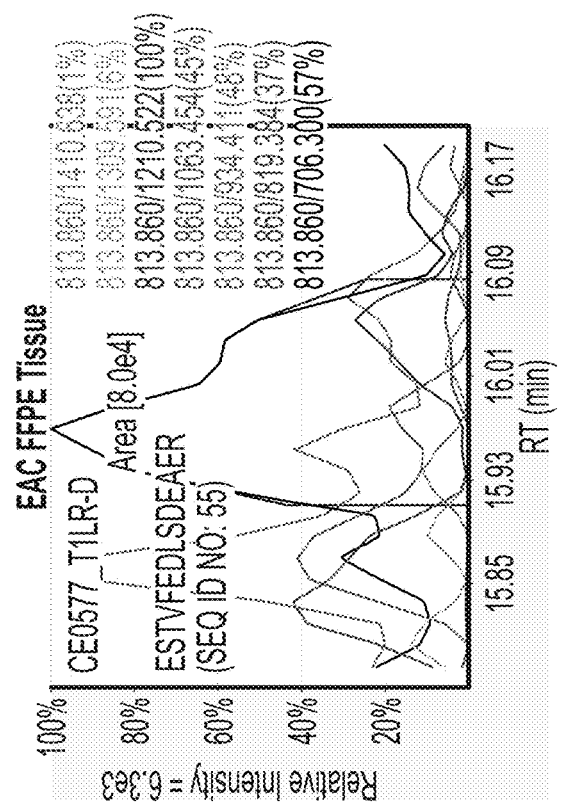
Figure 25E:
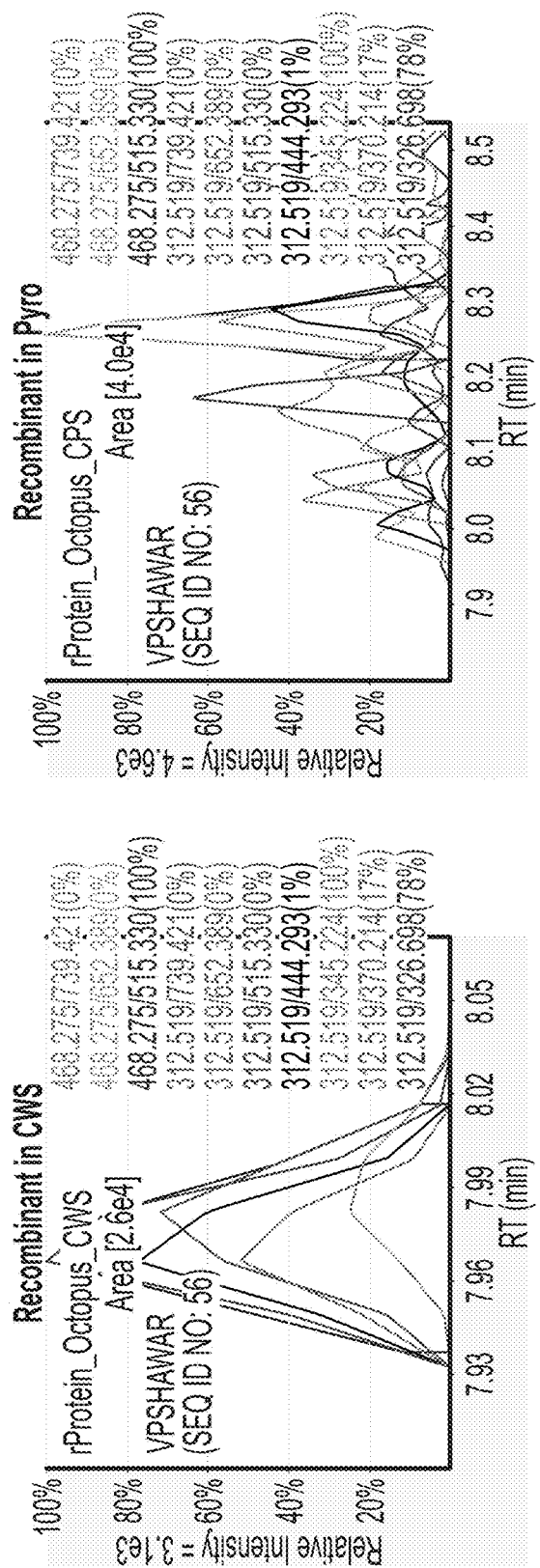
Figure 25E:
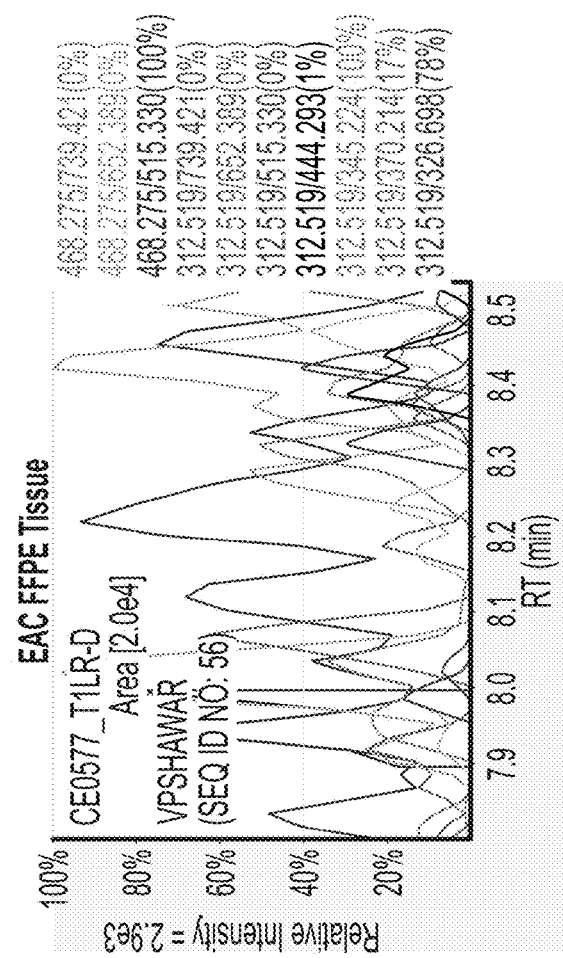
Figure 25F:
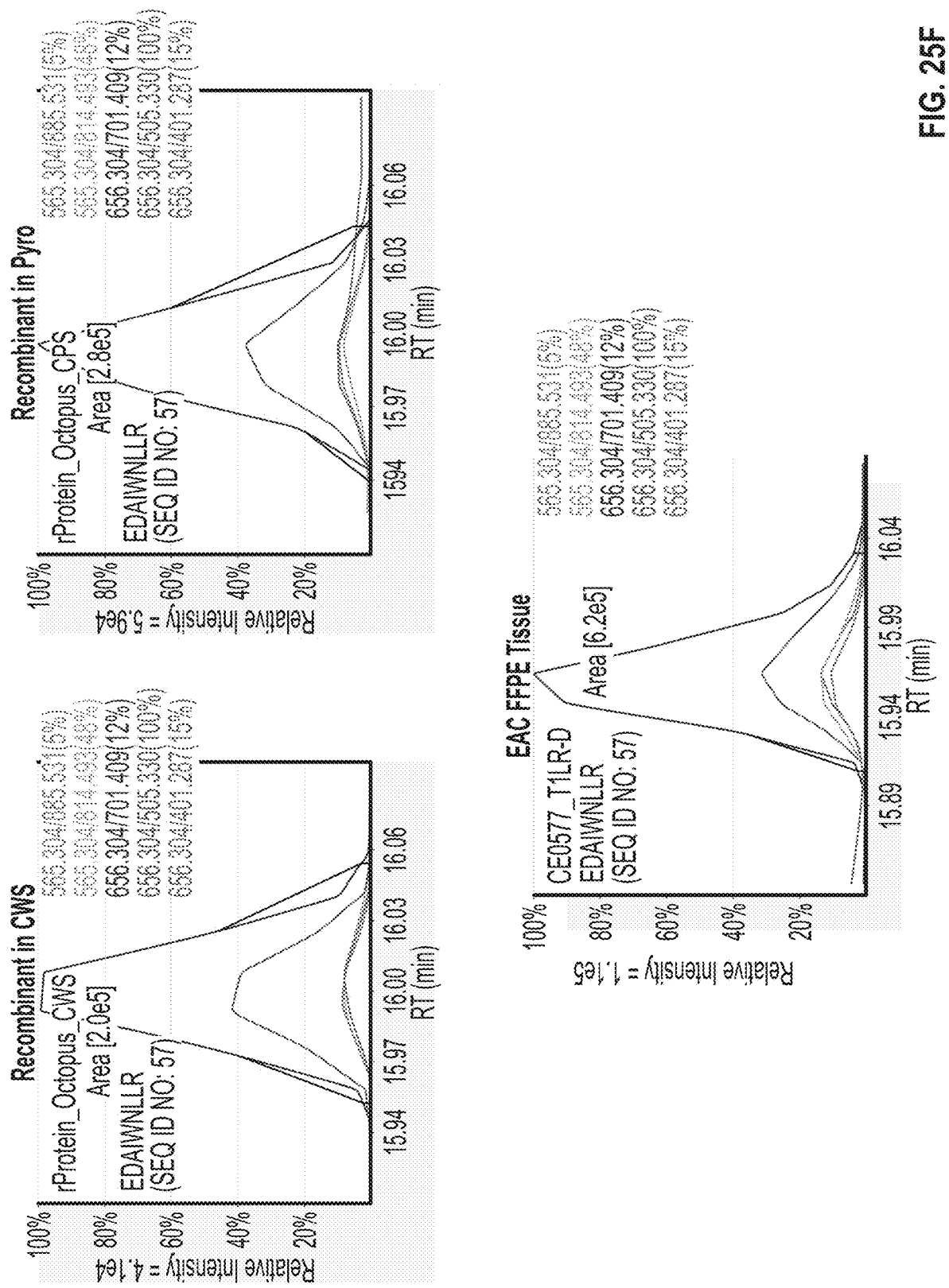
Figure 25G:
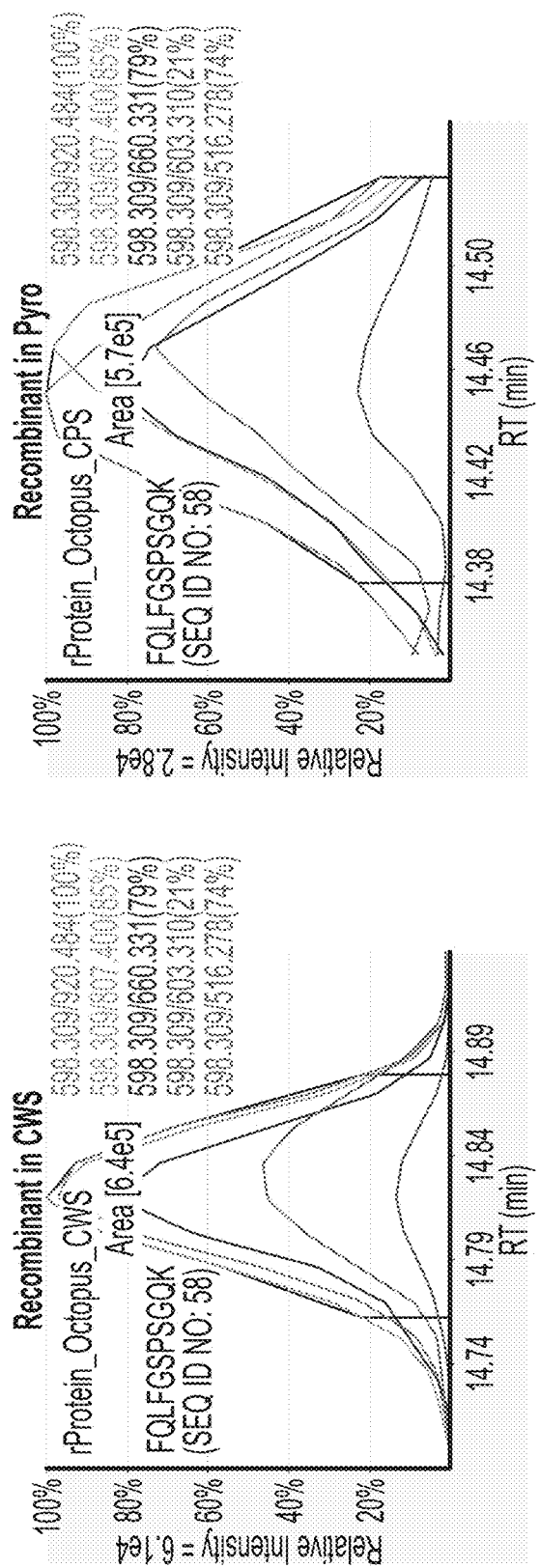
Figure 25G:
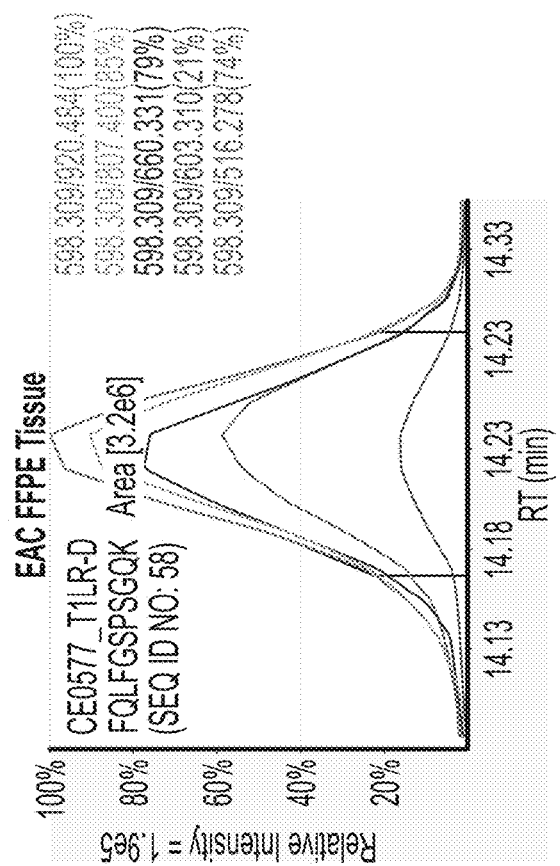
Figure 25H:
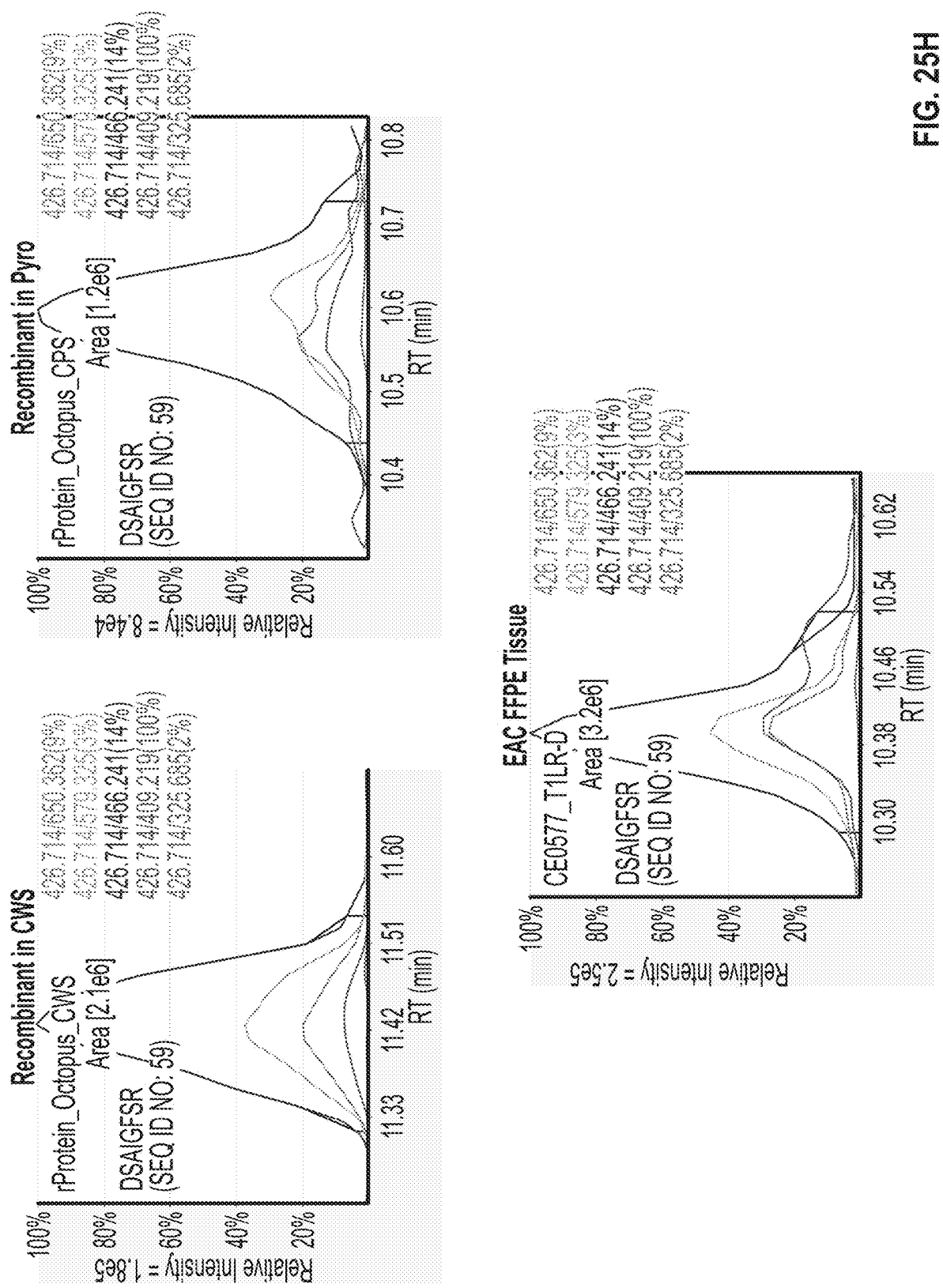
Figure 25I:
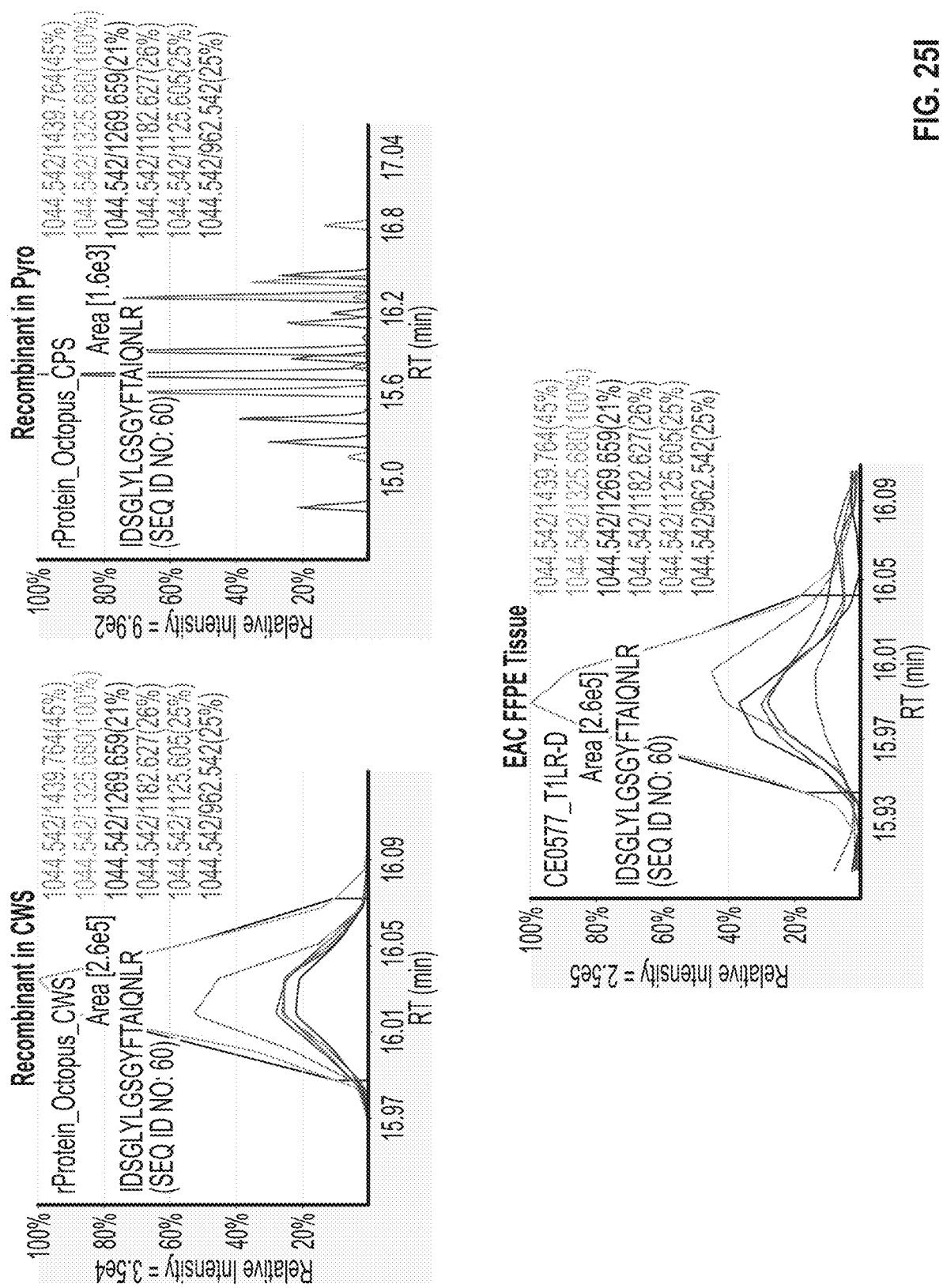
Figure 25J:
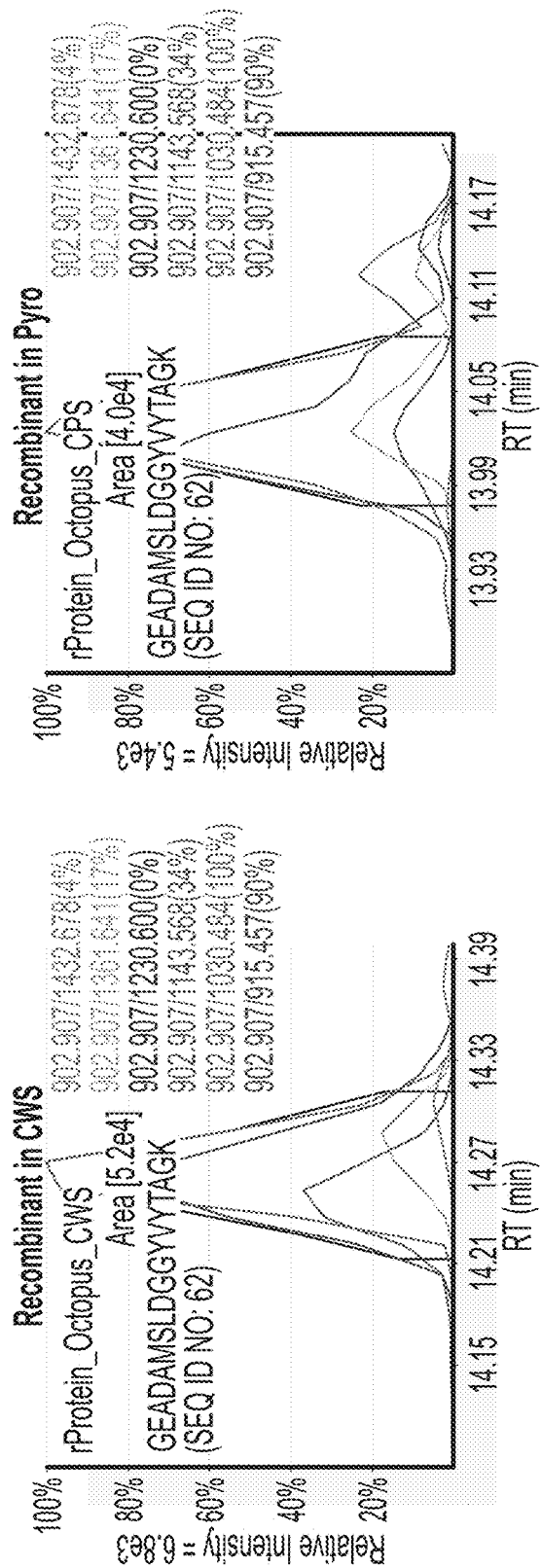
Figure 25J:
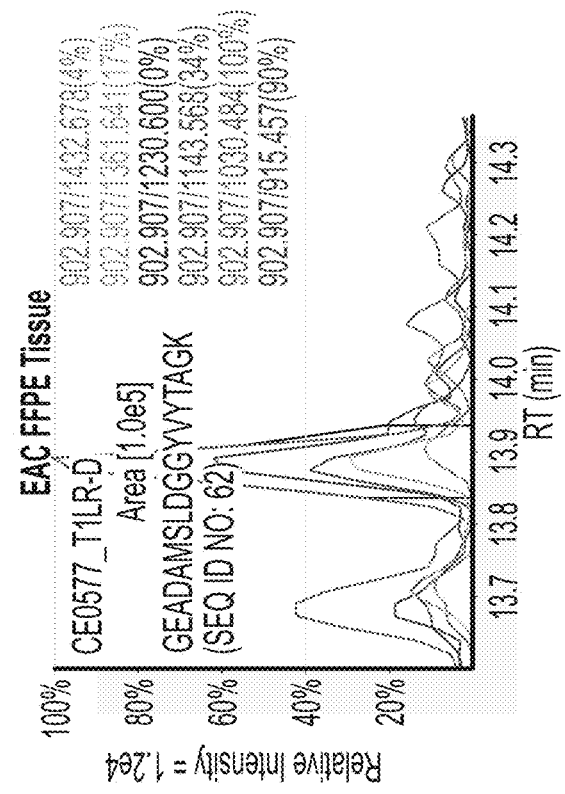
Figure 25K:
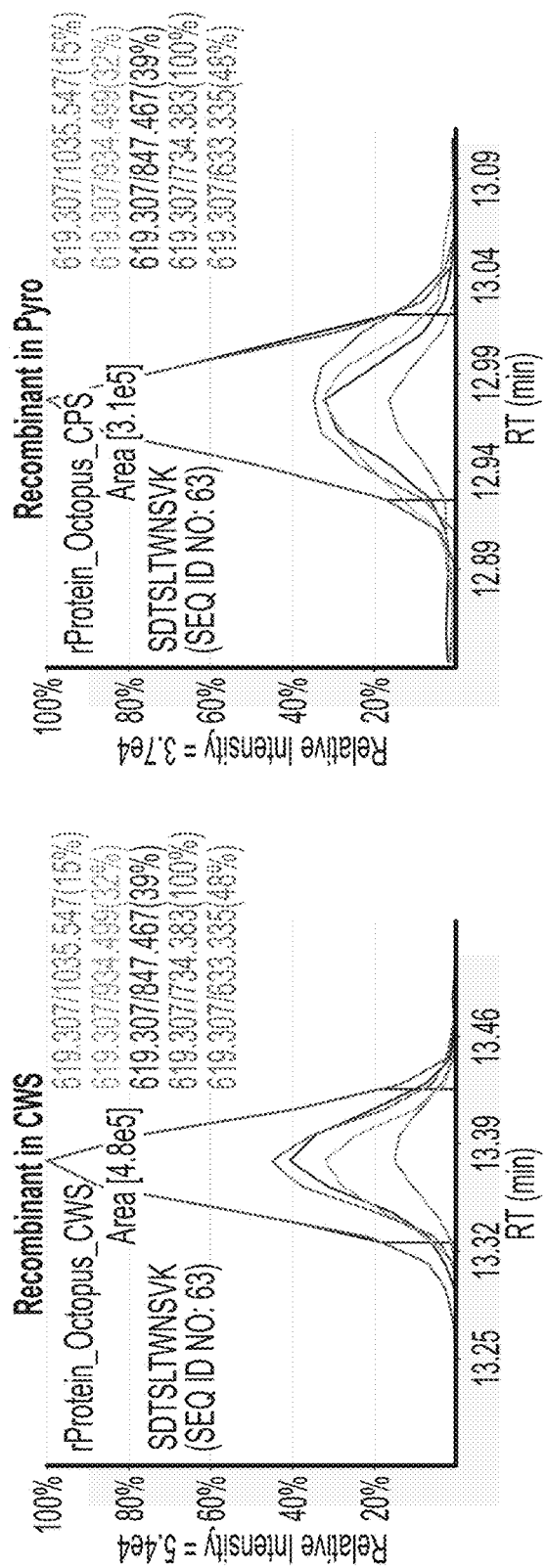
Figure 25K:
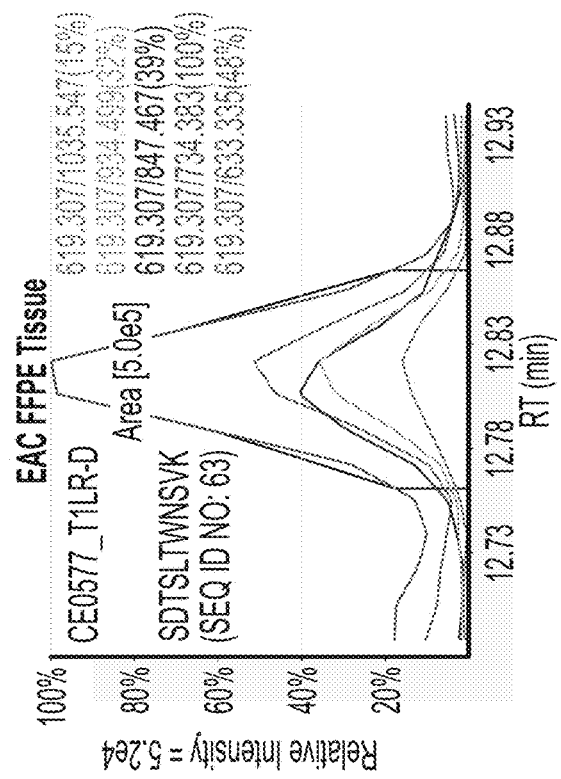
Figure 25L:
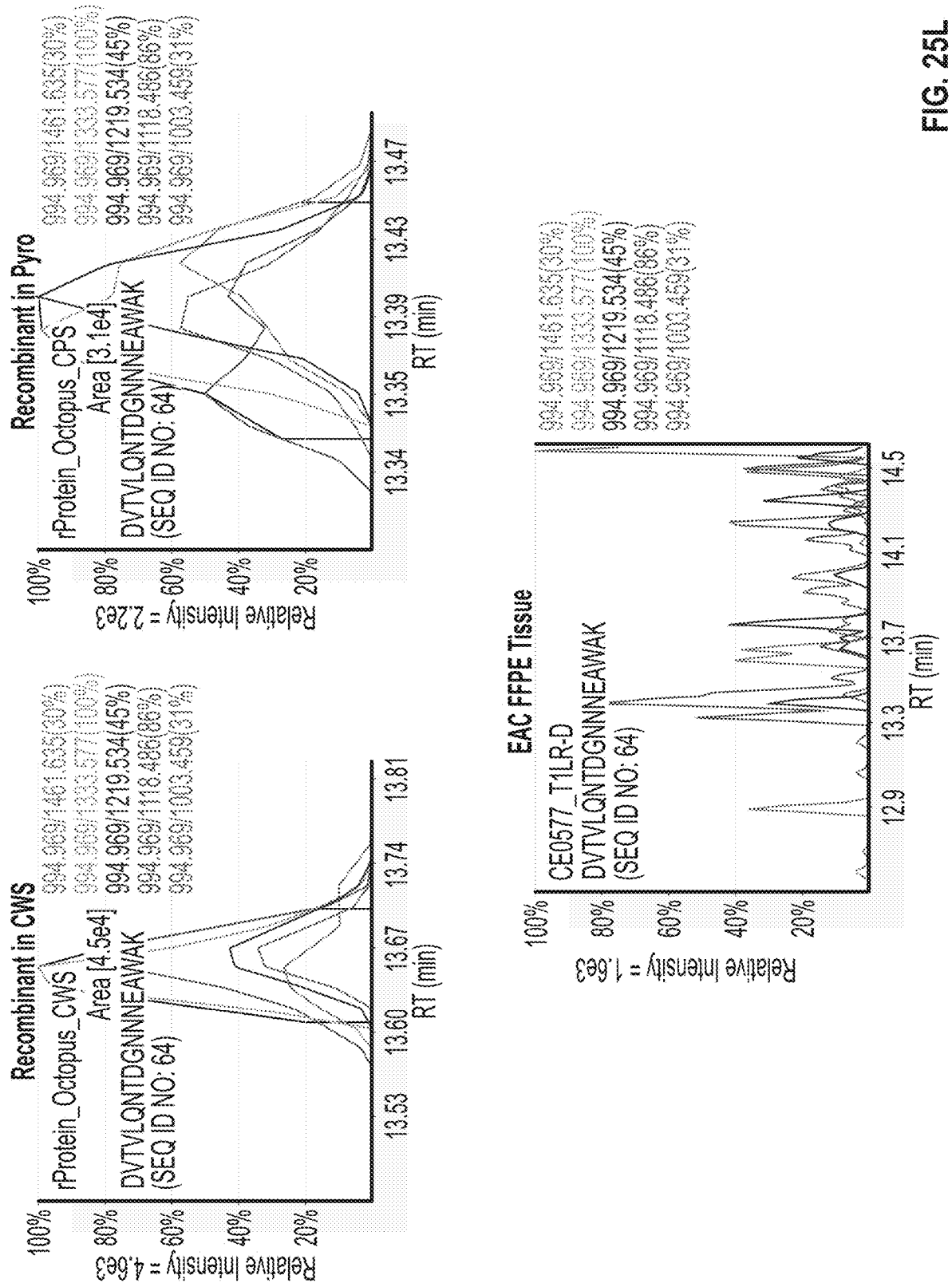
Figure 25M:
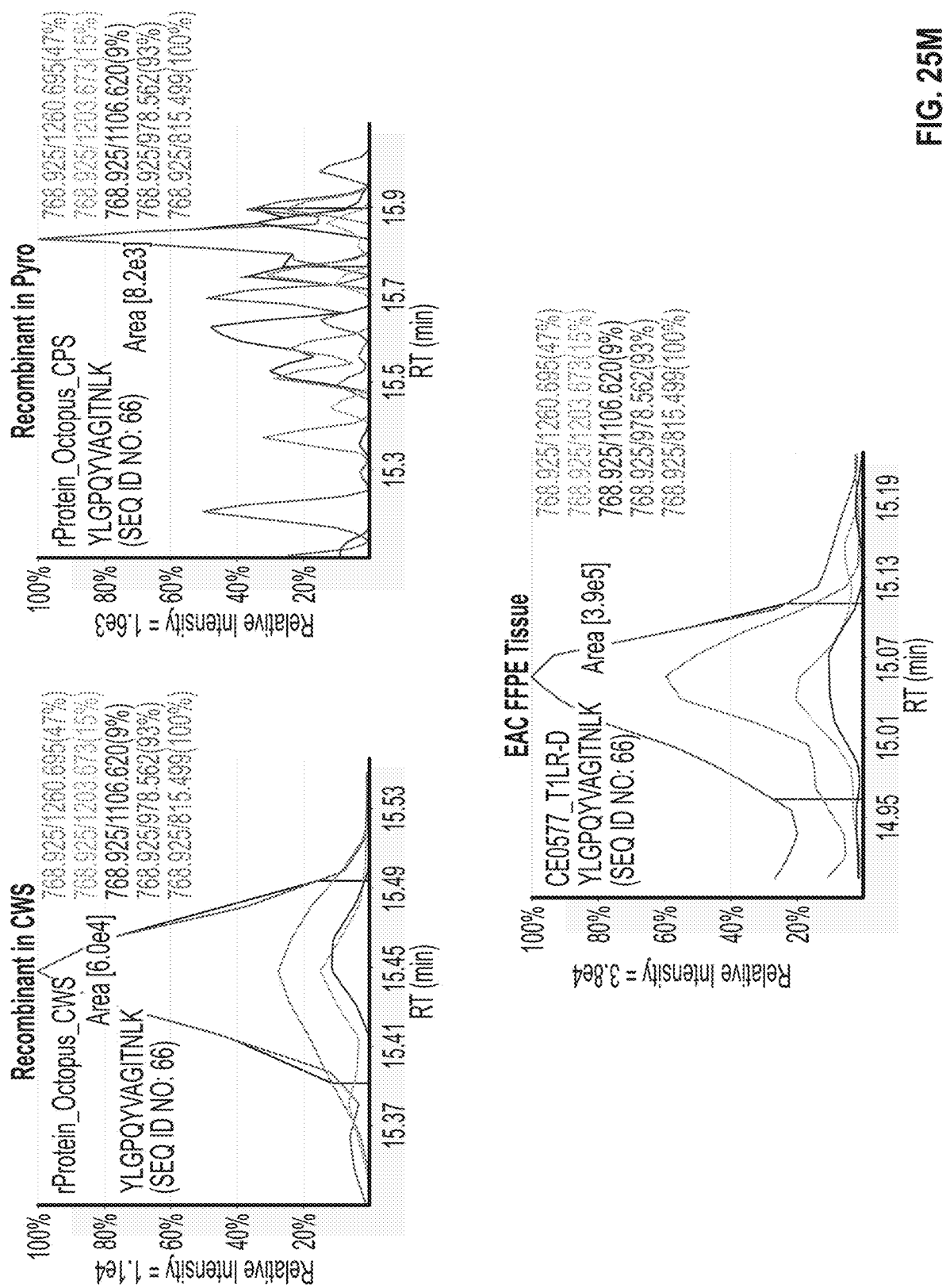

Representative tandem mass spectrometry spectra of the LTF protein in human samples using two of these peptides are shown in FIGS. 24A-24B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant LTF protein was used to screen unique peptides for SRM development. Specifically, 2 µg of human recombinant LTF protein was added to Liquid Tissue Buffer and treated with 0.5 µg of trypsin for 16 hours at 37° C. for a final concentration of 20 ng/µL. The reaction tube was heated at 95° C. for 5 minutes to inactivate trypsin. After hydrolysis, 2 µL of the LTF tryptic digests were mixed with 20 µL of carrier working solution (CWS), 5 µL HSM (to obtain retention time across the samples) and 23 µL of 0.100 formic acid of which 10 µL was injected for MS analysis. The data in Table 20 show the intensity that was observed in the MS analysis within this relatively simple matrix. In addition, 2 µL of the LTF tryptic digests were mixed with 5 µg of *Pyrococcus* (to observe the performance of the peptide in a more complex matrix), 5 µL HSM and 0.10% formic acid to a final volume of 50 µL of which 10 µL was injected for MS analysis as well. The data in Table 20 show the intensity that was observed in the MS analysis within this more complex matrix. In addition, the data in Table 20 show the intensity that was observed in a very complex lysate containing FFPE tissue from an esophageal adenocarcinoma tumor sample.

TABLE 18

Trypsin Digestion Mapping.

| Sequence | Recombinant Intensity in CWS | Recombinant Intensity in Pyro | FFPE EAC Intensity |
|---|---|---|---|
| ADAVTLDGGFIYEAGLAPYK (SEQ ID NO: 51) | ND | ND | ND |
| THYYAVAVVK (SEQ ID NO: 52) | 1e4 | ND | 9e4 |
| GGSFQLNELQGLK (SEQ ID NO: 53) | 1e4 | 5e3 | 1e5 |
| DGAGDVAFIR (SEQ ID NO: 54) | 7e4 | 5e4 | 6e5 |
| ESTVFEDLSDEAER (SEQ ID NO: 55) | 7e3 | ND | ND |
| VPSHAVVAR (SEQ ID NO: 56) | 3e3 | ND | ND |
| EDAIWNLLR (SEQ ID NO: 57) | 5e4 | 4e4 | 1e5 |
| FQLFGSPSGQK (SEQ ID NO: 58) | 6e4 | 2.8e4 | 1.9e5 |
| DSAIGFSR (SEQ ID NO: 59) | 1.8e5 | 8e4 | 2e5 |
| IDSGLYLGSGYFTAIQNLR (SEQ ID NO: 60) | 3e4 | ND | 2e4 |
| SEEEVAAR (SEQ ID NO: 61) | ND | ND | ND |
| GEADAMSLDGGYVYTAGK (SEQ ID NO: 62) | 6e3 | 5e3 | 1.2e4 |
| SDTSLTWNSVK (SEQ ID NO: 63) | 5e4 | 3e4 | 5e4 |
| DVTVLQNTDGNNNEAWAK (SEQ ID NO: 64) | 4e3 | ND | ND |

TABLE 18-continued

Trypsin Digestion Mapping.

| Sequence | Recombinant Intensity in CWS | Recombinant Intensity in Pyro | FFPE EAC Intensity |
|---|---|---|---|
| QVLLHQQAK (SEQ ID NO: 65) | ND | ND | ND |
| YLGPQYVAGITNLK (SEQ ID NO: 66) | 1e4 | ND | 3e4 |

Detection of the peptides in the protein digest is shown in FIGS. 25A-25M. Of the sixteen unique peptides screened, ten peptides were observed in at least one FFPE ECA tissue. Peptides DGAGDVAFIR (SEQ ID NO: 54) and FQLFGSPSGQK (SEQ ID NO: 58) showed high intensity and consistent product ion ratios in the recombinant protein and FFPE ECA tissues.

S100P

S100P (UniProt P25815) target peptides were evaluated for target feasibility for targeted mass spectrometry. The following exclusion criteria were used for in silico mapping: no methionine (M), no cysteine (C), and no arginine (R) or lysine (K) followed by a proline (P) (i.e., no RP or KP). The following inclusion criteria were used for in silico mapping: peptide sequence length between 5-25 amino acids, and fully tryptic sequences only. Based on these criteria, the peptides in Table 21, which are unique to S100P, were chosen.

TABLE 21

Unique S100P Peptides.

| Sequence | S100P Isoform | Post-Translational Modifications | Start Position | End Position |
|---|---|---|---|---|
| YSGSEGSTQTLTK (SEQ ID NO: 67) | 1 | S21-p, S24-p, T25-p, K30-ub | 18 | 30 |
| ELPGFLQSGK (SEQ ID NO: 68) | 1 | K49-ac, K49-ub, K49-sc | 40 | 49 |

Figure 26A:
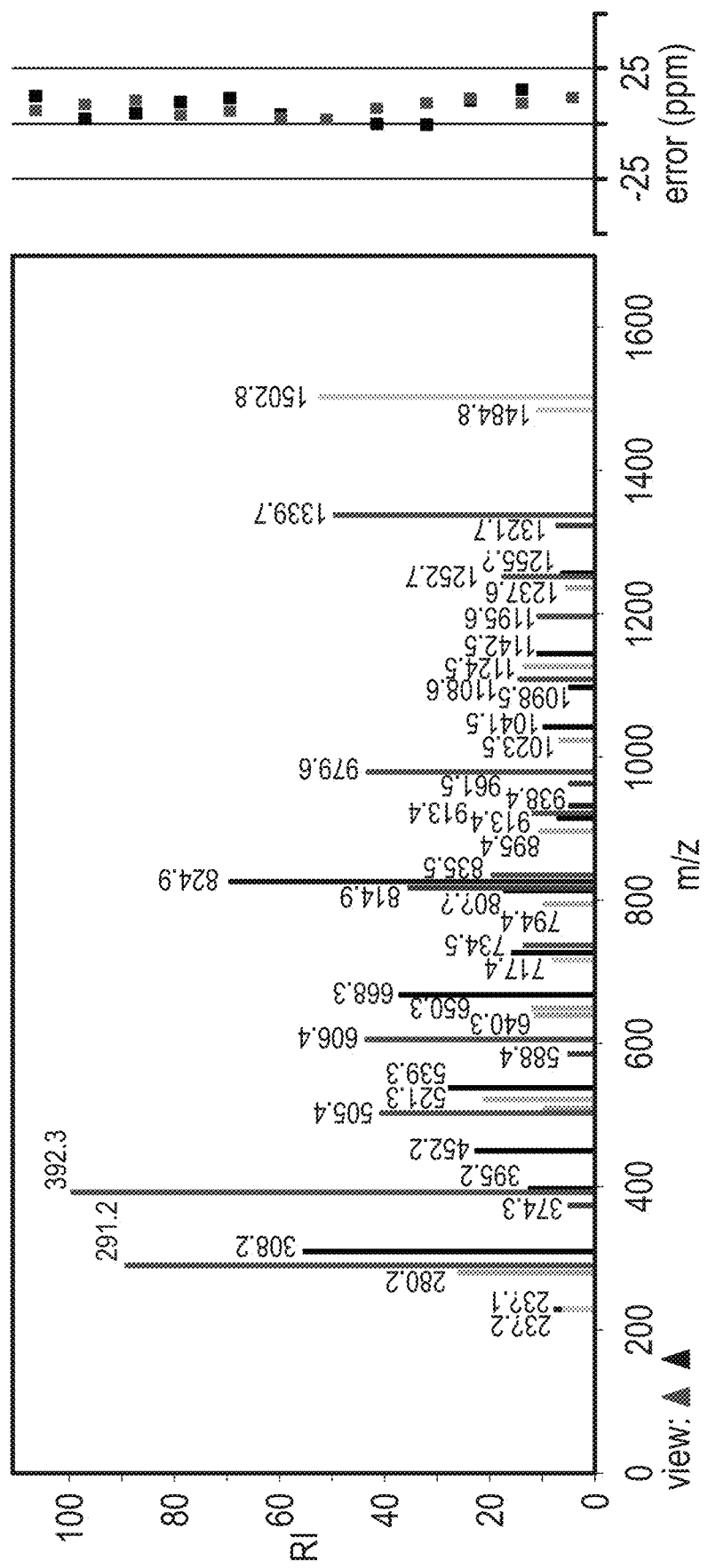
FIGS. 26A-26B. Representative tandem mass spectrometry spectra of the S100P protein in human samples using S100P peptides.
Figure 26B:
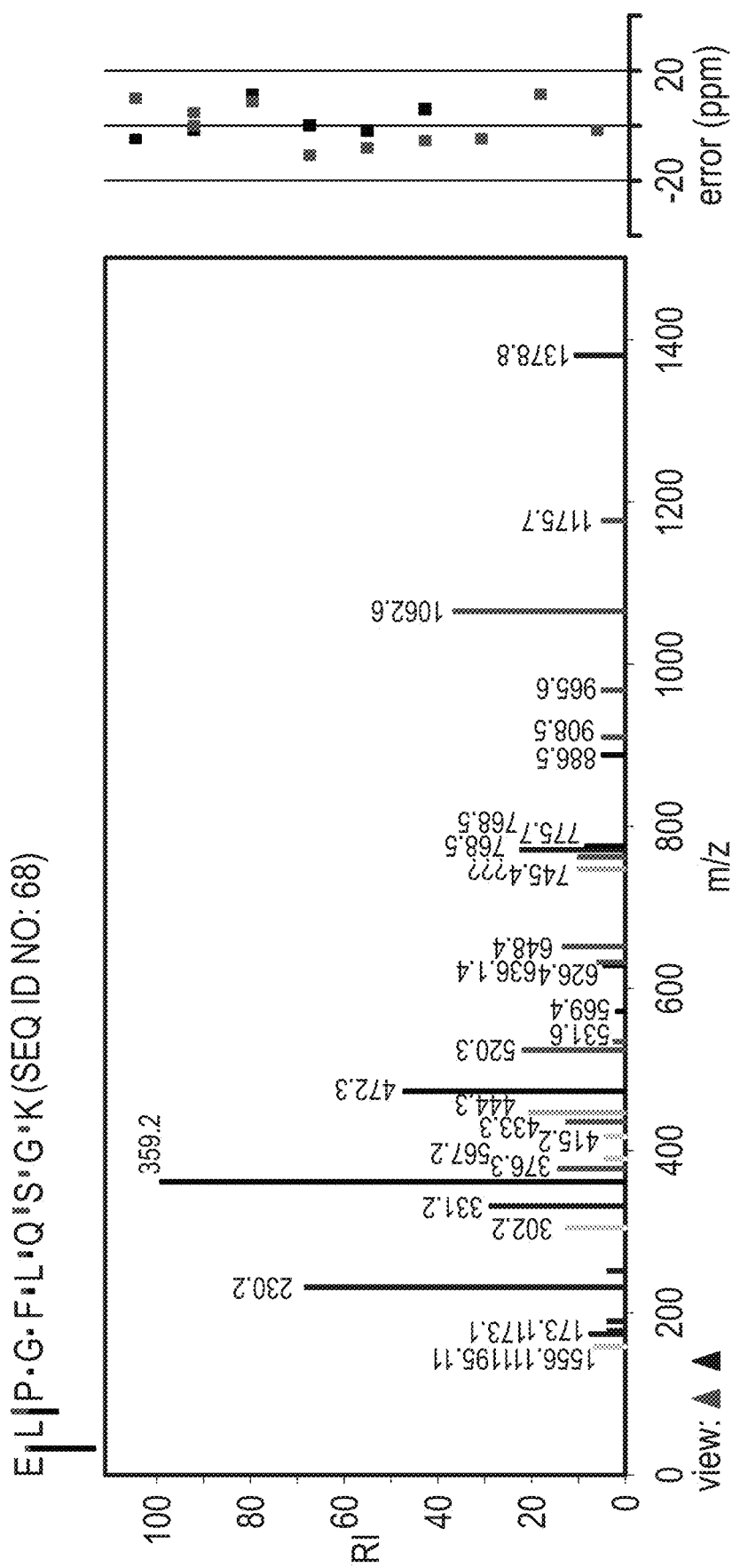

Representative tandem mass spectrometry spectra of the S100P protein in human samples using two of these peptides are shown in FIGS. 26A-26B. The spectra demonstrate we were able to detect these markers at high levels in heterogenous and formalin-fixed specimens.

Seven formalin-fixed paraffin-embedded (FFPE) clinical esophageal adenocarcinoma (EAC) tissues were then screened. Recombinant material (recombinant protein, overexpression lysate, or crude peptides) was used to screen the candidate peptides in FFPE cell lines or clinical samples. Trypsin-digested human recombinant S100P protein was used to screen unique peptides for SRM development. Specifically, 2 μg of human recombinant S100P protein was added to Liquid Tissue Buffer and treated with 0.5 μg of trypsin for 16 hours at 37° C. for a final concentration of 20 ng/μL. The reaction tube was heated at 95° C. for 5 minutes to inactivate trypsin. After hydrolysis, 2 μL of the S100P tryptic digests were mixed with 20 μL of carrier working solution (CWS), 5 μL HSM (to obtain retention time across the samples) and 23 μL of 0.1% formic acid of which 10 μL was injected for MS analysis. The data in Table 22 show the intensity that was observed in the MS analysis within this relatively simple matrix. In addition, 2 L of the S100P tryptic digests were mixed with 5 μg of *Pyrococcus* (to observe the performance of the peptide in a more complex matrix), 5 μL HSM and 0.1% formic acid to a final volume of 50 μL of which 10 μL was injected for MS analysis as well. The data in Table 22 show the intensity that was observed in the MS analysis within this more complex matrix. In addition, the data in Table 22 show the intensity that was observed in a very complex lysate containing FFPE tissue from an esophageal adenocarcinoma tumor sample.

TABLE 22

Trypsin Digestion Mapping.

| Sequence | Recombinant Intensity in CWS | Recombinant Intensity in Pyro | FFPE EAC Intensity |
|---|---|---|---|
| YSGSEGSTQTLTK (SEQ ID NO: 67) | 9e5 | 4e5 | 7e5 |
| ELPGFLQSGK (SEQ ID NO: 68) | 2e6 | 2e6 | 1e6 |

Figure 27A:
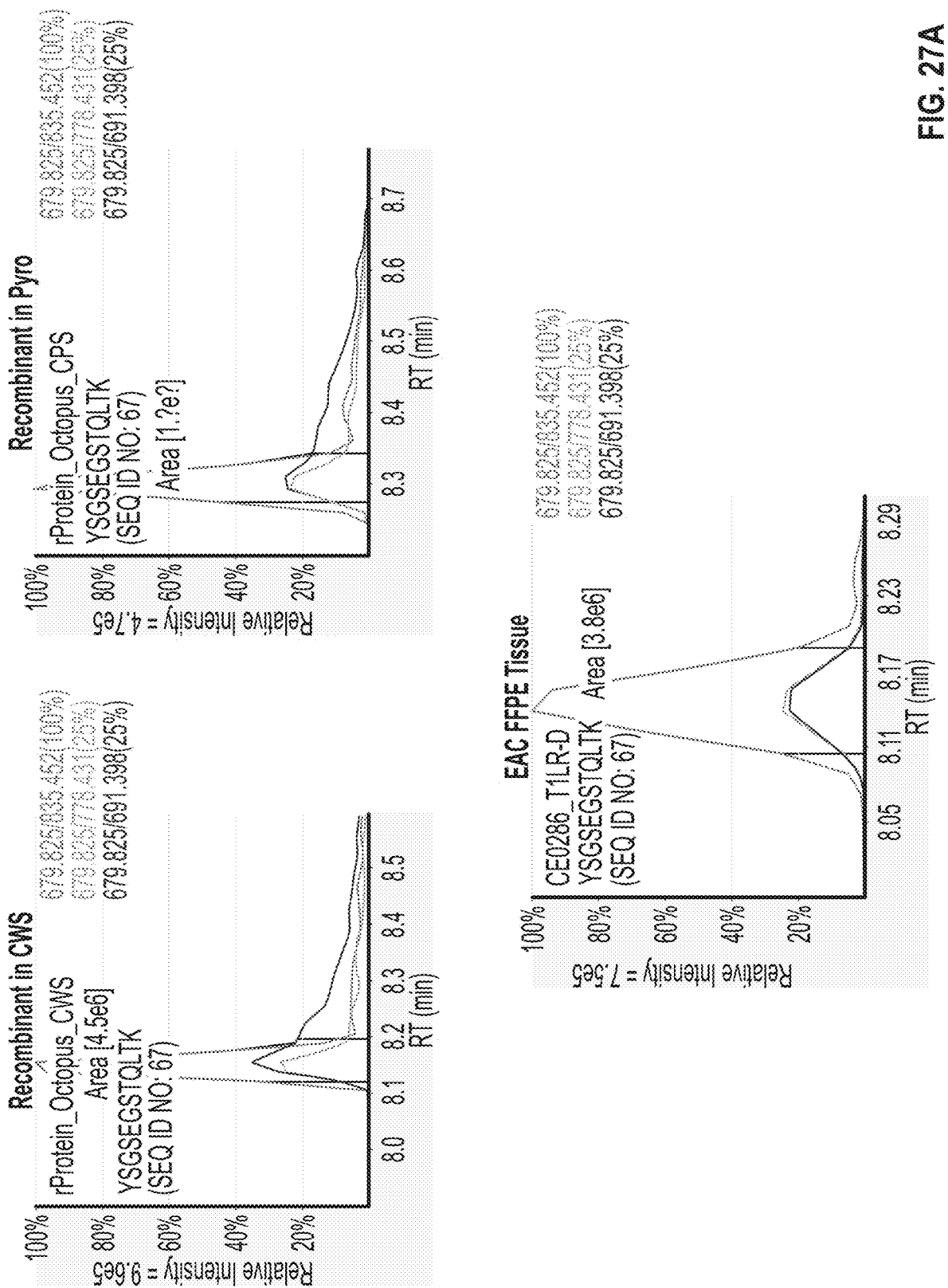
FIGS. 27A-27B. Detection of recombinant S100P peptides in carrier working solution (CWS) and a solution with *Pyrococcus* (pyro), and detection of S100P peptides in formalin-fixed paraffin-embedded esophageal adenocarcinoma tissues.
Figure 27B:
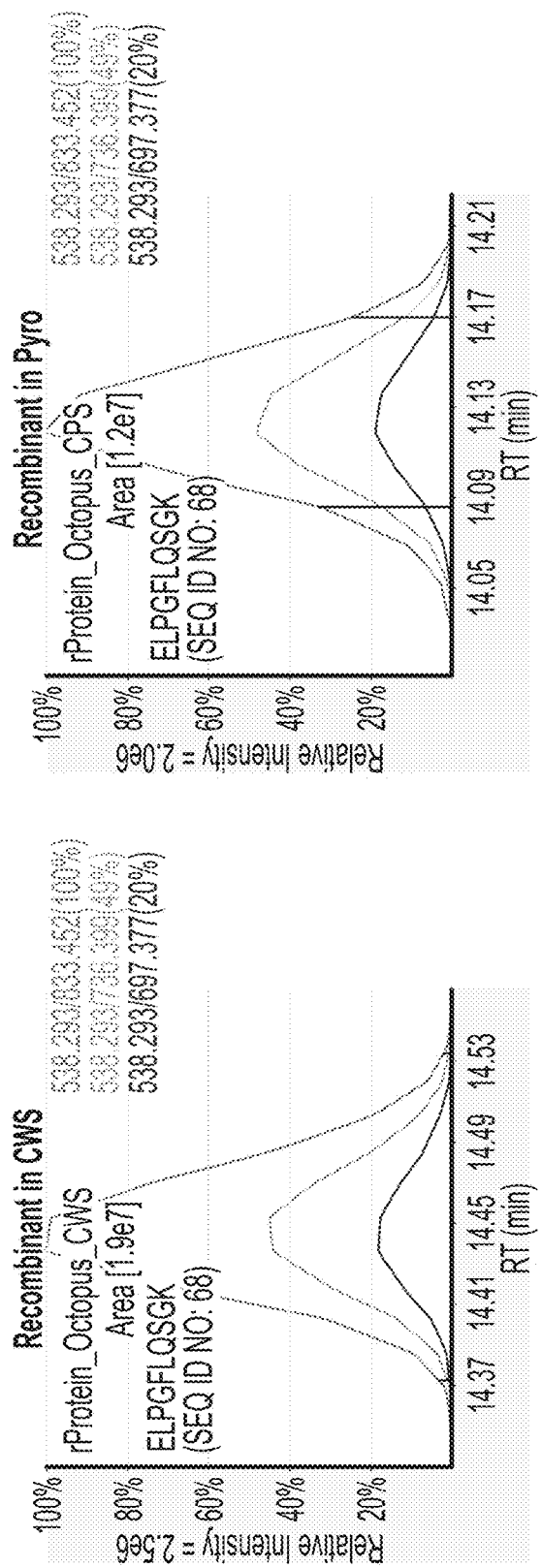
Figure 27B:
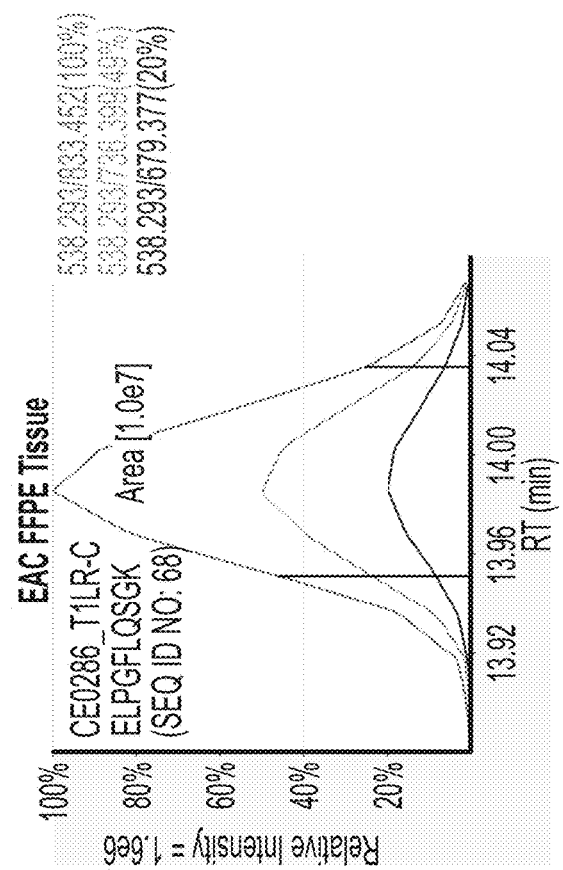

Detection of the peptides in the protein digest is shown in FIGS. 27A-27B. Both peptides were observed in all FFPE ECA tissues screened. Peptides YSGSEGSTQTLTK (SEQ ID NO: 67) and ELPGFLQSGK (SEQ ID NO: 68) showed high intensity and consistent product ion ratios in the recombinant protein and FFPE ECA tissues.

Example 3. Confirmation of Barrett's Esophagus Pathogenesis and Esophageal Adenocarcinoma Progression by Targeted Mass Spectrometry Materials and Methods 1. Preparation of Reagents and Solutions.

1.1. Prepare 1 Liter of 85% Ethanol/Reagent Alcohol by adding 150 mL of distilled water to 850 mL of Ethanol/Reagent Alcohol.

1.2. Prepare 1 Liter of 70% Ethanol/Reagent Alcohol by adding 300 mL of distilled water to 700 mL of Ethanol/Reagent Alcohol.

1.3. Prepare an aliquot of Mayer's Hematoxylin Stain in a 50 mL tube, sufficient for the number of slides to be processed. Protect from light by wrapping the tube in foil or placing it inside a drawer or cabinet when not in use.

2. Slide and Process Preparation.

2.1. Refer to the table below for the appropriate container and volume of reagent for the number of slides being processed.

2.2. A minimum of 5 mL of reagent per slide is suggested. Fresh aliquots of solutions are used when processing additional batches of slides.

| Number of Slides | Container | Volume |
|---|---|---|
| <4 | Slide Mailer | 20 mL |
| 4-10 | Coplin jar | 50 mL |
| Up to 24 | Staining Dish | Minimum 120 mL |

2.3. Label and fill the appropriate containers as follows:

| Container # | Reagent | Slide Mailer | Coplin Jar | Staining Dish |
|---|---|---|---|---|
| 1 | Xylene or Sub-X #1 | 20 mL | 50 mL | Minimum 120 mL |
| 2 | Xylene or Sub-X #2 | 20 mL | 50 mL | Minimum 120 mL |
| 3 | 100% Ethanol/ Reagent Alcohol #1 | 20 mL | 50 mL | Minimum 120 mL |
| 4 | 100% Ethanol/ Reagent Alcohol #2 | 20 mL | 50 mL | Minimum 120 mL |
| 5 | 85% Ethanol/ Reagent Alcohol | 20 mL | 50 mL | Minimum 120 mL |
| 6 | 70% Ethanol/ Reagent Alcohol | 20 mL | 50 mL | Minimum 120 mL |
| 7 | Distilled Water #1 | 20 mL | 50 mL | Minimum 120 mL |
| 8 | Distilled Water #2 | 20 mL | 50 mL | Minimum 120 mL |

2.4. Collect the slides to be processed label.

2.5. Place the slides with cut tissue sections to be processed on the Aluminum Slide Tray in a 58° C. to 61° C. oven for 30 to 60 minutes to melt the paraffin and to adhere the tissue section to the slide. Record the oven temperature, date, and time of incubation.

3. Deparaffinization and Rehydration.

Note 1: Use containers appropriate for Xylene, such as glass Coplin jars or green stain dishes. DO NOT USE polystyrene petri dishes. If using Xylene, all steps using this reagent are performed in a fume hood.

Note 2: If multiple sets of tissue are being processed, reagents are changed between each set of tissues. Inspect the containers to make sure that no tissue debris or residue remains in the container when reagents are being changed. If necessary, rinse container with 100% Ethanol/Reagent Alcohol to remove the debris and allow the container to air dry.

3.1. Sequentially process the slides through each step below. Slides are transferred to the successive container using forceps or the slide holder. Excess liquid can be removed by touching the slide to the side of the container and/or touching the end of the slide to a clean paper towel.

3.2. The slides are moved up and down 3 to 4 times in the solution when they are placed in a new container to facilitate reagent exchange. At the end of the incubation, move the slides up and down again and then drain. Note: If this is not possible due to unadhered sections, transfer the slides to a Petri dish for processing (Xylene cannot be used in polystyrene petri dishes).

3.2.1. Place the slides in container of Xylene or SubX #1 for 5 minutes.

3.2.2. Transfer the slides to the container of Xylene or SubX #2 for 5 minutes.

3.2.3. Transfer the slides to the container of 100% Ethanol #1 for 5 minutes.

3.2.4. Transfer the slides to the container of 100% Ethanol #2 for 5 minutes.

3.2.5. Transfer the slides to the container of 85% Ethanol for 1 minute.

3.2.6. Transfer the slides to the container of 70% Ethanol for 1 minute.

3.2.7. Transfer the slides to the container of Distilled Water #1 for 1 minute.

Note 3: If using staining dishes, after removing the slides from the slide holder following the Distilled Water #1 rinse, the slide holder is rinsed in a container of 100% Ethanol/Reagent Alcohol and air dried prior to use for processing additional slides.

4. Mayer's Hematoxylin Stain.

4.1 The application of Mayer's Hematoxylin Stain can be done with the slide lying flat in a Petri dish. However, the Distilled Water and graded alcohol steps can either be done in the Petri dish, a Coplin jar, Slide Mailer, or Staining Dish depending on what is appropriate for the number of slides in the specific set being processed.

4.2. Slides that have tissue sections that have become loose can be processed flat in a Petri dish for all of the steps so the loose tissue can be controlled and loss reduced.

4.3. Record any observation of loose tissue.

4.4. Using forceps, drain the slide on paper towels to remove excess water, then place the slide flat in a clean Petri dish.

4.5. Pipet enough Mayer's Hematoxylin Stain on the slide to completely cover only the tissue. Approximately 200 µl of stain is enough to cover most tissue sections, although larger volumes may be needed for large tissue sections.

4.6. Gently tilt the dish to move the fluid around on the tissue for even staining. Using the calibrated timer, incubate for 3 minutes at room temperature.

4.7. Using forceps, remove the slide from the Petri dish and drain off the Mayer's Hematoxylin onto paper towels. Alternatively, tilt the Petri dish so that the stain drains off the tissue and remove the stain with a pipette.

4.8. If continuing the processing in the Petri dish:

4.8.1. Using the forceps, place the slide lying flat in the dish.

4.8.2. Carefully add distilled water #2 to the Petri dish to completely cover the slide. Note: Do not add water directly on top of the tissue but direct the flow of water to the side of the slide.

4.8.3. Rinse the slide in distilled water #2 for 30 seconds. Repeat the distilled water rinse a minimum of 2 times. If the water is not clear, rinse again to remove excess dye.

4.8.4. Using forceps, remove the slide from the Petri dish and place upright in a Teflon slide rack to air dry overnight (16 to 24 hours) at room temperature.

4.9. If continuing the processing in a Coplin jar, Slide Mailer, or Staining Dish:

4.9.1. Using the forceps, place the slide into the container.

4.9.2. Rinse the slide in distilled water #2 for 30 seconds. Repeat the distilled water rinse a minimum of 2 times. If the water is not clear, rinse again to remove excess dye.

4.9.3. Using forceps, remove the slide from the container and place upright in a Teflon slide rack to air dry overnight (16 to 24 hours) at room temperature.

4.9.4. Inspect the slides to make sure that the paraffin has been completely removed.

4.9.5. If all of the paraffin has not been removed, reprocess the slides through Sub-X and 100% ethanol by following only Steps 3.2.1 to 3.2.4, and then air dry. If paraffin still remains, repeat Steps 3.2.1 to 3.2.2 using Xylene, then continue with Steps 3.2.3 and 3.2.4 only, and then air dry.

4.10. When the slides are completely dry, transfer them to a slide box.

4.11. Store the slides at room temperature prior to scanning the slide image for documentation.

Targeted Sample Collection Using Laser Microdissection

6. Microdissection.

Figure 29A:
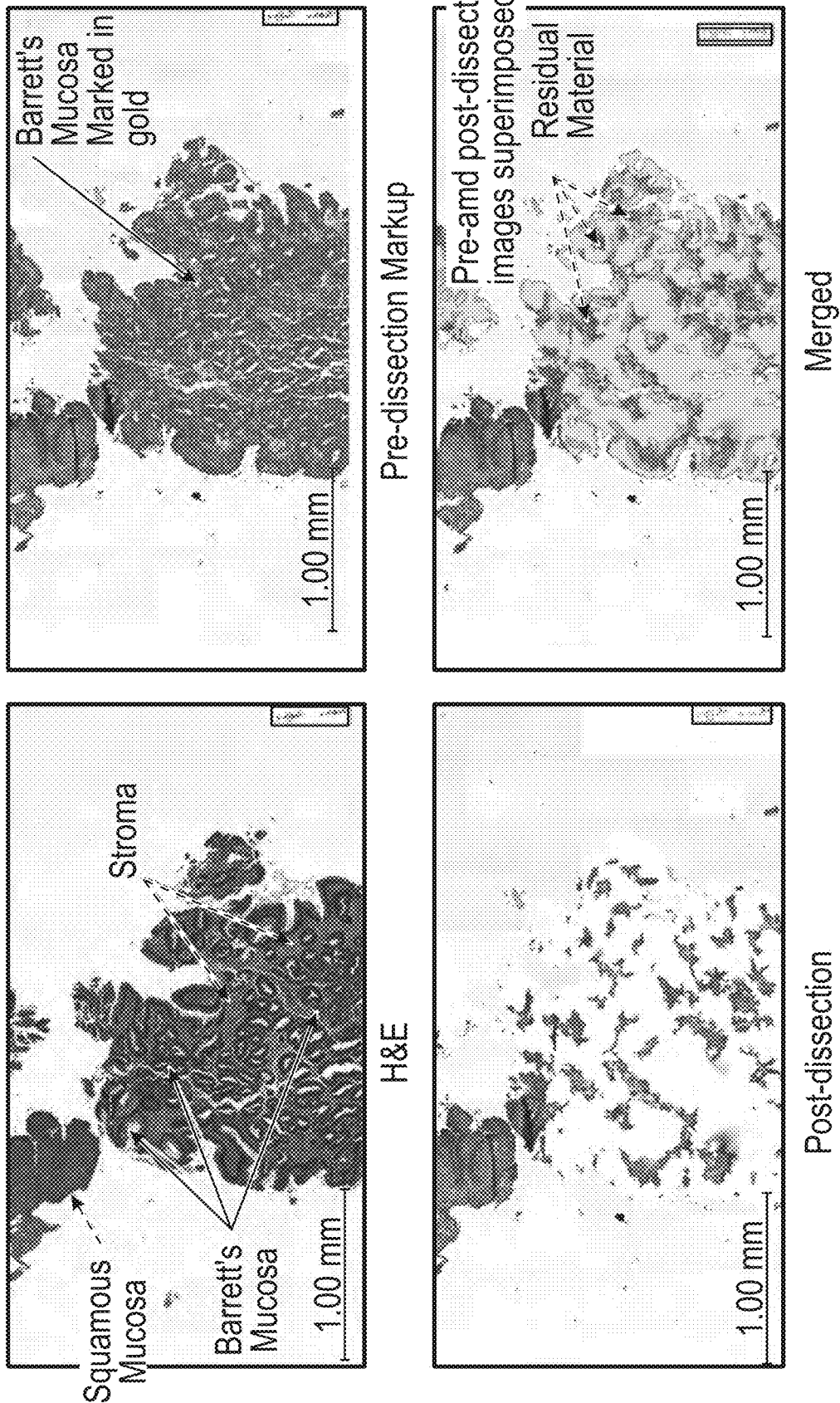
FIG. 29A. Microdissection of Barrett's mucosa.
Figure 29B:
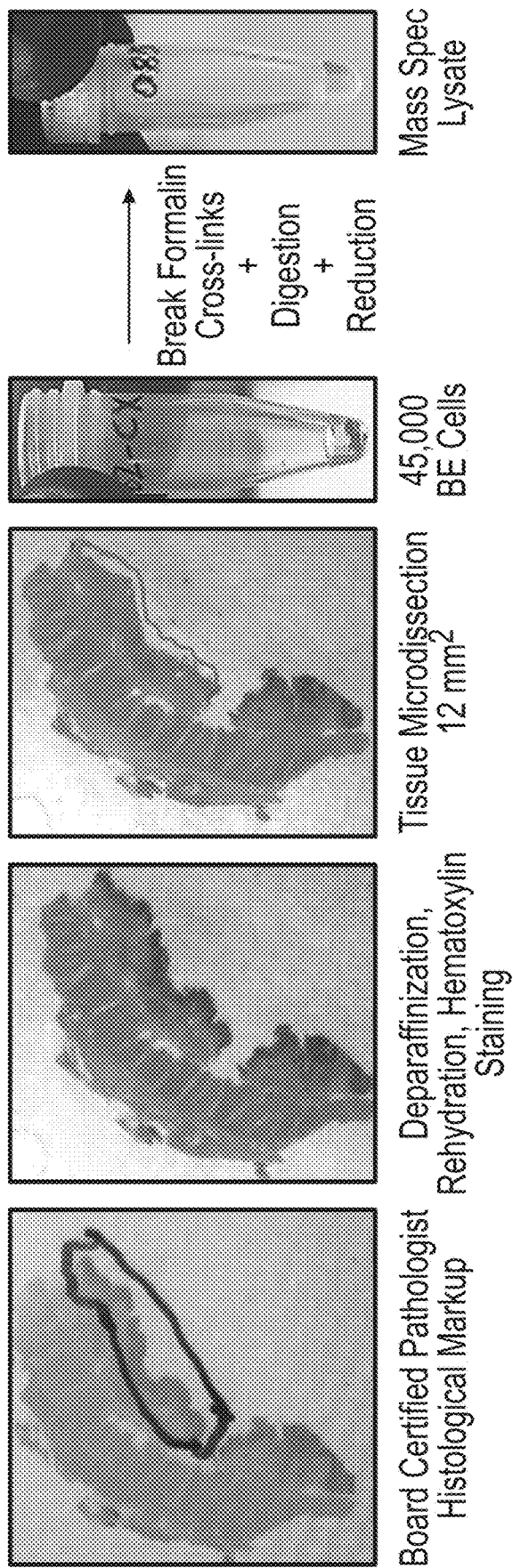
FIG. 29B. Needle dissection of Barrett's mucosa.

6.1. Tissue areas of interest were marked up by a board-certified pathologist and then laser microdissected using a laser microdissector (CellCut, MMI, Germany) to collect the tissue pellets. The microdissection was carried out at a scale to provide at least 8 mm² of tissue material for determination of the expression levels of study target proteins. FIG. 29A is a figure showing microdissection of Barrett's mucosa. Alternatively, needle dissection can be used, as shown in FIG. 29B.

6.2. The "Volume Dissected (mm³)" of cells collected is extrapolated from the total area of the sample microdissected and the thickness of the sample section on the slide.

Mass Spec-Compatible Lysate Processing

7. General Information.

7.1. To avoid introducing contamination, work in a clean area and clean gloves can be worn throughout the protocol. Avoid touching the clean gloves to surfaces that may introduce foreign particles. Reduce the exposure of samples, reagents, equipment and supplies to contamination sources, such as skin, hair, clothing, dust, and particulates.

7.2. The standard LT-MS preparation reaction size is a total microdissected volume of 0.12 mm³ in 30 µL of salt/detergent-free Buffer. This document describes the processing instructions for standard reaction sizes; the reaction volume may be scaled as long as the ratio of cells to buffer remains constant.

7.3. Label each Reaction Tube with the Sample UID. Record all required information during the execution of this procedure.

7.4. The trypsin component is labile and has specific requirements for reuse of the reconstituted reagent.

7.5. Components: Salt and detergent-free buffer, trypsin diluent, and reduction reagent (100 mM DTT) are used before the expiry date and can be frozen and thawed up to 5 times.

8. Heating Step.

8.1. Obtain the Total Microdissected Volume (mm³). Calculate the volume of salt/detergent-free buffer to be added to each tube using the following equation: Salt/Detergent-free Buffer (µL)=Total Microdissected Volume (mm³)+0.004 µL/mm³.

8.2. Observe the tube bottom for the presence of a cell pellet prior to processing. Record this information.

8.3. Thaw the salt/detergent-free buffer. Mix the tube, then microcentrifuge briefly to collect the buffer in the bottom of the tube.

8.4. Pipet the appropriate volume of salt/detergent-free buffer into the reaction tubes. Mix the tubes to resuspend the cells in the buffer.

8.5. Return any unused buffer to storage.

8.6. For samples collected in 1.5 mL screw cap Reaction Tubes, place the Reaction Tubes containing the procured cells in the salt/detergent-free buffer into a heating block preheated to 95° C. (±1° C.), set a timer for 90 minutes, and proceed to Step 8.8. Record the date, time, and temperature.

8.7. For samples in 0.65 or 0.5 mL PCR Reaction Tubes, vortex lightly, then, place the tubes into a preheated thermal cycler block at 95° C. (±1° C.), spacing them as evenly as possible in the block. Set a timer for 90 minutes and proceed to Step 8.8. Record the date, time, and temperature.

8.8. Every 20 minutes remove the tubes and shake down the buffer that has condensed so that it covers the cells. Alternately, quickly microcentrifuge for 5 to 10 seconds at 10,000 rcf.

8.9. Gently resuspend the cells in the buffer and immediately place the tube back into the 95° C. (±1° C.) heating block or the thermal cycler. DO NOT allow the tubes to cool down completely. If using a thermal cycler, after shaking all of the tubes, close the lid over the tubes again.

8.11. After 90 minutes, remove the tubes from the 95° C. (±1° C.) heat block or thermal cycler, and microcentrifuge the tube(s) at 10,000 ref for 1 minute. Record the date, time, and temperature and note the presence of any pellet.

8.11.1. If using a thermal cycler, stop the run and leave the lid of the thermal cycler open to cool.

8.12. Cool the tube(s) on ice for 1 to 2 minutes.

9. Pooling Stage.

9.1. If more than one tube was processed for a sample, the tubes for that sample can be pooled together.

10. Trypsin Digestion 10.1. Calculate the volume of Trypsin to be added to each Reaction Tube, based on the volume of the digested lysate preparation. A volume of 0.05 µL of 1 µg/µL Trypsin Solution is used for every 1 µL of salt/detergent-free buffer. Record the information. For example:

|  | Sample #1 | Sample #2 |
|---|---|---|
| Salt/detergent-free buffer volume | 30 µL | 60 µL |
| Trypsin volume (1 µg/µL solution) | 1.5 µL (1.5 µg) | 3.0 µL (3.0 µg) |

10.2. Determine the total amount of Trypsin required for the number of samples being processed.

10.3. If a frozen aliquot of reconstituted trypsin is used, record the number of freeze/thaw cycles in addition to the part/lot number and date information.

10.4. If needed, reconstitute the appropriate number of 20 µg vials of the lyophilized enzyme.

10.4.1. Add 20 µl of the Trypsin Diluent from the kit to each vial of Trypsin, then mix the vial(s) briefly to ensure the trypsin is dissolved. Place vial on ice for 5 minutes, then mix briefly again. Use reconstituted trypsin within 15 minutes.

10.4.2. Record the part/lot number and date information.

10.4.3. Label the tubes containing the unused reconstituted trypsin solution and store in the −20° C. freezer.

10.4.4. Unused solution is stable for at least 3 freeze thaw cycles.

10.5. Add the appropriate volume of the Trypsin Solution to each Reaction Tube. Mix and briefly microcentrifuge to collect the solution at the bottom of the Reaction Tube.

10.6. For 1.5 mL screw cap Reaction Tubes, place the Reaction Tubes in a water bath at 37° C. (±1° C.) and then proceed to step 10.9.

10.7. For 0.65- or 0.5-mL PCR Reaction Tubes, prepare the thermal cycler for heating the Reaction Tubes at 37° C. (±1° C.).

10.8. Place the Reaction Tubes into the PREHEATED thermal cycler block, spacing them as evenly as possible in the block. Close the lid over the tubes and proceed to step 10.9.

10.9. Heat the Reaction Tube(s) at 37° C. (±1° C.); record the temperature and time of day when the tubes are placed at 37° C. (±1° C.).

10.10. For the first hour, every 20 minutes, remove the tubes, and vortex rigorously for 10 to 15 seconds. Shake the buffer down to the bottom of the tube so that it covers the cells before placing the tube back into the 37° C. (±1° C.) water bath or the thermal cycler. If using a thermal cycler, after vortexing all of the tubes, clamp the lid over the tubes again.

10.11. Continue incubating at 37° C. (±1° C.) overnight (16 to 18 hours). Record the time of day the tubes are removed from the water bath or thermal cycler.

10.12. Microcentrifuge the tube(s) at 10,000 rcf for 1 minute. Note the presence of any pellet.

10.13. For samples collected in 1.5 mL screw cap reaction tubes, place the reaction tubes into a preheated heat block at 95° C. (±1° C.) for 5 minutes. Record the date, time, and temperature.

10.14. For samples in 0.65- or 0.5-mL PCR Reaction Tubes, place the tubes into a preheated thermal cycler block at 95° C. (±1° C.) for 5 minutes. Record the date, time, and temperature.

10.15. Microcentrifuge the tube(s) at 10,000 rcf for 1 minute. Note the presence of any pellet.

11. Protein Determination.

11.1. A Micro BCA Assay is performed to determine the protein concentration.

11.2. The Micro BCA Assay is performed on an aliquot of the mass spec-compatible lysate preparation prior to the addition of Reduction Reagent (DTT), since DTT interferes with the protein determination. Store the remaining MS lysate preparation in the reaction tubes in the −20° C. freezer until the protein determination assay has been completed.

11.3. "Micro BCA Assay for Protein Quantitation."

11.4. A summary table is generated including the Trypsin-corrected protein concentration and Trypsin-corrected total protein yield. Input the Trypsin-corrected concentration results (μg/μ:) into Form LM-010.01-F02, "Sample Calculations Workbook.xls" and proceed to Step 12.

Reduction Reaction.

12.1. The volume of Reduction Reagent (100 mM DTT) to be added to each Reaction Tube is calculated based on the final volume of the MS lysate preparation after addition of Trypsin and removal of aliquots for the protein determination.

12.1.1. The final concentration of the DTT must be 10 mM:

|  | Sample #1 | Sample #2 |
|---|---|---|
| Final MS lysate preparation volume | 25.5 μL | 57.0 μL |
| Reduction Reagent (100 mM DTT) volume | 2.6 μL | 5.7 μL |

12.1.2. Thaw the 100 mM DTT. Mix the tube, then microcentrifuge briefly to collect the reagent in the bottom of the tube.

12.1.3. Add the calculated volume of 100 mM DTT to each reaction tube. Mix and briefly microcentrifuge to collect the solution at the bottom of the reaction tube.

12.1.4. Determine the final protein concentration and total protein yield based on the adjusted volume following addition of DTT.

12.1.5. Return any unused 100 mM DTT to storage.

12.2. For samples collected in 1.5 mL screw cap reaction tubes, place the reaction tubes into a preheated heat block at 95° C. (±1° C.) for 5 minutes. Record the date, time, and temperature.

12.3. For samples in 0.65- or 0.5-mL PCR Reaction Tubes, place the tubes into a preheated thermal cycler block at 95° C. (±1° C.) for 5 minutes. Record the date, time, and temperature.

12.4. Microcentrifuge the tube(s) at 10,000 rcf for 1 minute.

12.5. Ensure that the reaction tubes are labeled with the Sample UID. Store the MS lysate preparation reaction tubes in the −20° C. freezer until ready for mass spectrometry analysis.

13. Mass Spectrometer Analysis.

13.1. Quality Control Systems Check.

13.1.1. Prior to Study sample analysis, several samples are run on the TSQ-Quantiva Mass Spectrometer system with a Nano-Flow HPLC as a Systems Check for quality control purposes to confirm that the platform is acceptable for data acquisition. Study sample analysis is initiated on completion of a successful Systems Check QC using the following samples:

| Sample type | Purpose in Systems Check |
|---|---|
| System Blank | Consists of Buffer A; analyzed using the analytical method for the System Check Supermix analytes to confirm there is no carryover from previous mass spectrometer runs. |
| Systems Check Supermix | Consists of the following peptides in the quantities indicated below, injected in the presence of a complex proteomics matrix. |

| | | Amount on Column: |
|---|---|---|
| Peptide Name: | Heavy Peptide | Light Peptide |
| RT-XXXXX-H (477) | 100 amol | 1 fmol |
| RT-XXXXX-H (610) | 250 amol | 1 fmol |
| RT-XXXXX-H (608) | 1000 amol | 0 |

| | The quantitative results from this sample are used to confirm acceptable operational performance parameters of the mass spectrometer system. Each peptide is reviewed by operator in real time and must meet parameter specifications described in the standard operating procedures. |
|---|---|
| System Blank | Re-analysis of Buffer A, using the analytical method for the System Check Supermix analytes to confirm there is no carryover from the previous sample run. |

13.2. Sample Processing for Quantitative Analysis 13.2.1. An aliquot of each mass spec compatible lysate preparation was diluted with 0.1% formic acid, and a cocktail of heavy isotope-labeled internal standard peptides was added.

13.2.2. Following a centrifugation step at 10,000×g for 10 minutes, the supernatants were placed in an empty well of a 96 well plate in the mass spectrometer system autosampler chamber.

13.2.3. A volume for each sample, containing 1.0 μg total protein and 5 fmol of internal standard peptide cocktail was injected into the system at a flow rate of 5 μL/minute, and peptides were eluted at 0.8 μL/minute. All study samples were analyzed with single injection. The mass spectrometer was run in the SRM mode using a cycle time of 1 second.

13.2.4. The assay was monitored in tissue samples using actin and tubulin as internal procedural controls to verify sample quality and integrity and efficacy of the dissection.

13.3. Data Analysis Process.

13.3.1. SRM data was inspected using the Xcalibur software program from Thermo Scientific and analyzed using Pinnacle software (Optys Tech; version 83). Individual data points and mass spectrometry peaks acquired from each sample were confirmed by manual review of the data in the Pinnacle software. Correct peak integrations were confirmed by direct visualization of product ion ratios.

13.3.2. Quantitative measurements of all analytes were determined by peak area (AUC) comparison between the spiked internal standard peptides and the endogenous peptides by calculating the ratio of endogenous analyte signal to the internal standard signal and multiplying by the amount of internal standard spiked into the sample.

13.3.3. Each sample was normalized to a 1.0 µg injection.

Total Analyte (amol/µg)=[(Endogenous Analyte AUC)/(Heavy Internal Standard AUC)*(5 fmol Heavy Internal Standard)]/(1.0 µg injection)

Figure 28:
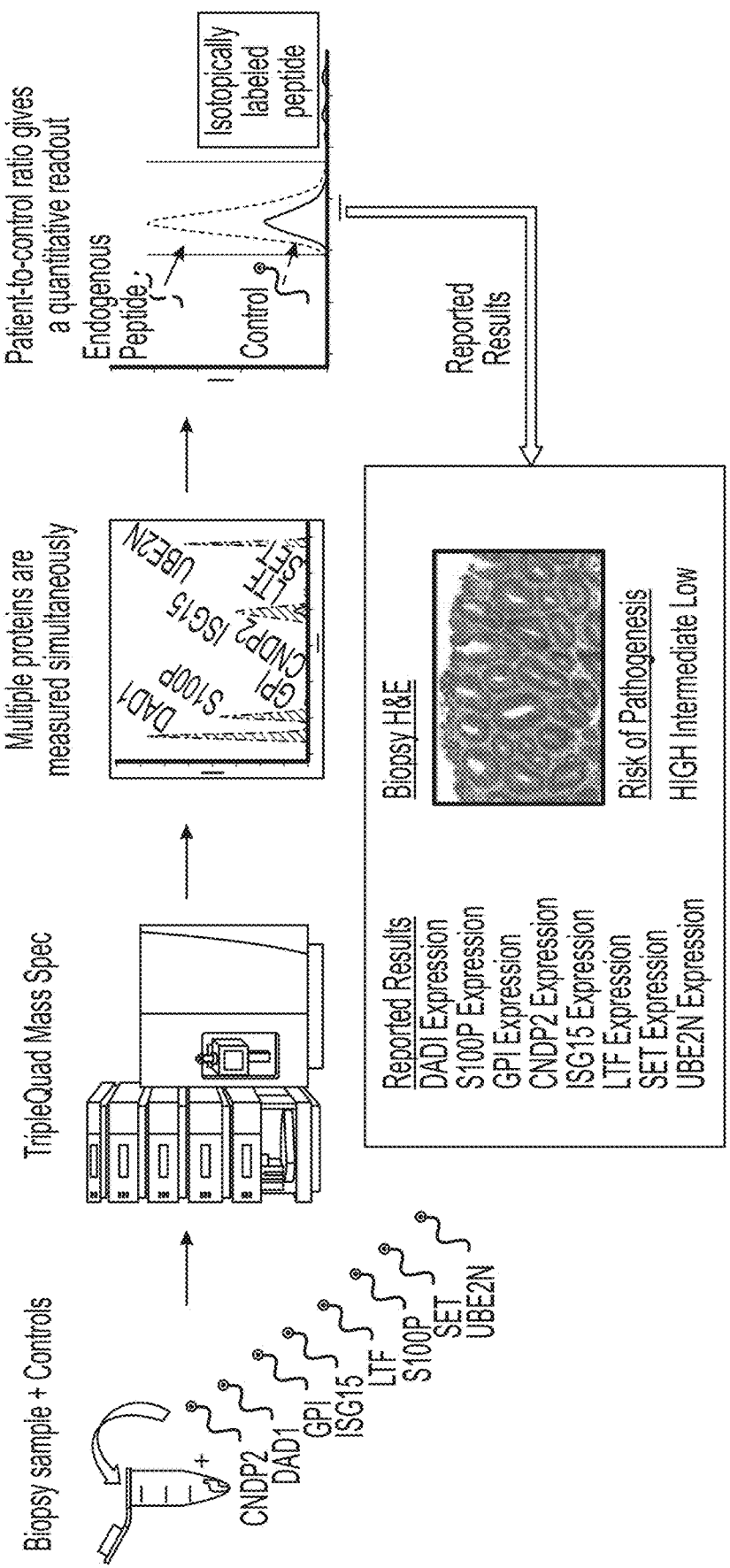
FIG. 28. Image illustrating an exemplary targeted mass spectrometry workflow.

An exemplary targeted mass spectrometry workflow is shown in FIG. 28.

Results

Figure 30A:
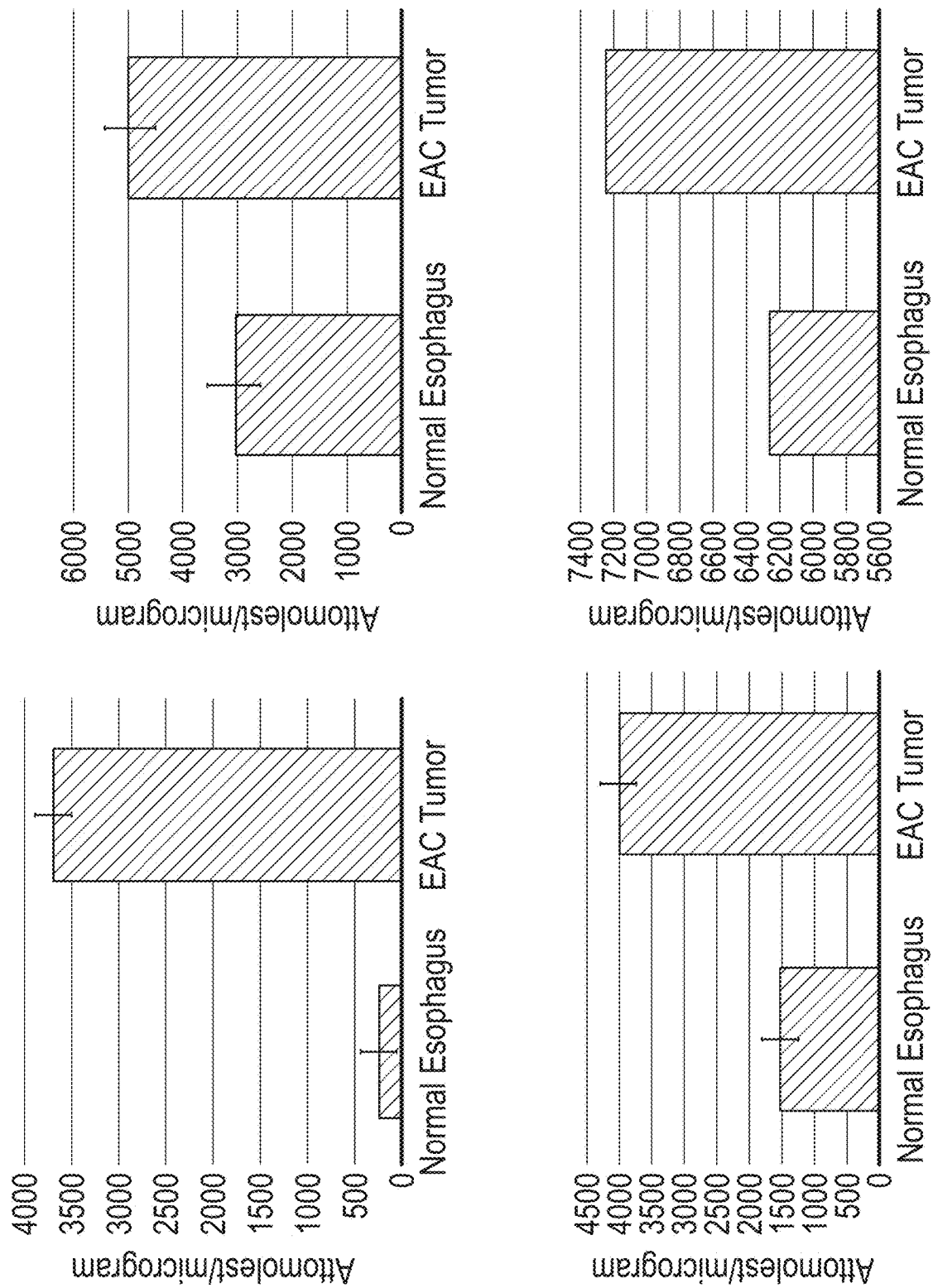
FIGS. 30A-30B. Graphs illustrating expression of ISG15, CNDP2, DAD1, and GPI (FIG. 30A) and LTF, S100P, SET, and UBE2N (FIG. 30B) in normal squamous esophageal epithelium and esophageal adenocarcinoma as determined by targeted mass spectrometry.
Figure 30B:
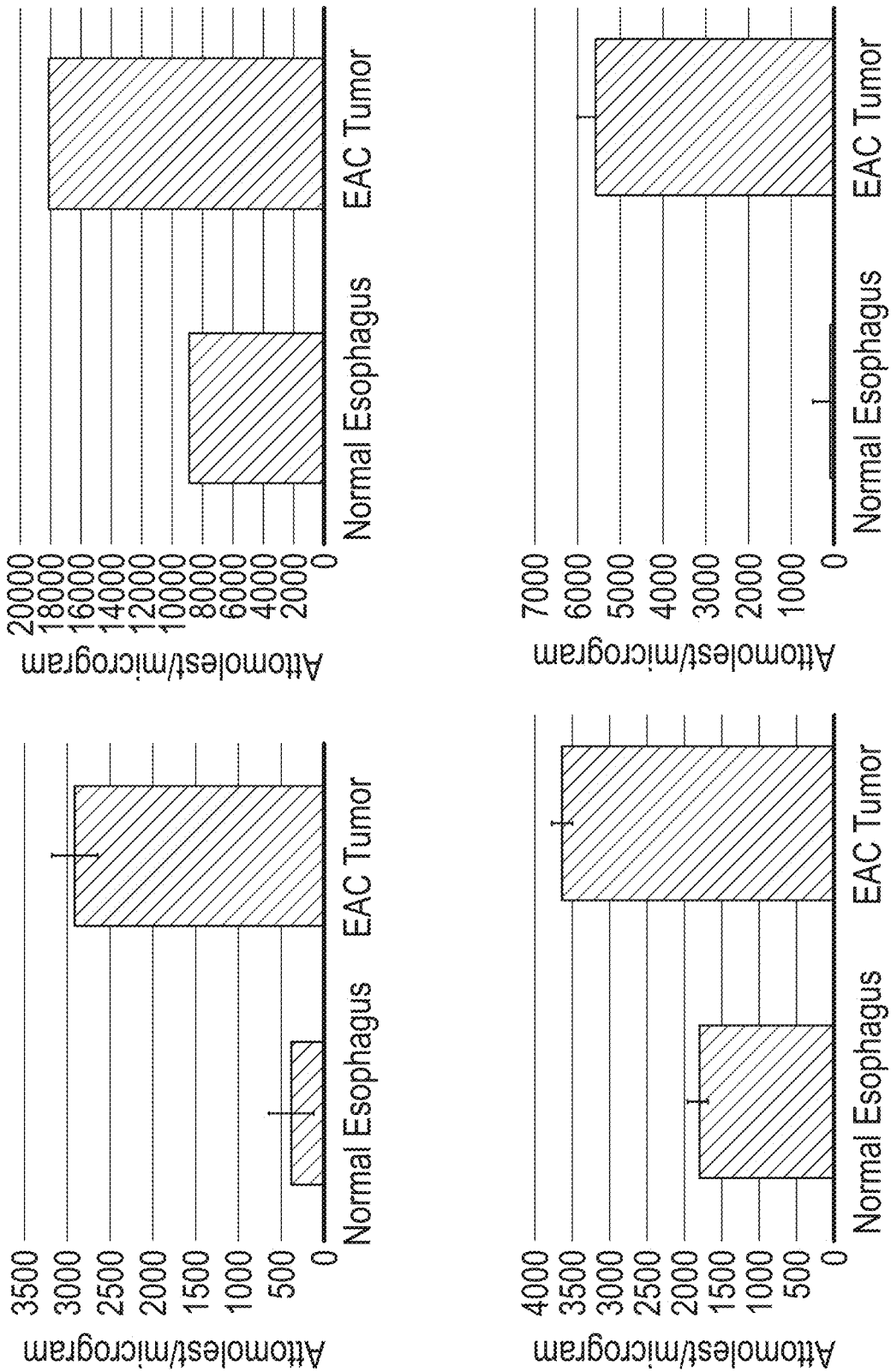

Normal esophagus and esophageal adenocarcinoma FFPE samples were processed as described above, and the samples were analyzed for expression of CNDP2, DAD1, GPI, ISG15, LTF, S100P, SET, and UBE2N using targeted mass spectrometry (as described above) and using the peptides described in Example 2. The results, shown in Table 23 and FIGS. 30A-30B, confirm what was observed using discovery mass spectrometry in Example 1. We have found consistent overexpression of these novel markers in esophageal adenocarcinoma, which is significant because the only biomarker approved for targeted therapy, HER2, is only overexpressed in 18% of esophageal adenocarcinoma (EAC) tumors. In contrast, ISG15 was overexpressed in 90% of the EAC tumors tested, LTF was overexpressed in 70% of the EAC tumors tested, CNDP2 was overexpressed in 100% of the EAC tumors tested, DAD1 was overexpressed in 70% of the EAC tumors tested, SET was overexpressed in 90% of the EAC tumors tested, UBE2N was overexpressed in 70% of the EAC tumors tested, S100P was overexpressed in 90% of the EAC tumors tested, and GPI was overexpressed in 60% of the EAC tumors tested. This not only confirms the consistent upregulation of these markers during carcinogenesis, but reveals potential new targets to inhibit via targeted therapy.

TABLE 23

Results for Targeted Mass Spectrometry - Normal vs. EAC.

| Marker | Peptide | Normal tissue expression (amol/µg) | | EAC Tumor Expression (amol/µg) | | *Median Overexpression Ratio (Tumor/Normal) |
|---|---|---|---|---|---|---|
| | | Mean | Median | Mean | Median | |
| CNDP2 | LPDGSEIPLPPILLGR (SEQ ID NO: 20) | 4279.2 ± 1286.6 | 2606.0 | 4974.2 ± 691.3 | 4800.0 | 1.8:1 |
| | TVFGVEPDLTR (SEQ ID NO: 31) | 3044.9 ± 888.1 | 1791.6 | 3842.3 ± 481.2 | 4133.6 | 2.3:1 |
| DAD1 | FLEEYLSSTPQR (SEQ ID NO: 7) | 2784.7 ± 705.6 | 1874.8 | 4035.4 ± 454.5 | 4221.6 | 2.3:1 |
| | ADFQGISPER (SEQ ID NO: 9) | 1549.1 ± 374.1 | 1032.8 | 2034.3 ± 226.5 | 2108.1 | 2.0:1 |
| GPI | LQQWYR (SEQ ID NO: 35) | 6263.4 ± 384.2 | 6418.8 | 7253.0 ± 944.6 | 6882.8 | 1.1:1 |
| ISG15 | IGVHAFQQR (SEQ ID NO: 11) | 78.5 ± 47.9 | 0.0 | 1084.0 ± 258.1 | 762.5 | 13.8:1 |
| | LAVHPSGVALQDR (SEQ ID NO: 12) | 244.6 ± 182.6 | 0.0 | 3702.8 ± 756.5 | 2676.4 | 15.1:1 |
| LTF | DGAGDVAFIR (SEQ ID NO: 54) | 397.2 ± 256.2 | 0.0 | 2925.1 ± 1004.6 | 2125.1 | 7.4:1 |
| | FQLFGSPSGQK (SEQ ID NO: 58) | 228.9 ± 176.9 | 0.0 | 1573.6 ± 532.2 | 1246.8 | 6.9:1 |
| S100P | YSGSEGSTQTLTK (SEQ ID NO: 67) | 8880.5 ± 6654.8 | 686.0 | 14521.1 ± 7757.6 | 4977.7 | 7.3:1 |
| | ELPGFLQSGK (SEQ ID NO: 68) | 11017.0 ± 8380.5 | 877.6 | 18145.8 ± 9866.7 | 5834.9 | 6.6:1 |
| SET | LNEQASEEILK (SEQ ID NO: 50) | 1814.0 ± 118.7 | 1754.6 | 3637.1 ± 423.1 | 3477.5 | 2.0:1 |
| UBE2N | YFHVVIAGPQDSPFEGGTFK (SEQ ID NO: 3) | 0.0 ± 0.0 | 0.0 | 5571.6 ± 420.5 | 5152.3 | 103.0:1 |

*For those sets of samples in which the median expression was zero in normal tissue, the mean overexpression ratio (tumor/normal) is shown.

In Table 23, for the targeted mass spectrometry using the peptide set forth in SEQ ID NO: 20, 9 of 11 normal tissue samples were below 2,900 amol/µg, and 2 of 11 normal tissue samples were 11,195 and 14,351 amol/µg. For the targeted mass spectrometry using the peptide set forth in SEQ ID NO: 31, 9 of 11 normal tissue samples were below 2,220 amol/µg, and 2 of 11 normal tissue samples were 8,368 and 9,534 amol/µg, respectively. For the targeted mass spectrometry using the peptide set forth in SEQ ID NO: 67, 9 of 11 normal tissue samples were below 742 amol/µg, and 2 of 11 normal tissue samples were 17,849 and 73,589 amol/µg, respectively. For the targeted mass spectrometry using the peptide set forth in SEQ ID NO: 68, 9 of 11 normal tissue samples were below 1,312 amol/µg, and 2 of 11 normal tissue samples were 92,680 and 21,546 amol/µg, respectively. For the targeted mass spectrometry using the peptide set forth in SEQ ID NO: 67, 9 of 10 esophageal adenocarcinoma samples were above 2,040 amol/µg, and 1 of 10 esophageal adenocarcinoma samples had zero quantification in amol/µg. For the targeted mass spectrometry using the peptide set forth in SEQ ID NO: 68, 9 of 10 esophageal adenocarcinoma samples were above 2,695 amol/µg, and 1 of 10 esophageal adenocarcinoma samples had zero quantification in amol/µg. For the targeted mass spectrometry using the peptide set forth in SEQ ID NO: 7, 9 of 11 normal tissue samples were below 2,900 amol/µg, and 2 of 11 normal tissue samples were 11,195 and 14,351 amol/µg, respectively. For the targeted mass spectrometry using the peptide set forth in SEQ ID NO: 9, 9 of 11 samples were below 1,215 amol/µg, and 2 of 11 samples were 3,946 and 4133 amol/µg, respectively.

Figure 31A:
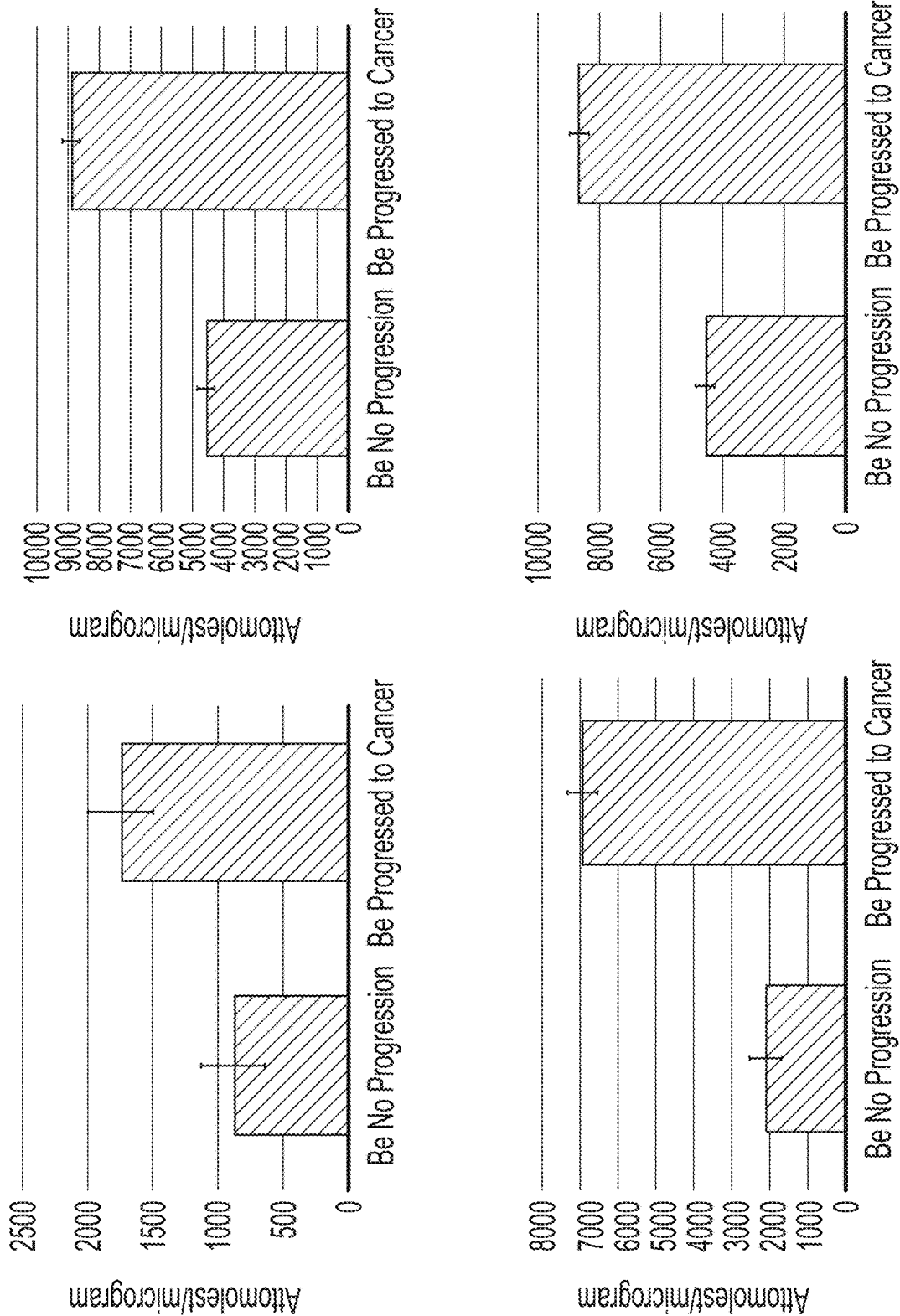
FIGS. 31A-31B. Graphs illustrating expression of ISG15, CNDP2, DAD1, and GPI (FIG. 31A) and LTF, S100P, SET, and UBE2N (FIG. 31B) in Barrett's esophagus samples from subjects that never progressed to esophageal adenocarcinoma and Barrett's esophagus samples from subjects who did progress to esophageal adenocarcinoma as determined by targeted mass spectrometry.
Figure 31B:
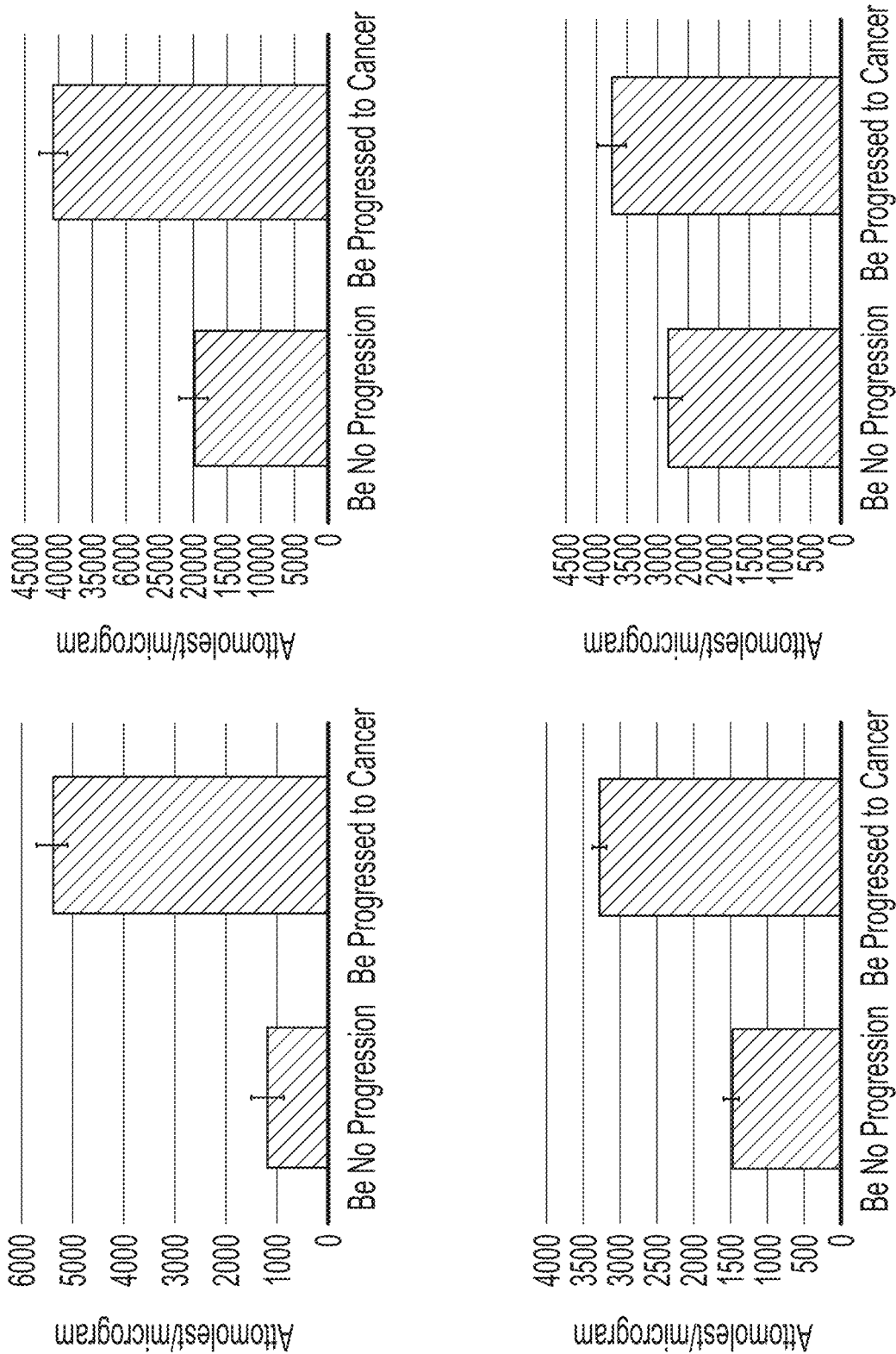

FFPE samples of Barrett's esophagus from subjects that never progressed to esophageal adenocarcinoma over 10 years and FFPE samples of Barrett's esophagus from subjects who did progress to esophageal adenocarcinoma were then processed as described above, and the samples were analyzed for expression of CNDP2, DAD1, GPI, ISG15, LTF, S100P, SET, and UBE2N using targeted mass spectrometry (as described above) and using the peptides described in Example 2. Regarding the Barrett's esophagus samples that progressed to esophageal adenocarcinoma, the subjects progressed to esophageal adenocarcinoma on average 334 days after the Barrett's esophagus sample was taken (median of 322 days, lower end of 30 days, higher end of 874 days). Four developed esophageal adenocarcinoma more than one year after high-grade dysplasia diagnosis, and five developed carcinoma less than one year after high-grade dysplasia diagnosis. The results, shown in Table 24 and FIGS. 31A-31B, show that we can determine if a Barrett's esophagus sample possesses hallmarks of malignant transformation in Barrett's tissue retrieved during routine screening protocols, and we can predict whether the Barrett's esophagus will progress to esophageal adenocarcinoma.

TABLE 24

Results for Targeted Mass Spectrometry - Non-Progressing BE vs. BE Progressing to EAC.

| Marker | Peptide | BE (No Progression) Expression (amol/µg) | | BE (Progressed to EAC) Expression (amol/µg) | | Mean Overexpression Ratio (Progressed/No Progression) |
|---|---|---|---|---|---|---|
| | | Mean | Median | Mean | Median | |
| CNDP2 | LPDGSEIPLPPILLGR (SEQ ID NO: 20) | 5675.1 ± 268.9 | 5637.9 | 8903.8 ± 940.6 | 8412.1 | 1.6:1 |
| | TVFGVEPDLTR (SEQ ID NO: 31) | 4584.7 ± 247 | 4598.4 | 5839.6 ± 734.9 | 5492 | 1.3:1 |
| DAD1 | FLEEYLSSTPQR (SEQ ID NO: 7) | 4300.1 ± 155.2 | 4353.1 | 6944.3 ± 389.4 | 7055 | 1.6:1 |
| | ADFQGISPER (SEQ ID NO: 9) | 2090.4 ± 108.8 | 1992.6 | 3443.8 ± 296.7 | 3739.8 | 1.6:1 |
| GPI | LQQWYR (SEQ ID NO: 35) | 4546.8 ± 245.5 | 4357.5 | 8668 ± 572.2 | 8377.1 | 1.9:1 |
| ISG15 | IGVHAFQQR (SEQ ID NO: 11) | 293.1 ± 37 | 267.1 | 501 ± 77.5 | 410.8 | 1.7:1 |
| | LAVHPSGVALQDR (SEQ ID NO: 12) | 885.4 ± 166.3 | 772.3 | 1744.2 ± 241.9 | 1368.3 | 2.0:1 |
| LTF | DGAGDVAFIR (SEQ ID NO: 54) | 1158 ± 292.4 | 756.8 | 5379.7 ± 1084.9 | 5608.4 | 4.6:1 |
| | FQLFGSPSGQK (SEQ ID NO: 58) | 363 ± 151.4 | 0.0 | 3084.7 ± 503.8 | 3226.8 | 8.5:1 |
| S100P | YSGSEGSTQTLTK (SEQ ID NO: 67) | 20025.9 ± 1900.4 | 20609 | 30963.1 ± 4520 | 33782.1 | 1.5:1 |
| | ELPGFLQSGK (SEQ ID NO: 68) | 25367.7 ± 2567.8 | 23708.5 | 40788.7 ± 5617 | 39050.1 | 1.6:1 |
| SET | LNEQASEEILK (SEQ ID NO: 50) | 1483.1 ± 88.3 | 1506.3 | 3265.8 ± 291.5 | 2898.4 | 2.2:1 |
| UBE2N | YFHVVIAGPQDSPFEGGTFK (SEQ ID NO: 3) | 2808 ± 214.2 | 2849 | 3735.1 ± 229 | 3603.3 | 1.3:1 |

Although upregulation or overexpression of any one of the markers by itself is predictive of Barrett's esophagus progression into esophageal adenocarcinoma, the upregulation or overexpression of LTF, ISG15, or DAD1 is highly predictive of Barrett's esophagus progression into esophageal adenocarcinoma. Discovery mass spectrometry determined these three markers are consistently upregulated and highly active in esophageal adenocarcinoma when compared to normal esophageal squamous mucosa. This was also confirmed with the targeted mass spectrometry method. When looking at these markers with targeted mass spectrometry in Barrett's tissue that remained stable over a ten year period, we found low to no expression of these markers. In Barrett's tissue that ultimately progressed to esophageal adenocarcinoma over a period of greater than one year, these three markers were found to be consistently overexpressed, indicating high predictability and sensitivity when assessing the risk of Barrett's tissue undergoing a malignant transformation. There were few to no outliers in these markers when looking at expression levels in normal, non-progressive Barrett's, progressive Barrett's, and esophageal adenocarcinoma specimens.

Similarly, the upregulation or overexpression of CNDP2, GPI, or SET is very predictive of Barrett's esophagus progression into esophageal adenocarcinoma. Discovery mass spectrometry determined these three markers are consistently upregulated and highly active in esophageal adenocarcinoma when compared to normal esophageal squamous mucosa. This was also confirmed with the targeted mass spectrometry method. Although a few outliers existed, there was consistent overexpression observed in Barrett's tissue that progressed to esophageal adenocarcinoma greater than one year from biopsy retrieval when compared to Barrett's tissue that did not progress to a worsened disease over a ten year period.

The upregulation or overexpression of S100P or UBE2N is also predictive of Barrett's esophagus progression into esophageal adenocarcinoma. Discovery mass spectrometry determined these two markers are consistently overexpressed and highly active in esophageal adenocarcinoma when compared to normal esophageal squamous mucosa. This was also confirmed with the targeted mass spectrometry method. High overexpression of these markers was predictive of Barrett's esophagus progression to esophageal adenocarcinoma. In addition, due to the upstream position of these markers to pathways that signal for progressive disease mechanisms, knowing the expression levels of these markers is clinically informative.

---

What is claimed is:

1. A composition, comprising:
(a) a LTF peptide comprising the sequence set forth in SEQ ID NO:54; and
one or more of
(b) a CNDP2 peptide,
(c) a SET peptide, and
(d) a GPI peptide,
wherein each peptide is 6 to 16 amino acids in length and is labeled with a heavy isotope label peptide, and
wherein the composition is formulated for use as a standard in a targeted mass spectrometry assay.

2. The composition of claim 1, wherein the CNDP2 peptide comprises the sequence set forth in SEQ ID NO:20 or SEQ ID NO:31.

3. The composition of claim 1, wherein the SET peptide comprises the sequence set forth in SEQ ID NO:50.

4. The composition of claim 1, wherein the GPI peptide comprises the sequence set forth in SEQ ID NO:35 or SEQ ID NO:39.

5. The composition of claim 1, comprising at least two peptides of (a)-(d), at least three peptides of (a)-(d), or all four peptides of (a)-(d).

6. The composition of claim 1, further comprising one or more of:
(e) an ISG15 peptide,
(f) a DAD1 peptide,
(g) a UBE2N peptide, and
(h) a S100P peptide,
wherein each peptide in (e)-(h) is 6 to 16 amino acids in length and is labeled with a heavy isotope label peptide.

7. The composition of claim 6, wherein the ISG15 peptide comprises the sequence set forth in SEQ ID NO:11 or SEQ ID NO:12.

8. The composition of claim 6, wherein the DAD1 peptide comprises the sequence set forth in SEQ ID NO:7 or SEQ ID NO:9.

9. The composition of claim 6, wherein the UBE2N peptide comprises the sequence set forth in SEQ ID NO:1 or SEQ ID NO:5.

10. The composition of claim 6, wherein the S100P peptide comprises the sequence set forth in SEQ ID NO:67 or SEQ ID NO:68.

11. The composition of claim 6, comprising at least two peptides of (e)-(h), at least three peptides of (e)-(h), or all four peptides of (e)-(h).

12. A composition, comprising:
(a) a LTF peptide comprising the sequence set forth in SEQ ID NO:54,
(b) a CNDP2 peptide,
(c) a SET peptide,
(d) a GPI peptide,
(e) an ISG15 peptide,
(f) a DAD1 peptide,
(g) a UBE2N, and
(h) a S100P peptide,
wherein each peptide is 6 to 16 amino acids in length and is labeled with a heavy isotope label peptide, and
wherein the composition is formulated as for use as a standard in a targeted mass spectrometry assay.

13. The composition of claim 12, wherein
the CNDP2 peptide comprises the sequence set forth in SEQ ID NO:20 or SEQ ID NO: 31;
the SET peptide comprises the sequence set forth in SEQ ID NO:50;
the GPI peptide comprises the sequence set forth in SEQ ID NO:35 or SEQ ID NO:39;
the ISG15 peptide comprises the sequence set forth in SEQ ID NO:11 or SEQ ID NO:12;
the DAD1 peptide comprises the sequence set forth in SEQ ID NO:7 or SEQ ID NO:9;
the UBE2N peptide comprises the sequence set forth in SEQ ID NO:1 or SEQ ID NO:5; and
the S100P peptide comprises the sequence set forth in SEQ ID NO:67 or SEQ ID NO:68.

14. A method of measuring levels of LTF, CNDP2, SET, GPI, ISG15, DAD1, UBE2N, and S100P in a tissue sample, the method comprising:
performing a targeted mass spectrometry assay on the tissue sample using a set of heavy isotope labeled peptides comprising a LTF peptide, a CNDP2 peptide, a SET peptide, a GPI peptide, an ISG15 peptide, a DAD1 peptide, a UBE2N peptide, and a S100P peptide as internal standards.

15. The method of claim 14, wherein
(a) the LTF peptide comprises the sequence set forth in SEQ ID NO:54 or SEQ ID NO: 58,
(b) the CNDP2 peptide comprises the sequence set forth in SEQ ID NO:20 or 31,
(c) the SET peptide protein comprising an amino acid comprises the sequence set forth in SEQ ID NO:50,
(d) the GPI peptide comprises the sequence set forth in SEQ ID NO:35 or SEQ ID NO: 39,
(e) the ISG15 peptide comprises the sequence set forth in SEQ ID NO:11 or SEQ ID NO: 12,
(f) the DAD1 peptide comprises the sequence set forth in SEQ ID NO:7 or SEQ ID NO: 9,
(g) the UBE2N peptide comprises the sequence set forth in SEQ ID NO:1 or SEQ ID NO: 5, and
(h) the S100P peptide comprises the sequence set forth in SEQ ID NO:67 or SEQ ID NO: 68,
wherein each peptide is 6 to 16 amino acids in length and is labeled with a heavy isotope label peptide.

16. A composition, comprising:
a LTF peptide comprising the sequence set forth in SEQ ID NO:54;
an ISG15 peptide, and
a DAD1 peptide,
wherein each peptide is 6 to 16 amino acids in length and is labeled with a heavy isotope label peptide, and
wherein the composition is formulated for use as a standard in a targeted mass spectrometry assay.

17. The composition of claim 16,
wherein the ISG15 peptide comprises the sequence set forth in SEQ ID NO:11 or SEQ ID NO:12, and
wherein the DAD1 peptide comprises the sequence set forth in SEQ ID NO:7 or SEQ ID NO: 9.

18. The composition of claim 16, further comprising one or more of
a CNDP2 peptide,
a SET peptide,
a GPI peptide,
a UBE2N peptide, and
a S100P peptide,
wherein each peptide is 6 to 16 amino acids in length and is labeled with a heavy isotope label peptide.

19. A composition, comprising:
a CNDP2 peptide comprising the sequence set forth in SEQ ID NO:20;
a GPI peptide, and
a SET peptide,
wherein each peptide is 6 to 16 amino acids in length and is labeled with a heavy isotope label peptide, and
wherein the composition is formulated for use as a standard in a targeted mass spectrometry assay.

20. The composition of claim 19,
wherein the GPI peptide comprises the sequence set forth in SEQ ID NO:35 or SEQ ID NO: 39, and
wherein the SET peptide comprises the sequence set forth in SEQ ID NO:50.

21. The composition of claim 19, further comprising one or more of
a LTF peptide,
an ISG15 peptide,
a DAD1 peptide,
a UBE2N peptide, and
a S100P peptide,
wherein each peptide is 6 to 16 amino acids in length and is labeled with a heavy isotope label peptide.

22. A composition, comprising:
a UBE2N peptide comprising the sequence set forth in SEQ ID NO:1, and
a S100P peptide,
wherein each peptide is 6 to 16 amino acids in length and is labeled with a heavy isotope label peptide, and
wherein the composition is formulated for use as a standard in a targeted mass spectrometry assay.

23. The composition of claim 22,
wherein the S100P peptide comprises the sequence set forth in SEQ ID NO:67 or SEQ ID NO:68.

24. The composition of claim 22, further comprising one or more of
a CNDP2 peptide,
a GPI peptide,
a SET peptide,
a LTF peptide,
an ISG15 peptide, and
a DAD1 peptide,
wherein each peptide is 6 to 16 amino acids in length and is labeled with a heavy isotope label peptide.

25. A composition, comprising:
a LTF peptide comprising the sequence of SEQ ID NO:54; and at least one of
a CNDP2 peptide comprising the sequence of SEQ ID NO:20;
a SET peptide comprising the sequence of SEQ ID NO:50;
a GPI peptide comprising the sequence of SEQ ID NO:35;
an ISG15 peptide comprising the sequence of SEQ ID NO:11;
a DAD1 peptide comprising the sequence of SEQ ID NO:7;
a UBE2N peptide comprising the sequence of SEQ ID NO:1; and
a S100P peptide comprising the sequence of SEQ ID NO:67;
wherein the peptide is labeled with a heavy isotope label peptide, and
wherein the composition is formulated for use as a standard in a targeted mass spectrometry assay.

26. The composition of claim 25, wherein the composition comprises at least 2 peptides, at least 3 peptides, at least 4 peptides, at least 5 peptides, at least 6 peptides, at least 7 peptides, or all at least 8 peptides.

* * * * *

SEQUENCE LISTING

```
Sequence total quantity: 68
SEQ ID NO: 1            moltype = AA  length = 10
FEATURE                 Location/Qualifiers
REGION                  1..10
                        note = UBE2N peptide
source                  1..10
                        mol_type = protein
                        organism = synthetic construct
SEQUENCE: 1
LLAEPVPGIK                                                                  10

SEQ ID NO: 2            moltype = AA  length = 9
FEATURE                 Location/Qualifiers
REGION                  1..9
                        note = UBE2N peptide
source                  1..9
                        mol_type = protein
                        organism = synthetic construct
SEQUENCE: 2
AEPDESNAR                                                                    9

SEQ ID NO: 3            moltype = AA  length = 20
FEATURE                 Location/Qualifiers
REGION                  1..20
                        note = UBE2N peptide
source                  1..20
                        mol_type = protein
                        organism = synthetic construct
SEQUENCE: 3
YFHVVIAGPQ DSPFEGGTFK                                                       20

SEQ ID NO: 4            moltype = AA  length = 8
FEATURE                 Location/Qualifiers
REGION                  1..8
                        note = UBE2N peptide
source                  1..8
                        mol_type = protein
                        organism = synthetic construct
SEQUENCE: 4
IYHPNVDK                                                                     8

SEQ ID NO: 5            moltype = AA  length = 8
FEATURE                 Location/Qualifiers
REGION                  1..8
                        note = UBE2N peptide
source                  1..8
                        mol_type = protein
```

```
SEQUENCE: 5
WSPALQIR                                                                8

SEQ ID NO: 6            moltype = AA   length = 11
FEATURE                 Location/Qualifiers
REGION                  1..11
                        note = UBE2N peptide
source                  1..11
                        mol_type = protein
                        organism = synthetic construct
SEQUENCE: 6
TNEAQAIETA R                                                           11

SEQ ID NO: 7            moltype = AA   length = 12
FEATURE                 Location/Qualifiers
REGION                  1..12
                        note = DAD1 peptide
source                  1..12
                        mol_type = protein
                        organism = synthetic construct
SEQUENCE: 7
FLEEYLSSTP QR                                                          12

SEQ ID NO: 8            moltype = AA   length = 8
FEATURE                 Location/Qualifiers
REGION                  1..8
                        note = DAD1 peptide
source                  1..8
                        mol_type = protein
                        organism = synthetic construct
SEQUENCE: 8
IQINPQNK                                                                8

SEQ ID NO: 9            moltype = AA   length = 10
FEATURE                 Location/Qualifiers
REGION                  1..10
                        note = DAD1 peptide
source                  1..10
                        mol_type = protein
                        organism = synthetic construct
SEQUENCE: 9
ADFQGISPER                                                             10

SEQ ID NO: 10           moltype = AA   length = 6
FEATURE                 Location/Qualifiers
REGION                  1..6
                        note = ISG15 peptide
source                  1..6
                        mol_type = protein
                        organism = synthetic construct
SEQUENCE: 10
AQITQK                                                                  6

SEQ ID NO: 11           moltype = AA   length = 9
FEATURE                 Location/Qualifiers
REGION                  1..9
                        note = ISG15 peptide
source                  1..9
                        mol_type = protein
                        organism = synthetic construct
SEQUENCE: 11
IGVHAFQQR                                                               9

SEQ ID NO: 12           moltype = AA   length = 13
FEATURE                 Location/Qualifiers
REGION                  1..13
                        note = ISG15 peptide
source                  1..13
                        mol_type = protein
                        organism = synthetic construct
SEQUENCE: 12
LAVHPSGVAL QDR                                                         13

SEQ ID NO: 13           moltype = AA   length = 20
FEATURE                 Location/Qualifiers
REGION                  1..20
                        note = ISG15 peptide
source                  1..20
```

```
                             -continued mol_type = protein
                        organism = synthetic construct
SEQUENCE: 13
VPLASQGLGP GSTVLLVVDK                                               20

SEQ ID NO: 14           moltype = AA  length = 7
FEATURE                 Location/Qualifiers
REGION                  1..7
                        note = ISG15 peptide
source                  1..7
                        mol_type = protein
                        organism = synthetic construct
SEQUENCE: 14
SSTYEVR                                                              7

SEQ ID NO: 15           moltype = AA  length = 9
FEATURE                 Location/Qualifiers
REGION                  1..9
                        note = ISG15 peptide
source                  1..9
                        mol_type = protein
                        organism = synthetic construct
SEQUENCE: 15
LTQTVAHLK                                                            9

SEQ ID NO: 16           moltype = AA  length = 9
FEATURE                 Location/Qualifiers
REGION                  1..9
                        note = ISG15 peptide
source                  1..9
                        mol_type = protein
                        organism = synthetic construct
SEQUENCE: 16
GGGTEPGGR                                                            9

SEQ ID NO: 17           moltype = AA  length = 8
FEATURE                 Location/Qualifiers
REGION                  1..8
                        note = CNDP2 peptide
source                  1..8
                        mol_type = protein
                        organism = synthetic construct
SEQUENCE: 17
YIDENQDR                                                             8

SEQ ID NO: 18           moltype = AA  length = 13
FEATURE                 Location/Qualifiers
REGION                  1..13
                        note = CNDP2 peptide
source                  1..13
                        mol_type = protein
                        organism = synthetic construct
SEQUENCE: 18
WVAIQSVSAW PEK                                                      13

SEQ ID NO: 19           moltype = AA  length = 13
FEATURE                 Location/Qualifiers
REGION                  1..13
                        note = CNDP2 peptide
source                  1..13
                        mol_type = protein
                        organism = synthetic construct
SEQUENCE: 19
QLGGSVELVD IGK                                                      13

SEQ ID NO: 20           moltype = AA  length = 16
FEATURE                 Location/Qualifiers
REGION                  1..16
                        note = CNDP2 peptide
source                  1..16
                        mol_type = protein
                        organism = synthetic construct
SEQUENCE: 20
LPDGSEIPLP PILLGR                                                   16

SEQ ID NO: 21           moltype = AA  length = 7
FEATURE                 Location/Qualifiers
REGION                  1..7
                        note = CNDP2 peptide
```

| | | |
|---|---|---|
| source | 1..7<br>mol_type = protein<br>organism = synthetic construct | |
| SEQUENCE: 21<br>LGSDPQK | | 7 |
| SEQ ID NO: 22<br>FEATURE<br>REGION<br>source | moltype = AA  length = 6<br>Location/Qualifiers<br>1..6<br>note = CNDP2 peptide<br>1..6<br>mol_type = protein<br>organism = synthetic construct | |
| SEQUENCE: 22<br>GSTDDK | | 6 |
| SEQ ID NO: 23<br>FEATURE<br>REGION<br>source | moltype = AA  length = 15<br>Location/Qualifiers<br>1..15<br>note = CNDP2 peptide<br>1..15<br>mol_type = protein<br>organism = synthetic construct | |
| SEQUENCE: 23<br>GPVAGWINAL EAYQK | | 15 |
| SEQ ID NO: 24<br>FEATURE<br>REGION<br>source | moltype = AA  length = 10<br>Location/Qualifiers<br>1..10<br>note = CNDP2 peptide<br>1..10<br>mol_type = protein<br>organism = synthetic construct | |
| SEQUENCE: 24<br>TGQEIPVNVR | | 10 |
| SEQ ID NO: 25<br>FEATURE<br>REGION<br>source | moltype = AA  length = 5<br>Location/Qualifiers<br>1..5<br>note = CNDP2 peptide<br>1..5<br>mol_type = protein<br>organism = synthetic construct | |
| SEQUENCE: 25<br>DTFFK | | 5 |
| SEQ ID NO: 26<br>FEATURE<br>REGION<br>source | moltype = AA  length = 21<br>Location/Qualifiers<br>1..21<br>note = CNDP2 peptide<br>1..21<br>mol_type = protein<br>organism = synthetic construct | |
| SEQUENCE: 26<br>GNILIPGINE AVAAVTEEEH K | | 21 |
| SEQ ID NO: 27<br>FEATURE<br>REGION<br>source | moltype = AA  length = 14<br>Location/Qualifiers<br>1..14<br>note = CNDP2 peptide<br>1..14<br>mol_type = protein<br>organism = synthetic construct | |
| SEQUENCE: 27<br>LYDDIDFDIE EFAK | | 14 |
| SEQ ID NO: 28<br>FEATURE<br>REGION<br>source | moltype = AA  length = 12<br>Location/Qualifiers<br>1..12<br>note = CNDP2 peptide<br>1..12<br>mol_type = protein<br>organism = synthetic construct | |
| SEQUENCE: 28<br>DVGAQILLHS HK | | 12 |
| SEQ ID NO: 29<br>FEATURE<br>REGION | moltype = AA  length = 19<br>Location/Qualifiers<br>1..19 | |

```
                                note = CNDP2 peptide
source                          1..19
                                mol_type = protein
                                organism = synthetic construct
SEQUENCE: 29
YPSLSLHGIE GAFSGSGAK                                                    19

SEQ ID NO: 30                   moltype = AA   length = 6
FEATURE                         Location/Qualifiers
REGION                          1..6
                                note = CNDP2 peptide
source                          1..6
                                mol_type = protein
                                organism = synthetic construct
SEQUENCE: 30
SPNEFK                                                                   6

SEQ ID NO: 31                   moltype = AA   length = 11
FEATURE                         Location/Qualifiers
REGION                          1..11
                                note = CNDP2 peptide
source                          1..11
                                mol_type = protein
                                organism = synthetic construct
SEQUENCE: 31
TVFGVEPDLT R                                                            11

SEQ ID NO: 32                   moltype = AA   length = 17
FEATURE                         Location/Qualifiers
REGION                          1..17
                                note = CNDP2 peptide
source                          1..17
                                mol_type = protein
                                organism = synthetic construct
SEQUENCE: 32
EGGSIPVTLT FQEATGK                                                      17

SEQ ID NO: 33                   moltype = AA   length = 8
FEATURE                         Location/Qualifiers
REGION                          1..8
                                note = CNDP2 peptide
source                          1..8
                                mol_type = protein
                                organism = synthetic construct
SEQUENCE: 33
YNYIEGTK                                                                 8

SEQ ID NO: 34                   moltype = AA   length = 6
FEATURE                         Location/Qualifiers
REGION                          1..6
                                note = GPI peptide
source                          1..6
                                mol_type = protein
                                organism = synthetic construct
SEQUENCE: 34
DPQFQK                                                                   6

SEQ ID NO: 35                   moltype = AA   length = 6
FEATURE                         Location/Qualifiers
REGION                          1..6
                                note = GPI peptide
source                          1..6
                                mol_type = protein
                                organism = synthetic construct
SEQUENCE: 35
LQQWYR                                                                   6

SEQ ID NO: 36                   moltype = AA   length = 6
FEATURE                         Location/Qualifiers
REGION                          1..6
                                note = GPI peptide
source                          1..6
                                mol_type = protein
                                organism = synthetic construct
SEQUENCE: 36
SELNLR                                                                   6

SEQ ID NO: 37                   moltype = AA   length = 21
FEATURE                         Location/Qualifiers
```

```
                                    -continued

REGION                  1..21
                        note = GPI peptide
source                  1..21
                        mol_type = protein
                        organism = synthetic construct
SEQUENCE: 37
FNHFSLTLNT NHGHILVDYS K                                              21

SEQ ID NO: 38           moltype = AA  length = 7
FEATURE                 Location/Qualifiers
REGION                  1..7
                        note = GPI peptide
source                  1..7
                        mol_type = protein
                        organism = synthetic construct
SEQUENCE: 38
INYTEGR                                                              7

SEQ ID NO: 39           moltype = AA  length = 8
FEATURE                 Location/Qualifiers
REGION                  1..8
                        note = GPI peptide
source                  1..8
                        mol_type = protein
                        organism = synthetic construct
SEQUENCE: 39
AVLHVALR                                                             8

SEQ ID NO: 40           moltype = AA  length = 10
FEATURE                 Location/Qualifiers
REGION                  1..10
                        note = GPI peptide
source                  1..10
                        mol_type = protein
                        organism = synthetic construct
SEQUENCE: 40
SNTPILVDGK                                                           10

SEQ ID NO: 41           moltype = AA  length = 14
FEATURE                 Location/Qualifiers
REGION                  1..14
                        note = GPI peptide
source                  1..14
                        mol_type = protein
                        organism = synthetic construct
SEQUENCE: 41
VWYVSNIDGT HIAK                                                      14

SEQ ID NO: 42           moltype = AA  length = 17
FEATURE                 Location/Qualifiers
REGION                  1..17
                        note = GPI peptide
source                  1..17
                        mol_type = protein
                        organism = synthetic construct
SEQUENCE: 42
TLAQLNPESS LFIIASK                                                   17

SEQ ID NO: 43           moltype = AA  length = 15
FEATURE                 Location/Qualifiers
REGION                  1..15
                        note = GPI peptide
source                  1..15
                        mol_type = protein
                        organism = synthetic construct
SEQUENCE: 43
TFTTQETITN AETAK                                                     15

SEQ ID NO: 44           moltype = AA  length = 8
FEATURE                 Location/Qualifiers
REGION                  1..8
                        note = GPI peptide
source                  1..8
                        mol_type = protein
                        organism = synthetic construct
SEQUENCE: 44
EWFLQAAK                                                             8

SEQ ID NO: 45           moltype = AA  length = 7
```

```
FEATURE              Location/Qualifiers
REGION               1..7
                     note = GPI peptide
source               1..7
                     mol_type = protein
                     organism = synthetic construct
SEQUENCE: 45
DPSAVAK                                                                              7

SEQ ID NO: 46        moltype = AA  length = 11
FEATURE              Location/Qualifiers
REGION               1..11
                     note = GPI peptide
source               1..11
                     mol_type = protein
                     organism = synthetic construct
SEQUENCE: 46
HFVALSTNTT K                                                                        11

SEQ ID NO: 47        moltype = AA  length = 7
FEATURE              Location/Qualifiers
REGION               1..7
                     note = GPI peptide
source               1..7
                     mol_type = protein
                     organism = synthetic construct
SEQUENCE: 47
ELQAAGK                                                                              7

SEQ ID NO: 48        moltype = AA  length = 22
FEATURE              Location/Qualifiers
REGION               1..22
                     note = GPI peptide
source               1..22
                     mol_type = protein
                     organism = synthetic construct
SEQUENCE: 48
IFVQGIIWDI NSFDQWGVEL GK                                                            22

SEQ ID NO: 49        moltype = AA  length = 8
FEATURE              Location/Qualifiers
REGION               1..8
                     note = SET peptide
source               1..8
                     mol_type = protein
                     organism = synthetic construct
SEQUENCE: 49
QSPLPPQK                                                                             8

SEQ ID NO: 50        moltype = AA  length = 11
FEATURE              Location/Qualifiers
REGION               1..11
                     note = SET peptide
source               1..11
                     mol_type = protein
                     organism = synthetic construct
SEQUENCE: 50
LNEQASEEIL K                                                                        11

SEQ ID NO: 51        moltype = AA  length = 20
FEATURE              Location/Qualifiers
REGION               1..20
                     note = LTF peptide
source               1..20
                     mol_type = protein
                     organism = synthetic construct
SEQUENCE: 51
ADAVTLDGGF IYEAGLAPYK                                                               20

SEQ ID NO: 52        moltype = AA  length = 10
FEATURE              Location/Qualifiers
REGION               1..10
                     note = LTF peptide
source               1..10
                     mol_type = protein
                     organism = synthetic construct
SEQUENCE: 52
THYYAVAVVK                                                                          10
```

```
SEQ ID NO: 53         moltype = AA  length = 13
FEATURE               Location/Qualifiers
REGION                1..13
                      note = LTF peptide
source                1..13
                      mol_type = protein
                      organism = synthetic construct
SEQUENCE: 53
GGSFQLNELQ GLK                                                          13

SEQ ID NO: 54         moltype = AA  length = 10
FEATURE               Location/Qualifiers
REGION                1..10
                      note = LTF peptide
source                1..10
                      mol_type = protein
                      organism = synthetic construct
SEQUENCE: 54
DGAGDVAFIR                                                              10

SEQ ID NO: 55         moltype = AA  length = 14
FEATURE               Location/Qualifiers
REGION                1..14
                      note = LTF peptide
source                1..14
                      mol_type = protein
                      organism = synthetic construct
SEQUENCE: 55
ESTVFEDLSD EAER                                                         14

SEQ ID NO: 56         moltype = AA  length = 9
FEATURE               Location/Qualifiers
REGION                1..9
                      note = LTF peptide
source                1..9
                      mol_type = protein
                      organism = synthetic construct
SEQUENCE: 56
VPSHAVVAR                                                               9

SEQ ID NO: 57         moltype = AA  length = 9
FEATURE               Location/Qualifiers
REGION                1..9
                      note = LTF peptide
source                1..9
                      mol_type = protein
                      organism = synthetic construct
SEQUENCE: 57
EDAIWNLLR                                                               9

SEQ ID NO: 58         moltype = AA  length = 11
FEATURE               Location/Qualifiers
REGION                1..11
                      note = LTF peptide
source                1..11
                      mol_type = protein
                      organism = synthetic construct
SEQUENCE: 58
FQLFGSPSGQ K                                                            11

SEQ ID NO: 59         moltype = AA  length = 8
FEATURE               Location/Qualifiers
REGION                1..8
                      note = LTF peptide
source                1..8
                      mol_type = protein
                      organism = synthetic construct
SEQUENCE: 59
DSAIGFSR                                                                8

SEQ ID NO: 60         moltype = AA  length = 19
FEATURE               Location/Qualifiers
REGION                1..19
                      note = LTF peptide
source                1..19
                      mol_type = protein
                      organism = synthetic construct
SEQUENCE: 60
IDSGLYLGSG YFTAIQNLR                                                    19
```

```
SEQ ID NO: 61           moltype = AA   length = 8
FEATURE                 Location/Qualifiers
REGION                  1..8
                        note = LTF peptide
source                  1..8
                        mol_type = protein
                        organism = synthetic construct
SEQUENCE: 61
SEEEVAAR                                                                 8

SEQ ID NO: 62           moltype = AA   length = 18
FEATURE                 Location/Qualifiers
REGION                  1..18
                        note = LTF peptide
source                  1..18
                        mol_type = protein
                        organism = synthetic construct
SEQUENCE: 62
GEADAMSLDG GYVYTAGK                                                     18

SEQ ID NO: 63           moltype = AA   length = 11
FEATURE                 Location/Qualifiers
REGION                  1..11
                        note = LTF peptide
source                  1..11
                        mol_type = protein
                        organism = synthetic construct
SEQUENCE: 63
SDTSLTWNSV K                                                            11

SEQ ID NO: 64           moltype = AA   length = 18
FEATURE                 Location/Qualifiers
REGION                  1..18
                        note = LTF peptide
source                  1..18
                        mol_type = protein
                        organism = synthetic construct
SEQUENCE: 64
DVTVLQNTDG NNNEAWAK                                                     18

SEQ ID NO: 65           moltype = AA   length = 9
FEATURE                 Location/Qualifiers
REGION                  1..9
                        note = LTF peptide
source                  1..9
                        mol_type = protein
                        organism = synthetic construct
SEQUENCE: 65
QVLLHQQAK                                                                9

SEQ ID NO: 66           moltype = AA   length = 14
FEATURE                 Location/Qualifiers
REGION                  1..14
                        note = LTF peptide
source                  1..14
                        mol_type = protein
                        organism = synthetic construct
SEQUENCE: 66
YLGPQYVAGI TNLK                                                         14

SEQ ID NO: 67           moltype = AA   length = 13
FEATURE                 Location/Qualifiers
REGION                  1..13
                        note = S100P peptide
source                  1..13
                        mol_type = protein
                        organism = synthetic construct
SEQUENCE: 67
YSGSEGSTQT LTK                                                          13
```

```
SEQ ID NO: 68         moltype = AA  length = 10
FEATURE               Location/Qualifiers
REGION                1..10
                      note = S100P peptide
source                1..10
                      mol_type = protein
                      organism = synthetic construct
SEQUENCE: 68
ELPGFLQSGK                                                              10
```